US011939389B2

(12) United States Patent
Abujoub et al.

(10) Patent No.: US 11,939,389 B2
(45) Date of Patent: Mar. 26, 2024

(54) BCMA CHIMERIC ANTIGEN RECEPTORS AND USES THEREOF

(71) Applicant: Novartis AG, Basel (CH)

(72) Inventors: Aida Abujoub, Winchester, MA (US); John Blankenship, Acton, MA (US); Dexiu Bu, Melrose, MA (US); Tony Fleming, Stow, MA (US); Brian Holmberg, Somerville, MA (US); Connie Hong, Somerville, MA (US); Lu Huang, West Roxbury, MA (US); Chonghui Zhang, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 18/170,969

(22) Filed: Feb. 17, 2023

(65) Prior Publication Data

US 2023/0183368 A1 Jun. 15, 2023

Related U.S. Application Data

(62) Division of application No. 16/439,495, filed on Jun. 12, 2019, now Pat. No. 11,608,382.

(60) Provisional application No. 62/832,991, filed on Apr. 12, 2019, provisional application No. 62/684,628, filed on Jun. 13, 2018.

(51) Int. Cl.

| | |
|---|---|
| ***C07K 16/28*** | (2006.01) |
| ***A61K 35/17*** | (2015.01) |
| ***A61P 35/00*** | (2006.01) |
| ***C07K 14/705*** | (2006.01) |
| ***C07K 14/725*** | (2006.01) |
| ***C12N 5/0783*** | (2010.01) |
| *A61K 38/00* | (2006.01) |

(52) U.S. Cl.

CPC .......... *C07K 16/2878* (2013.01); *A61K 35/17* (2013.01); *A61P 35/00* (2018.01); *C07K 14/7051* (2013.01); *C07K 14/70578* (2013.01); *C12N 5/0636* (2013.01); *A61K 38/00* (2013.01); *C07K 2317/565* (2013.01); *C07K 2317/622* (2013.01); *C07K 2317/732* (2013.01); *C07K 2317/76* (2013.01); *C07K 2319/02* (2013.01); *C07K 2319/03* (2013.01); *C07K 2319/30* (2013.01); *C07K 2319/33* (2013.01)

(58) Field of Classification Search

None

See application file for complete search history.

(56) References Cited

U.S. PATENT DOCUMENTS

| | | | |
|---|---|---|---|
| 3,929,992 | A | 12/1975 | Sehgal et al. |
| 5,359,046 | A | 10/1994 | Capon et al. |
| 5,665,772 | A | 9/1997 | Cottens et al. |
| 5,686,281 | A | 11/1997 | Roberts |
| 5,712,149 | A | 1/1998 | Roberts |
| 5,858,358 | A | 1/1999 | June et al. |
| 5,874,240 | A | 2/1999 | Ni et al. |
| 5,883,223 | A | 3/1999 | Gray |
| 5,906,936 | A | 5/1999 | Eshhar et al. |
| 5,912,172 | A | 6/1999 | Eshhar et al. |
| 6,103,521 | A | 8/2000 | Capon et al. |
| 6,319,494 | B1 | 11/2001 | Capon et al. |
| 6,352,694 | B1 | 3/2002 | June et al. |
| 6,355,779 | B1 | 3/2002 | Goodwin et al. |
| 6,407,213 | B1 | 6/2002 | Carter et al. |
| 6,410,319 | B1 | 6/2002 | Raubitschek et al. |
| 6,475,481 | B2 | 11/2002 | Talmadge |
| 6,534,055 | B1 | 3/2003 | June et al. |
| 6,569,997 | B1 | 5/2003 | Kwon |
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,049,136 | B2 | 5/2006 | Seed et al. |
| 7,052,906 | B1 | 5/2006 | Lawson et al. |
| 7,067,318 | B2 | 6/2006 | June et al. |
| 7,070,995 | B2 | 7/2006 | Jensen |
| 7,083,785 | B2 | 8/2006 | Browning et al. |
| 7,129,332 | B2 | 10/2006 | Pastan et al. |
| 7,144,575 | B2 | 12/2006 | June et al. |
| 7,172,869 | B2 | 2/2007 | June et al. |

(Continued)

FOREIGN PATENT DOCUMENTS

| | | |
|---|---|---|
| CN | 1795009 A | 6/2006 |
| CN | 101210048 A | 7/2008 |

(Continued)

OTHER PUBLICATIONS

Rennert et al. (JEM, vol. 192, No. 11, Dec. 4, 2000 1677-1683). (Year: 2000).*

Salazar-Camarena et al. (Lupus (2016) 25, 582-592). (Year: 2016).*

Yuen et al., Trends Cancer. Dec. 2016 ; 2(12): 747-757, renumbered as pp. 1-18. (Year: 2016).*

Gavioli et al., "Protein kinase C mediates human neutrophil cytotoxicity" Biochemical and Biophysical Research Communications 148(3): 1290-1294 (1987).

Geiger and Jyothi, "Development and Application of Receptor-Modified T Lymphocytes for Adoptive Immunotherapy" Transfusion Medicine Reviews (2001) vol. 15 No. 1 pp. 21-34.

(Continued)

*Primary Examiner* — Zachary S Skelding

(74) *Attorney, Agent, or Firm* — K&L Gates LLP

(57) ABSTRACT

The invention provides compositions and methods for treating diseases associated with expression of BCMA. The invention also relates to chimeric antigen receptor (CAR) specific to BCMA, vectors encoding the same, and recombinant T cells comprising the BCMA CAR. The invention also includes methods of administering a genetically modified T cell expressing a CAR that comprises a BCMA binding domain.

90 Claims, 8 Drawing Sheets

Specification includes a Sequence Listing.

(56) References Cited

U.S. PATENT DOCUMENTS

| | | | |
|---|---|---|---|
| 7,175,843 | B2 | 2/2007 | June et al. |
| 7,232,566 | B2 | 6/2007 | June et al. |
| 7,265,209 | B2 | 9/2007 | Jensen |
| 7,319,143 | B2 | 1/2008 | Gross et al. |
| 7,320,787 | B2 | 1/2008 | Seed et al. |
| 7,446,190 | B2 | 11/2008 | Sadelain et al. |
| 7,446,191 | B2 | 11/2008 | Jensen |
| 7,514,537 | B2 | 4/2009 | Jensen |
| 7,627,643 | B1 | 12/2009 | Ignatoff et al. |
| 7,628,986 | B2 | 12/2009 | Weber et al. |
| 7,638,326 | B2 | 12/2009 | June et al. |
| 7,741,465 | B1 | 6/2010 | Eshhar et al. |
| 7,745,140 | B2 | 6/2010 | June et al. |
| 7,754,482 | B2 | 7/2010 | Riley et al. |
| 7,943,743 | B2 | 5/2011 | Korman et al. |
| 7,994,298 | B2 | 8/2011 | Zhang et al. |
| 8,211,422 | B2 | 7/2012 | Eshhar et al. |
| 8,252,914 | B2 | 8/2012 | Zhang et al. |
| 8,389,282 | B2 | 3/2013 | Sadelain et al. |
| 8,399,645 | B2 | 3/2013 | Campana et al. |
| 8,465,743 | B2 | 6/2013 | Rosenberg et al. |
| 8,637,307 | B2 | 1/2014 | June et al. |
| 8,722,400 | B2 | 5/2014 | Riley et al. |
| 8,852,551 | B2 | 10/2014 | Jordan |
| 8,906,682 | B2 | 12/2014 | June et al. |
| 8,911,993 | B2 | 12/2014 | June et al. |
| 8,916,381 | B1 | 12/2014 | June et al. |
| 8,975,071 | B1 | 3/2015 | June et al. |
| 9,101,584 | B2 | 8/2015 | June et al. |
| 9,102,760 | B2 | 8/2015 | June et al. |
| 9,102,761 | B2 | 8/2015 | June et al. |
| 9,272,002 | B2 | 3/2016 | Powell, Jr. et al. |
| 9,328,156 | B2 | 5/2016 | June et al. |
| 9,365,641 | B2 | 6/2016 | June et al. |
| 9,394,368 | B2 | 7/2016 | Brogdon et al. |
| 9,402,865 | B2 | 8/2016 | Powell et al. |
| 9,422,351 | B2 | 8/2016 | Scholler et al. |
| 9,446,105 | B2 | 9/2016 | Powell, Jr. |
| 9,464,140 | B2 | 10/2016 | June et al. |
| 9,481,728 | B2 | 11/2016 | June et al. |
| 9,499,629 | B2 | 11/2016 | June et al. |
| 9,518,123 | B2 | 12/2016 | June et al. |
| 9,540,445 | B2 | 1/2017 | June et al. |
| 9,572,836 | B2 | 2/2017 | June et al. |
| 9,573,988 | B2 | 2/2017 | Brogdon et al. |
| 9,598,489 | B2 | 3/2017 | Powell, Jr. |
| 9,708,384 | B2 | 7/2017 | Scholler et al. |
| 9,714,278 | B2 | 7/2017 | June et al. |
| 9,745,368 | B2 | 8/2017 | Milone et al. |
| 9,765,156 | B2 | 9/2017 | June et al. |
| 9,777,061 | B2 | 10/2017 | Ebersbach et al. |
| 9,815,901 | B2 | 11/2017 | Brogdon et al. |
| 9,937,205 | B2 | 4/2018 | Albelda et al. |
| 10,174,095 | B2 | 1/2019 | Brogdon et al. |
| 11,608,382 | B2 | 3/2023 | Abujoub et al. |
| 2003/0060444 | A1 | 3/2003 | Finney et al. |
| 2003/0077249 | A1 | 4/2003 | Bebbington et al. |
| 2003/0147869 | A1 | 8/2003 | Riley et al. |
| 2003/0148982 | A1 | 8/2003 | Brenner et al. |
| 2003/0171546 | A1 | 9/2003 | Jensen |
| 2003/0224520 | A1 | 12/2003 | June et al. |
| 2004/0038886 | A1 | 2/2004 | Finney et al. |
| 2004/0043401 | A1 | 3/2004 | Sadelain et al. |
| 2004/0101519 | A1 | 5/2004 | June et al. |
| 2004/0110290 | A1 | 6/2004 | June et al. |
| 2005/0019429 | A1 | 1/2005 | Ivanov et al. |
| 2005/0113564 | A1 | 5/2005 | Campana et al. |
| 2005/0129671 | A1 | 6/2005 | Cooper et al. |
| 2006/0034810 | A1 | 2/2006 | Riley et al. |
| 2006/0121005 | A1 | 6/2006 | Berenson et al. |
| 2006/0246548 | A1 | 11/2006 | Jensen |
| 2007/0036773 | A1 | 2/2007 | Cooper et al. |
| 2008/0058316 | A1 | 3/2008 | Eberhart et al. |
| 2008/0131415 | A1 | 6/2008 | Riddell et al. |
| 2009/0088373 | A1 | 4/2009 | Gallo et al. |
| 2009/0092611 | A1 | 4/2009 | Kindsvogel |
| 2009/0148419 | A1 | 6/2009 | Gonzalez De La Pena et al. |
| 2009/0257994 | A1 | 10/2009 | Jensen |
| 2009/0325167 | A1 | 12/2009 | Chappell et al. |
| 2010/0105136 | A1 | 4/2010 | Carter et al. |
| 2010/0196311 | A1 | 8/2010 | Kim et al. |
| 2010/0261269 | A1 | 10/2010 | June et al. |
| 2010/0273797 | A1 | 10/2010 | Boman et al. |
| 2011/0052554 | A1 | 3/2011 | Zakrzewski et al. |
| 2011/0129496 | A1 | 6/2011 | Ahmed et al. |
| 2011/0262467 | A1 | 10/2011 | Riley et al. |
| 2011/0280894 | A1 | 11/2011 | Krackhardt et al. |
| 2012/0039906 | A1 | 2/2012 | Olive |
| 2012/0082661 | A1 | 4/2012 | Kalled et al. |
| 2012/0138858 | A1 | 6/2012 | Lee et al. |
| 2012/0148552 | A1 | 6/2012 | Jensen |
| 2012/0244116 | A1 | 9/2012 | Hiwase et al. |
| 2012/0282256 | A1 | 11/2012 | Campana et al. |
| 2012/0321667 | A1 | 12/2012 | Sentman |
| 2013/0040371 | A1 | 2/2013 | Abe et al. |
| 2013/0071409 | A1 | 3/2013 | Riley et al. |
| 2013/0071414 | A1 | 3/2013 | Dotti et al. |
| 2013/0149337 | A1 | 6/2013 | Cooper et al. |
| 2013/0155909 | A1 | 6/2013 | Jackson et al. |
| 2013/0280280 | A1 | 10/2013 | Algate et al. |
| 2013/0287748 | A1 | 10/2013 | June et al. |
| 2013/0288368 | A1 | 10/2013 | June et al. |
| 2013/0309258 | A1 | 11/2013 | June et al. |
| 2014/0050708 | A1 | 2/2014 | Powell et al. |
| 2014/0099309 | A1 | 4/2014 | Powell, Jr. et al. |
| 2014/0099340 | A1 | 4/2014 | June et al. |
| 2014/0106449 | A1 | 4/2014 | June et al. |
| 2014/0186947 | A1 | 7/2014 | June et al. |
| 2014/0212446 | A1 | 7/2014 | Riley et al. |
| 2014/0219975 | A1 | 8/2014 | June et al. |
| 2014/0227237 | A1 | 8/2014 | June et al. |
| 2014/0242049 | A1 | 8/2014 | Choi et al. |
| 2014/0255363 | A1 | 9/2014 | Metelitsa et al. |
| 2014/0271635 | A1 | 9/2014 | Brogdon et al. |
| 2014/0322169 | A1 | 10/2014 | Harper et al. |
| 2014/0322183 | A1 | 10/2014 | Milone et al. |
| 2014/0322212 | A1 | 10/2014 | Brogdon et al. |
| 2014/0322217 | A1 | 10/2014 | Moore et al. |
| 2014/0322275 | A1 | 10/2014 | Brogdon et al. |
| 2014/0370017 | A1 | 12/2014 | June et al. |
| 2014/0370045 | A1 | 12/2014 | June et al. |
| 2015/0017141 | A1 | 1/2015 | June et al. |
| 2015/0024482 | A1 | 1/2015 | Frigault et al. |
| 2015/0050729 | A1 | 2/2015 | June et al. |
| 2015/0093822 | A1 | 4/2015 | June et al. |
| 2015/0099299 | A1 | 4/2015 | June et al. |
| 2015/0118202 | A1 | 4/2015 | June et al. |
| 2015/0140019 | A1 | 5/2015 | June et al. |
| 2015/0190428 | A1 | 7/2015 | June et al. |
| 2015/0202286 | A1 | 7/2015 | June et al. |
| 2015/0283178 | A1 | 10/2015 | June et al. |
| 2015/0290244 | A1 | 10/2015 | June et al. |
| 2015/0342994 | A1 | 12/2015 | Riley et al. |
| 2016/0046724 | A1 | 2/2016 | Brogdon et al. |
| 2016/0051651 | A1 | 2/2016 | Brogdon et al. |
| 2016/0068601 | A1 | 3/2016 | Brogdon et al. |
| 2016/0096892 | A1 | 4/2016 | Brogdon et al. |
| 2016/0185861 | A1 | 6/2016 | Bedoya et al. |
| 2016/0311907 | A1 | 10/2016 | Brogdon et al. |
| 2016/0311917 | A1 | 10/2016 | Beatty et al. |
| 2016/0340406 | A1 | 11/2016 | Zhao et al. |
| 2016/0362472 | A1 | 12/2016 | Bitter et al. |
| 2017/0008963 | A1 | 1/2017 | Brogdon et al. |
| 2017/0081411 | A1 | 3/2017 | Engels et al. |
| 2017/0137783 | A1 | 5/2017 | Bedoya et al. |
| 2017/0183415 | A1 | 6/2017 | Brogdon et al. |
| 2017/0209492 | A1 | 7/2017 | June et al. |
| 2017/0211055 | A1 | 7/2017 | Brogdon et al. |
| 2017/0226216 | A1 | 8/2017 | Morgan et al. |
| 2017/0226495 | A1 | 8/2017 | Guimaraes |
| 2017/0239294 | A1 | 8/2017 | Thomas-Tikhonenko et al. |
| 2017/0260268 | A1 | 9/2017 | Beatty et al. |
| 2017/0274014 | A1 | 9/2017 | Brogdon et al. |
| 2017/0306416 | A1 | 10/2017 | Bedoya et al. |

(56) References Cited

U.S. PATENT DOCUMENTS

| | | | |
|---|---|---|---|
| 2017/0335281 | A1 | 11/2017 | Loew et al. |
| 2018/0022795 | A1 | 1/2018 | Milone et al. |
| 2018/0044423 | A1 | 2/2018 | Ebersbach et al. |
| 2018/0044424 | A1 | 2/2018 | June et al. |
| 2018/0118834 | A1 | 5/2018 | Brogdon et al. |
| 2018/0125892 | A1 | 5/2018 | Brannetti et al. |
| 2018/0133296 | A1 | 5/2018 | Barrett et al. |
| 2018/0140602 | A1 | 5/2018 | Angst et al. |
| 2018/0230193 | A1 | 8/2018 | Loew et al. |
| 2018/0252727 | A1 | 9/2018 | Garfall et al. |
| 2018/0258149 | A1 | 9/2018 | Motz et al. |
| 2018/0298068 | A1 | 10/2018 | Albelda |
| 2018/0312595 | A1 | 11/2018 | Brogdon et al. |
| 2019/0000880 | A1 | 1/2019 | Motz et al. |
| 2019/0000944 | A1 | 1/2019 | Brogdon et al. |
| 2019/0135940 | A1 | 5/2019 | Brogdon et al. |
| 2019/0151365 | A1 | 5/2019 | Anak et al. |
| 2019/0153061 | A1 | 5/2019 | Brogdon et al. |
| 2019/0161542 | A1 | 5/2019 | Gill et al. |
| 2019/0263914 | A1 | 8/2019 | Brogdon et al. |
| 2019/0269727 | A1 | 9/2019 | Fachin et al. |
| 2019/0292238 | A1 | 9/2019 | Bitter et al. |
| 2019/0292257 | A1 | 9/2019 | Bedoya et al. |
| 2019/0298715 | A1 | 10/2019 | Motz et al. |
| 2019/0330356 | A1 | 10/2019 | Brogdon et al. |
| 2019/0336504 | A1 | 11/2019 | Gill et al. |
| 2019/0375815 | A1 | 12/2019 | Engels et al. |
| 2019/0382500 | A1 | 12/2019 | Abujoub et al. |
| 2019/0388471 | A1 | 12/2019 | June et al. |
| 2019/0389928 | A1 | 12/2019 | Posey et al. |
| 2020/0048359 | A1 | 2/2020 | Albelda et al. |
| 2020/0055948 | A1 | 2/2020 | Daley et al. |
| 2020/0061113 | A1 | 2/2020 | Kassim et al. |
| 2020/0085869 | A1 | 3/2020 | Schuster et al. |
| 2020/0087376 | A1 | 3/2020 | Fraietta et al. |
| 2020/0113941 | A1 | 4/2020 | Brannetti et al. |
| 2020/0179511 | A1 | 6/2020 | Daley et al. |
| 2020/0215171 | A1 | 7/2020 | Brogdon et al. |
| 2020/0281973 | A1 | 9/2020 | Dranoff |
| 2020/0283729 | A1 | 9/2020 | Loew et al. |
| 2020/0291354 | A1 | 9/2020 | Johnson et al. |
| 2020/0339704 | A1 | 10/2020 | Bradner et al. |
| 2020/0360431 | A1 | 11/2020 | Garfall et al. |
| 2020/0368268 | A1 | 11/2020 | Johnson et al. |
| 2020/0370012 | A1 | 11/2020 | Fraietta et al. |
| 2020/0371091 | A1 | 11/2020 | Pruteanu-Malinici et al. |
| 2020/0399383 | A1 | 12/2020 | Scholler et al. |
| 2021/0002377 | A1 | 1/2021 | Brogdon et al. |
| 2021/0047405 | A1 | 2/2021 | Nobles et al. |
| 2021/0079073 | A1 | 3/2021 | Milone et al. |
| 2021/0087279 | A1 | 3/2021 | Engels et al. |
| 2021/0139595 | A1 | 5/2021 | Ebersbach et al. |
| 2021/0171909 | A1 | 6/2021 | Golovina |
| 2021/0172020 | A1 | 6/2021 | Bedoya et al. |
| 2021/0177896 | A1 | 6/2021 | Porter et al. |
| 2021/0177900 | A1 | 6/2021 | Engels et al. |
| 2021/0213063 | A1 | 7/2021 | Isaacs et al. |
| 2021/0220404 | A1 | 7/2021 | Abujoub et al. |
| 2021/0246423 | A1 | 8/2021 | Bedoya et al. |
| 2021/0284752 | A1 | 9/2021 | Brogdon et al. |
| 2021/0317183 | A1 | 10/2021 | Zhao et al. |
| 2021/0347851 | A1 | 11/2021 | Isaacs et al. |
| 2021/0396739 | A1 | 12/2021 | Pruteanu-Malinici et al. |
| 2022/0021653 | A1 | 1/2022 | Metz |
| 2022/0047633 | A1 | 2/2022 | Grupp |
| 2022/0064316 | A1 | 3/2022 | Brogdon et al. |
| 2022/0089750 | A1 | 3/2022 | June et al. |
| 2022/0152150 | A1 | 5/2022 | Koshy et al. |
| 2022/0168389 | A1 | 6/2022 | Ghassemi et al. |
| 2022/0195010 | A1 | 6/2022 | Bitter et al. |
| 2022/0251152 | A1 | 8/2022 | Carbonneau et al. |
| 2022/0364055 | A1 | 11/2022 | Treanor et al. |
| 2022/0387486 | A1 | 12/2022 | Brannetti et al. |
| 2023/0026049 | A1 | 1/2023 | Brogdon et al. |
| 2023/0071283 | A1 | 3/2023 | Golosov et al. |
| 2023/0074800 | A1 | 3/2023 | Berger et al. |
| 2023/0111593 | A1 | 4/2023 | Schuster et al. |
| 2023/0139800 | A1 | 5/2023 | Motz et al. |
| 2023/0174933 | A1 | 6/2023 | Brogdon et al. |
| 2023/0183368 | A1 | 6/2023 | Abujoub et al. |
| 2023/0220090 | A1 | 7/2023 | Brogdon et al. |
| 2023/0250179 | A1 | 8/2023 | Abujoub et al. |
| 2023/0256017 | A1 | 8/2023 | Brogdon et al. |
| 2023/0295296 | A1 | 9/2023 | Bedoya et al. |
| 2023/0302155 | A1 | 9/2023 | Koshy et al. |
| 2023/0312677 | A1 | 10/2023 | Posey et al. |
| 2023/0332104 | A1 | 10/2023 | Estevez Silva et al. |

FOREIGN PATENT DOCUMENTS

| | | | |
|---|---|---|---|
| CN | 101495516 | A | 7/2009 |
| CN | 102796198 | A | 11/2012 |
| CN | 102875685 | A | 1/2013 |
| CN | 102952191 | A | 3/2013 |
| CN | 103113470 | A | 5/2013 |
| CN | 103347897 | A | 10/2013 |
| EP | 0574512 | A1 | 12/1993 |
| EP | 0871495 | A1 | 10/1998 |
| EP | 1226244 | A2 | 7/2002 |
| EP | 1975231 | B1 | 8/2011 |
| EP | 2649086 | A1 | 10/2013 |
| EP | 2694549 | A1 | 2/2014 |
| JP | 6359520 | B2 | 7/2018 |
| RU | 2016146486 | A | 6/2018 |
| WO | 1992015322 | A1 | 9/1992 |
| WO | 9409010 | A1 | 4/1994 |
| WO | 9418317 | A1 | 8/1994 |
| WO | 199530014 | A1 | 11/1995 |
| WO | 9623814 | A1 | 8/1996 |
| WO | 9624671 | A1 | 8/1996 |
| WO | 9625953 | A1 | 8/1996 |
| WO | 9640140 | A1 | 12/1996 |
| WO | 1997015669 | A1 | 5/1997 |
| WO | 9723613 | A2 | 7/1997 |
| WO | 1997024373 | A1 | 7/1997 |
| WO | 9818809 | A1 | 5/1998 |
| WO | 9900494 | A2 | 1/1999 |
| WO | 9957268 | A1 | 11/1999 |
| WO | 0014257 | A1 | 3/2000 |
| WO | 0063374 | A1 | 10/2000 |
| WO | 01062931 | A2 | 8/2001 |
| WO | 01072325 | A1 | 10/2001 |
| WO | 2002033101 | A1 | 4/2002 |
| WO | 02077029 | A2 | 10/2002 |
| WO | 02088334 | A1 | 11/2002 |
| WO | 2003013598 | A2 | 2/2003 |
| WO | 2003057171 | A2 | 7/2003 |
| WO | 2004106381 | A1 | 12/2004 |
| WO | 2005000894 | A2 | 1/2005 |
| WO | 2005019429 | A2 | 3/2005 |
| WO | 2005044996 | A2 | 5/2005 |
| WO | 2005090990 | A2 | 9/2005 |
| WO | 2005118788 | A2 | 12/2005 |
| WO | 2006034106 | A2 | 3/2006 |
| WO | 2006060878 | A1 | 6/2006 |
| WO | 2006077428 | A1 | 7/2006 |
| WO | 2006130458 | A2 | 12/2006 |
| WO | 2007005874 | A2 | 1/2007 |
| WO | 2008045437 | A2 | 4/2008 |
| WO | 2008110491 | A2 | 9/2008 |
| WO | 2008121420 | A1 | 10/2008 |
| WO | 2008127735 | A1 | 10/2008 |
| WO | 2009007124 | A1 | 1/2009 |
| WO | 2009051974 | A1 | 4/2009 |
| WO | 2009091826 | A2 | 7/2009 |
| WO | 2010019570 | A2 | 2/2010 |
| WO | 2010025177 | A1 | 3/2010 |
| WO | 2010056754 | A2 | 5/2010 |
| WO | 2010077634 | A1 | 7/2010 |
| WO | 2010085660 | A2 | 7/2010 |
| WO | 2010095031 | A2 | 8/2010 |
| WO | 2010104949 | A2 | 9/2010 |
| WO | 2010126066 | A1 | 11/2010 |
| WO | 2011041093 | A1 | 4/2011 |

(56) References Cited

FOREIGN PATENT DOCUMENTS

| | | | |
|---|---|---|---|
| WO | 2011059836 | A2 | 5/2011 |
| WO | 2011070109 | A1 | 6/2011 |
| WO | 2011097477 | A1 | 8/2011 |
| WO | 2011119773 | A1 | 9/2011 |
| WO | 2011156860 | A1 | 12/2011 |
| WO | 2012007414 | A2 | 1/2012 |
| WO | 2012025530 | A1 | 3/2012 |
| WO | 2012031744 | A1 | 3/2012 |
| WO | 2012033885 | A1 | 3/2012 |
| WO | 2012058460 | A2 | 5/2012 |
| WO | 2012066058 | A1 | 5/2012 |
| WO | 2012079000 | A1 | 6/2012 |
| WO | 2012082841 | A2 | 6/2012 |
| WO | 2012099973 | A2 | 7/2012 |
| WO | 2012123755 | A1 | 9/2012 |
| WO | 2012127464 | A2 | 9/2012 |
| WO | 2012129514 | A1 | 9/2012 |
| WO | 2012135854 | A2 | 10/2012 |
| WO | 2012138475 | A1 | 10/2012 |
| WO | 2012138858 | A1 | 10/2012 |
| WO | 2012163805 | A1 | 12/2012 |
| WO | 2013009690 | A2 | 1/2013 |
| WO | 2013019615 | A2 | 2/2013 |
| WO | 2013026833 | A1 | 2/2013 |
| WO | 2013026837 | A1 | 2/2013 |
| WO | 2013026839 | A1 | 2/2013 |
| WO | 2013033626 | A2 | 3/2013 |
| WO | 2013040371 | A2 | 3/2013 |
| WO | 2013040557 | A2 | 3/2013 |
| WO | 2013059593 | A1 | 4/2013 |
| WO | 2013063419 | A2 | 5/2013 |
| WO | 2013074916 | A1 | 5/2013 |
| WO | 2013092001 | A1 | 6/2013 |
| WO | 2013123061 | A1 | 8/2013 |
| WO | 2013126712 | A1 | 8/2013 |
| WO | 2013126726 | A1 | 8/2013 |
| WO | 2013126729 | A1 | 8/2013 |
| WO | 2013126733 | A1 | 8/2013 |
| WO | 2013142034 | A1 | 9/2013 |
| WO | 2013154760 | A1 | 10/2013 |
| WO | 2013169625 | A1 | 11/2013 |
| WO | 2013173820 | A2 | 11/2013 |
| WO | 2013185552 | A1 | 12/2013 |
| WO | 2014011984 | A1 | 1/2014 |
| WO | 2014011987 | A1 | 1/2014 |
| WO | 2014011988 | A2 | 1/2014 |
| WO | 2014011993 | A2 | 1/2014 |
| WO | 2014011996 | A1 | 1/2014 |
| WO | 2014012001 | A2 | 1/2014 |
| WO | 2014031687 | A1 | 2/2014 |
| WO | 2014039513 | A2 | 3/2014 |
| WO | 2014048920 | A1 | 4/2014 |
| WO | 2014051433 | A1 | 4/2014 |
| WO | 2014055442 | A2 | 4/2014 |
| WO | 2014055657 | A1 | 4/2014 |
| WO | 2014055668 | A1 | 4/2014 |
| WO | 2014066527 | A2 | 5/2014 |
| WO | 2014068079 | A1 | 5/2014 |
| WO | 2014100385 | A1 | 6/2014 |
| WO | 2014124143 | A1 | 8/2014 |
| WO | 2014127261 | A1 | 8/2014 |
| WO | 2014130635 | A1 | 8/2014 |
| WO | 2014130657 | A1 | 8/2014 |
| WO | 2014134165 | A1 | 9/2014 |
| WO | 2014138704 | A1 | 9/2014 |
| WO | 2014138805 | A1 | 9/2014 |
| WO | 2014138819 | A1 | 9/2014 |
| WO | 2014140248 | A1 | 9/2014 |
| WO | 2014140904 | A2 | 9/2014 |
| WO | 2014144622 | A2 | 9/2014 |
| WO | 2014145252 | A2 | 9/2014 |
| WO | 2014153270 | A1 | 9/2014 |
| WO | 2014164554 | A1 | 10/2014 |
| WO | 2014165707 | A2 | 10/2014 |
| WO | 2014172584 | A1 | 10/2014 |
| WO | 2014186469 | A2 | 11/2014 |
| WO | 2015044386 | A1 | 4/2015 |
| WO | 2015090229 | A1 | 6/2015 |
| WO | 2015090230 | A1 | 6/2015 |
| WO | 2015112626 | A1 | 7/2015 |
| WO | 2015124715 | A1 | 8/2015 |
| WO | 2015142661 | A1 | 9/2015 |
| WO | 2015142675 | A2 | 9/2015 |
| WO | 2015157252 | A1 | 10/2015 |
| WO | 2016014501 | A1 | 1/2016 |
| WO | 2016014530 | A1 | 1/2016 |
| WO | 2016014535 | A1 | 1/2016 |
| WO | 2016014553 | A1 | 1/2016 |
| WO | 2016014565 | A2 | 1/2016 |
| WO | 2016014576 | A1 | 1/2016 |
| WO | 2016019300 | A1 | 2/2016 |
| WO | 2016025880 | A1 | 2/2016 |
| WO | 2016028896 | A1 | 2/2016 |
| WO | 2016044605 | A1 | 3/2016 |
| WO | 2016057705 | A1 | 4/2016 |
| WO | 2016079177 | A1 | 5/2016 |
| WO | 2016090320 | A1 | 6/2016 |
| WO | 2016094304 | A2 | 6/2016 |
| WO | 2016105450 | A2 | 6/2016 |
| WO | 2016109410 | A2 | 7/2016 |
| WO | 2016166629 | A1 | 10/2016 |
| WO | 2016166630 | A1 | 10/2016 |
| WO | 2017015427 | A1 | 1/2017 |
| WO | 2017019496 | A1 | 2/2017 |
| WO | 2017031104 | A1 | 2/2017 |
| WO | 2017068421 | A1 | 4/2017 |
| WO | 2017075389 | A1 | 5/2017 |
| WO | 2017117112 | A1 | 7/2017 |
| WO | 2017130223 | A2 | 8/2017 |
| WO | 2017165245 | A2 | 9/2017 |
| WO | 2018067992 | A1 | 4/2018 |
| WO | 2018106732 | A1 | 6/2018 |
| WO | 2018151836 | A1 | 8/2018 |
| WO | 2019108900 | A1 | 6/2019 |
| WO | 2019133969 | A2 | 7/2019 |
| WO | 2019229701 | A1 | 12/2019 |
| WO | 2019241426 | A1 | 12/2019 |
| WO | 2020047452 | A2 | 3/2020 |

OTHER PUBLICATIONS

Geiger et al., "Integrated src kinase and constimulatory activity enhances signal transduction through single-chain chimeric receptors in T lymphocytes," Blood 98(8): 2364-2371 (2001).

GenBank Accession No. NP_000725.1 accessed on Jan. 7, 2016 from http://www.ncbi.nlm.nih.gov/protein/NP_000725.

GenBank Accession No. NP_932170.1 accessed Jan. 7, 2016 from http://www.ncbi.nlm.nih.gov/protein/NP_932170.

Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.

Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.

Gonzalez et al. "Genetic engineering of cytolytic T lymphocytes for adoptive T-cell therapy of neuroblastoma," The Journal of Gene Medicine 6(6): 704-711 (2004).

Gribben et al., "Stem cell transplantation for indolent lymphoma and chronic lymphocytic leukemia" Biol Blood Marrow Transplant (2011) vol. 17 (1 Suppl): S63-S70.

Griffin, "Development and applications of surface-linked single chain antibodies against T-cell antigens" Journal of Immunological Methods (2001) vol. 248 pp. 77-90.

Gross et al., "Endowing T cells with antibody specificity using chimeric T cell receptors," The FASEB Journal 6: 3370-3378 (1992).

Gross et al., "Expression of immunoglobulin-T-cell receptor chimeric molecules as functional receptors with antibody-type specificity," PNAS 86: 10024-10028 (1989) (discuss "gene pair approach:"

(56) References Cited

OTHER PUBLICATIONS

VH spliced to the C-region gene segment of alpha or beta TcR chain, or gamma or zeta TcR chain, VL is attached to the other chain).

Grupp et al. "Chimeric Antigen Receptor-Modified T Cells for Acute Lymphoid Leukemia", New England Journal of Medicine (2013) vol. 368 No. 16 pp. 1509-1518.

Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.

Hekele et al., "Growth Retardation of Tumors By Adoptive Transfer of Cytotoxic T Lymphocytes Reprogrammed By CD44V6-Specific SCFV:~-Chimera" Int J. Cancer (1996) vol. 68 pp. 232-238.

Ho et al., "Adoptive immunotherapy: Engineering T cell responses as biological weapons for tumor mass destruction" Cancer Cell (2003) vol. 3 pp. 431-437.

Hollyman et al. "Manufacturing validation of biologically functional T cells targeted to CD19 antigen for autologous adoptive cell therapy" J Immunother (2009) vol. 32 No. 2 pp. 169-180.

Holm et al., Functional mapping and single chain construction of the anti-cytokeratin 8 monoclonal antibody TS1, Molecular Immunology (2077) vol. 44, pp. 1075-1084.

Homback et al., "OX40 costimulation by a chimeric antigen receptor abrogates CD28 and IL-2 induced IL-10 secretion by redirected CD4+ T cells," OncoImmunology (2012) vol. 1, Issue 4, pp. 458-466.

Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).

Huye E L et al.: 'Combining mTor Inhibitors With Rapamycin-resistant T Cells: A Two-pronged Approach to Tumor Elimination',Molecular Therapy, vol. 19, No. 12,Aug. 30, 2011 (Aug. 30, 2011), pp. 2239-2248, XP055191016, GB, ISSN: 1525-0016, DOI: 10.1038/mt.2011.179 the whole document.

Im et al., "Immunotherapy in hematologic malignancies: past, present, and future," Journal of Hematology & Oncology (2017) vol. 10, Article 94, 10 pages.

Imai et al., "Chimeric receptors with 4-1BB signaling capacity provoke potent cytotoxicity against acute lymphoblastic leukemia," Leukemia 18: 676-684 (2004).

Imai et al., "Genetic modification of primary natural killer cells overcomes inhibitory signals and induces specific killing of leukemic cells" Blood (2005) vol. 106 No 1 pp. 376-383.

International Search Report and Written Opinion for International Application No. PCT/US2019/036830 dated Oct. 18, 2019.

International Search Report from PCT/US2011/064191 dated Jan. 5, 2012.

Irving et al., "The cytoplasmic domain of the T cell receptor zeta chain is sufficient to couple to receptor-associated signal transduction pathways," Cell 64: 891-901 (1991).

Jang et al., "Human 4-1BB (CD137) Signals Are Mediated by TRAF2 and Activate Nuclear Factor-KB," Biomedical and Biophysical Research Communications (1998) vol. 242, pp. 613-620.

Jena, Bipulendu et al. "Redirecting T-cell specificity by introducing a tumor-specific chimeric antigen receptor, Blood, May 3, 2010", vol. 116, No. 7, pp. 1035-1044.

Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.

Johnson et al., "Gene therapy with human and mouse T-cell receptors mediates cancer regression and targets hormal tissues expressing cognate antigen" Blood (2009) vol. 114 No. 3 pp. 535-545.

June et al., "Engineering lymphocyte subsets: tools, trials and tribulations" Nat Rev Immunol (2009) vol. 9 No. 10 pp. 704-716.

Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.

Kerkar. "Model T' Cells: A Time-Tested Vehicle for Gene Therapy." Frontiers in Immunology 4 (2013): 304. PMC. Web. Aug. 18, 2015.

Kershaw et al., "A Phase I Study on Adoptive Immunotherapy Using Gene-Modified T Cells for Ovarian Cancer," Clin. Cancer Res. 12(20 Pt 1): 6106-6115 (2006).

Kim et al., "Human 4-1BB regulates CD28 co-stimulation to promote Th1 cell responses" Eur. J. Immunol. (1998) vol. 28 pp. 881-890.

Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180, 52nd Annual Meeting of the American-Society-Of-Hematology (ASH); Orlando, FL, USA; Dec. 4-7, 2010 abstract.

Kochenderfer et al. "Construction and Pre-clinical Evaluation of an Anti-CD19 Chimeric Antigen Receptor", J Immunother (2009) vol. 32, No. 7, pp. 689-702.

Kochenderfer et al., "Eradication of B-lineage cells and regression of lymphoma in a patient treated with autologous T cells genetically-engineered to recognize CD19," Blood 116: 4099-4102 (2010).

Kofler etal., "CD28 Costimulation Impairs the Efficacy of a Redirected T-cell Antitumor Attack in the Presence of Regulatory T cells Which Can Be Overcome by Preventing Lck Activation," Molecular Therapy (2011) vol. 19, No. 4, pp. 760-767.

Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.

Krebs et al. "Genetically Modified T Cells to Target Glioblastoma", Frontiers in Oncology, vol. 3, Jan. 1, 2013.

Kuhn, et al., "Determinants of intracellular RNA pharmacokinetics: Implication for RNA-based immunotherapeutics" RNA Biology, 8(1):35-43 (2011).

Kuwana et al., "Expression of Chimeric Receptor Composed of Immunoglobulin-derived V Resions and T-cell Receptor-derived C Regions" Biochem. Biophys. Res. Commun. 149: 964-968 (1987).

Kwon et al., "cDNA sequences of two inducible T-cell genes". Proc. Natl. Acad. Sci. U.S.A. 86(6): 1963-1967 (1989).

Laabi et al. "The BCMA gene, preferentially expressed during B lymphoid maturation, is bidirectionally transcribed", Nucleic Acids Research (1994) vol. 22, No. 7, pp. 1147-1154.

Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.

Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).

Lanitis et al., "Redirected Antitumor Activity of Primary Human Lymphocytes Transduced With a Fully Human Anti-mesothelin Chimeric Receptor" Molecular Therapy, 20(3):633-643 (2012).

Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.

Arch et al, "4-1BB and Ox40 Are Members of a Tumor Necrosis Factor (TNF)-Nerve Growth Factor Receptor Subfamily That Bind TNF Receptor-Associated Factors and Activate Nuclear Factor kB" Molecular and Cellular Biology (1998) vol. 18, No. 1, pp. 558-565.

Avagacestat: https://www.selleckchem.com/products/BMS-708163.html, retrieved on Jun. 30, 2022.

Baeksgaard & Sorensen, "Acute tumor lysis syndrome in solid tumors—a case report and review of the literature" Cancer Chemotherapy Pharmacology (2003) vol. 51 pp. 187-192.

Bakker et al. "C-type lectin-like molecule-1: a novel myeloid cell surface marker associated with acute myeloid leukemia", Cancer Research (2004) vol. 64, No. 22,pp. 8443-8450.

(56) References Cited

OTHER PUBLICATIONS

Barao et al., "The TNF receptor-ligands 4-1BB-4-1 BBL and GITR-GITRL in NK cell responses," Frontiers in Immunology (2013) vol. 3, Article 402, 8 pages.
Barrett, et al., "Pre-clinical model of eradication of B cell leukemia with lentiviral transduced anti-CD19 chimeric immunoreceptor-modified T cells" Cancer Research:AACR 101st Annual Meeting, Abstract 2933 (Apr. 17-21, 2010).
Barrett, et al., "Treatment of Advanced Leukemia in Mice with mRNA Engineered T Cells" Human Gene Therapy, 22(12):1575-1586 (2011).
BCMA: https://en.wikipedia.org/wiki/B-cell_maturation_antigen, retrieved Jun. 30, 2022.
Beers, et al., "Immunotoxins with Increased Activity against Epidermal Growth Factor Receptor vIII-expressing Cells Produced by Antibody Phage Display" Clinical Cancer Research, 6:2835-2843 (2000).
Bendig, M.M. Humanization of rodent monoclonal antibodies by CDR grafting. Methods: A Companion to Methods in Enzymology, 1995; vol. 8, p. 83-93.
Birkholz et al. "Transfer of mRNA encoding recombinant immunoreceptors reprograms CD4+ and CD8+ T cells for use in the adoptive immunotherapy of cancer," Gene Therapy 16:596-604 (2009).
Bondanza et al. "Suicide gene therapy of graft-versus-host disease induced by central memory human T lymphocytes" Blood (2006) vol. 107 No 5 pp. 1828-1836.
Bork "Powers and Pitfalls in Sequence Analysis: The 70% Hurdle" Genome Research (2000) vol. 10, pp. 398-400.
Brenner "Errors in genome annotation" TIG (1999) vol. 15, No. 4, pp. 132-133.
Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.
Brocker and Karjalainen, "Signals through T Cell Receptor-Chain alone Are Insufficient to Prime Resting T Lymphocytes" J. Exp. Med. (1995) vol. 181 pp. 1653-1659.
Call & Wucherpfennig, "The T Cell Receptor: Critical Role of the Membrane Environment in Receptor Assembly and Function" Annu. Rev. Immunol. (2005) vol. 23 pp. 101-125.
Carpenito et al. "Control of large, established tumor xenografts with genetically retargeted human T cells containing CD28 and CD137 domains", Proc Natl Acad Sci USA (2009) vol. 106 pp. 3360-3365.
Carpenter et al. "B-cell Maturation Antigen Is a Promising Target for Adoptive T-cell Therapy of Multiple Myeloma" Clinical Cancer Research (2013) vol. 19, No. 8, pp. 2048-2060.
Cartellieri et al., "Chimeric Antigen Receptor-Engineered T Cells for Immunotherapy of Cancer," Journal of Biomedicine and Biotechnology (2010) vol. 2010, Article 956304, 13 pages.
Casset et al. "A peptide mimetic of an anti-CD4 monoclonal antibody by rational design" Biochemical and Biophysical Research Communications (2003) vol. 307, pp. 198-205.
Casucci et al. "CD44v6-targeted T cells mediate potent antitumor effects against acute myeloid leukemia and multiple myeloma", Blood (2013) vol. 122 No. 20 pp. 3461-3472.
Chames et al., "Therapeutic antibodies: successes, limitations and hopes for the future" British J. of Pharmacology (2009) vol. 57, pp. 220-233.
Chen et al. "Selection and Analysis of an Optimized Anti-VEGF Antibody: Crystal Structure of an Affinity-matured Fab in Complex with Antigen" J Mol Biol. (1999) vol. 293, 865-881.
Chinnasamy et al. "Local Delivery of Interleukin-12 Using T Cells Targeting VEGF Receptor-2 Eradicates Multiple Vascularized Tumors in Mice", Clinical Cancer Research, vol. 18, No. 6, Jan. 30, 2012, pp. 1672-1683.
Chiu et al. "Hodgkin lymphoma cells express TACI and BCMAreceptors and generate survival and proliferation signals in response to BAFF and APRIL", Blood (2007) vol. 109 No. 2, pp. 729-739.
Chmielewski et al. "IL-12 Release by Engineered T Cells Expressing Chimeric Antigen Receptors Can Effectively Muster an Antigen Receptors Can Effectively Muster an Antigen-Independent Macrophage Response on Tumor Cells That Have Shut Down Tumor Antigen Expression", Cancer Research, vol. 71, No. 17, Jul. 8, 2011, pp. 5697-7506.
Claudio et al. "A molecular compendium of genes expressed in multiple myeloma", Blood (2002) vol. 100 No. 6, pp. 2175-2186.
Cohen et al. "Safety and Efficacy of B-Cell Maturation Antigen (BCMA)-Specific Chimeric Antigen Receptor T Cells (CART-BCMA) with Cyclophosphamide Conditioning for Refractory Multiple Myeloma (MM)" Blood (2017) vol. 130, Supplement 1, No. 505 (Abstract), pp. 1-3.
Cooper, "Test-driving CARs," Blood (2018) vol. 112, No. 8, p. 2172-2173.
Coquery et al., "Regulatory Roles of the Tumor Necrosis Factor Receptor BCMA" Crit Rev Immunol. (2012) vol. 32, No. 4, pp. 287-305.
Davila et al. "B Cell Aplasia In a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
Deshayes et al. "Abnormal production of the TNF-homologue APRIL increases the proliferation of human malignant glioblastoma cell lines via a specific receptor", Oncogene (2004) vol. 23 No. 17, pp. 3005-3012.
Doerks et al. "Protein annotation: detective work for function prediction" TIG (1998) vol. 14, No. 6, pp. 248-250.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dotti et al. "Design and development of therapies using chimeric antigen receptor-expressing T cells", Immunological Reviews, vol. 257, No. 1, Dec. 13, 2013, pp. 107-126.
Dropulic and June, "Gene-Based Immunotherapy for Human Immunodeficiency Virus Infection and Acquired Immunodeficiency Syndrome" Human Gene Therapy (2006) vol. 17 pp. 577-588.
Du et al., "New Immunotoxins Targeting CD123, a Stem Cell Antigen on Acute Myeloid Leukemia Cells" J. Immunother. vol. 30, No. 6 pp. 607-613 (2007).
Dull et al., "A Third-Generation Lentivirus Vector with a Conditional Packaging System" Journal of Virology (1998) vol. 72 No. 11 pp. 8463-8471.
Elsawa et al. "Cytokines in the Microenvironment of WaldenstrÃ¶m's Macroglobulinemia", Clin Lymphoma Myeloma (2009) vol. 9 No. 1 pp. 43-45.
Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).
Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).

(56) References Cited

OTHER PUBLICATIONS

Finney et al., "Chimeric receptors providing both primary and costimulatory signaling in T cells from a single gene product," J. Immunol. 161: 2791-2797 (1998).

Frey, N. "Genetically Engineered Lymphocyte Therapy in Treating Patients With B-Cell Leukemia or Lymphoma That is Resistant or Refractory to Chemotherapy" (2015) Clinical Trial NCT01029366.

Friedmann-Morvinski et al., "Redirected primary T cells harboring a chimeric receptor require costimulation for their antigen-specific activation," Blood 105: 3087-3093 (2005).

Riet et al. "Nonviral RNA transfection to transiently modify T cells with chimeric antigen receptors for adoptive therapy", Methods in Molecular Biology, Humana Press, Inc, US, vol. 969, Jan. 1, 2013, pp. 187-201.

Roederer, "T-cell dynamics of immunodeficiency" Nature Medicine (1995) vol. 1 No. 7 pp. 621-622.

Romeo et al., "Cellular immunity to HIV activated by CD4 fused to T cell or Fc receptor polypeptides," Cell 64:1037-1046 (1991).

Rouas et al. "Lentiviral-mediated gene delivery in human monocyte-derived dendritic cells: Optimized design and procedures for highly efficient transduction compatible with clinical constraints". Cancer Gene Therapy (2002) vol. 9 pp. 715-724.

Rudikoff et al. "Single amino acid substitution altering antigen-binding specificity" Proc Natl Acad Sci (1982) vol. 79, pp. 1979-1983.

Ryan et al., "Antibody targeting of B-cell maturation antigen on malignant plasma cells," Mol Cancer Ther (2007) vol. 6, No. 11, pp. 3009-3018.

Sabbagh et al., "TNF family ligands define niches for T cell memory" Trends in Immunology (2007) vol. 28 No. 8 pp. 333-339.

Sadelain et al. "The promise and potential pitfalls of chimeric antigen receptors." Current Opinion Immunology (2009) vol. 21 No. 2 pp. 215-223.

Sadelain et al., "Targeting Tumours with Genetically Enhanced T Lymphocytes," Nature Reviews: Cancer 3: 35-45 (2003).

Sadelain et al., "The Basic Principles of Chimeric Antigen Receptor Design," Cancer Discov (2013) vol. 3, No. 4, pp. 388-398.

Sagiv-Barfi, et al., "Ibrutinib enhances the antitumor immune response induced by intratumoral injection of a TLR9 ligand in mouse lymphoma" Blood, 125(13):2079-2086 (2015).

Sagiv-Barfi, et al., "Therapeutic antitumor immunity by checkpoint blockade is enhanced by ibrutinib, an inhibitor of both BTK and ITK" PNAS, 112(9):E966-E972 (2015).

Sampson, et al., "EGFRvIII mCAR-Modified T-Cell Therapy Cures Mice with Established Intracerebral Glioma and Generates Host Immunity against Tumor-Antigen Loss" Clinical Cancer Research, 20(4):972-984 (2013).

Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.

Sebestyen et al., "Human TCR That Incorporate CD3 Induce Highly Preferred Pairing between TCR and Chains following Gene Transfer" Journal of Immunology (2008) vol. 180 pp. 7736-7746.

Shirasu et al., "Functional Design of Chimeric T-Cell Antigen Receptors for Adoptive Immunotherapy of Cancer: Architecture and Outcomes," AntiCancer Res. 32: 2377-2384 (2012).

Singapore Search Report and Written Opinion for Singapore Application No. 11201700476V dated Nov. 6, 2017.

Singh, et al., "Third Generation Chimeric Antigen Receptors Containing CD137 or CD134 Signaling Endodomains Augment CD19-Specific T-Cell Effector Function" Blood: Ash Annual Meeting Abstracts; 114:22 (2009).

Skolnick et al. "From genes to protein structure and function: novel applications of computational approachesin the genomic era" TIBTECH (2000) vol. 18, pp. 34-39.

Smirnova et al. "Identification of new splice variants of the genes BAFF and BCMA", Molecular Immunology (2008) vol. 45, pp. 1179-1183.

Song et al. "CD27 costimulation augments the survival and antitumor activity of redirected human T cells in vivo" Blood (2012) Bol 119, No. 3, pp. 696-706.

Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.

Stromnes et al. "Abrogation of Src Homology Region 2 Domain-Containing Phosphatase 1 in Tumor-Specific T Cells Improves Efficacy of Adoptive Immunotherapy by Enhancing the Effector Function and Accumulation of Short-Lived Effector T Cells In Vivo", The Journal of Immunology, (2012) vol. 189, No. 4, pp. 1812-1825.

Tai et al. "Novel anti-B-cell maturation antigen antibody-drug conjugate (GSK2857916) selectively induces killing of multiple myeloma" Blood (2014) vol. 123, No. 20, p. 3128-3138.

Terakura et al. "Generation of CD19-chimeric antigen receptor modified CD8+ T cells derived from virus-specific central memory T cells" Blood (2012) vol. 119, No. 1, pp. 72-82.

Tettamanti et al., "Targeting of the acute myeloid leukemia stem cells through immunotherapy: development of novel chimeric receptors specific for the CD123 antigen," OMICS group conference 2nd world congress on biotechology (2011) retrieved from internet www.omicsonline.org/biotechnology2011.

Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.

Uckun et al., "Detailed studies on expression and function of CD19 surface determinant by using B43 monoclonal antibody and the clinical potential of anti-CD19 immunotoxins" Blood (1988) vol. 71 pp. 13-29.

Uniprot identifier Q02223-2 accessed Sep. 28, 2015 from <http://www.uniprot.org/uniprot/Q02223>.

Urbanska et al., "A Universal Strategy For Adoptive Immunotherapy Of Cancer Through Use Of A Novel T-Cell Antigen Receptor," Cancer Res. 72(7): 1844-1852 (2012).

Vajdos et al. "Comprehensive Functional Maps of the Antigen Ă-binding Site of an Anti-Erb82 Antibody Obtained with Shotgun Scanning Mutagenesis" J Mol Biol (2002) vol. 320, pp. 415-428.

Van Duyne et al. "Atomic Structure of the Rapamycin Human Immunophilin FKBP-12 Complex" American Chemical Society (1991) vol. 113, pp. 7433-7434.

Vinay and Kwon, "Role of 4-1BB in immune responses" Immunology (1998) vol. 10 pp. 481-489.

Wang et al. "A Chimeric Antigen Receptor (CARs) Based Upon a Killer Immunoglobulin-Like Receptor (KIR) Triggers Robust Cytotoxic Activity in Solid Tumors" Molecular Therapy (2014) vol. 22, Supplement 1, pp. S57.

Wang et al. "Generation of Potent T-cell Immunotherapy for Cancer Using DAP12-Based, Multichain, Chimeric Immunoreceptors" Cancer Immunology Research (2015) vol. 3, No. 7, pp. 815-826.

Wang et al. "Overcoming intrinsic inhibitory pathways to augment the antineoplastic activity of adoptively transferred T cells: Re-tuning your CAR before hitting a rocky road", Oncoimmunology (2013) vol. 2, No. 11, p. e264921-3.

Weijtens, "Immuno-gene therapy for renal cancer chimeric receptor-mediated lysis of tumorcells," Thesis: 1-128 (2001).

Wells "Additivity of Mutational Effects in Proteins" Biochemistry (1990) vol. 29, No. 37, pp. 8509-8517.

Willemsen et al., "Genetic Engineering of T Cell Specificity for Immunotherapy of Cancer" Human Immunology (2003) vol. 64 pp. 56-68.

Worcester et al "GSI inhibition may boost BCMA CAR T-cell therapy efficacy in myeloma" Hematology News (2017) Retrieved from the Internet: URL:https://www.mdedge.com/hematologynews/article/152733/multiple-myeloma/gsi-inhibition-may-boost-bcma-car-t-cell-therapy[retrieved on Jun. 19, 2018].

Written Opinion for PCT Application No. PCT/US2014/034570 dated Oct. 17, 2015.

Written Opinion for PCT/US13/63083, dated Jan. 17, 2014.

Written Opinion of the International Searching Authority for International Application No. PCT/US13/032029, dated Oct. 11, 2014.

(56) References Cited

OTHER PUBLICATIONS

Wu et al., "Humanization of a Murine Monoclonal Antibody by Simultaneous Optimization of Framework and CDR Residues," J Mol Biol (1999) vol. 294, pp. 151-162.
Xu V et al: "Closely related T-memory stem cells correlate with in vivo expansion of CAR.CD19-T cells and are preserved by IL-7 and IL-15", Blood, vol. 123, No. 24, Apr. 29, 2014 (Apr. 29, 2014), pp. 3750-3759, XP055201372, ISSN: 0006-4971, DOI:10.1182/blood-2014-01-552174.
Yang et al. "B Cell Maturation Antigen, the Receptor for a Proliferation-Inducing Ligand and B Cell-Activating Factor of the TNF Family, Induces Antigen Presentation in B Cells" J Immunol (2005) vol. 175, pp. 2814-2824.
Zhao et al. "Targeting C-type lectin-like molecule-1 for antibody-mediated immunotherapy in acute myeloid leukemia", Haematologica (2010) vol. 95 No. 1 pp. 71-78.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zhao et al., "A Herceptin-Based Chimeric Antigen Receptor with Modified Signaling Domains Leads to Enhanced Survival of Transduced T Lymphocytes and Antitumor Activity," J Immunol (2009) vol. 183, No. 9, pp. 5563-5574.
Zhong et al., "Enhanced T cell response due to diacylglycerol kinase deficiency" Nature Immunology 4(9): 882-890 (2003).
Zufferey et al., "Multiply attenuated lentiviral vector achieves efficient gene delivery in vivo" Nature Biotechnology (1997) vol. 15 pp. 871-876.
Laurent et al. "γ-secretase directly sheds the survival receptor BCMA from plasma cells" Nature Communications (2015) vol. 6, No. 7333, pp. 1-12.
Lee et al., "In vivo Inhibition of Human CD19-Targeted Effector T Cells by Natural T Regulatory Cells in a Kenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.
Liu et al, "Metformin and the mTOR Inhibitor Everolimus (RAD001) Sensitize Breast Cancer Cells to the Cytotoxic Effect of Chemotherapeutic Drugs In Vitro", Anticancer Research, 32: 1627-1638 (2012).
Lorimer, et al., "Recombinant immunotoxins specific for a mutant epidermal growth factor receptor: Targeting with a single chain antibody variable domain isolated by phage display" Proc. Natl. Acad. Sci. USA, 93:14815-14820 (1996).
Macallan et al., "Measurement and modeling of human T cell kinetics" European Journal of Immunology (2003) vol. 33 pp. 2316-2326.
Maccallum et al., "Antibody-Antigen Interactions: Contact Analysis and Binding Site Topography," J Mol Biol (1996) vol. 262, pp. 732-745.
Maher et al., "Human T lymphocyte cytotoxicity and proliferation directed by a single chimeric TCRzeta/CD28 receptor," Nat. Biotechnol. 20: 70-75 (2002).
Marcus et al. "Allogenic chimeric antigen receptor-modified cells for adoptive cell therapy of cancer" Expert Opinion on Biological Therapy (2014) vol. 14, No. 7, pp. 947-954.
Mardiros et al., "CD123-Specific Chimeric Antigen Receptor Redirected T Cells Exhibit Potent Cytolytic Activity and Multiple Effector Functions Against Acute Myeloid Leukemia without Altering Normal Hematopoietic Colony Formation in Vitro" Blood 120(21): abstract 950 (2011).
Maus et al. "Antibody-modified T cells: CARs take the front seat for hematologic malignancies" Blood (2014) vol. 123, No. 17, pp. 2625-2635.
Maus et al., "T cells expressing chimeric antigen receptors can cause anaphylaxis in humans" Cancel Immunol Res, 1:26-31 (2013).
Maus, Marcela V. et al. "Zoom zoom: racing CARs for multiple myeloma", Clinical Cancer Research, Apr. 15, 2013, vol. 19 No. 8, pp. 1917-1919.
McAlpine et al. "Revised NMR Assignments for Rapamycin", The Journal of Antibiotics (1991) vol. 44 No. 6, pp. 688-690.
McCormack et al., "Bi-specific TCR-anti CD3 redirected T-cell targeting of NY-ESO-1-and LAGE-1-positive tumors," Cancer Immunol. Immunother. 62:773-785 (2013).
McGuinness et al., "Anti-tumor activity of human T cells expressing the CC49-zeta chimeric immune receptor," Hum. Gene Ther. 10: 165-173 (1999).
Melero et al., "Amplification of Tumor Immunity by Gene Transfer of the Co-Stimulatory 4-1BB Ligand: Synergy with the CD28 Co-Stimulatory Pathway," Eur. J. Immunol. 28(3): 1116-1121 abstract (1998).
Milone et al, "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Moon, et al., "A PD1-CD28 'Switch Receptor' Is Able to Augment Mesothelin-Directed Chimeric Antigen Receptor T Cell Therapy in a Resistant In Vivo Model of Human Tumor" 17th Annual Meeting of the American Society of Gene and Cell Therapy, Abstract 520 (May 21-24, 2014).
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.
NCBI accession NM_001192.2 accessed Sep. 28, 2015 from http://www.ncbi.nlm.nih.gov/nuccore/23238191>.
NCBI accession NP_001183.2 accessed Sep. 28, 2015 from http://www.ncbi.nlm.nih.gov/protein/23238192>.
Ngo et al. "The Protein Folding Problem and Tertiary Structure Prediction, Chapter 14:Computational Complexity, Protein Structure Prediction and Levinthal Paradox" (1994) pp. 433-440.
Nicholson et al., "Construction and Characterisation of a Function CD19 Specific Single Chain Fv Fragment for Immunotherapy of B Lineage Leukaemia and Lymphoma," Molecular Immunology 34(I6-I7): 1157-1165 (1997).
Novak et al. "Expression of BCMA, TACI, and BAFF-R in multiple myeloma: a mechanism for growth and survival", Blood (2004) vol. 103 No. 2, pp. 689-694.
Ohno, et al., "Expression of miR-17-92 enhances anti-tumor activity of T-cells transduced with the anti-EGFRvIII chimeric antigen receptor in mice bearing human GBM xenografts" Journal of ImmunoTherapy of Cancer, 1:21 (2013).
Ohno, et al., "Retrovirally engineered T-cell-based immunotherapy targeting type III variant epidermal growth factor receptor, a glioma-associated antigen" Cancer Science, 101(12):2518-2524 (2010).
Okamoto, et al., "Monoclonal antibody against the fusion junction of a deletion-mutant epidermal growth factor receptor" British Journal of Cancer, 73:1366-1372 (1996).

(56) References Cited

OTHER PUBLICATIONS

Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al., "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Patel et al., "Impact of chimeric immune receptor extracellular protein domains on T cell function" Gene Therapy (1999) vol. 6 pp. 412-419.
Paul, W.E. Fundamental Immunology, 3rd Edition, 1993, pp. 292-295.
Pelekanou et al. "BAFF, APRIL, TWEAK, BCMA, TACI and Fn14 Proteins Are Related to Human Glioma Tumor Grade: Immunohistochemistry and Public Microarray Data Meta-Analysis" Plos One (2013) vol. 8 No. 12 pp. 1-11.
Pizzitola et al., "Chimeric antigen receptors against CD33/CD123 antigens efficiently target primary acute myeloid leukemia cells in vivo", Leukemia (2014) vol. 28 No. 8 pp. 1596-1605.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Prinz et al., "High DGK-a and Disabled MAPK Pathways cause Dysfunction of Human Tumor-Infiltrating CD8+ T Cells That Is Reversable by Pharmacologic Intervention," The Journal of Immunology 188: 5990-6000, 2012.
Prosser, et al., "Tumor PD-L1 co-stimulates primary human CD8+ cytotoxic T cells modified to express a PD1: CD28 chimeric receptor" Molecular Immunology, 51:263-272 (2012).
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rambaldi et al., "Cell-based strategies to manage leukemia relapse: efficacy and feasibility of immunotherapy approaches",Leukemia (2014)., vol. 29, No. 1, pp. 1-10.
Rapoport et al., "Restoration of immunity in lymphopenic individuals with cancer by vaccination and adoptive T-cell transfer" Nature Medicine (2005) vol. 11 No. 11 pp. 1230-1237.
Riese et al "Enhanced Effector Responses in Activated CD8+ T Cells Deficient in Diacylglycerol Kinases", Cancer Research (2013) vol. 73 No. 12 pp. 3566-3577.
Ali et al., "T cells expressing an anti-B-cell maturation antigen chimeric antigen receptor cause remissions of multiple myeloma," Blood (2016) vol. 128, No. 13, pp. 1688-1700.
Fraietta et al., "Biomarkers of Response to Anti-CD19 Chimeric Antigen Receptor (CAR) T-Cell Therapy in Patients with Chronic Lymphocytic Leukemia," Blood (2016) vol. 128, Issue 22, Abstract 642, 6 pages.
Porter et al., "Chimeric antigen receptor T cells persist and induce sustained remissions in relapsed refractory chronic lymphocytic leukemia" Science Translational Medicine (2015) vol. 7 No. 303 303ra139.
[No Author Listed] ClinicalTrials.Gov Identifier NCT03502577, "BCMA-Specific CAR T-Cells Combined With a Gamma Secretase Inhibitor (LY3039478) to Treat Relapsed or Persistent Multiple Myeloma," retrieved from clinicaltrials.gov/ct2/show/NCT03502577?term=ly3039478&rank=5 on Jun. 27, 2018, 12 pages.
Altvater et al. "2B4 (CD244) Signaling by Recombinant Antigen-specific Chimeric Receptors Costimulates Natural Killer Cell Activation to Leukemia and Neuroblastoma Cells" Clinical Cancer Research (2009) vol. 15, No. 15, pp. 4857-4866.
Berg et al. "Selective Expansion of a Peripheral Blood CD81 Memory T Cell Subset Expressing Both Granzyme B and L-Selectin During Primary Viral Infection in Renal Allograft Recipients" Transplant Proc. (1998) vol. 30, No. 8, pp. 3975-3977.
Brunner et al., "Cytotoxic T cells; Double-barreled shot guns," Nature Medicine (1999) vol. 5, No. 1, pp. 20.
Bullain, et al., "Genetically engineered T cells to target EGFRvIII expressing glioblastoma" J Neurooncol, 94:373-382 (2009).
Chen et al. "Gene Expression of Gamma Secretase (GS) Complex-Related Proteins, the Enzyme That Sheds B-Cell Maturation Antigen (BCMA), Among Patients with Multiple Myeloma (MM) and Effects of the GS Inhibitor LSN424354 on Solubilized Boma in MM and Chronic Lymphocytic Leukemia" Blood (2016) vol. 128, No. 22, Abstract 5641.
Chmielewski et al. "Of CARs and TRUCKs: chimeric antigen receptor (CAR) T cells engineered with an inducible cytokine to modulate the tumor stroma", Immunological Reviews, vol. 257, No. 1, Jan. 13, 2014, pp. 83-90.
Cohen et al., "B cell maturation antigen-specific CAR T cells are clinically active in multiple myeloma" J Clin Invest (2019) vol. 129, No. 6, pp. 2210-2221.
Coico et al., "Immunology," translated Serebryabaya, Moscow (2008) p. 37.
Colman et al., "Effects of amino acid sequence changes on antibody-antigen interactions," Research in Immunology, (1994) vol. 145, No. 1, p. 33-36.
Dimasi et al., "Development of a Trispecific Antibody Designed to Simultaneously and Efficiently Target Three Different Antigens on Tumor Cells" Mol. Pharmaceutics (2015) vol. 12, pp. 3490-3501.
Fraietta et al., "Determinants of response and resistance to CD19 chimeric antigen receptor (CAR) T cell therapy of chronic lymphocytic leukemia" Nat Med (2018) vol. 24, No. 5, pp. 563-571.
Galla et al., "Retroviral Pseudotransduction for Targeted Cell Manipulation" Mol Cell (2004) vol. 16, No. 2, pp. 309-315.
Garfall, et al. "Imunotherapy with chimeric antigen receptors for multiple myeloma." Discovery Medicine. 17 (91) (pp. 37-46), Jan. 2014.
Garland et al. "The use of Teflon cell culture bags to expand functionally active CD8q cytotoxic T lymphocytes" Journal of Immunological Methods (1999) vol. 227, pp. 53-56.
Gattinoni et al. "Acquisition of full effector function in vitro paradoxically impairs the in vivo antitumor efficacy of adoptively transferred CD8+ T cells" The Journal of Clinical Investigation (2005) vol. 115, No. 6, pp. 1616-1626.
Gentile et al., "Perspectives in the treatment of multiple myeloma," Expert Opin Bio Ther (2013) vol. 13(Supp. 1), S1-S22.
Giavridis et al "CAR T cell-induced cytokine release syndrome is mediated by macrophages and abated by IL-1 plockade" Nat Med (2018) vol. 24, No. 6, pp. 731-738.
Gill et al. "Preclinical targeting of human acute myeloid leukemia and myeloablation using chimeric antigen receptor-modified T cells", Blood (2014) vol. 123 No. 23 pp. 2343-2345.
Gupta, et al., "Development of an EGFRvIII specific recombinant antibody" BMC Biotechnology, 10(72):1-13 (2010).
Gura, "Systems for Identifying New Drugs Are Often Faulty" Science (1997) vol. 278, pp. 1041-1042.
Haanen et al., "Selective Expansion of Cross-reactive CD81 Memory T Cells by Viral Variants" J. Exp. Med. (1999) vol. 190, No. 9, pp. 1319-1328.
Haapasalo et al., "The Many Substrates of Presenilin/gamma-Secretase," J Alzheimers Dis (2011) vol. 25, No. 1, pp. 3-28.
Haas et al., "Critical factors influencing stable transduction of human CD34(+) cells with HIV-1-derived lentiviral vectors" Mol Ther (2000) vol. 2, No. 1, pp. 71-80.
Hallett et al., "Immunosuppressive Effects of Multiple Myeloma Are Overcome by PD-L1 Blockade," Biol Blood Marrow Transplant (2011) vol. 17, pp. 1133-1145.
Holtkamp, et al., "Modification of antigen-encoding RNA increases stability, translational efficacy, and T-cell stimulatory capacity of dendritic cells" Blood, 108(13):4009-4071 (2006).

(56) References Cited

OTHER PUBLICATIONS

Hoyos et al. "Engineering CD19-specific T lymphocytes with interleukin-15 and a suicide gene to enhance their anti-lymphoma/leukemia effects and safety", Leukemia, vol. 24, No. 6, Apr. 29, 2010, pp. 1160-1170.
Hunder et al., "Treatment of Metastic Melanoma with Autologous CD4+ T Cells against NY-ESO-'1." The New England Journal of Medicine 358(25): 2698-2703 (2008).
International Preliminary Report on Patentability for International Application No. PCT/US2019/049127 dated Mar. 2, 2021.
International Search Report and Written Opinion for International Application No. PCT/CN2014/090501, dated Jun. 5, 2015.
International Search Report and Written Opinion for International Application No. PCT/US13/032029, dated Jun. 20, 2013.
International Search Report and Written Opinion for International Application No. PCT/US2015/041378 dated Jan. 21, 2016.
International Search Report and Written Opinion for International Application No. PCT/US2018/029955 dated Sep. 27, 2018.
International Search Report and Written Opinion for International Application No. PCT/US2018/029963 dated Jun. 29, 2018.
International Search Report and Written Opinion for International Application No. PCT/US2018/063255 dated May 13, 2019.
International Search Report and Written Opinion for PCT Application No. PCT/US2014/034570 dated Aug. 12, 2014.
International Search Report and Written Opinion of the International Search Authority for International Application No. PCT/CN2014/082586 dated Apr. 24, 2015.
International Search Report and Written Opinion of the International Search Authority for International Application No. PCT/US2015/012284 dated May 8, 2015.
International Search Report for International Application No. PCT/US13/63083, dated Jan. 17, 2014.
Irving et al. "Functional Characterization of a Signal Transducing Motif Present in the T Cell Antigen Receptor" J Exp Med (1993) vol. 177, pp. 1093-1103.
Jena et al. "Chimeric Antigen Receptor (CAR)-Specific Monoclonal Antibody to Detect CD19-Specific T Cells in Clinical Trials," PLOS 8(3): e57838 (2013).
Jensen et al. "Design and implementation of adoptive therapy with chimeric antigen receptor-modified T cells" Immunological Reviews (2014) vol. 257, pp. 127-144.
John et al., "Anti-PD-1 antibody therapy potently enhances the eradication of established tumors by gene-modified T cells", Clinical Cancer Research, The American Association for Cancer Research, US (2013) vol. 19, No. 20, pp. 5636-5646.
Kaiser, "First pass at cancer genoome reveals complex landscape" Science (2006) vol. 313, p. 1370.
Kalos et al. "Adoptive T Cell Transfer for Cancer Immunotherapy in the Era of Synthetic Biology", Immunity, Cell Press, US, vol. 39, No. 1, Jul. 25, 2013. pp. 49-60.
Kershaw et al. "Gene-engineered T cells for cancer therapy", Nature Reviews Cancer, vol. 13, No. 8, Jul. 24, 2013, pp. 525-541.
Lu et al. "A Rapid Cell Expansion Process for Production of Engineered Autologous CART-T Cell Therapies" Human Gene Therapy Methods (2016) vol. 27, No. 6, pp. 209-218.
Mariuzza et al., "The Structural Basis of Antigen-Antibody Recognition," Ann Rev Biophys Biophys Chem (1987) vol. 16, pp. 139-159.
Markley et al. "IL-7 and IL-21 are superior to IL-2 and IL-15 in promoting human T cell-mediated rejection of systemic lymphoma in immunodeficient mice" Blood (2010) vol. 115, No. 17, pp. 3508-3519.
Morgan, et al., "Recognition of Glioma Stem Cells by Genetically Modified T Cells Targeting EGFRvIII and Development of Adoptive Cell Therapy for Glioma" Human Gene Therapy, 23:1043-1053 (2012).
Mueller et al: "Cellular kinetics of CTL019 in relapsed/refractory B-cell acute lymphoblastic leukemia and chronic lymphocytic leukemia" Blood (2017) vol. 130, No. 21, pp. 2317-2325.
Nakayashiki, et al., "Production of a Single-chain Variable Fragment Antibody Recognizing Type III Mutant Epidermal Growth Factor Receptor" Jpn. J. Cancer Res., 91:1035-1043 (2000).
Neurauter et al. "Cell Isolation and Expansion Using Dynabeads" Adv Biochem Engin/Biotechnol (2007) vol. 106, pp. 41-73.
Norelli et al "Monocyte-derived IL-1 and IL-6 are differentially required for cytokine-release syndrome and neurotoxicity due to CAR T cells" Nat Med. (2018) vol. 24, No. 6, pp. 739-748.
Park et al. "A phase Ib GOELAMS study of the mTOR inhibitor RAD001 in association with chemotherapy for AML patients in first relapse" Leukemia (2013) vol. 27, No. 7, pp. 1479-1486.
Pascalis et al. "Grafting of "Abbreviated" Complementarity-Determining Regions Containing Specificity-Determining Residues Essential for Ligand Contact to Engineer a Less Immunogenic Humanized Monoclonal Antibody" The Journal of Immunology (2002) vol. 169, pp. 3076-3084.
Patel et al. "Engineering an APRIL-specific B Cell Maturation Antigen" The Journal of Biological Chemistry (2004) vol. 279, No. 16, pp. 16727-16735.
Pont et al., "Gamma-Secretase inhibition increases efficacy of BCMA-specific chimeric antigen receptor T cells in multiple myeloma," Blood (2019) vol. 134, No. 19, pp. 1585-1597.
Prazma et al. "Dendritic cell CD83: A therapeutic target or innocent bystander?" Immunology Letters (2008) vol. 115, pp. 1-8.
Radhika et al., "Targeting Leukemias by CD123 Specific Chimerica Antigen Receptor" Blood(ASH Annual Meeting Abstracts) 118(21): abstract 1908 (2011).
Ran et al., "gamma-Secretase inhibitors in ancer clinical trials are pharmacologically and functionally distinct," EMBO Molecular Medicine (2017) vol. 9, pp. 950-966.
Roitt et al., "Immunology," Moscow, "Mir" (2000) pp. 110-111. Russian language.
Roitt, et al., "Immunology," Moscow, Mir, 2000, pp. 4-6.
Smith et al., "Ex vivo expansion of human T cells for adoptive immunotherapy using the novel Xeno-free CTSTM Immune Cell Serum Replacement" Clinical and Translational Immunology (2015) vol. 4, No. 1, e31, pp. 1-10.
Stephan et al., "T cell-encoded CD80 and 4-1BBL induce auto- and transcostimulation, resulting in potent tumor rejection," Nature Medicine (2007) vol. 13, No. 12, pp. 1440-1449.
Wang et al. "Clinical manufacturing of CAR T cells: foundation of a promising therapy" Molecular Therapy—Oncolytics (2016) vol. 3, No. 16015, pp. 1-7.
Zhang et al., "Research progress on chimeric antigen receptor T cell therapy for multiple myeloma," Chin J Cell Mol Immunol (2019) vol. 34, No. 5, pp. 469-473.
Zhu et al. "Closed-system manufacturing of CD19 and dual-targeted CD20/19 chimeric antigen receptor T cells using the CliniMACS Prodigy device at an academic medical center" Cytotherapy (2018) vol. 20, pp. 394-406.

* cited by examiner

BCMA CHIMERIC ANTIGEN RECEPTORS AND USES THEREOF

RELATED APPLICATIONS

This application is a divisional of U.S. patent application Ser. No. 16/439,495, filed on Jun. 12, 2019, now allowed, which claims priority to U.S. Ser. No. 62/684,628 filed on Jun. 13, 2018, and U.S. Ser. No. 62/832,991 filed on Apr. 12, 2019, the contents of each of which are incorporated herein by reference in their entirety.

SEQUENCE LISTING

The instant application contains a Sequence Listing which has been submitted electronically in XML format and is hereby incorporated by reference in its entirety. Said XML copy, created on Feb. 15, 2023, is named N2067-715541FT_SL.xml and is 398,916 bytes in size.

FIELD OF THE INVENTION

The present invention relates generally to the use of immune effector cells (e.g., T cells, NK cells) engineered to express a Chimeric Antigen Receptor (CAR) to treat a disease associated with expression of the B-cell maturation antigen protein (BCMA).

BACKGROUND OF THE INVENTION

B-cell maturation antigen (BCMA) is a tumor necrosis family receptor (TNFR) member expressed cells of the B-cell lineage. BCMA expression is the highest on terminally differentiated B cells. BCMA is involved in mediating the survival of plasma cells for maintaining long-term humoral immunity. The expression of BCMA has been recently linked to a number of cancers, autoimmune disorders, and infectious diseases. Cancers with increased expression of BCMA include some hematological cancers, such as multiple myeloma, Hodgkin's and non-Hodgkin's lymphoma, various leukemias, and glioblastoma.

SUMMARY OF THE INVENTION

In one aspect, this invention features an isolated nucleic acid molecule encoding a chimeric antigen receptor (CAR), wherein the CAR comprises an anti-BCMA binding domain (e.g., a human anti-BCMA binding domain, e.g., a human anti-BCMA binding domain described herein), a transmembrane domain, and an intracellular signaling domain.

In another aspect, this invention provides an isolated CAR, wherein the CAR comprises an anti-BCMA binding domain (e.g., a human anti-BCMA binding domain, e.g., a human anti-BCMA binding domain described herein), a transmembrane domain, and an intracellular signaling domain.

In some embodiments, the anti-BCMA binding domain (e.g., human anti-BCMA binding domain) comprises one or more (e.g., all three) heavy chain complementarity determining region 1 (HC CDR1), heavy chain complementarity determining region 2 (HC CDR2), and heavy chain complementarity determining region 3 (HC CDR3) of an anti-BCMA binding domain described herein, and/or one or more (e.g., all three) light chain complementarity determining region 1 (LC CDR1), light chain complementarity determining region 2 (LC CDR2), and light chain complementarity determining region 3 (LC CDR3) of an anti- BCMA binding domain described herein. In some embodiments, the anti-BCMA binding domain comprises a heavy chain variable region described herein (e.g., in Table 2, 6, or 10) and/or a light chain variable region described herein (e.g., in Table 2, 6, or 10). In some embodiments, the anti-BCMA binding domain comprises a scFv comprising a light chain and a heavy chain of an amino acid sequence of Table 2, 6, or 10. In some embodiments, the anti-BCMA binding domain comprises a scFv described herein (e.g., in Table 2, 6, or 10). In some embodiments, the CAR comprises a CAR sequence disclosed herein (e.g., in Table 2, 6, or 10).

In some embodiments, the anti-BCMA binding domain comprises a HC CDR1, a HC CDR2, and a HC CDR3 of any anti-BCMA heavy chain binding domain amino acid sequence listed in Tables 2-13 (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)). In some embodiments, the anti-BCMA binding domain comprises a LC CDR1, a LC CDR2, and a LC CDR3 of any anti-BCMA light chain binding domain amino acid sequence listed in Tables 2-13 (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)).

In some embodiments, the HC CDR1, HC CDR2, and HC CDR3 are the HC CDR sequences listed in Tables 3-5 (e.g., in a single row of Tables 3-5) (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)). In some embodiments, the LC CDR1, LC CDR2, and LC CDR3 are the LC CDR sequences listed in Tables 3-5 (e.g., in a single row of Tables 3-5) (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)). In some embodiments, the HC CDR1, HC CDR2, and HC CDR3 comprise the amino acid sequences of SEQ ID NOs: 44, 45, and 84, respectively (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)). In some embodiments, the HC CDR1, HC CDR2, and HC CDR3 comprise the amino acid sequences of: (i) SEQ ID NOs: 44, 45, and 46, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); (ii) SEQ ID NOs: 44, 45, and 68, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); or (iii) SEQ ID NOs: 44, 45, and 76, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions).

In some embodiments, the LC CDR1, LC CDR2, and LC CDR3 comprise the amino acid sequences of SEQ ID NOs: 54, 55, and 56, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions).

In some embodiments, the HC CDR1, HC CDR2, HC CDR3, LC CDR1, LC CDR2, and LC CDR3 comprise the amino acid sequences of: (i) SEQ ID NOs: 44, 45, 46, 54, 55, and 56, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions); (ii) SEQ ID NOs: 44, 45, 68, 54, 55, and 56, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions); or (iii) SEQ ID NOs: 44, 45, 76, 54, 55, and 56, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions).

In some embodiments, the anti-BCMA binding domain comprises a heavy chain variable region (VH) comprising the amino acid sequence of SEQ ID NO: 52, 70, or 78, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions).

In some embodiments, the anti-BCMA binding domain comprises a VH, wherein the nucleic acid molecule comprises a nucleic acid sequence encoding the VH, wherein the nucleic acid sequence comprises the nucleic acid sequence of SEQ ID NO: 53, 71, or 79, or a nucleic acid sequence having at least about 85%, 90%, 95%, or 99% sequence identity thereto.

In some embodiments, the anti-BCMA binding domain comprises a light chain variable region (VL) comprising the amino acid sequence of SEQ ID NO: 61, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions).

In some embodiments, the anti-BCMA binding domain comprises a VL, wherein the nucleic acid molecule comprises a nucleic acid sequence encoding the VL, wherein the nucleic acid sequence comprises the nucleic acid sequence of SEQ ID NO: 62, or a nucleic acid sequence having at least about 85%, 90%, 95%, or 99% sequence identity thereto.

In some embodiments, the anti-BCMA binding domain comprises a VH and VL, wherein the VH and VL comprise the amino acid sequences of: (i) SEQ ID NOs: 52 and 61, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions), (ii) SEQ ID NOs: 70 and 61, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions), or (iii) SEQ ID NOs: 78 and 61, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions).

In some embodiments, the anti-BCMA binding domain comprises a single-chain fragment variable (scFv) comprising the amino acid sequence of SEQ ID NO: 64, 72, or 80, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the anti-BCMA binding domain comprises a single-chain fragment variable (scFv), wherein the nucleic acid molecule comprises a nucleic acid sequence encoding the scFv, wherein the nucleic acid sequence comprises the nucleic acid sequence of SEQ ID NO: 65, 73, or 81, or a nucleic acid sequence having at least about 85%, 90%, 95%, or 99% sequence identity thereto.

In some embodiments, the CAR comprises the amino acid sequence of SEQ ID NO: 66, 74, or 82, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the nucleic acid molecule comprises the nucleic acid sequence of SEQ ID NO: 67, 75, or 83, or a nucleic acid sequence having at least about 85%, 90%, 95%, or 99% sequence identity thereto.

In some embodiments, the HC CDR1, HC CDR2, and HC CDR3 are the HC CDR sequences listed in Tables 7-9 (e.g., in a single row of Tables 7-9) (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)). In some embodiments, the LC CDR1, LC CDR2, and LC CDR3 are the LC CDR sequences listed in Tables 7-9 (e.g., in a single row of Tables 7-9) (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)).

In some embodiments, the HC CDR1, HC CDR2, and HC CDR3 comprise the amino acid sequences of SEQ ID NOs: 86, 130, and 88, respectively (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)). In some embodiments, the HC CDR1, HC CDR2, and HC CDR3 comprise the amino acid sequences of: (i) SEQ ID NOs: 86, 87, and 88, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); (ii) SEQ ID NOs: 86, 109, and 88, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); or (iii) SEQ ID NOs: 86, 109, and 88, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions).

In some embodiments, the LC CDR1, LC CDR2, and LC CDR3 comprise the amino acid sequences of SEQ ID NOs: 95, 131, and 132, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions). In some embodiments, the LC CDR1, LC CDR2, and LC CDR3 comprise the amino acid sequences of: (i) SEQ ID NOs: 95, 96, and 97, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); (ii) SEQ ID NOs: 95, 114, and 115, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); or (iii) SEQ ID NOs: 95, 114, and 97, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions).

In some embodiments, the HC CDR1, HC CDR2, HC CDR3, LC CDR1, LC CDR2, and LC CDR3 comprise the amino acid sequences of: (i) SEQ ID NOs: 86, 87, 88, 95, 96, and 97, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions); (ii) SEQ ID NOs: 86, 109, 88, 95, 114, and 115, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions); or (iii) SEQ ID NOs: 86, 109, 88, 95, 114, and 97, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions).

In some embodiments, the anti-BCMA binding domain comprises a heavy chain variable region (VH) comprising the amino acid sequence of SEQ ID NO: 93 or 112, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the anti-BCMA binding domain comprises a VH, wherein the nucleic acid molecule comprises a nucleic acid sequence encoding the VH, wherein the nucleic acid sequence comprises the nucleic acid sequence of SEQ ID NO: 260, 94, or 113, or a nucleic acid sequence having at least about 85%, 90%, 95%, or 99% sequence identity thereto.

In some embodiments, the anti-BCMA binding domain comprises a light chain variable region (VL) comprising the amino acid sequence of SEQ ID NO: 102, 118, or 124, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the anti-BCMA binding domain comprises a VL, wherein the nucleic acid molecule comprises a nucleic acid sequence encoding the VL, wherein the nucleic acid sequence comprises the nucleic acid sequence of SEQ ID NO: 261, 103, 119, or 125, or a nucleic acid sequence having at least about 85%, 90%, 95%, or 99% sequence identity thereto.

In some embodiments, the anti-BCMA binding domain comprises a VH and VL, wherein the VH and VL comprise the amino acid sequences of: (i) SEQ ID NOs: 93 and 102, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions, (ii) SEQ ID NOs: 112 and 118, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions, or (iii) SEQ ID NOs: 112 and 124, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions.

In some embodiments, the anti-BCMA binding domain comprises a single-chain fragment variable (scFv) comprising the amino acid sequence of SEQ ID NO: 105, 120, or 126, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the anti-BCMA binding domain comprises a single-chain fragment variable (scFv), wherein the nucleic acid molecule comprises a nucleic acid sequence encoding the scFv, wherein the nucleic acid sequence comprises the nucleic acid sequence of SEQ ID NO: 253, 106, 121, or 127, or a nucleic acid sequence having at least about 85%, 90%, 95%, or 99% sequence identity thereto.

In some embodiments, the CAR comprises the amino acid sequence of SEQ ID NO: 107, 122, or 128, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the nucleic acid molecule comprises the nucleic acid sequence of SEQ ID NO: 259, 108, 123, or 129, or a nucleic acid sequence having at least about 85%, 90%, 95%, or 99% sequence identity thereto. In some embodiments, the nucleic acid molecule comprises the nucleic acid sequence of SEQ ID NO: 258, or a nucleic acid sequence having at least about 85%, 90%, 95%, or 99% sequence identity thereto.

In some embodiments, the HC CDR1, HC CDR2, and HC CDR3 are the HC CDR sequences listed in Tables 11-13 (e.g., in a single row of Tables 11-13) (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)). In some embodiments, the LC CDR1, LC CDR2, and LC CDR3 are the LC CDR sequences listed in Tables 11-13 (e.g., in a single row of Tables 11-13) (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)).

In some embodiments, the HC CDR1, HC CDR2, and HC CDR3 comprise the amino acid sequences of SEQ ID NOs: 179, 180, and 181, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions). In some embodiments, the HC CDR1, HC CDR2, and HC CDR3 comprise the amino acid sequences of: (i) SEQ ID NOs: 137, 138, and 139, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); or (ii) SEQ ID NOs: 160, 161, and 162, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions).

In some embodiments, the LC CDR1, LC CDR2, and LC CDR3 comprise the amino acid sequences of SEQ ID NOs: 147, 182, and 183, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions). In some embodiments, the LC CDR1, LC CDR2, and LC CDR3 comprise the amino acid sequences of: (i) SEQ ID NOs: 147, 148, and 149, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); or (ii) SEQ ID NOs: 147, 170, and 171, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions).

In some embodiments, the HC CDR1, HC CDR2, HC CDR3, LC CDR1, LC CDR2, and LC CDR3 comprise the amino acid sequences of: (i) SEQ ID NOs: 137, 138, 139, 147, 148, and 149, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions); or (ii) SEQ ID NOs: 160, 161, 162, 147, 170, and 171, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions).

In some embodiments, the anti-BCMA binding domain comprises a heavy chain variable region (VH) comprising the amino acid sequence of SEQ ID NO: 145 or 168, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the anti-BCMA binding domain comprises a VH, wherein the nucleic acid molecule comprises a nucleic acid sequence encoding the VH, wherein the nucleic acid sequence comprises the nucleic acid sequence of SEQ ID NO: 146 or 169, or a nucleic acid sequence having at least about 85%, 90%, 95%, or 99% sequence identity thereto.

In some embodiments, the anti-BCMA binding domain comprises a light chain variable region (VL) comprising the amino acid sequence of SEQ ID NO: 154 or 173, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the anti-BCMA binding domain comprises a VL, wherein the nucleic acid molecule comprises a nucleic acid sequence encoding the VL, wherein the nucleic acid sequence comprises the nucleic acid sequence of SEQ ID NO: 155 or 174, or a nucleic acid sequence having at least about 85%, 90%, 95%, or 99% sequence identity thereto.

In some embodiments, the anti-BCMA binding domain comprises a VH and VL, wherein the VH and VL comprise the amino acid sequences of: (i) SEQ ID NOs: 145 and 154, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions), or (ii) SEQ ID NOs: 168 and 173, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions).

In some embodiments, the anti-BCMA binding domain comprises a single-chain fragment variable (scFv) comprising the amino acid sequence of SEQ ID NO: 156 or 175, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the anti-BCMA binding domain comprises a single-chain fragment variable (scFv), wherein the nucleic acid molecule comprises a nucleic acid sequence encoding the scFv, wherein the nucleic acid sequence comprises the nucleic acid sequence of SEQ ID NO: 157 or 176, or a nucleic acid sequence having at least about 85%, 90%, 95%, or 99% sequence identity thereto.

In some embodiments, the CAR comprises the amino acid sequence of SEQ ID NO: 158 or 177, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the nucleic acid molecule comprises the nucleic acid sequence of SEQ ID NO: 159 or 178, or a nucleic acid sequence having at least about 85%, 90%, 95%, or 99% sequence identity thereto.

In some embodiments, the anti-BCMA binding domain comprises a VH and a VL, wherein the VH and VL are connected by a linker, e.g., a linker described herein, optionally wherein the linker comprises the amino acid sequence of SEQ ID NO: 63 or 104, or an amino acid sequence having at least about 85%, 90%, 95%, or 99% sequence identity thereto.

In some embodiments, the transmembrane domain comprises a transmembrane domain of a protein chosen from the alpha, beta or zeta chain of T-cell receptor, CD28, CD3 epsilon, CD45, CD4, CD5, CD8, CD9, CD16, CD22, CD33, CD37, CD64, CD80, CD86, CD134, CD137 and CD154. In some embodiments, the transmembrane domain comprises the amino acid sequence of SEQ ID NO: 6, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the nucleic acid molecule comprises a nucleic acid sequence encoding the transmembrane domain, wherein the nucleic acid sequence comprises the nucleic acid sequence of SEQ ID NO: 17, or a nucleic acid sequence having at least about 85%, 90%, 95%, or 99% sequence identity thereto.

In some embodiments, the anti-BCMA binding domain is connected to the transmembrane domain by a hinge region. In some embodiments, the hinge region comprises the amino acid sequence of SEQ ID NO: 2, 3, or 4, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the nucleic acid molecule comprises a nucleic acid sequence encoding the hinge region, wherein the nucleic acid sequence comprises the nucleic acid sequence of SEQ ID NO: 13, 14, or 15, or a nucleic acid sequence having at least about 85%, 90%, 95%, or 99% sequence identity thereto.

In some embodiments, the transmembrane domain and the hinge region comprise the amino acid sequence of SEQ ID NO: 202, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the transmembrane domain and the hinge region are encoded by the nucleic acid sequence of SEQ ID NO: 254, or a nucleic acid sequence having at least about 85%, 90%, 95%, or 99% sequence identity thereto.

In some embodiments, the intracellular signaling domain comprises a primary signaling domain, e.g., a primary signaling domain described herein, optionally wherein the primary signaling domain comprises a functional signaling domain derived from CD3 zeta, TCR zeta, FcR gamma, FcR beta, CD3 gamma, CD3 delta, CD3 epsilon, CD5, CD22, CD79a, CD79b, CD278 (ICOS), FcεRI, DAP10, DAP12, or CD66d. In some embodiments, the primary signaling domain comprises the amino acid sequence of SEQ ID NO: 9 or 10, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the nucleic acid molecule comprises a nucleic acid sequence encoding the primary signaling domain, wherein the nucleic acid sequence comprises the nucleic acid sequence of SEQ ID NO: 20 or 21, or a nucleic acid sequence having at least about 85%, 90%, 95%, or 99% sequence identity thereto. In some embodiments, the nucleic acid molecule comprises a nucleic acid sequence encoding the primary signaling domain, wherein the nucleic acid sequence comprises the nucleic acid sequence of SEQ ID NO: 256, or a nucleic acid sequence having at least about 85%, 90%, 95%, or 99% sequence identity thereto.

In some embodiments, the intracellular signaling domain comprises a costimulatory signaling domain, e.g., a costimulatory signaling domain described herein, optionally wherein the costimulatory signaling domain comprises a functional signaling domain derived from a MHC class I molecule, a TNF receptor protein, an Immunoglobulin-like protein, a cytokine receptor, an integrin, a signalling lymphocytic activation molecule (SLAM protein), an activating NK cell receptor, BTLA, a Toll ligand receptor, OX40, CD2, CD7, CD27, CD28, CD30, CD40, CDS, ICAM-1, 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD28-OX40, CD28-4-1BB, or a ligand that specifically binds with CD83. In some embodiments, the costimulatory signaling domain comprises the amino acid sequence of SEQ ID NO: 7, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the nucleic acid molecule comprises a nucleic acid sequence encoding the costimulatory signaling domain, wherein the nucleic acid sequence comprises the nucleic acid sequence of SEQ ID NO: 18, or a nucleic acid sequence having at least about 85%, 90%, 95%, or 99% sequence identity thereto. In some embodiments, the nucleic acid molecule comprises a nucleic acid sequence encoding the costimulatory signaling domain, wherein the nucleic acid sequence comprises the nucleic acid sequence of SEQ ID NO: 255, or a nucleic acid sequence having at least about 85%, 90%, 95%, or 99% sequence identity thereto.

In some embodiments, the intracellular signaling domain comprises a functional signaling domain derived from 4-1BB and a functional signaling domain derived from CD3 zeta, optionally wherein the intracellular signaling domain comprises the amino acid sequence of SEQ ID NO: 7 (or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions)) and the amino acid sequence of SEQ ID NO: 9 or 10 (or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions)), optionally wherein the intracellular signaling domain comprises the amino acid sequence of SEQ ID NO: 7 and the amino acid sequence of SEQ ID NO: 9 or 10.

In some embodiments, the CAR further comprises a leader sequence comprising the amino acid sequence of SEQ ID NO: 1.

In some embodiments, the CAR comprises one or more (e.g., 1, 2 or all) of the following properties: (i) the CAR, when expressed in a cell (e.g., a T cell), activates NFAT signaling in the cell in the presence of BCMA-expressing cells, e.g., as measured by the JNL Screening Reporter Assay described in Example 1, e.g., as assessed using methods described in Example 1 with respect to FIG. 1A or 1C; (ii) the CAR, when expressed in a cell (e.g., a T cell), induces cytotoxicity of BCMA-expressing cells, e.g., as assessed using methods described in Example 1 with respect to FIG. 3A; and (iii) the CAR, when expressed in a cell (e.g., a T cell), induces expression of a cytokine (e.g., IFN-γ) in the cell in the presence of BCMA-expressing cells, e.g., as assessed using methods described in Example 1 with respect to FIG. 3C.

In another aspect, this invention provides an anti-BCMA binding domain comprising a heavy chain variable region (VH) comprising a heavy chain complementarity determining region 1 (HC CDR1), a heavy chain complementarity determining region 2 (HC CDR2), and a heavy chain complementarity determining region 3 (HC CDR3), and a light chain variable region (VL) comprising a light chain complementarity determining region 1 (LC CDR1), a light chain complementarity determining region 2 (LC CDR2), and a light chain complementarity determining region 3 (LC CDR3), wherein the HC CDR1, HC CDR2, HC CDR3, LC CDR1, LC CDR2, and LC CDR3 comprise CDR amino acid sequences disclosed herein.

In some embodiments, the HC CDR1, HC CDR2, and HC CDR3 are the HC CDR sequences listed in Tables 3-5 (e.g., in a single row of Tables 3-5) (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)). In some embodiments, the LC CDR1, LC CDR2, and LC CDR3 are the LC CDR sequences listed in Tables 3-5 (e.g., in a single row of Tables 3-5) (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)). In some embodiments, the HC CDR1, HC CDR2, and HC CDR3 comprise the amino acid sequences of SEQ ID NOs: 44, 45, and 84, respectively (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)). In some embodiments, the HC CDR1, HC CDR2, and HC CDR3 comprise the amino acid sequences of: (i) SEQ ID NOs: 44, 45, and 46, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); (ii) SEQ ID NOs: 44, 45, and 68, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); or (iii) SEQ ID NOs: 44, 45, and 76, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions).

In some embodiments, the LC CDR1, LC CDR2, and LC CDR3 comprise the amino acid sequences of SEQ ID NOs: 54, 55, and 56, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions).

In some embodiments, the HC CDR1, HC CDR2, HC CDR3, LC CDR1, LC CDR2, and LC CDR3 comprise the amino acid sequences of: (i) SEQ ID NOs: 44, 45, 46, 54, 55, and 56, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions); (ii) SEQ ID NOs: 44, 45, 68, 54, 55, and 56, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions); or (iii) SEQ ID NOs: 44, 45, 76, 54, 55, and 56, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions).

In some embodiments, the anti-BCMA binding domain comprises a heavy chain variable region (VH) comprising the amino acid sequence of SEQ ID NO: 52, 70, or 78, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions).

In some embodiments, the anti-BCMA binding domain comprises a VH, wherein the nucleic acid molecule comprises a nucleic acid sequence encoding the VH, wherein the nucleic acid sequence comprises the nucleic acid sequence of SEQ ID NO: 53, 71, or 79, or a nucleic acid sequence having at least about 85%, 90%, 95%, or 99% sequence identity thereto.

In some embodiments, the anti-BCMA binding domain comprises a light chain variable region (VL) comprising the amino acid sequence of SEQ ID NO: 61, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions).

In some embodiments, the anti-BCMA binding domain comprises a VL, wherein the nucleic acid molecule comprises a nucleic acid sequence encoding the VL, wherein the nucleic acid sequence comprises the nucleic acid sequence of SEQ ID NO: 62, or a nucleic acid sequence having at least about 85%, 90%, 95%, or 99% sequence identity thereto.

In some embodiments, the anti-BCMA binding domain comprises a VH and VL, wherein the VH and VL comprise the amino acid sequences of: (i) SEQ ID NOs: 52 and 61, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions), (ii) SEQ ID NOs: 70 and 61, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions), or (iii) SEQ ID NOs: 78 and 61, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions).

In some embodiments, the HC CDR1, HC CDR2, and HC CDR3 are the HC CDR sequences listed in Tables 7-9 (e.g., in a single row of Tables 7-9) (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)). In some embodiments, the LC CDR1, LC CDR2, and LC CDR3 are the LC CDR sequences listed in Tables 7-9 (e.g., in a single row of Tables 7-9) (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)).

In some embodiments, the HC CDR1, HC CDR2, and HC CDR3 comprise the amino acid sequences of SEQ ID NOs: 86, 130, and 88, respectively (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)). In some embodiments, the HC CDR1, HC CDR2, and HC CDR3 comprise the amino acid sequences of: (i) SEQ ID NOs: 86, 87, and 88, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); (ii) SEQ ID NOs: 86, 109, and 88, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); or (iii) SEQ ID NOs: 86, 109, and 88, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions).

In some embodiments, the LC CDR1, LC CDR2, and LC CDR3 comprise the amino acid sequences of SEQ ID NOs: 95, 131, and 132, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions). In some embodiments, the LC CDR1, LC CDR2, and LC CDR3 comprise the amino acid sequences of: (i) SEQ ID NOs: 95, 96, and 97, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); (ii) SEQ ID NOs: 95, 114, and 115, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); or (iii) SEQ ID NOs: 95, 114, and 97, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions).

In some embodiments, the HC CDR1, HC CDR2, HC CDR3, LC CDR1, LC CDR2, and LC CDR3 comprise the amino acid sequences of: (i) SEQ ID NOs: 86, 87, 88, 95, 96, and 97, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions); (ii) SEQ ID NOs: 86, 109, 88, 95, 114, and 115, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions); or (iii) SEQ ID NOs: 86, 109, 88, 95, 114, and 97, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions).

In some embodiments, the anti-BCMA binding domain comprises a heavy chain variable region (VH) comprising the amino acid sequence of SEQ ID NO: 93 or 112, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the anti-BCMA binding domain comprises a VH, wherein the nucleic acid molecule comprises a nucleic acid sequence encoding the VH, wherein the nucleic acid sequence comprises the nucleic acid sequence of SEQ ID NO: 260, 94, or 113, or a nucleic acid sequence having at least about 85%, 90%, 95%, or 99% sequence identity thereto.

In some embodiments, the anti-BCMA binding domain comprises a light chain variable region (VL) comprising the amino acid sequence of SEQ ID NO: 102, 118, or 124, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the anti-BCMA binding domain comprises a VL, wherein the nucleic acid molecule comprises a nucleic acid sequence encoding the VL, wherein the nucleic acid sequence comprises the nucleic acid sequence of SEQ ID NO: 261, 103, 119, or 125, or a nucleic acid sequence having at least about 85%, 90%, 95%, or 99% sequence identity thereto.

In some embodiments, the anti-BCMA binding domain comprises a VH and VL, wherein the VH and VL comprise the amino acid sequences of: (i) SEQ ID NOs: 93 and 102, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions, (ii) SEQ ID NOs: 112 and 118, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions, or (iii) SEQ ID NOs: 112 and 124, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions.

In some embodiments, the HC CDR1, HC CDR2, and HC CDR3 are the HC CDR sequences listed in Tables 11-13 (e.g., in a single row of Tables 11-13) (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)). In some embodiments, the LC CDR1, LC CDR2, and LC CDR3 are the LC CDR sequences listed in Tables 11-13 (e.g., in a single row of Tables 11-13) (or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions)).

In some embodiments, the HC CDR1, HC CDR2, and HC CDR3 comprise the amino acid sequences of SEQ ID NOs: 179, 180, and 181, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions). In some embodiments, the HC CDR1, HC CDR2, and HC CDR3 comprise the amino acid sequences of: (i) SEQ ID NOs: 137, 138, and 139, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); or (ii) SEQ ID NOs: 160, 161, and 162, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions).

In some embodiments, the LC CDR1, LC CDR2, and LC CDR3 comprise the amino acid sequences of SEQ ID NOs:

147, 182, and 183, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions). In some embodiments, the LC CDR1, LC CDR2, and LC CDR3 comprise the amino acid sequences of: (i) SEQ ID NOs: 147, 148, and 149, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions); or (ii) SEQ ID NOs: 147, 170, and 171, respectively, or an amino acid sequence having at least about 85%, 90%, 95%, or 99% sequence identity thereto, or an amino acid sequence having at least one, two, or three modifications (e.g., substitutions, e.g., conservative substitutions) but not more than seven, six, or five modifications (e.g., substitutions, e.g., conservative substitutions).

In some embodiments, the HC CDR1, HC CDR2, HC CDR3, LC CDR1, LC CDR2, and LC CDR3 comprise the amino acid sequences of: (i) SEQ ID NOs: 137, 138, 139, 147, 148, and 149, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions); or (ii) SEQ ID NOs: 160, 161, 162, 147, 170, and 171, respectively, or a sequence having at least about 85%, 90%, 95%, or 99% sequence identity thereto, or a sequence having at least one, two, or three modifications (e.g., substitutions, e.g., conservative substitutions) but not more than seven, six, or five modifications (e.g., substitutions, e.g., conservative substitutions).

In some embodiments, the anti-BCMA binding domain comprises a heavy chain variable region (VH) comprising the amino acid sequence of SEQ ID NO: 145 or 168, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the anti-BCMA binding domain comprises a VH, wherein the nucleic acid molecule comprises a nucleic acid sequence encoding the VH, wherein the nucleic acid sequence comprises the nucleic acid sequence of SEQ ID NO: 146 or 169, or a nucleic acid sequence having at least about 85%, 90%, 95%, or 99% sequence identity thereto.

In some embodiments, the anti-BCMA binding domain comprises a light chain variable region (VL) comprising the amino acid sequence of SEQ ID NO: 154 or 173, or an amino acid sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions). In some embodiments, the anti-BCMA binding domain comprises a VL, wherein the nucleic acid molecule comprises a nucleic acid sequence encoding the VL, wherein the nucleic acid sequence comprises the nucleic acid sequence of SEQ ID NO: 155 or 174, or a nucleic acid sequence having at least about 85%, 90%, 95%, or 99% sequence identity thereto.

In some embodiments, the anti-BCMA binding domain comprises a VH and VL, wherein the VH and VL comprise the amino acid sequences of: (i) SEQ ID NOs: 145 and 154, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions), or (ii) SEQ ID NOs: 168 and 173, respectively, or a sequence having at least about 85%, 90%, 95%, or 99% sequence identity thereto, or an amino acid sequence having at least one, two, or three modifications (e.g., substitutions, e.g., conservative substitutions) but not more than 30, 20, or 10 modifications (e.g., substitutions, e.g., conservative substitutions).

In one aspect, this invention provides an isolated polypeptide molecule encoded by a nucleic acid molecule described herein. In one aspect, this invention provides a vector comprising a nucleic acid molecule described herein, or a nucleic acid molecule encoding a CAR described herein. In some embodiments, the vector is chosen from a DNA vector, a RNA vector, a plasmid, a lentivirus vector, an adenoviral vector, or a retrovirus vector. In some embodiments, the vector comprises an EF-1 promoter comprising the nucleic acid sequence of SEQ ID NO: 11. In one aspect, this invention provides a cell (e.g., a T cell or an NK cell) comprising a nucleic acid molecule described herein, a CAR described herein, a polypeptide molecule described herein, or a vector described herein. In some embodiments, the cell further expresses an inhibitory agent that comprises a first polypeptide that comprises at least a portion of an inhibitory molecule, associated with a second polypeptide that comprises a positive signal from an intracellular signaling domain, optionally wherein the inhibitory agent comprises a first polypeptide comprising at least a portion of PD-1 and a second polypeptide comprising a costimulatory domain and a primary signaling domain.

In one aspect, this invention provides a method of making a cell comprising transducing a cell (e.g., a T cell or an NK cell) with a vector described herein. In one aspect, this invention provides a method of making an RNA-engineered cell comprising introducing an in vitro transcribed RNA or synthetic RNA into a cell (e.g., a T cell or an NK cell), where the RNA comprises a nucleic acid molecule described herein, or a nucleic acid molecule encoding a CAR described herein.

In one aspect, this invention provides a method of providing an anti-tumor immunity in a subject comprising administering to the subject an effective amount of a cell described herein. In one aspect, this invention provides a method of treating a subject having a disease associated with expression of BCMA comprising administering to the subject an effective amount of a cell described herein. In some embodiments, the cell is an autologous T cell or an allogeneic T cell. In some embodiments, the disease associated with BCMA expression is: (i) a cancer or malignancy, or a precancerous condition chosen from one or more of a myelodysplasia, a myelodysplastic syndrome or a preleukemia, or (ii) a non-cancer related indication associated with expression of BCMA. In some embodiments, the disease is a hematologic cancer or a solid cancer. In some embodiments, the disease is chosen from: acute leukemia, B-cell acute lymphoid leukemia ("BALL"), T-cell acute lymphoid leukemia ("TALL"), acute lymphoid leukemia (ALL), chronic myelogenous leukemia (CML), chronic lymphocytic leukemia (CLL), B cell prolymphocytic leukemia, blastic plasmacytoid dendritic cell neoplasm, Burkitt's lymphoma, diffuse large B cell lymphoma, follicular lymphoma, hairy cell leukemia, small cell- or large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, prostate cancer (e.g., castrate-resistant or therapy-resistant prostate cancer, or metastatic prostate cancer), pancreatic cancer, lung cancer, a plasma cell proliferative disorder (e.g., asymptomatic myeloma (smoldering multiple myeloma or indolent myeloma), monoclonal gammapathy of undetermined significance (MGUS), Waldenstrom's macroglobulinemia, plasmacytoma (e.g., plasma cell dyscrasia, solitary myeloma, solitary plasmacytoma, extramedullary plasmacytoma, and multiple plasmacytoma), systemic amyloid light chain amyloidosis, or POEMS syndrome (also known as Crow-Fukase syndrome, Takatsuki disease, and PEP syndrome)), or a combination thereof. In some embodiments, the disease is multiple myeloma. In some embodiments, the method further comprises administering to the subject a second therapeutic agent. In some embodiments, the second therapeutic agent is a PD-1 inhibitor, optionally wherein the PD-1 inhibitor is selected from the group consisting of PDR001, Nivolumab, Pembrolizumab, Pidilizumab, MEDI0680, REGN2810, TSR-042, PF-06801591, and AMP-224. In some embodiments, the second therapeutic agent is a PD-L1 inhibitor, optionally wherein the PD-L1 inhibitor is selected from the group consisting of FAZ053, Atezolizumab, Avelumab, Durvalumab, and BMS-936559. In some embodiments, the second therapeutic agent is a LAG-3 inhibitor, optionally wherein the LAG-3 inhibitor is selected from the group consisting of LAG525, BMS-986016, TSR-033, MK-4280 and REGN3767. In some embodiments, the second therapeutic agent is a TIM-3 inhibitor, optionally wherein the TIM-3 inhibitor is selected from the group consisting of MBG453, TSR-022, and LY3321367. In some embodiments, the second therapeutic agent is a CTLA-4 inhibitor, optionally wherein the CTLA-4 inhibitor is Ipilimumab or Tremelimumab. In some embodiments, the second therapeutic agent is an interleukin-15 (IL-15) polypeptide, an interleukin-15 receptor alpha (IL-15Ra) polypeptide, or a combination of both an IL-15 polypeptide and an IL-15Ra polypeptide, e.g., hetIL-15. In some embodiments, the second therapeutic agent is an interleukin-12 (IL-12) polypeptide. In some embodiments, the second therapeutic agent is an mTOR inhibitor, optionally wherein the mTOR inhibitor is RAD001 or rapamycin.

The anti-BCMA binding domains disclosed herein, as well as CARs comprising such anti-BCMA binding domains, have improved properties over previous anti-BCMA binding domains and CARs comprising them, for example, increased binding affinity to BCMA, increased CAR expression levels in cells (e.g., T cells or NK cells), and/or enhanced ability to mediate cytotoxicity and/or cytokine production of cells (e.g., T cells or NK cells).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. Headings, sub-headings or numbered or lettered elements, e.g., (a), (b), (i) etc, are presented merely for ease of reading. The use of headings or numbered or lettered elements in this document does not require the steps or elements be performed in alphabetical order or that the steps or elements are necessarily discrete from one another. Other features, objects, and advantages of the invention will be apparent from the description and drawings, and from the claims.

BRIEF DESCRIPTION OF THE DRAWINGS

FIGS. 1B and 1D are graphs showing expression level of BCMA CARs on JNL cells were detected by flow cytometry using a human recombinant (r)BCMA_Fc-AF647. 1× or 2× platform indicated 40,000 of H293 cells or 80,000 of H293 cells seeded for viral production.

FIG. 3A: CART cells were co-cultured with KMS11-luc target cells at the indicated E:T ratios. % cell killing was determined by the difference in luciferase signal between target cells without effector T cells (control) and with effector T cells (experimental), expressed as a percent of the control. UTD represents untransduced T cells. FIG. 3B: Background killing was observed for the BCMA-negative line NALM6. FIG. 3C: IFNγ was measured by MSD in the supernatants collected at 24 h from these co-culture systems with a E:T ratio of 2.5. All data is expressed as the average+/−standard deviation.

DETAILED DESCRIPTION

Definitions

Figure 1A:
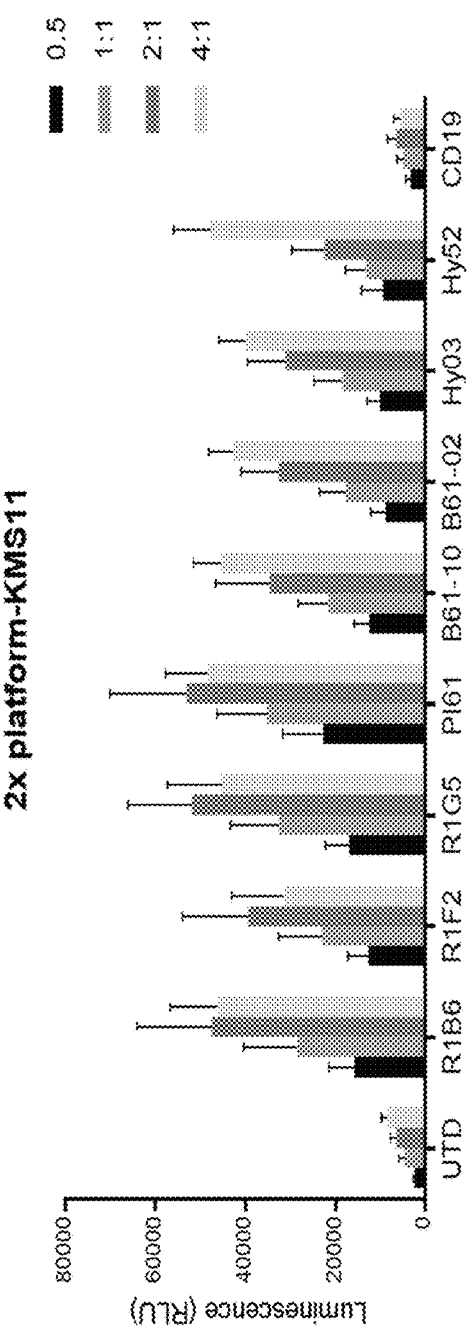
FIGS. 1A-1H. Jurkat NFAT Luciferase (JNL) reporter assay using an automated system was used to test the function of BCMA CARs. CAR clones were evaluated in the JNL reporter assay for antigen-dependent activity. JNL cells containing the indicated CAR clones or untransduced JNL cells (UTD) were co-cultured with media alone (FIGS. 1G and 1H) or with target cells lines (KMS11 as a BCMA-positive cell line (FIGS. 1A and 1C) and NALM6 as a BCMA-negative cell line (FIGS. 1E and 1F)) at different ratios and luciferase activity was measured as luminescence intensity. Clones were considered active when the luminescence intensity exceeded 2-fold the level of UTD cells in the presence of antigen-expressing cells. Luminescence readout is a direct measurement of CAR stimulation.

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The compositions and methods of the present invention encompass polypeptides and nucleic acids having the sequences specified, or sequences substantially identical or similar thereto, e.g., sequences at least 85%, 90%, or 95% identical or higher to the sequence specified. In the context of an amino acid sequence, the term "substantially identical" is used herein to refer to a first amino acid sequence that contains a sufficient or minimum number of amino acid residues that are i) identical to, or ii) conservative substitutions of aligned amino acid residues in a second amino acid sequence such that the first and second amino acid sequences can have a common structural domain and/or common functional activity, for example, amino acid sequences that contain a common structural domain having at least about 85%, 90%. 91%, 92%, 93%, 94%, 95%, 96%, 97%, 98% or 99% identity to a reference sequence, e.g., a sequence provided herein.

In the context of a nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity, for example, nucleotide sequences having at least about 85%, 90%, 91%, 92%, 93%, 94%, 95%, 96%, 97%, 98% or 99% identity to a reference sequence, e.g., a sequence provided herein.

The term "variant" refers to a polypeptide that has a substantially identical amino acid sequence to a reference amino acid sequence, or is encoded by a substantially identical nucleotide sequence. In some embodiments, the variant is a functional variant.

The term "functional variant" refers to a polypeptide that has a substantially identical amino acid sequence to a reference amino acid sequence, or is encoded by a substantially identical nucleotide sequence, and is capable of having one or more activities of the reference amino acid sequence.

As used herein, the term "BCMA" refers to B-cell maturation antigen. BCMA (also known as TNFRSF17, BCM or CD269) is a member of the tumor necrosis receptor (TNFR) family and is predominantly expressed on terminally differentiated B cells, e.g., memory B cells, and plasma cells. Its ligand is called B-cell activator of the TNF family (BAFF) and a proliferation inducing ligand (APRIL). BCMA is involved in mediating the survival of plasma cells for maintaining long-term humoral immunity. The gene for BCMA is encoded on chromosome 16 producing a primary mRNA transcript of 994 nucleotides in length (NCBI accession NM_001192.2) that encodes a protein of 184 amino acids (NP_001183.2). A second antisense transcript derived from the BCMA locus has been described, which may play a role in regulating BCMA expression. (Laabi Y. et al., Nucleic Acids Res., 1994, 22:1147-1154). Additional transcript variants have been described with unknown significance (Smirnova A S et al. Mol Immunol., 2008, 45(4): 1179-1183. A second isoform, also known as TV4, has been identified (Uniprot identifier Q02223-2). As used herein, "BCMA" includes proteins comprising mutations, e.g., point mutations, fragments, insertions, deletions and splice variants of full length wild-type BCMA.

The term "Chimeric Antigen Receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, e.g., comprise a chimeric fusion protein. In some embodiments, the domains in the CAR polypeptide construct are not contiguous with each other, e.g., are in different polypeptide chains, e.g., as provided in an RCAR as described herein.

In one aspect, the cytoplasmic signaling domain comprises a primary signaling domain (e.g., a primary signaling domain of CD3-zeta). In one aspect, the cytoplasmic signaling domain further comprises one or more functional signaling domains derived from at least one costimulatory molecule as defined below. In one aspect, the costimulatory molecule is chosen from 41BB (i.e., CD137), CD27, ICOS, and/or CD28. In one aspect, the CAR comprises a chimeric fusion protein comprising an extracellular antigen recognition domain, a transmembrane domain and an intracellular signaling domain comprising a functional signaling domain derived from a stimulatory molecule. In one aspect, the CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. In one aspect, the CAR comprises a chimeric fusion protein comprising an extracellular antigen recognition domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen recognition domain, wherein the leader sequence is optionally cleaved from the antigen recognition domain (e.g., an scFv) during cellular processing and localization of the CAR to the cellular membrane.

A CAR that comprises an antigen binding domain (e.g., an scFv, a single domain antibody, or TCR (e.g., a TCR alpha binding domain or TCR beta binding domain)) that targets a specific tumor marker X, wherein X can be a tumor marker as described herein, is also referred to as XCAR. For example, a CAR that comprises an antigen binding domain that targets BCMA is referred to as BCMA CAR. The CAR can be expressed in any cell, e.g., an immune effector cell as described herein (e.g., a T cell or an NK cell).

The term "signaling domain" refers to the functional portion of a protein which acts by transmitting information within the cell to regulate cellular activity via defined signaling pathways by generating second messengers or functioning as effectors by responding to such messengers.

The term "antibody," as used herein, refers to a protein, or polypeptide sequence derived from an immunoglobulin molecule, which specifically binds with an antigen. Antibodies can be polyclonal or monoclonal, multiple or single chain, or intact immunoglobulins, and may be derived from natural sources or from recombinant sources. Antibodies can be tetramers of immunoglobulin molecules.

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')2, and Fv fragments, scFv antibody fragments, linear antibodies, single domain antibodies such as sdAb (either VL or VH), camelid VHH domains, and multi-specific molecules formed from antibody fragments such as a bivalent fragment comprising two or more, e.g., two, Fab fragments linked by a disulfide brudge at the hinge region, or two or more, e.g., two isolated CDR or other epitope binding fragments of an antibody linked. An antibody fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antibody fragments can also be grafted into scaffolds based on polypeptides such as a fibronectin type III (Fn3) (see U.S. Pat. No. 6,703,199, which describes fibronectin polypeptide minibodies).

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The terms "complementarity determining region" or "CDR," as used herein, refer to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), or a combination thereof. In a combined Kabat and Chothia numbering scheme, in some embodiments, the CDRs correspond to the amino acid residues that are part of a Kabat CDR, a Chothia CDR, or both.

The portion of the CAR composition of the invention comprising an antibody or antibody fragment thereof may exist in a variety of forms, for example, where the antigen binding domain is expressed as part of a polypeptide chain including, for example, a single domain antibody fragment (sdAb), a single chain antibody (scFv), or e.g., a human or humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises an scFv.

As used herein, the term "binding domain" or "antibody molecule" (also referred to herein as "anti-target binding domain") refers to a protein, e.g., an immunoglobulin chain or fragment thereof, comprising at least one immunoglobulin variable domain sequence. The term "binding domain" or "antibody molecule" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-tumor effect" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anti-cancer effect" can also be manifested by the ability of the peptides, polynucleotides, cells and antibodies in prevention of the occurrence of cancer in the first place. The term "anti-tumor effect" refers to a biological effect which can be manifested by various means, including but not limited to, e.g., a decrease in tumor volume, a decrease in the number of tumor cells, a decrease in tumor cell proliferation, or a decrease in tumor cell survival. The term "autologous" refers to any material derived from the same individual to whom it is later to be re-introduced into the individual.

The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "apheresis" as used herein refers to the art-recognized extracorporeal process by which the blood of a donor or patient is removed from the donor or patient and passed through an apparatus that separates out selected particular constituent(s) and returns the remainder to the circulation of the donor or patient, e.g., by retransfusion. Thus, in the context of "an apheresis sample" refers to a sample obtained using apheresis.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. Preferred cancers treated by the methods described herein include multiple myeloma, Hodgkin's lymphoma or non-Hodgkin's lymphoma.

The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

"Derived from" as that term is used herein, indicates a relationship between a first and a second molecule. It generally refers to structural similarity between the first molecule and a second molecule and does not connotate or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connotate or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

The phrase "disease associated with expression of BCMA" includes, but is not limited to, a disease associated with a cell which expresses BCMA (e.g., wild-type or mutant BCMA) or condition associated with a cell which expresses BCMA (e.g., wild-type or mutant BCMA) including, e.g., proliferative diseases such as a cancer or malignancy or a precancerous condition such as a myelodysplasia, a myelodysplastic syndrome or a preleukemia; or a noncancer related indication associated with a cell which expresses BCMA (e.g., wild-type or mutant BCMA). For the avoidance of doubt, a disease associated with expression of BCMA may include a condition associated with a cell which does not presently express BCMA, e.g., because BCMA expression has been downregulated, e.g., due to treatment with a molecule targeting BCMA, e.g., a BCMA inhibitor described herein, but which at one time expressed BCMA. In one aspect, a cancer associated with expression of BCMA (e.g., wild-type or mutant BCMA) is a hematological cancer. In one aspect, the hematological cancer is a leukemia or a lymphoma. In one aspect, a cancer associated with expression of BCMA (e.g., wild-type or mutant BCMA) is a malignancy of differentiated plasma B cells. In one aspect, a cancer associated with expression of BCMA (e.g., wild-type or mutant BCMA) includes cancers and malignancies including, but not limited to, e.g., one or more acute leukemias including but not limited to, e.g., B-cell acute Lymphoid Leukemia ("BALL"), T-cell acute Lymphoid Leukemia ("TALL"), acute lymphoid leukemia (ALL); one or more chronic leukemias including but not limited to, e.g., chronic myelogenous leukemia (CML), Chronic Lymphoid Leukemia (CLL). Additional cancers or hematologic conditions associated with expression of BCMA (e.g., wild-type or mutant BCMA) comprise, but are not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. In some embodiments, the cancer is multiple myeloma, Hodgkin's lymphoma, non-Hodgkin's lymphoma, or glioblastoma. In embodiments, a disease associated with expression of BCMA includes a plasma cell proliferative disorder, e.g., asymptomatic myeloma (smoldering multiple myeloma or indolent myeloma), monoclonal gammapathy of undetermined significance (MGUS), Waldenstrom's macroglobulinemia, plasmacytomas (e.g., plasma cell dyscrasia, solitary myeloma, solitary plasmacytoma, extramedullary plasmacytoma, and multiple plasmacytoma), systemic amyloid light chain amyloidosis, and POEMS syndrome (also known as Crow-Fukase syndrome, Takatsuki disease, and PEP syndrome). Further diseases associated with expression of BCMA (e.g., wild-type or mutant BCMA) expression include, but not limited to, e.g., atypical and/or non-classical cancers, malignancies, precancerous conditions or proliferative diseases associated with expression of BCMA (e.g., wild-type or mutant BCMA), e.g., a cancer described herein, e.g., a prostate cancer (e.g., castrate-resistant or therapy-resistant prostate cancer, or metastatic prostate cancer), pancreatic cancer, or lung cancer.

Non-cancer related conditions that are associated with BCMA (e.g., wild-type or mutant BCMA) include viral infections; e.g., HIV, fungal infections, e.g., *C. neoformans*; autoimmune disease; e.g. rheumatoid arthritis, system lupus erythematosus (SLE or lupus), pemphigus vulgaris, and Sjogren's syndrome; inflammatory bowel disease, ulcerative colitis; transplant-related allospecific immunity disorders related to mucosal immunity; and unwanted immune responses towards biologics (e.g., Factor VIII) where humoral immunity is important. In embodiments, a non-cancer related indication associated with expression of BCMA includes but is not limited to, e.g., autoimmune disease, (e.g., lupus), inflammatory disorders (allergy and asthma) and transplantation. In some embodiments, the tumor antigen-expressing cell expresses, or at any time expressed, mRNA encoding the tumor antigen. In an embodiment, the tumor antigen-expressing cell produces the tumor antigen protein (e.g., wild-type or mutant), and the tumor antigen protein may be present at normal levels or reduced levels. In an embodiment, the tumor antigen-expressing cell produced detectable levels of a tumor antigen protein at one point, and subsequently produced substantially no detectable tumor antigen protein.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested using the functional assays described herein.

The term "stimulation," refers to a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

The term "stimulatory molecule," refers to a molecule expressed by a T cell that provides the primary cytoplasmic signaling sequence(s) that regulate primary activation of the TCR complex in a stimulatory way for at least some aspect of the T cell signaling pathway. In some embodiments, the ITAM-containing domain within the CAR recapitulates the signaling of the primary TCR independently of endogenous TCR complexes. In one aspect, the primary signal is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS"), FcεRI and CD66d, DAP10 and DAP12. In a specific CAR of the invention, the intracellular signaling domain in any one or more CARS of the invention comprises an intracellular signaling sequence, e.g., a primary signaling sequence of CD3-zeta. The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. In embodiments, the intracellular signal domain transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, CD278 (also known as "ICOS"), FcεRI, CD66d, DAP10 and DAP12.

The term "zeta" or alternatively "zeta chain", "CD3-zeta" or "TCR-zeta" refers to CD247. Swiss-Prot accession number P20963 provides exemplary human CD3 zeta amino acid sequences. A "zeta stimulatory domain" or alternatively a "CD3-zeta stimulatory domain" or a "TCR-zeta stimulatory domain" refers to a stimulatory domain of CD3-zeta or a variant thereof (e.g., a molecule having mutations, e.g., point mutations, fragments, insertions, or deletions). In some embodiments, the cytoplasmic domain of zeta comprises residues 52 through 164 of GenBank Acc. No. BAG36664.1 or a variant thereof (e.g., a molecule having mutations, e.g., point mutations, fragments, insertions, or deletions). In some embodiments, the "zeta stimulatory domain" or a "CD3-zeta stimulatory domain" is the sequence provided as SEQ ID NO: 9 or 10, or a variant thereof (e.g., a molecule having mutations, e.g., point mutations, fragments, insertions, or deletions).

The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an MHC class I molecule, TNF receptor proteins, Immunoglobulin-like proteins, cytokine receptors, integrins, signaling lymphocytic activation molecules (SLAM proteins), activating NK cell receptors, BTLA, Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD28-OX40, CD28-4-1BB, and a ligand that specifically binds with CD83.

A costimulatory intracellular signaling domain refers to the intracellular portion of a costimulatory molecule.

The intracellular signaling domain can comprise the entire intracellular portion, or the entire native intracellular signaling domain, of the molecule from which it is derived, or a functional fragment thereof.

The term "4-1BB" refers to CD137 or Tumor necrosis factor receptor superfamily member 9. Swiss-Prot accession number P20963 provides exemplary human 4-1BB amino acid sequences. A "4-1BB costimulatory domain" refers to a costimulatory domain of 4-1BB, or a variant thereof (e.g., a molecule having mutations, e.g., point mutations, fragments, insertions, or deletions). In some embodiments, the "4-1BB costimulatory domain" is the sequence provided as SEQ ID NO: 7 or a variant thereof (e.g., a molecule having mutations, e.g., point mutations, fragments, insertions, or deletions).

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloic-derived phagocytes.

"Immune effector function or immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "effector function" refers to a specialized function of a cell. Effector function of a T cell, for example, may be cytolytic activity or helper activity including the secretion of cytokines.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or a RNA may also include introns to the extent that the nucleotide sequence encoding the protein may in some version contain an intron(s).

The term "effective amount" or "therapeutically effective amount" are used interchangeably herein, and refer to an amount of a compound, formulation, material, or composition, as described herein effective to achieve a particular biological result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence. In some embodiments, expression comprises translation of an mRNA introduced into a cell.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementarity determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid," "nucleic acid molecule," "polynucleotide," or "polynucleotide molecule" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. In some embodiments, a "nucleic acid," "nucleic acid molecule," "polynucleotide," or "polynucleotide molecule" comprise a nucleotide/nucleoside derivative or analog. Unless otherwise indicated, a particular nucleic acid sequence also implicitly encompasses conservatively modified variants thereof (e.g., degenerate codon substitutions, e.g., conservative substitutions), alleles, orthologs, SNPs, and complementary sequences as well as the sequence explicitly indicated. Specifically, degenerate codon substitutions, e.g., conservative substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The terms "cancer associated antigen" or "tumor antigen" interchangeably refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs of the present invention includes CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+ T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

The term "tumor-supporting antigen" or "cancer-supporting antigen" interchangeably refer to a molecule (typically a protein, carbohydrate or lipid) that is expressed on the surface of a cell that is, itself, not cancerous, but supports the cancer cells, e.g., by promoting their growth or survival e.g., resistance to immune cells. Exemplary cells of this type include stromal cells and myeloid-derived suppressor cells (MDSCs). The tumor-supporting antigen itself need not play a role in supporting the tumor cells so long as the antigen is present on a cell that supports cancer cells.

The term "flexible polypeptide linker" or "linker" as used in the context of an scFv refers to a peptide linker that consists of amino acids such as glycine and/or serine residues used alone or in combination, to link variable heavy and variable light chain regions together. In some embodiments, the flexible polypeptide linker is a Gly/Ser linker and comprises the amino acid sequence (Gly-Gly-Gly-Ser)n, where n is a positive integer equal to or greater than 1. For example, n=1, n=2, n=3. n=4, n=5 and n=6, n=7, n=8, n=9 and n=10 (SEQ ID NO: 42). In some embodiments, the flexible polypeptide linkers include, but are not limited to, (Gly4 Ser)4 (SEQ ID NO: 27) or (Gly4 Ser)3 (SEQ ID NO: 28). In another embodiment, the linkers include multiple repeats of (Gly2Ser), (GlySer) or (Gly3Ser) (SEQ ID NO: 29). Also included within the scope of the invention are linkers described in WO2012/138475, incorporated herein by reference.

As used herein, a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 30), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin lymphoma, Hodgkin lymphoma, leukemias, uterine cancer, cervical cancer, bladder cancer, kidney cancer and adenocarcinomas such as breast cancer, prostate cancer (e.g., castrate-resistant or therapy-resistant prostate cancer, or metastatic prostate cancer), ovarian cancer, pancreatic cancer, and the like, or a plasma cell proliferative disorder, e.g., asymptomatic myeloma (smoldering multiple myeloma or indolent myeloma), monoclonal gammapathy of undetermined significance (MGUS), Waldenstrom's macroglobulinemia, plasmacytomas (e.g., plasma cell dyscrasia, solitary myeloma, solitary plasmacytoma, extramedullary plasmacytoma, and multiple plasmacytoma), systemic amyloid light chain amyloidosis, and POEMS syndrome (also known as Crow-Fukase syndrome, Takatsuki disease, and PEP syndrome).

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

"Regulatable chimeric antigen receptor (RCAR)," as used herein, refers to a set of polypeptides, typically two in the simplest embodiments, which when in an immune effector cell, provides the cell with specificity for a target cell, typically a cancer cell, and with intracellular signal generation. In some embodiments, an RCAR comprises at least an extracellular antigen binding domain, a transmembrane domain and a cytoplasmic signaling domain (also referred to herein as "an intracellular signaling domain") comprising a functional signaling domain derived from a stimulatory molecule and/or costimulatory molecule as defined herein in the context of a CAR molecule. In some embodiments, the set of polypeptides in the RCAR are not contiguous with each other, e.g., are in different polypeptide chains. In some embodiments, the RCAR includes a dimerization switch that, upon the presence of a dimerization molecule, can couple the polypeptides to one another, e.g., can couple an antigen binding domain to an intracellular signaling domain. In some embodiments, the RCAR is expressed in a cell (e.g., an immune effector cell) as described herein, e.g., an RCAR-expressing cell (also referred to herein as "RCARX cell"). In an embodiment the RCARX cell is a T cell, and is referred to as a RCART cell. In an embodiment the RCARX cell is an NK cell, and is referred to as a RCARN cell. The RCAR can provide the RCAR-expressing cell with specificity for a target cell, typically a cancer cell, and with regulatable intracellular signal generation or proliferation, which can optimize an immune effector property of the RCAR-expressing cell. In embodiments, an RCAR cell relies at least in part, on an antigen binding domain to provide specificity to a target cell that comprises the antigen bound by the antigen binding domain.

"Membrane anchor" or "membrane tethering domain", as that term is used herein, refers to a polypeptide or moiety, e.g., a myristoyl group, sufficient to anchor an extracellular or intracellular domain to the plasma membrane.

"Switch domain," as that term is used herein, e.g., when referring to an RCAR, refers to an entity, typically a polypeptide-based entity, that, in the presence of a dimerization molecule, associates with another switch domain. The association results in a functional coupling of a first entity linked to, e.g., fused to, a first switch domain, and a second entity linked to, e.g., fused to, a second switch domain. A first and second switch domain are collectively referred to as a dimerization switch. In embodiments, the first and second switch domains are the same as one another, e.g., they are polypeptides having the same primary amino acid sequence, and are referred to collectively as a homodimerization switch. In embodiments, the first and second switch domains are different from one another, e.g., they are polypeptides having different primary amino acid sequences, and are referred to collectively as a heterodimerization switch. In embodiments, the switch is intracellular. In embodiments, the switch is extracellular. In embodiments, the switch domain is a polypeptide-based entity, e.g., FKBP or FRB-based, and the dimerization molecule is small molecule, e.g., a rapalogue. In embodiments, the switch domain is a polypeptide-based entity, e.g., an scFv that binds a myc peptide, and the dimerization molecule is a polypeptide, a fragment thereof, or a multimer of a polypeptide, e.g., a myc ligand or multimers of a myc ligand that bind to one or more myc scFvs. In embodiments, the switch domain is a polypeptide-based entity, e.g., myc receptor, and the dimerization molecule is an antibody or fragments thereof, e.g., myc antibody.

"Dimerization molecule," as that term is used herein, e.g., when referring to an RCAR, refers to a molecule that promotes the association of a first switch domain with a second switch domain. In embodiments, the dimerization molecule does not naturally occur in the subject, or does not occur in concentrations that would result in significant dimerization. In embodiments, the dimerization molecule is a small molecule, e.g., rapamycin or a rapalogue, e.g, RAD001.

The term "low, immune enhancing, dose" when used in conjuction with an mTOR inhibitor, e.g., an allosteric mTOR inhibitor, e.g., RAD001 or rapamycin, or a catalytic mTOR inhibitor, refers to a dose of mTOR inhibitor that partially, but not fully, inhibits mTOR activity, e.g., as measured by the inhibition of P70 S6 kinase activity. Methods for evaluating mTOR activity, e.g., by inhibition of P70 S6 kinase, are discussed herein. The dose is insufficient to result in complete immune suppression but is sufficient to enhance the immune response. In an embodiment, the low, immune enhancing, dose of mTOR inhibitor results in a decrease in the number of PD-1 positive T cells and/or an increase in the number of PD-1 negative T cells, or an increase in the ratio of PD-1 negative T cells/PD-1 positive T cells. In an embodiment, the low, immune enhancing, dose of mTOR inhibitor results in an increase in the number of naive T cells. In an embodiment, the low, immune enhancing, dose of mTOR inhibitor results in one or more of the following:

an increase in the expression of one or more of the following markers: $CD62L^{high}$, $CD127^{high}$, $CD27^{+}$, and BCL2, e.g., on memory T cells, e.g., memory T cell precursors;

a decrease in the expression of KLRG1, e.g., on memory T cells, e.g., memory T cell precursors; and an increase in the number of memory T cell precursors, e.g., cells with any one or combination of the following characteristics: increased $CD62L^{high}$, increased $CD127^{high}$, increased $CD27^{+}$, decreased KLRG1, and increased BCL2;

wherein any of the changes described above occurs, e.g., at least transiently, e.g., as compared to a non-treated subject.

"Refractory" as used herein refers to a disease, e.g., cancer, that does not respond to a treatment. In embodiments, a refractory cancer can be resistant to a treatment before or at the beginning of the treatment. In other embodiments, the refractory cancer can become resistant during a treatment. A refractory cancer is also called a resistant cancer.

"Relapsed" or "relapse" as used herein refers to the return or reappearance of a disease (e.g., cancer) or the signs and symptoms of a disease such as cancer after a period of improvement or responsiveness, e.g., after prior treatment of a therapy, e.g., cancer therapy. The initial period of responsiveness may involve the level of cancer cells falling below a certain threshold, e.g., below 20%, 1%, 10%, 5%, 4%, 3%, 2%, or 1%. The reappearance may involve the level of cancer cells rising above a certain threshold, e.g., above 20%, 1%, 10%, 5%, 4%, 3%, 2%, or 1%. For example, e.g., in the context of B-ALL, the reappearance may involve, e.g., a reappearance of blasts in the blood, bone marrow (>5%), or any extramedullary site, after a complete response. A complete response, in this context, may involve <5% BM blast. More generally, in an embodiment, a response (e.g., complete response or partial response) can involve the absence of detectable MRD (minimal residual disease). In an embodiment, the initial period of responsiveness lasts at least 1, 2, 3, 4, 5, or 6 days; at least 1, 2, 3, or 4 weeks; at least 1, 2, 3, 4, 6, 8, 10, or 12 months; or at least 1, 2, 3, 4, or 5 years.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98%, or 99% identity, and includes subranges such as 96-99%, 96-98%, 96-97%, 97-99%, 97-98%, and 98-99% identity. This applies regardless of the breadth of the range.

A "gene editing system" as the term is used herein, refers to a system, e.g., one or more molecules, that direct and effect an alteration, e.g., a deletion, of one or more nucleic acids at or near a site of genomic DNA targeted by said system. Gene editing systems are known in the art, and are described more fully below.

Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Various aspects of the compositions and methods herein are described in further detail below. Additional definitions are set out throughout the specification.

Description

Provided herein are compositions of matter and methods of use for the treatment of a disease such as cancer using cells expressing BCMA chimeric antigen receptors (CAR), e.g., CART-BCMA.

In one aspect, the invention provides a cell (e.g., an immune effector cell, e.g., T cell or NK cell) engineered to express a CAR, wherein the CAR T cell ("CART") or CAR NK cell exhibits an antitumor property. In one aspect a cell is transformed with the CAR and the CAR is expressed on the cell surface. In some embodiments, the cell (e.g., an immune effector cell, e.g., T cell or NK cell) is transduced with a viral vector encoding a CAR. In some embodiments, the viral vector is a retroviral vector. In some embodiments, the viral vector is a lentiviral vector. In some such embodiments, the cell may stably express the CAR. In another embodiment, the cell (e.g., an immune effector cell, e.g., T cell or NK cell) is transfected with a nucleic acid, e.g., mRNA, cDNA, DNA, encoding a CAR. In some such embodiments, the cell may transiently express the CAR.

In one aspect, the CARs of the invention combine an antigen binding domain of a specific antibody with an intracellular signaling molecule. For example, in some aspects, the intracellular signaling molecule includes, but is not limited to, CD3-zeta chain, 4-1BB and CD28 signaling modules and combinations thereof. In one aspect, the antigen binding domain binds to BCMA.

Furthermore, the present invention provides BCMA CAR compositions and their use in medicaments or methods for treating, among other diseases, cancer or any malignancy or autoimmune diseases involving cells or tissues which express BCMA.

In one aspect, the CAR of the invention can be used to eradicate BCMA-expressing normal cells, thereby applicable for use as a cellular conditioning therapy prior to cell transplantation. In one aspect, the BCMA-expressing normal cell is a BCMA-expressing normal stem cell and the cell transplantation is a stem cell transplantation.

In one aspect, the invention provides a cell (e.g., T cell or NK cell) engineered to express a chimeric antigen receptor (CAR), wherein the CAR T cell ("CART") or the CAR NK cell exhibits an antitumor property. A preferred antigen is BCMA. In one aspect, the antigen binding domain of the CAR comprises a human anti-BCMA antibody fragment. In one aspect, the antigen binding domain of the CAR comprises a human anti-BCMA antibody fragment comprising an scFv. Accordingly, the invention provides a BCMA-CAR that comprises a human anti-BCMA binding domain and is engineered into a cell, e.g., a T cell or NK cell, and methods of their use for adoptive therapy.

In one aspect, the BCMA-CAR comprises at least one intracellular domain selected from the group of a CD137 (4-1BB) signaling domain, a CD28 signaling domain, a CD3zeta signal domain, and any combination thereof. In one aspect, the BCMA-CAR comprises at least one intracellular signaling domain is from one or more co-stimulatory molecule(s) other than a CD137 (4-1BB) or CD28.

Chimeric Antigen Receptor (CAR)

The present invention provides a CAR (e.g., a CAR polypeptide) that comprises an anti-BCMA binding domain (e.g., human anti-BCMA binding domain as described herein), a transmembrane domain, and an intracellular signaling domain, wherein said anti-BCMA binding domain comprises a heavy chain complementarity determining region 1 (HC CDR1), a heavy chain complementarity determining region 2 (HC CDR2), and a heavy chain complementarity determining region 3 (HC CDR3) of any anti- BCMA heavy chain binding domain amino acid sequences listed in Tables 2-13. The anti-BCMA binding domain of the CAR can further comprise a light chain complementarity determining region 1 (LC CDR1), a light chain complementarity determining region 2 (LC CDR2), and a light chain complementarity determining region 3 (LC CDR3) of any anti-BCMA light chain binding domain amino acid sequences listed in Tables 2-13.

The present invention also provides nucleic acid molecules encoding the CAR as described herein, e.g., encoding a CAR that comprises an anti-BCMA binding domain (e.g., human anti-BCMA binding domain as described herein), a transmembrane domain, and an intracellular signaling domain, wherein said anti-BCMA binding domain comprises a HC CDR1, a HC CDR2, and a HC CDR3 of any anti-BCMA heavy chain binding domain amino acid sequences listed in Tables 2-13. In some embodiments, the encoded anti-BCMA binding domain of the CAR can further comprise a LC CDR1, a LC CDR2, and a LC CDR3 of any anti-BCMA light chain binding domain amino acid sequences listed in Tables 2-13.

In one aspect, an exemplary BCMA CAR constructs comprise an optional leader sequence, an extracellular antigen binding domain, a hinge, a transmembrane domain, and an intracellular stimulatory domain. An exemplary leader sequence is provided as SEQ ID NO: 1. An exemplary nucleic acid sequence encoding the leader sequence is provided as SEQ ID NO: 12. An exemplary hinge/spacer sequence is provided as SEQ ID NO: 2, 3, 4, or 5. An exemplary transmembrane domain sequence is provided as SEQ ID NO: 6. An exemplary sequence of the intracellular signaling domain of the 4-1BB protein is provided as SEQ ID NO: 7. An exemplary sequence of the intracellular signaling domain of CD27 is provided as SEQ ID NO: 8. An exemplary CD3zeta domain sequence is provided as SEQ ID NO: 9 or 10. In certain embodiments, the domains are contiguous with and in the same reading frame to form a single fusion protein. In other embodiments, the domain are in separate polypeptides, e.g., as in an RCAR molecule as described herein.

The CAR construct can include a Gly/Ser linker having one or more of the following sequences: GGGGS (SEQ ID NO: 25); encompassing 1-6 "Gly Gly Gly Gly Ser" repeating units, e.g., GGGGSGGGGS GGGGSGGGGS GGGGSGGGGS (SEQ ID NO: 26); GGGGSGGGGS GGGGSGGGGS (SEQ ID NO: 27); GGGGSGGGGS GGGGS (SEQ ID NO: 28); GGGS (SEQ ID NO: 29); or encompassing 1-10 "Gly Gly Gly Ser" repeating units, e.g., GGGSGGGSGG GSGGGSGGGS GGGSGGGSGG GSGGGSGGGS (SEQ ID NO: 42).

In embodiments, the CAR construct include a poly A sequence, e.g., a sequence encompassing 50-5000 or 100-5000 adenines (SEQ ID NOS 30 and 33, respectively) (e.g., SEQ ID NO: 30, SEQ ID NO: 33, SEQ ID NO: 34 or SEQ ID NO: 35), or a sequence encompassing 50-5000 thymines (SEQ ID NO: 32) (e.g., SEQ ID NO: 31, SEQ ID NO: 32). Alternatively, the CAR construct can include, for example, a linker including the sequence GSTSGSGKPGSGEGSTKG (SEQ ID NO: 43).

In certain embodiments, the full length BCMA CAR molecule includes the amino acid sequence of, or is encoded by the nucleotide sequence of, R1B6, R1F2, R1G5, PI61, B61-02, B61-10, Hy03, or Hy52, provided in Tables 2-13, or a sequence substantially (e.g., 95-99%) identical thereto. In certain embodiments, the BCMA CAR molecule, or the anti-BCMA antigen binding domain, includes the scFv amino acid sequence of R1B6, R1F2, R1G5, PI61, B61-02, B61-10, Hy03, or Hy52, provided in Tables 2, 6, and 10, or a sequence substantially (e.g., 95-99%) identical thereto. In certain embodiments, the BCMA CAR molecule, or the anti-BCMA antigen binding domain, includes the heavy chain variable region and/or the light chain variable region of R1B6, R1F2, R1G5, PI61, B61-02, B61-10, Hy03, or Hy52, provided in Tables 2, 6, and 10, or a sequence substantially (e.g., 95-99%) identical thereto. In certain embodiments, the BCMA CAR molecule, or the anti-BCMA antigen binding domain, includes one, two or three CDRs from the heavy chain variable region (e.g., HCDR1, HCDR2 and/or HCDR3), and/or one, two or three CDRs from the light chain variable region (e.g., LCDR1, LCDR2 and/or LCDR3) of R1B6, R1F2, R1G5, PI61, B61-02, B61-10, Hy3, or Hy52, provided in Tables 2-13, or a sequence substantially (e.g., 95-99%) identical thereto.

Sequences of non-limiting examples of various components that can be part of a CAR molecule described herein are listed in Table 1, where "aa" stands for amino acids, and "na" stands for nucleic acids that encode the corresponding peptide.

TABLE 1

Sequences of various components of CAR

| SEQ ID NO | Description | Sequence |
|---|---|---|
| SEQ ID NO: 11 | EF-1 promoter (na) | CGTGAGGCTCCGGTGCCCGTCAGTGGGCAGAGCGCACATCG<br>CCCACAGTCCCCGAGAAGTTGGGGGGAGGGGTCGGCAATTG<br>AACCGGTGCCTAGAGAAGGTGGCGCGGGGTAAACTGGGAAA<br>GTGATGTCGTGTACTGGCTCCGCCTTTTTCCCGAGGGTGGGG<br>GAGAACCGTATATAAGTGCAGTAGTCGCCGTGAACGTTCTTT<br>TTCGCAACGGGTTTGCCGCCAGAACACAGGTAAGTGCCGTGT<br>GTGGTTCCCGCGGGCCTGGCCTCTTTACGGGTTATGGCCCTT<br>GCGTGCCTTGAATTACTTCCACCTGGCTGCAGTACGTGATTCT<br>TGATCCCGAGCTTCGGGTTGGAAGTGGGTGGGAGAGTTCGA<br>GGCCTTGCGCTTAAGGAGCCCCTTCGCCTCGTGCTTGAGTTG<br>AGGCCTGGCCTGGGCGCTGGGGCCGCCGCGTGCGAATCTGGT<br>GGCACCTTCGCGCCTGTCTCGCTGCTTTCGATAAGTCTCTAGC<br>CATTTAAAATTTTTGATGACCTGCTGCGACGCTTTTTTTCTGG<br>CAAGATAGTCTTGTAAATGCGGGCCAAGATCTGCACACTGGT<br>ATTTCGGTTTTTGGGGCCGCGGGCGGCGACGGGGCCCGTGCG<br>TCCCAGCGCACATGTTCGGCGAGGCGGGGCCTGCGAGCGCG<br>GCCACCGAGAATCGGACGGGGGTAGTCTCAAGCTGGCCGGC<br>CTGCTCTGGTGCCTGGCCTCGCGCCGCCGTGTATCGCCCCGC<br>CCTGGGCGGCAAGGCTGGCCCGGTCGGCACCAGTTGCGTGA |

TABLE 1-continued

Sequences of various components of CAR

| SEQ ID NO | Description | Sequence |
|---|---|---|
| | | GCGGAAAGATGGCCGCTTCCCGGCCCTGCTGCAGGGAGCTC AAAATGGAGGACGCGGCGCTCGGGAGAGCGGGCGGGTGAGT CACCCACACAAAGGAAAAGGGCCTTTCCGTCCTCAGCCGTCG CTTCATGTGACTCCACGGAGTACCGGGCGCCGTCCAGGCACC TCGATTAGTTCTCGAGCTTTTGGAGTACGTCGTCTTTAGGTTG GGGGGAGGGGTTTTATGCGATGGAGTTTCCCCACACTGAGTG GGTGGAGACTGAAGTTAGGCCAGCTTGGCACTTGATGTAATT CTCCTTGGAATTTGCCCTTTTTGAGTTTGGATCTTGGTTCATT CTCAAGCCTCAGACAGTGGTTCAAAGTTTTTTTCTTCCATTTC AGGTGTCGTGA |
| SEQ ID NO: 1 | Leader (aa) | MALPVTALLLPLALLLHAARP |
| SEQ ID NO: 12 | Leader (na) | ATGGCCCTGCCTGTGACAGCCCTGCTGCTGCCTCTGGCTCTG CTGCTGCATGCCGCTAGACCC |
| SEQ ID NO: 2 | CD8 hinge (aa) | TTTPAPRPPTPAPTIASQPLSLRPEACRPAAGGAVHTRGLDFACD |
| SEQ ID NO: 13 | CD8 hinge (na) | ACCACGACGCCAGCGCCGCGACCACCAACACCGGCGCCCAC CATCGCGTCGCAGCCCCTGTCCCTGCGCCCAGAGGCGTGCCG GCCAGCGGCGGGGGGCGCAGTGCACACGAGGGGGCTGGACT TCGCCTGTGAT |
| SEQ ID NO: 3 | Ig4 hinge (aa) | ESKYGPPCPPCPAPEFLGGPSVFLFPPKPKDTLMISRTPEVTCVV VDVSQEDPEVQFNWYVDGVEVHNAKTKPREEQFNSTYRVVSV LTVLHQDWLNGKEYKCKVSNKGLPSSIEKTISKAKGQPREPQV YTLPPSQEEMTKNQVSLTCLVKGFYPSDIAVEWESNGQPENNY KTTPPVLDSDGSFFLYSRLTVDKSRWQEGNVFSCSVMHEALHN HYTQKSLSLSLGKM |
| SEQ ID NO: 14 | Ig4 hinge (na) | GAGAGCAAGTACGGCCCTCCCTGCCCCCCTTGCCCTGCCCCC GAGTTCCTGGGCGGACCCAGCGTGTTCCTGTTCCCCCCCAAG CCCAAGGACACCCTGATGATCAGCCGGACCCCCGAGGTGAC CTGTGTGGTGGTGGACGTGTCCCAGGAGGACCCCGAGGTCCA GTTCAACTGGTACGTGGACGGCGTGGAGGTGCACAACGCCA AGACCAAGCCCCGGGAGGAGCAGTTCAATAGCACCTACCGG GTGGTGTCCGTGCTGACCGTGCTGCACCAGGACTGGCTGAAC GGCAAGGAATACAAGTGTAAGGTGTCCAACAAGGGCCTGCC CAGCAGCATCGAGAAAACCATCAGCAAGGCCAAGGGCCAGC CTCGGGAGCCCCAGGTGTACACCCTGCCCCCTAGCCAAGAGG AGATGACCAAGAACCAGGTGTCCCTGACCTGCCTGGTGAAG GGCTTCTACCCCAGCGACATCGCCGTGGAGTGGGAGAGCAA CGGCCAGCCCGAGAACAACTACAAGACCACCCCCCCTGTGCT GGACAGCGACGGCAGCTTCTTCCTGTACAGCCGGCTGACCGT GGACAAGAGCCGGTGGCAGGAGGGCAACGTCTTTAGCTGCT CCGTGATGCACGAGGCCCTGCACAACCACTACACCCAGAAG AGCCTGAGCCTGTCCCTGGGCAAGATG |
| SEQ ID NO: 4 | IgD hinge (aa) | RWPESPKAQASSVPTAQPQAEGSLAKATTAPATTRNTGRGGEE KKKEKEKEEQEERETKTPECPSHTQPLGVYLLTPAVQDLWLRD KATFTCFVVGSDLKDAHLTWEVAGKVPTGGVEEGLLERHSNGS QSQHSRLTLPRSLWNAGTSVTCTLNHPSLPPQRLMALREPAAQ APVKLSLNLLASSDPPEAASWLLCEVSGFSPPNILLMWLEDQRE VNTSGFAPARPPPQPGSTTFWAWSVLRVPAPPSPQPATYTCVVS HEDSRTLLNASRSLEVSYVTDH |
| SEQ ID NO: 15 | IgD hinge (na) | AGGTGGCCCGAAAGTCCCAAGGCCCAGGCATCTAGTGTTCCT ACTGCACAGCCCCAGGCAGAAGGCAGCCTAGCCAAAGCTAC TACTGCACCTGCCACTACGCGCAATACTGGCCGTGGCGGGGA GGAGAAGAAAAAGGAGAAAGAGAAAGAAGAACAGGAAGAG AGGGAGACCAAGACCCCTGAATGTCCATCCCATACCCAGCC GCTGGGCGTCTATCTCTTGACTCCCGCAGTACAGGACTTGTG GCTTAGAGATAAGGCCACCTTTACATGTTTCGTCGTGGGCTC TGACCTGAAGGATGCCCATTTGACTTGGGAGGTTGCCGGAAA GGTACCCACAGGGGGGGTTGAGGAAGGGTTGCTGGAGCGCC ATTCCAATGGCTCTCAGAGCCAGCACTCAAGACTCACCCTTC CGAGATCCCTGTGGAACGCCGGGACCTCTGTCACATGTACTC TAAATCATCCTAGCCTGCCCCCACAGCGTCTGATGGCCCTTA GAGAGCCAGCCGCCCAGGCACCAGTTAAGCTTAGCCTGAAT CTGCTCGCCAGTAGTGATCCCCCAGAGGCCGCCAGCTGGCTC TTATGCGAAGTGTCCGGCTTTAGCCCGCCCAACATCTTGCTC ATGTGGCTGGAGGACCAGCGAGAAGTGAACACCAGCGGCTT CGCTCCAGCCCGGCCCCCACCCCAGCCGGGTTCTACCACATT |

TABLE 1-continued

Sequences of various components of CAR

| SEQ ID NO | Description | Sequence |
|---|---|---|
| | | CTGGGCCTGGAGTGTCTTAAGGGTCCCAGCACCACCTAGCCC CCAGCCAGCCACATACACCTGTGTTGTGTCCCATGAAGATAG CAGGACCCTGCTAAATGCTTCTAGGAGTCTGGAGGTTTCCTA CGTGACTGACCATT |
| SEQ ID NO: 6 | CD8 Transmembrane (aa) | IYIWAPLAGTCGVLLLSLVITLYC |
| SEQ ID NO: 17 | CD8 Transmembrane (na) | ATCTACATCTGGGCGCCCTTGGCCGGGACTTGTGGGGTCCTT CTCCTGTCACTGGTTATCACCCTTTACTGC |
| SEQ ID NO: 7 | 4-1BB intracellular domain (aa) | KRGRKKLLYIFKQPFMRPVQTTQEEDGCSCRFPEEEEGGCEL |
| SEQ ID NO: 18 | 4-1BB intracellular domain (na) | AAACGGGGCAGAAAGAAACTCCTGTATATATTCAAACAACC ATTTATGAGACCAGTACAAACTACTCAAGAGGAAGATGGCT GTAGCTGCCGATTTCCAGAAGAAGAAGAAGGAGGATGTGAA CTG |
| SEQ ID NO: 8 | CD27 (aa) | QRRKYRSNKGESPVEPAEPCRYSCPREEEGSTIPIQEDYRKPEPA CSP |
| SEQ ID NO: 19 | CD27 (na) | AGGAGTAAGAGGAGCAGGCTCCTGCACAGTGACTACATGAA CATGACTCCCCGCCGCCCCGGGCCCACCCGCAAGCATTACCA GCCCTATGCCCCACCACGCGACTTCGCAGCCTATCGCTCC |
| SEQ ID NO: 9 | CD3-zeta (aa) (Q/K mutant) | RVKFSRSADAPAYKQGQNQLYNELNLGRREEYDVLDKRRGRD PEMGGKPRRKNPQEGLYNELQKDKMAEAYSEIGMKGERRRGK GHDGLYQGLSTATKDTYDALHMQALPPR |
| SEQ ID NO: 20 | CD3-zeta (na) (Q/K mutant) | AGAGTGAAGTTCAGCAGGAGCGCAGACGCCCCCGCGTACAA GCAGGGCCAGAACCAGCTCTATAACGAGCTCAATCTAGGAC GAAGAGAGGAGTACGATGTTTTGGACAAGAGACGTGGCCGG GACCCTGAGATGGGGGGAAAGCCGAGAAGGAAGAACCCTCA GGAAGGCCTGTACAATGAACTGCAGAAAGATAAGATGGCGG AGGCCTACAGTGAGATTGGGATGAAAGGCGAGCGCCGGAGG GGCAAGGGGCACGATGGCCTTTACCAGGGTCTCAGTACAGC CACCAAGGACACCTACGACGCCCTTCACATGCAGGCCCTGCC CCCTCGC |
| SEQ ID NO: 10 | CD3-zeta (aa) (NCBI Reference Sequence NM_000734.3) | RVKFSRSADAPAYQQGQNQLYNELNLGRREEYDVLDKRRGRD PEMGGKPRRKNPQEGLYNELQKDKMAEAYSEIGMKGERRRGK GHDGLYQGLSTATKDTYDALHMQALPPR |
| SEQ ID NO: 21 | CD3-zeta (na) (NCBI Reference Sequence NM_000734.3) | AGAGTGAAGTTCAGCAGGAGCGCAGACGCCCCCGCGTACCA GCAGGGCCAGAACCAGCTCTATAACGAGCTCAATCTAGGAC GAAGAGAGGAGTACGATGTTTTGGACAAGAGACGTGGCCGG GACCCTGAGATGGGGGGAAAGCCGAGAAGGAAGAACCCTCA GGAAGGCCTGTACAATGAACTGCAGAAAGATAAGATGGCGG AGGCCTACAGTGAGATTGGGATGAAAGGCGAGCGCCGGAGG GGCAAGGGGCACGATGGCCTTTACCAGGGTCTCAGTACAGC CACCAAGGACACCTACGACGCCCTTCACATGCAGGCCCTGCC CCCTCGC |
| SEQ ID NO: 36 | CD28 Intracellular domain (amino acid sequence) | RSKRSRLLHSDYMNMTPRRPGPTRKHYQPYAPPRDFAAYRS |
| SEQ ID NO: 37 | CD28 Intracellular domain (nucleotide sequence) | AGGAGTAAGAGGAGCAGGCTCCTGCACAGTGACTACATGAA CATGACTCCCCGCCGCCCCGGGCCCACCCGCAAGCATTACCA GCCCTATGCCCCACCACGCGACTTCGCAGCCTATCGCTCC |

TABLE 1-continued

Sequences of various components of CAR

| SEQ ID NO | Description | Sequence |
|---|---|---|
| SEQ ID NO: 38 | ICOS Intracellular domain (amino acid sequence) | TKKKYSSSVHDPNGEYMFMRAVNTAKKSRLT DVTL |
| SEQ ID NO: 39 | ICOS Intracellular domain (nucleotide sequence) | ACAAAAAAGAAGTATTCATCCAGTGTGCACGACCCTAACGG TGAATACATGTTCATGAGAGCAGTGAACACAGCCAAAAAAT CCAGACTCACAGATGTGACCCTA |
| SEQ ID NO: 5 | GS hinge/linker (aa) | GGGGSGGGGS |
| SEQ ID NO: 16 | GS hinge/linker (na) | GGTGGCGGAGGTTCTGGAGGTGGAGGTTCC |
| SEQ ID NO: 40 | GS hinge/linker (na) | GGTGGCGGAGGTTCTGGAGGTGGGGGTTCC |
| SEQ ID NO: 25 | linker | GGGGS |
| SEQ ID NO: 26 | linker | (Gly-Gly-Gly-Gly-Ser)n, where n = 1-6, e.g., GGGGSGGGGS GGGGSGGGGS GGGGSGGGGS |
| SEQ ID NO: 27 | linker | GGGGSGGGGSGGGGSGGGGS |
| SEQ ID NO: 28 | linker | GGGGSGGGGSGGGGS |
| SEQ ID NO: 29 | linker | GGGS |
| SEQ ID NO: 41 | linker | (Gly-Gly-Gly-Ser)n where n is a positive integer equal to or greater than 1 |
| SEQ ID NO: 42 | linker | (Gly-Gly-Gly-Ser)n, where n = 1-10, e.g., GGGSGGGSGG GSGGGSGGGS GGGSGGGSGG GSGGGSGGGS |
| SEQ ID NO: 43 | linker | GSTSGSGKPGSGEGSTKG |
| SEQ ID NO: 30 | polyA | $(A)_{5000}$ This sequence may encompass 50-5000 adenines. |
| SEQ ID NO: 31 | polyT | $(T)_{100}$ |
| SEQ ID NO: 32 | polyT | $(T)_{5000}$ This sequence may encompass 50-5000 thymines. |
| SEQ ID NO: 33 | polyA | $(A)_{5000}$ This sequence may encompass 100-5000 adenines. |
| SEQ ID NO: 34 | polyA | $(A)_{400}$ This sequence may encompass 100-400 adenines. |
| SEQ ID NO: 35 | polyA | $(A)_{2000}$ This sequence may encompass 50-2000 adenines. |
| SEQ ID NO: 22 | PD1 CAR (aa) | pgwfldspdrpwnpptfspallvvtegdnatftcsfsntsesfvlnwyrmspsnqtdklaafpedr sqpgqdcrfrvtqlpngrdfhmsvvrarrndsgtylcgaislapkaqikeslraelrvterraevpta hpspsprpagqfqtlvtttpaprpptpaptiasqplslrpeacrpaaggavhtrgldfacdiviwapl agtcgvlllslvitlyckrgrkkllyifkqpfmrpvqttqeedgcscrfpeeeeggcelrvkfsrsad apaykqgqnqlynelnlgrreeydvldkrrgrdpemggkprrknpqeglynelqkdkmaeayse igmkgerrrgkghdglyqglstatkdtydalhmqalppr |

TABLE 1-continued

Sequences of various components of CAR

| SEQ ID NO | Description | Sequence |
|---|---|---|
| SEQ ID NO: 23 | PD-1 CAR (na) (PD1 ECD underlined) | atggccctccctgtcactgccctgcttctccccctcgcactcctgctccacgccgctagaccacccggatggtttctggactctccggatcgcccgtggaatcccccaaccttctcaccggcactcttggttgtgactgagggcgataatgcgaccttcacgtgctcgttctccaacacctccgaatcattcgtgctgaactggtaccgcatgagcccgtcaaaccagaccgacaagctcgccgcgtttccggaagatcggtcgcaaccgggacaggattgtcggttccgcgtgactcaactgccgaatggcagagacttccacatgagcgtggtccgcgctaggcgaaacgactccgggacctacctgtgcggagccatctcgctggcgcctaaggcccaaatcaaagagagcttgagggccgaactgagagtgaccgagcgcagagctgaggtgccaactgcacatccatccccatcgcctcggcctgcggggcagtttcagaccctggtcacgaccactccggcgccgcgcccaccgactccggccccaactatcgcgagccagcccctgtcgctgaggccggaagcatgccgccctgccgccggaggtgctgtgcatacccggggattggacttcgcatgcgacatctacatttgggctcctctcgccggaacttgtggcgtgctccttctgtccctggtcatcaccctgtactgcaagcggggtcggaaaaagcttctgtacattttcaagcagcccttcatgaggcccgtgcaaaccacccaggaggaggacggttgctcctgccggttccccgaagaggaagaaggaggttgcgagctgcgcgtgaagttctcccggagcgccgacgcccccgcctataagcagggccagaaccagctgtacaacgaactgaacctgggacggcgggaagagtacgatgtgctggacaagcggcgcggccgggaccccgaaatgggcgggaagcctagaagaaagaaccctcaggaaggcctgtataacgagctgcagaaggacaagatggccgaggcctactccgaaattgggatgaagggagagcggcggaggggaaaggggcacgacggcctgtaccaaggactgtccaccgccaccaaggacacatacgatgccctgcacatgcaggcccttccccctcgc |
| SEQ ID NO: 24 | PD-1 CAR underlined) (aa) with signal (PD1 ECD | Malpvtalllplalllhaarppgwfldspdrpwnpptfspallvvtegdnatftcsfsntsesfvlnwyrmspsnqtdklaafpedrsqpgqdcrfrvtqlpngrdfhmsvvrarrndsgtylegaislapkaqikeslraelrvterraevptahpspsprpagqfcitlvtttpaprpptpaptiasqplslrpeacrpaaggavhtrgldfacdiyiwaplagtcgvlllslvitlyckrgrkkllyifkqpfmrpvqttqeedgcscrfpeeeeggcelrvkfsrsadapaykqgqnqlynelnlgrreeydvldkrrgrdpemggkprrknpqeglynelqkdkmaeayseigmkgerrrgkghdglyqglstatkdtydalhmqalppr |

CAR Antigen Binding Domain

In one aspect, the portion of the CAR comprising the antigen binding domain comprises an antigen binding domain that targets a tumor antigen, e.g., a tumor antigen described herein. In one aspect, the CAR of the present invention comprises a binding domain that specifically binds BCMA (e.g., human BCMA).

The antigen binding domain can be any protein that binds to the antigen including, but not limited to, a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, and the like.

Exemplary anti-BCMA binding domain amino acid sequences are provided in Tables 2-13. In one aspect, the antigen binding domain comprises a human antibody or a human antibody fragment. In some embodiments, the human anti-BCMA binding domain comprises one or more (e.g., all three) LC CDR1, LC CDR2, and LC CDR3 of a human anti-BCMA binding domain described herein (e.g., in Tables 2-13), and/or one or more (e.g., all three) HC CDR1, HC CDR2, and HC CDR3 of a human anti-BCMA binding domain described herein (e.g., in Tables 2-13). In some embodiments, the human anti-BCMA binding domain comprises a human VL described herein (e.g., in Tables 2, 6, and 10) and/or a human VH described herein (e.g., in Tables 2, 6, and 10). In some embodiments, the anti-BCMA binding domain is a scFv comprising a VL and a VH of an amino acid sequence of Tables 2, 6, and 10. In an embodiment, the anti-BCMA binding domain (e.g., an scFv) comprises: a VL comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence provided in Tables 2, 6, and 10, or a sequence with 95-99% identity with an amino acid sequence of Tables 2, 6, and 10; and/or a VH comprising an amino acid sequence having at least one, two or three modifications (e.g., substitutions, e.g., conservative substitutions) but not more than 30, 20 or 10 modifications (e.g., substitutions, e.g., conservative substitutions) of an amino acid sequence provided in Tables 2, 6, and 10, or a sequence with 95-99% identity to an amino acid sequence of Tables 2, 6, and 10.

TABLE 2

Amino acid and nucleic acid sequences of exemplary PALLAS-derived anti-BCMA molecules

| SEQ ID NO | Name/ Description | Sequence |
|---|---|---|
| R1B6 | | |
| SEQ ID NO: 44 | HCDR1 (Kabat) | SYAMS |
| SEQ ID NO: 45 | HCDR2 (Kabat) | AISGSGGSTYYADSVKG |
| SEQ ID NO: 46 | HCDR3 (Kabat) | REWVPYDVSWYFDY |

TABLE 2-continued

Amino acid and nucleic acid sequences of exemplary PALLAS-derived anti-BCMA molecules

| SEQ ID NO | Name/ Description | Sequence |
|---|---|---|
| SEQ ID NO: 47 | HCDR1 (Chothia) | GFTFSSY |
| SEQ ID NO: 48 | HCDR2 (Chothia) | SGSGGS |
| SEQ ID NO: 46 | HCDR3 (Chothia) | REWVPYDVSWYFDY |
| SEQ ID NO: 49 | HCDR1 (IMGT) | GFTFSSYA |
| SEQ ID NO: 50 | HCDR2 (IMGT) | ISGSGGST |
| SEQ ID NO: 51 | HCDR3 (IMGT) | ARREWVPYDVSWYFDY |
| SEQ ID NO: 52 | VH | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCARREWVPYDVSWYFDYWGQGTLVTVSS |
| SEQ ID NO: 53 | DNA VH | GAAGTGCAGTTGCTGGAGTCAGGCGGAGGACTGGTGCAGCCCG GAGGATCGCTTCGCTTGAGCTGCGCAGCCTCAGGCTTTACCTTC TCCTCCTACGCCATGTCCTGGGTCAGACAGGCTCCCGGGAAGG GACTGGAATGGGTGTCCGCCATTAGCGGTTCCGGCGGAAGCAC TTACTATGCCGACTCTGTGAAGGGCCGCTTCACTATCTCCCGGG ACAACTCCAAGAACACCCTGTATCTCCAAATGAATTCCCTGAGG GCCGAAGATACCGCGGTGTACTACTGCGCTAGACGGGAGTGGG TGCCCTACGATGTCAGCTGGTACTTCGACTACTGGGGACAGGGC ACTCTCGTGACTGTGTCCTCC |
| SEQ ID NO: 54 | LCDR1 (Kabat) | RASQSISSYLN |
| SEQ ID NO: 55 | LCDR2 (Kabat) | AASSLQS |
| SEQ ID NO: 56 | LCDR3 (Kabat) | QQSYSTPLT |
| SEQ ID NO: 57 | LCDR1 (Chothia) | SQSISSY |
| SEQ ID NO: 58 | LCDR2 (Chothia) | AAS |
| SEQ ID NO: 59 | LCDR3 (Chothia) | SYSTPL |
| SEQ ID NO: 60 | LCDR1 (IMGT) | QSISSY |
| SEQ ID NO: 58 | LCDR2 (IMGT) | AAS |
| SEQ ID NO: 56 | LCDR3 (IMGT) | QQSYSTPLT |
| SEQ ID NO: 61 | VL | DIQMTQSPSSLSASVGDRVTITCRASQSISSYLNWYQQKPGKAPKL LIYAASSLQSGVPSRFSGSGSGTDFTLTISSLQPEDFATYYCQQSYS TPLTFGQGTKVEIK |
| SEQ ID NO: 62 | DNA VL | GACATTCAAATGACTCAGTCCCCGTCCTCCCTCTCCGCCTCCGT GGGAGATCGCGTCACGATCACGTGCAGGGCCAGCCAGAGCATC TCCAGCTACCTGAACTGGTACCAGCAGAAGCCAGGGAAGGCAC CGAAGCTCCTGATCTACGCCGCTAGCTCGCTGCAGTCCGGCGTC CCTTCACGGTTCTCGGGATCGGGCTCAGGCACCGACTTCACCCT GACCATTAGCAGCCTGCAGCCGGAGGACTTCGCGACATACTAC TGTCAGCAGTCATACTCCACCCCTCTGACCTTCGGCCAAGGGAC CAAAGTGGAGATCAAG |

TABLE 2-continued

Amino acid and nucleic acid sequences of exemplary PALLAS-derived anti-BCMA molecules

| SEQ ID NO | Name/ Description | Sequence |
|---|---|---|
| SEQ ID NO: 63 | Linker | GGGGSGGGGSGGGGSGGGGS |
| SEQ ID NO: 64 | scFv (VH-linker-VL) | EVQLLESGGGLVQPGGSLRLSCAASGFTFSSYAMSWVRQAPGKGL<br>EWVSAISGSGGSTYYADSVKGRFTISRDNSKNTLYLQMNSLRAED<br>TAVYYCARREWVPYDVSWYFDYWGQGTLVTVSSGGGGSGGGGS<br>GGGGSGGGGSDIQMTQSPSSLSASVGDRVTITCRASQSISSYLNWY<br>QQKPGKAPKLLIYAASSLQSGVPSRFSGSGSGTDFTLTISSLQPEDF<br>ATYYCQQSYSTPLTFGQGTKVEIK |
| SEQ ID NO: 65 | DNA scFv | GAAGTGCAGTTGCTGGAGTCAGGCGGAGGACTGGTGCAGCCCG<br>GAGGATCGCTTCGCTTGAGCTGCGCAGCCTCAGGCTTTACCTTC<br>TCCTCCTACGCCATGTCCTGGGTCAGACAGGCTCCCGGGAAGG<br>GACTGGAATGGGTGTCCGCCATTAGCGGTTCCGGCGGAAGCAC<br>TTACTATGCCGACTCTGTGAAGGGCCGCTTCACTATCTCCCGGG<br>ACAACTCCAAGAACACCCTGTATCTCCAAATGAATTCCCTGAGG<br>GCCGAAGATACCGCGGTGTACTACTGCGCTAGACGGGAGTGGG<br>TGCCCTACGATGTCAGCTGGTACTTCGACTACTGGGGACAGGGC<br>ACTCTCGTGACTGTGTCCTCCGGTGGTGGTGGATCGGGGGGTGG<br>TGGTTCGGGCGGAGGAGGATCTGGAGGAGGAGGGTCGGACATT<br>CAAATGACTCAGTCCCCGTCCTCCCTCTCCGCCTCCGTGGGAGA<br>TCGCGTCACGATCACGTGCAGGGCCAGCCAGAGCATCTCCAGC<br>TACCTGAACTGGTACCAGCAGAAGCCAGGGAAGGCACCGAAGC<br>TCCTGATCTACGCCGCTAGCTCGCTGCAGTCCGGCGTCCCTTCA<br>CGGTTCTCGGGATCGGGCTCAGGCACCGACTTCACCCTGACCAT<br>TAGCAGCCTGCAGCCGGAGGACTTCGCGACATACTACTGTCAG<br>CAGTCATACTCCACCCCTCTGACCTTCGGCCAAGGGACCAAAGT<br>GGAGATCAAG |
| SEQ ID NO: 66 | Full CAR amino acid sequence | EVQLLESGGGLVQPGGSLRLSCAASGFTFSSYAMSWVRQAPGKGL<br>EWVSAISGSGGSTYYADSVKGRFTISRDNSKNTLYLQMNSLRAED<br>TAVYYCARREWVPYDVSWYFDYWGQGTLVTVSSGGGGSGGGGS<br>GGGGSGGGGSDIQMTQSPSSLSASVGDRVTITCRASQSISSYLNWY<br>QQKPGKAPKLLIYAASSLQSGVPSRFSGSGSGTDFTLTISSLQPEDF<br>ATYYCQQSYSTPLTFGQGTKVEIKTTTPAPRPPTPAPTIASQPLSLRP<br>EACRPAAGGAVHTRGLDFACDIYIWAPLAGTCGVLLLSLVITLYC<br>KRGRKKLLYIFKQPFMRPVQTTQEEDGCSCRFPEEEEGGCELRVKF<br>SRSADAPAYQQGQNQLYNELNLGRREEYDVLDKRRGRDPEMGG<br>KPRRKNPQEGLYNELQKDKMAEAYSEIGMKGERRRGKGHDGLY<br>QGLSTATKDTYDALHMQALPPR |
| SEQ ID NO: 67 | Full CAR DNA sequence | GAAGTGCAGTTGCTGGAGTCAGGCGGAGGACTGGTGCAGCCCG<br>GAGGATCGCTTCGCTTGAGCTGCGCAGCCTCAGGCTTTACCTTC<br>TCCTCCTACGCCATGTCCTGGGTCAGACAGGCTCCCGGGAAGG<br>GACTGGAATGGGTGTCCGCCATTAGCGGTTCCGGCGGAAGCAC<br>TTACTATGCCGACTCTGTGAAGGGCCGCTTCACTATCTCCCGGG<br>ACAACTCCAAGAACACCCTGTATCTCCAAATGAATTCCCTGAGG<br>GCCGAAGATACCGCGGTGTACTACTGCGCTAGACGGGAGTGGG<br>TGCCCTACGATGTCAGCTGGTACTTCGACTACTGGGGACAGGGC<br>ACTCTCGTGACTGTGTCCTCCGGTGGTGGTGGATCGGGGGGTGG<br>TGGTTCGGGCGGAGGAGGATCTGGAGGAGGAGGGTCGGACATT<br>CAAATGACTCAGTCCCCGTCCTCCCTCTCCGCCTCCGTGGGAGA<br>TCGCGTCACGATCACGTGCAGGGCCAGCCAGAGCATCTCCAGC<br>TACCTGAACTGGTACCAGCAGAAGCCAGGGAAGGCACCGAAGC<br>TCCTGATCTACGCCGCTAGCTCGCTGCAGTCCGGCGTCCCTTCA<br>CGGTTCTCGGGATCGGGCTCAGGCACCGACTTCACCCTGACCAT<br>TAGCAGCCTGCAGCCGGAGGACTTCGCGACATACTACTGTCAG<br>CAGTCATACTCCACCCCTCTGACCTTCGGCCAAGGGACCAAAGT<br>GGAGATCAAGACCACTACCCCAGCACCGAGGCCACCCACCCCG<br>GCTCCTACCATCGCCTCCCAGCCTCTGTCCCTGCGTCCGGAGGC<br>ATGTAGACCCGCAGCTGGTGGGGCCGTGCATACCCGGGGTCTT<br>GACTTCGCCTGCGATATCTACATTTGGGCCCCTCTGGCTGGTAC<br>TTGCGGGGTCCTGCTGCTTTCACTCGTGATCACTCTTTACTGTAA<br>GCGCGGTCGGAAGAAGCTGCTGTACATCTTTAAGCAACCCTTCA<br>TGAGGCCTGTGCAGACTACTCAAGAGGAGGACGGCTGTTCATG<br>CCGGTTCCCAGAGGAGGAGGAAGGCGGCTGCGAACTGCGCGTG<br>AAATTCAGCCGCAGCGCAGATGCTCCAGCCTACCAGCAGGGGC<br>AGAACCAGCTCTACAACGAACTCAATCTTGGTCGGAGAGAGGA<br>GTACGACGTGCTGGACAAGCGGAGAGGACGGGACCCAGAAAT<br>GGGCGGGAAGCCGCGCAGAAAGAATCCCCAAGAGGGCCTGTA |

TABLE 2-continued

| SEQ ID NO | Name/ Description | Sequence |
|---|---|---|
| Amino acid and nucleic acid sequences of exemplary PALLAS-derived anti-BCMA molecules | | |
| | | CAACGAGCTCCAAAAGGATAAGATGGCAGAAGCCTATAGCGAG ATTGGTATGAAAGGGGAACGCAGAAGAGGCAAAGGCCACGAC GGACTGTACCAGGGACTCAGCACCGCCACCAAGGACACCTATG ACGCTCTTCACATGCAGGCCCTGCCGCCTCGG |
| R1F2 | | |
| SEQ ID NO: 44 | HCDR1 (Kabat) | SYAMS |
| SEQ ID NO: 45 | HCDR2 (Kabat) | AISGSGGSTYYADSVKG |
| SEQ ID NO: 68 | HCDR3 (Kabat) | REWWYDDWYLDY |
| SEQ ID NO: 47 | HCDR1 (Chothia) | GFTFSSY |
| SEQ ID NO: 48 | HCDR2 (Chothia) | SGSGGS |
| SEQ ID NO: 68 | HCDR3 (Chothia) | REWWYDDWYLDY |
| SEQ ID NO: 49 | HCDR1 (IMGT) | GFTFSSYA |
| SEQ ID NO: 50 | HCDR2 (IMGT) | ISGSGGST |
| SEQ ID NO: 69 | HCDR3 (IMGT) | ARREWWYDDWYLDY |
| SEQ ID NO: 70 | VH | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCARREWWYDDWYLDYWGQGTLVTVSS |
| SEQ ID NO: 71 | DNA VH | GAAGTGCAGTTGCTGGAGTCAGGCGGAGGACTGGTGCAGCCCG GAGGATCGCTTCGCTTGAGCTGCGCAGCCTCAGGCTTTACCTTC TCCTCCTACGCCATGTCCTGGGTCAGACAGGCTCCCGGGAAGG GACTGGAATGGGTGTCCGCCATTAGCGGTTCCGGCGGAAGCAC TTACTATGCCGACTCTGTGAAGGGCCGCTTCACTATCTCCCGGG ACAACTCCAAGAACACCCTGTATCTCCAAATGAATTCCCTGAGG GCCGAAGATACCGCGGTGTACTACTGCGCTAGACGGGAGTGGT GGTACGACGATTGGTACCTGGACTACTGGGGACAGGGCACTCT CGTGACTGTGTCCTCC |
| SEQ ID NO: 54 | LCDR1 (Kabat) | RASQSISSYLN |
| SEQ ID NO: 55 | LCDR2 (Kabat) | AASSLQS |
| SEQ ID NO: 56 | LCDR3 (Kabat) | QQSYSTPLT |
| SEQ ID NO: 57 | LCDR1 (Chothia) | SQSISSY |
| SEQ ID NO: 58 | LCDR2 (Chothia) | AAS |
| SEQ ID NO: 59 | LCDR3 (Chothia) | SYSTPL |
| SEQ ID NO: 60 | LCDR1 (IMGT) | QSISSY |
| SEQ ID NO: 58 | LCDR2 (IMGT) | AAS |
| SEQ ID NO: 56 | LCDR3 (IMGT) | QQSYSTPLT |

TABLE 2-continued

Amino acid and nucleic acid sequences of exemplary PALLAS-derived anti-BCMA molecules

| SEQ ID NO | Name/ Description | Sequence |
|---|---|---|
| SEQ ID NO: 61 | VL | DIQMTQSPSSLSASVGDRVTITCRASQSISSYLNWYQQKPGKAPKL LIYAASSLQSGVPSRFSGSGSGTDFTLTISSLQPEDFATYYCQQSYS TPLTFGQGTKVEIK |
| SEQ ID NO: 62 | DNA VL | GACATTCAAATGACTCAGTCCCCGTCCTCCCTCTCCGCCTCCGT GGGAGATCGCGTCACGATCACGTGCAGGGCCAGCCAGAGCATC TCCAGCTACCTGAACTGGTACCAGCAGAAGCCAGGGAAGGCAC CGAAGCTCCTGATCTACGCCGCTAGCTCGCTGCAGTCCGGCGTC CCTTCACGGTTCTCGGGATCGGGCTCAGGCACCGACTTCACCCT GACCATTAGCAGCCTGCAGCCGGAGGACTTCGCGACATACTAC TGTCAGCAGTCATACTCCACCCCTCTGACCTTCGGCCAAGGGAC CAAAGTGGAGATCAAG |
| SEQ ID NO: 63 | Linker | GGGGSGGGGSGGGGSGGGGS |
| SEQ ID NO: 72 | scFv (VH-linker-VL) | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCARREWWYDDWYLDYWGQGTLVTVSSGGGGSGGGGSG GGGSGGGGSDIQMTQSPSSLSASVGDRVTITCRASQSISSYLNWYQ QKPGKAPKLLIYAASSLQSGVPSRFSGSGSGTDFTLTISSLQPEDFA TYYCQQSYSTPLTFGQGTKVEIK |
| SEQ ID NO: 73 | DNA scFv | GAAGTGCAGTTGCTGGAGTCAGGCGGAGGACTGGTGCAGCCCG GAGGATCGCTTCGCTTGAGCTGCGCAGCCTCAGGCTTTACCTTC TCCTCCTACGCCATGTCCTGGGTCAGACAGGCTCCCGGGAAGG GACTGGAATGGGTGTCCGCCATTAGCGGTTCCGGCGGAAGCAC TTACTATGCCGACTCTGTGAAGGGCCGCTTCACTATCTCCCGGG ACAACTCCAAGAACACCCTGTATCTCCAAATGAATTCCCTGAGG GCCGAAGATACCGCGGTGTACTACTGCGCTAGACGGGAGTGGT GGTACGACGATTGGTACCTGGACTACTGGGGACAGGGCACTCT CGTGACTGTGTCCTCCGGTGGTGGTGGATCGGGGGGTGGTGGTT CGGGCGGAGGAGGATCTGGAGGAGGAGGGTCGGACATTCAAA TGACTCAGTCCCCGTCCTCCCTCTCCGCCTCCGTGGGAGATCGC GTCACGATCACGTGCAGGGCCAGCCAGAGCATCTCCAGCTACC TGAACTGGTACCAGCAGAAGCCAGGGAAGGCACCGAAGCTCCT GATCTACGCCGCTAGCTCGCTGCAGTCCGGCGTCCCTTCACGGT TCTCGGGATCGGGCTCAGGCACCGACTTCACCCTGACCATTAGC AGCCTGCAGCCGGAGGACTTCGCGACATACTACTGTCAGCAGT CATACTCCACCCCTCTGACCTTCGGCCAAGGGACCAAAGTGGA GATCAAG |
| SEQ ID NO: 74 | Full CAR amino acid sequence | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCARREWWYDDWYLDYWGQGTLVTVSSGGGGSGGGGSG GGGSGGGGSDIQMTQSPSSLSASVGDRVTITCRASQSISSYLNWYQ QKPGKAPKLLIYAASSLQSGVPSRFSGSGSGTDFTLTISSLQPEDFA TYYCQQSYSTPLTFGQGTKVEIKTTTPAPRPPTPAPTIASQPLSLRPE ACRPAAGGAVHTRGLDFACDIYIWAPLAGTCGVLLLSLVITLYCK RGRKKLLYIFKQPFMRPVQTTQEEDGCSCRFPEEEEGGCELRVKFS RSADAPAYQQGQNQLYNELNLGRREEYDVLDKRRGRDPEMGGK PRRKNPQEGLYNELQKDKMAEAYSEIGMKGERRRGKGHDGLYQ GLSTATKDTYDALHMQALPPR |
| SEQ ID NO: 75 | Full CAR DNA sequence | GAAGTGCAGTTGCTGGAGTCAGGCGGAGGACTGGTGCAGCCCG GAGGATCGCTTCGCTTGAGCTGCGCAGCCTCAGGCTTTACCTTC TCCTCCTACGCCATGTCCTGGGTCAGACAGGCTCCCGGGAAGG GACTGGAATGGGTGTCCGCCATTAGCGGTTCCGGCGGAAGCAC TTACTATGCCGACTCTGTGAAGGGCCGCTTCACTATCTCCCGGG ACAACTCCAAGAACACCCTGTATCTCCAAATGAATTCCCTGAGG GCCGAAGATACCGCGGTGTACTACTGCGCTAGACGGGAGTGGT GGTACGACGATTGGTACCTGGACTACTGGGGACAGGGCACTCT CGTGACTGTGTCCTCCGGTGGTGGTGGATCGGGGGGTGGTGGTT CGGGCGGAGGAGGATCTGGAGGAGGAGGGTCGGACATTCAAA TGACTCAGTCCCCGTCCTCCCTCTCCGCCTCCGTGGGAGATCGC GTCACGATCACGTGCAGGGCCAGCCAGAGCATCTCCAGCTACC TGAACTGGTACCAGCAGAAGCCAGGGAAGGCACCGAAGCTCCT GATCTACGCCGCTAGCTCGCTGCAGTCCGGCGTCCCTTCACGGT TCTCGGGATCGGGCTCAGGCACCGACTTCACCCTGACCATTAGC AGCCTGCAGCCGGAGGACTTCGCGACATACTACTGTCAGCAGT CATACTCCACCCCTCTGACCTTCGGCCAAGGGACCAAAGTGGA GATCAAGACCACTACCCCAGCACCGAGGCCACCCACCCCGGCT CCTACCATCGCCTCCCAGCCTCTGTCCCTGCGTCCGGAGGCATG |

TABLE 2-continued

| Amino acid and nucleic acid sequences of exemplary PALLAS-derived anti-BCMA molecules | | |
|---|---|---|
| SEQ ID NO | Name/ Description | Sequence |
| | | TAGACCCGCAGCTGGTGGGGCCGTGCATACCCGGGGTCTTGAC TTCGCCTGCGATATCTACATTTGGGCCCCTCTGGCTGGTACTTG CGGGGTCCTGCTGCTTTCACTCGTGATCACTCTTTACTGTAAGC GCGGTCGGAAGAAGCTGCTGTACATCTTTAAGCAACCCTTCATG AGGCCTGTGCAGACTACTCAAGAGGAGGACGGCTGTTCATGCC GGTTCCCAGAGGAGGAGGAAGGCGGCTGCGAACTGCGCGTGAA ATTCAGCCGCAGCGCAGATGCTCCAGCCTACCAGCAGGGGCAG AACCAGCTCTACAACGAACTCAATCTTGGTCGGAGAGAGGAGT ACGACGTGCTGGACAAGCGGAGAGGACGGGACCCAGAAATGG GCGGGAAGCCGCGCAGAAAGAATCCCCAAGAGGGCCTGTACA ACGAGCTCCAAAAGGATAAGATGGCAGAAGCCTATAGCGAGAT TGGTATGAAAGGGGAACGCAGAAGAGGCAAAGGCCACGACGG ACTGTACCAGGGACTCAGCACCGCCACCAAGGACACCTATGAC GCTCTTCACATGCAGGCCCTGCCGCCTCGG |
| R1G5 | | |
| SEQ ID NO: 44 | HCDR1 (Kabat) | SYAMS |
| SEQ ID NO: 45 | HCDR2 (Kabat) | AISGSGGSTYYADSVKG |
| SEQ ID NO: 76 | HCDR3 (Kabat) | REWWGESWLFDY |
| SEQ ID NO: 47 | HCDR1 (Chothia) | GFTFSSY |
| SEQ ID NO: 48 | HCDR2 (Chothia) | SGSGGS |
| SEQ ID NO: 76 | HCDR3 (Chothia) | REWWGESWLFDY |
| SEQ ID NO: 49 | HCDR1 (IMGT) | GFTFSSYA |
| SEQ ID NO: 50 | HCDR2 (IMGT) | ISGSGGST |
| SEQ ID NO: 77 | HCDR3 (IMGT) | ARREWWGESWLFDY |
| SEQ ID NO: 78 | VH | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCARREWWGESWLFDYWGQGTLVTVSS |
| SEQ ID NO: 79 | DNA VH | GAAGTGCAGTTGCTGGAGTCAGGCGGAGGACTGGTGCAGCCCG GAGGATCGCTTCGCTTGAGCTGCGCAGCCTCAGGCTTTACCTTC TCCTCCTACGCCATGTCCTGGGTCAGACAGGCTCCCGGGAAGG GACTGGAATGGGTGTCCGCCATTAGCGGTTCCGGCGGAAGCAC TTACTATGCCGACTCTGTGAAGGGCCGCTTCACTATCTCCCGGG ACAACTCCAAGAACACCCTGTATCTCCAAATGAATTCCCTGAGG GCCGAAGATACCGCGGTGTACTACTGCGCTAGACGGGAGTGGT GGGGAGAAAGCTGGCTGTTCGACTACTGGGGACAGGGCACTCT CGTGACTGTGTCCTCC |
| SEQ ID NO: 54 | LCDR1 (Kabat) | RASQSISSYLN |
| SEQ ID NO: 55 | LCDR2 (Kabat) | AASSLQS |
| SEQ ID NO: 56 | LCDR3 (Kabat) | QQSYSTPLT |
| SEQ ID NO: 57 | LCDR1 (Chothia) | SQSISSY |
| SEQ ID NO: 58 | LCDR2 (Chothia) | AAS |

TABLE 2-continued

Amino acid and nucleic acid sequences of exemplary PALLAS-derived anti-BCMA molecules

| SEQ ID NO | Name/ Description | Sequence |
|---|---|---|
| SEQ ID NO: 59 | LCDR3 (Chothia) | SYSTPL |
| SEQ ID NO: 60 | LCDR1 (IMGT) | QSISSY |
| SEQ ID NO: 58 | LCDR2 (IMGT) | AAS |
| SEQ ID NO: 56 | LCDR3 (IMGT) | QQSYSTPLT |
| SEQ ID NO: 61 | VL | DIQMTQSPSSLSASVGDRVTITCRASQSISSYLNWYQQKPGKAPKL LIYAASSLQSGVPSRFSGSGSGTDFTLTISSLQPEDFATYYCQQSYS TPLTFGQGTKVEIK |
| SEQ ID NO: 62 | DNA VL | GACATTCAAATGACTCAGTCCCCGTCCTCCCTCTCCGCCTCCGT GGGAGATCGCGTCACGATCACGTGCAGGGCCAGCCAGAGCATC TCCAGCTACCTGAACTGGTACCAGCAGAAGCCAGGGAAGGCAC CGAAGCTCCTGATCTACGCCGCTAGCTCGCTGCAGTCCGGCGTC CCTTCACGGTTCTCGGGATCGGGCTCAGGCACCGACTTCACCCT GACCATTAGCAGCCTGCAGCCGGAGGACTTCGCGACATACTAC TGTCAGCAGTCATACTCCACCCCTCTGACCTTCGGCCAAGGGAC CAAAGTGGAGATCAAG |
| SEQ ID NO: 63 | Linker | GGGGSGGGGSGGGGSGGGGS |
| SEQ ID NO: 80 | scFv (VH-linker-VL) | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCARREWWGESWLFDYWGQGTLVTVSSGGGGSGGGGSGG GGSGGGGSDIQMTQSPSSLSASVGDRVTITCRASQSISSYLNWYQQ KPGKAPKLLIYAASSLQSGVPSRFSGSGSGTDFTLTISSLQPEDFAT YYCQQSYSTPLTFGQGTKVEIK |
| SEQ ID NO: 81 | DNA scFv | GAAGTGCAGTTGCTGGAGTCAGGCGGAGGACTGGTGCAGCCCG GAGGATCGCTTCGCTTGAGCTGCGCAGCCTCAGGCTTTACCTTC TCCTCCTACGCCATGTCCTGGGTCAGACAGGCTCCCGGGAAGG GACTGGAATGGGTGTCCGCCATTAGCGGTTCCGGCGGAAGCAC TTACTATGCCGACTCTGTGAAGGGCCGCTTCACTATCTCCCGGG ACAACTCCAAGAACACCCTGTATCTCCAAATGAATTCCCTGAGG GCCGAAGATACCGCGGTGTACTACTGCGCTAGACGGGAGTGGT GGGGAGAAAGCTGGCTGTTCGACTACTGGGGACAGGGCACTCT CGTGACTGTGTCCTCCGGTGGTGGTGGATCGGGGGGTGGTGGTT CGGGCGGAGGAGGATCTGGAGGAGGAGGGTCGGACATTCAAA TGACTCAGTCCCCGTCCTCCCTCTCCGCCTCCGTGGGAGATCGC GTCACGATCACGTGCAGGGCCAGCCAGAGCATCTCCAGCTACC TGAACTGGTACCAGCAGAAGCCAGGGAAGGCACCGAAGCTCCT GATCTACGCCGCTAGCTCGCTGCAGTCCGGCGTCCCTTCACGGT TCTCGGGATCGGGCTCAGGCACCGACTTCACCCTGACCATTAGC AGCCTGCAGCCGGAGGACTTCGCGACATACTACTGTCAGCAGT CATACTCCACCCCTCTGACCTTCGGCCAAGGGACCAAAGTGGA GATCAAG |
| SEQ ID NO: 82 | Full CAR amino acid sequence | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCARREWWGESWLFDYWGQGTLVTVSSGGGGSGGGGSGG GGSGGGGSDIQMTQSPSSLSASVGDRVTITCRASQSISSYLNWYQQ KPGKAPKLLIYAASSLQSGVPSRFSGSGSGTDFTLTISSLQPEDFAT YYCQQSYSTPLTFGQGTKVEIKTTTPAPRPPTPAPTIASQPLSLRPEA CRPAAGGAVHTRGLDFACDIYIWAPLAGTCGVLLLSLVITLYCKR GRKKLLYIFKQPFMRPVQTTQEEDGCSCRFPEEEEGGCELRVKFSR SADAPAYQQGQNQLYNELNLGRREEYDVLDKRRGRDPEMGGKP RRKNPQEGLYNELQKDKMAEAYSEIGMKGERRRGKGHDGLYQG LSTATKDTYDALHMQALPPR |
| SEQ ID NO: 83 | Full CAR DNA sequence | GAAGTGCAGTTGCTGGAGTCAGGCGGAGGACTGGTGCAGCCCG GAGGATCGCTTCGCTTGAGCTGCGCAGCCTCAGGCTTTACCTTC TCCTCCTACGCCATGTCCTGGGTCAGACAGGCTCCCGGGAAGG GACTGGAATGGGTGTCCGCCATTAGCGGTTCCGGCGGAAGCAC TTACTATGCCGACTCTGTGAAGGGCCGCTTCACTATCTCCCGGG ACAACTCCAAGAACACCCTGTATCTCCAAATGAATTCCCTGAGG GCCGAAGATACCGCGGTGTACTACTGCGCTAGACGGGAGTGGT GGGGAGAAAGCTGGCTGTTCGACTACTGGGGACAGGGCACTCT |

TABLE 2-continued

| Amino acid and nucleic acid sequences of exemplary PALLAS-derived anti-BCMA molecules | | |
|---|---|---|
| SEQ ID NO | Name/ Description | Sequence |
| | | CGTGACTGTGTCCTCCGGTGGTGGTGGATCGGGGGGTGGTGGTT<br>CGGGCGGAGGAGGATCTGGAGGAGGAGGGTCGGACATTCAAA<br>TGACTCAGTCCCCGTCCTCCCTCTCCGCCTCCGTGGGAGATCGC<br>GTCACGATCACGTGCAGGGCCAGCCAGAGCATCTCCAGCTACC<br>TGAACTGGTACCAGCAGAAGCCAGGGAAGGCACCGAAGCTCCT<br>GATCTACGCCGCTAGCTCGCTGCAGTCCGGCGTCCCTTCACGGT<br>TCTCGGGATCGGGCTCAGGCACCGACTTCACCCTGACCATTAGC<br>AGCCTGCAGCCGGAGGACTTCGCGACATACTACTGTCAGCAGT<br>CATACTCCACCCCTCTGACCTTCGGCCAAGGGACCAAAGTGGA<br>GATCAAGACCACTACCCCAGCACCGAGGCCACCCACCCCGGCT<br>CCTACCATCGCCTCCCAGCCTCTGTCCCTGCGTCCGGAGGCATG<br>TAGACCCGCAGCTGGTGGGGCCGTGCATACCCGGGGTCTTGAC<br>TTCGCCTGCGATATCTACATTTGGGCCCCTCTGGCTGGTACTTG<br>CGGGGTCCTGCTGCTTTCACTCGTGATCACTCTTTACTGTAAGC<br>GCGGTCGGAAGAAGCTGCTGTACATCTTTAAGCAACCCTTCATG<br>AGGCCTGTGCAGACTACTCAAGAGGAGGACGGCTGTTCATGCC<br>GGTTCCCAGAGGAGGAGGAAGGCGGCTGCGAACTGCGCGTGAA<br>ATTCAGCCGCAGCGCAGATGCTCCAGCCTACCAGCAGGGGCAG<br>AACCAGCTCTACAACGAACTCAATCTTGGTCGGAGAGAGGAGT<br>ACGACGTGCTGGACAAGCGGAGAGGACGGGACCCAGAAATGG<br>GCGGGAAGCCGCGCAGAAAGAATCCCCAAGAGGGCCTGTACA<br>ACGAGCTCCAAAAGGATAAGATGGCAGAAGCCTATAGCGAGAT<br>TGGTATGAAAGGGGAACGCAGAAGAGGCAAAGGCCACGACGG<br>ACTGTACCAGGGACTCAGCACCGCCACCAAGGACACCTATGAC<br>GCTCTTCACATGCAGGCCCTGCCGCCTCGG |

TABLE 3

| Kabat CDRs of exemplary PALLAS-derived anti-BCMA molecules | | | | | | |
|---|---|---|---|---|---|---|
| Kabat | HCDR1 | HCDR2 | HCDR3 | LCDRI | LCDR2 | LCDR3 |
| R1B6 | SYAMS (SEQ ID NO: 44) | AISGSGGSTY YADSVKG (SEQ ID NO: 45) | REWVPYDVS WYFDY (SEQ ID NO: 46) | RASQSISS YLN (SEQ ID NO: 54) | AASSL QS (SEQ ID NO: 55) | QQSYSTP LT (SEQ ID NO: 56) |
| R1F2 | SYAMS (SEQ ID NO: 44) | AISGSGGSTY YADSVKG (SEQ ID NO: 45) | REWWYDD WYLDY (SEQ ID NO: 68) | RASQSISS YLN (SEQ ID NO: 54) | AASSL QS (SEQ ID NO: 55) | QQSYSTP LT (SEQ ID NO: 56) |
| R1G5 | SYAMS (SEQ ID NO: 44) | AISGSGGSTY YADSVKG (SEQ ID NO: 45) | REWWGESW LFDY (SEQ ID NO: 76) | RASQSISS YLN (SEQ ID NO: 54) | AASSL QS (SEQ ID NO: 55) | QQSYSTP LT (SEQ ID NO: 56) |
| Consensus | SYAMS (SEQ ID NO: 44) | AISGSGGSTY YADSVKG (SEQ ID NO: 45) | REW$X_1X_2X_3X_4$ $X_5X_6$W$X_7X_8$D Y, wherein $X_1$ is absent or V; $X_2$ is absent or P; $X_3$ is W or Y; $X_4$ is G, Y, or D; $X_5$ is E, D, or V; $X_6$ is S or D; $X_7$ is L or Y; and $X_8$ is F or L (SEQ ID NO: 84) | RASQSISS YLN (SEQ ID NO: 54) | AASSL QS (SEQ ID NO: 55) | QQSYSTP LT (SEQ ID NO: 56) |

TABLE 4

Chothia CDRs of exemplary PALLAS-derived anti-BCMA molecules

| Chothia | HCDR1 | HCDR2 | HCDR3 | LCDRI | LCDR2 | LCDR3 |
|---|---|---|---|---|---|---|
| R1B6 | GFTFSSY (SEQ ID NO: 47) | SGSGGS (SEQ ID NO: 48) | REWVPYDVS WYFDY (SEQ ID NO: 46) | SQSISSY (SEQ ID NO: 57) | AAS (SEQ ID NO: 58) | SYSTPL (SEQ ID NO: 59) |
| R1F2 | GFTFSSY (SEQ ID NO: 47) | SGSGGS (SEQ ID NO: 48) | REWWYDD WYLDY (SEQ ID NO: 68) | SQSISSY (SEQ ID NO: 57) | AAS (SEQ ID NO: 58) | SYSTPL (SEQ ID NO: 59) |
| R1G5 | GFTFSSY (SEQ ID NO: 47) | SGSGGS (SEQ ID NO: 48) | REWWGESW LFDY (SEQ ID NO: 76) | SQSISSY (SEQ ID NO: 57) | AAS (SEQ ID NO: 58) | SYSTPL (SEQ ID NO: 59) |
| Consensus | GFTFSSY (SEQ ID NO: 47) | SGSGGS (SEQ ID NO: 48) | REW$X_1X_2X_3X_4$ $X_5X_6$W$X_7X_8$D Y, wherein $X_1$ is absent or V; $X_2$ is absent or P; $X_3$ is W or Y; $X_4$ is G, Y, or D; $X_5$ is E, D, or V; $X_6$ is S or D; $X_7$ is L or Y; and $X_8$ is F or L (SEQ ID NO: 84) | SQSISSY (SEQ ID NO: 57) | AAS (SEQ ID NO: 58) | SYSTPL (SEQ ID NO: 59) |

TABLE 5

IMGT CDRs of exemplary PALLAS-derived anti-BCMA molecules

| IMGT | HCDR1 | HCDR2 | HCDR3 | LCDR1 | LCDR2 | LCDR3 |
|---|---|---|---|---|---|---|
| R1B6 | GFTFSSYA (SEQ ID NO: 49) | ISGSGGST (SEQ ID NO: 50) | ARREWVPY DVSWYFDY (SEQ ID NO: 51) | QSISSY (SEQ ID NO: 60) | AAS (SEQ ID NO: 58) | QQSYSTP LT (SEQ ID NO: 56) |
| R1F2 | GFTFSSYA (SEQ ID NO: 49) | ISGSGGST (SEQ ID NO: 50) | ARREWWYD DWYLDY (SEQ ID NO: 69) | QSISSY (SEQ ID NO: 60) | AAS (SEQ ID NO: 58) | QQSYSTP LT (SEQ ID NO: 56) |
| R1G5 | GFTFSSYA (SEQ ID NO: 49) | ISGSGGST (SEQ ID NO: 50) | ARREWWGE SWLFDY (SEQ ID NO: 77) | QSISSY (SEQ ID NO: 60) | AAS (SEQ ID NO: 58) | QQSYSTP LT (SEQ ID NO: 56) |
| Consensus | GFTFSSYA (SEQ ID NO: 49) | ISGSGGST (SEQ ID NO: 50) | ARREW$X_1X_2$ $X_3X_4X_5X_6$W$X_7$ $X_8$DY, wherein $X_1$ is absent or V; $X_2$ is absent or P; $X_3$ is W or Y; $X_4$ is G, Y, or D; $X_5$ is E, D, or V; $X_6$ is S or D; $X_7$ is L or Y; and $X_8$ is F or L (SEQ ID NO: 85) | QSISSY (SEQ ID NO: 60) | AAS (SEQ ID NO: 58) | QQSYSTP LT (SEQ ID NO: 56) |

TABLE 6

Amino acid and nucleic acid sequences of exemplary B cell-derived anti-BCMA molecules

| SEQ ID NO | Name/ Description | Sequence |
|---|---|---|
| PI61 | | |
| SEQ ID NO: 86 | HCDR1 (Kabat) | SYGMH |
| SEQ ID NO: 87 | HCDR2 (Kabat) | VISYDGSNKYYADSVKG |
| SEQ ID NO: 88 | HCDR3 (Kabat) | SGYALHDDYYGLDV |
| SEQ ID NO: 47 | HCDR1 (Chothia) | GFTFSSY |
| SEQ ID NO: 89 | HCDR2 (Chothia) | SYDGSN |
| SEQ ID NO: 88 | HCDR3 (Chothia) | SGYALHDDYYGLDV |
| SEQ ID NO: 90 | HCDR1 (IMGT) | GFTFSSYG |
| SEQ ID NO: 91 | HCDR2 (IMGT) | ISYDGSNK |
| SEQ ID NO: 92 | HCDR3 (IMGT) | GGSGYALHDDYYGLDV |
| SEQ ID NO: 93 | VH | QVQLQESGGGVVQPGRSLRLSCAASGFTFSSYGMHWVRQAPGKGL EWVAVISYDGSNKYYADSVKGRFTISRDNSKNTLYLQMNSLRAED TAVYYCGGSGYALHDDYYGLDVWGQGTLVTVSS |
| SEQ ID NO: 94 | DNA VH | CAAGTGCAGCTGCAGGAATCCGGTGGCGGAGTCGTGCAGCCTGG AAGGAGCCTGAGACTCTCATGCGCCGCGTCAGGGTTCACCTTTT CCTCCTACGGGATGCATTGGGTCAGACAGGCCCCCGGAAAGGGA CTCGAATGGGTGGCTGTGATCAGCTACGACGGCTCCAACAAGTA CTACGCCGACTCCGTGAAAGGCCGGTTCACTATCTCCCGGGACA ACTCCAAGAACACGCTGTATCTGCAAATGAATTCACTGCGCGCG GAGGATACCGCTGTGTACTACTGCGGTGGCTCCGGTTACGCCCT GCACGATGACTATTACGGCCTTGACGTCTGGGGCCAGGGAACCC TCGTGACTGTGTCCAGC |
| SEQ ID NO: 95 | LCDR1 (Kabat) | TGTSSDVGGYNYVS |
| SEQ ID NO: 96 | LCDR2 (Kabat) | DVSNRPS |
| SEQ ID NO: 97 | LCDR3 (Kabat) | SSYTSSSTLYV |
| SEQ ID NO: 98 | LCDR1 (Chothia) | TSSDVGGYNY |
| SEQ ID NO: 99 | LCDR2 (Chothia) | DVS |
| SEQ ID NO: 100 | LCDR3 (Chothia) | YTSSSTLY |
| SEQ ID NO: 101 | LCDR1 (IMGT) | SSDVGGYNY |
| SEQ ID NO: 99 | LCDR2 (IMGT) | DVS |
| SEQ ID NO: 97 | LCDR3 (IMGT) | SSYTSSSTLYV |
| SEQ ID NO: 102 | VL | QSALTQPASVSGSPGQSITISCTGTSSDVGGYNYVSWYQQHPGKAP KLMIYDVSNRPSGVSNRFSGSKSGNTASLTISGLQAEDEADYYCSSY TSSSTLYVFGSGTKVTVL |

TABLE 6-continued

Amino acid and nucleic acid sequences of exemplary B cell-derived anti-BCMA molecules

| SEQ ID NO | Name/ Description | Sequence |
|---|---|---|
| SEQ ID NO: 103 | DNA VL | CAGAGCGCACTGACTCAGCCGGCATCCGTGTCCGGTAGCCCCGG ACAGTCGATTACCATCTCCTGTACCGGCACCTCCTCCGACGTGG GAGGGTACAACTACGTGTCGTGGTACCAGCAGCACCCAGGAAA GGCCCCTAAGTTGATGATCTACGATGTGTCAAACCGCCCGTCTG GAGTCTCCAACCGGTTCTCCGGCTCCAAGTCCGGCAACACCGCC AGCCTGACCATTAGCGGGCTGCAAGCCGAGGATGAGGCCGACT ACTACTGCTCGAGCTACACATCCTCGAGCACCCTCTACGTGTTCG GCTCGGGGACTAAGGTCACCGTGCTG |
| SEQ ID NO: 104 | Linker | GGGGSGGGGSGGGGS |
| SEQ ID NO: 105 | scFv (VH-linker-VL) | QVQLQESGGGVVQPGRSLRLSCAASGFTFSSYGMHWVRQAPGKGL EWVAVISYDGSNKYYADSVKGRFTISRDNSKNTLYLQMNSLRAED TAVYYCGGSGYALHDDYYGLDVWGQGTLVTVSSGGGGSGGGGS GGGGSQSALTQPASVSGSPGQSITISCTGTSSDVGGYNYVSWYQQH PGKAPKLMIYDVSNRPSGVSNRFSGSKSGNTASLTISGLQAEDEAD YYCSSYTSSSTLYVFGSGTKVTVL |
| SEQ ID NO: 106 | DNA scFv | CAAGTGCAGCTGCAGGAATCCGGTGGCGGAGTCGTGCAGCCTGG AAGGAGCCTGAGACTCTCATGCGCCGCGTCAGGGTTCACCTTTT CCTCCTACGGGATGCATTGGGTCAGACAGGCCCCCGGAAAGGGA CTCGAATGGGTGGCTGTGATCAGCTACGACGGCTCCAACAAGTA CTACGCCGACTCCGTGAAAGGCCGGTTCACTATCTCCCGGGACA ACTCCAAGAACACGCTGTATCTGCAAATGAATTCACTGCGCGCG GAGGATACCGCTGTGTACTACTGCGGTGGCTCCGGTTACGCCCT GCACGATGACTATTACGGCCTTGACGTCTGGGGCCAGGGAACCC TCGTGACTGTGTCCAGCGGTGGAGGAGGTTCGGGCGGAGGAGG ATCAGGAGGGGGTGGATCGCAGAGCGCACTGACTCAGCCGGCA TCCGTGTCCGGTAGCCCCGGACAGTCGATTACCATCTCCTGTACC GGCACCTCCTCCGACGTGGGAGGGTACAACTACGTGTCGTGGTA CCAGCAGCACCCAGGAAAGGCCCCTAAGTTGATGATCTACGATG TGTCAAACCGCCCGTCTGGAGTCTCCAACCGGTTCTCCGGCTCCA AGTCCGGCAACACCGCCAGCCTGACCATTAGCGGGCTGCAAGCC GAGGATGAGGCCGACTACTACTGCTCGAGCTACACATCCTCGAG CACCCTCTACGTGTTCGGCTCGGGGACTAAGGTCACCGTGCTG |
| SEQ ID NO: 107 | Full CAR amino acid sequence | QVQLQESGGGVVQPGRSLRLSCAASGFTFSSYGMHWVRQAPGKGL EWVAVISYDGSNKYYADSVKGRFTISRDNSKNTLYLQMNSLRAED TAVYYCGGSGYALHDDYYGLDVWGQGTLVTVSSGGGGSGGGGS GGGGSQSALTQPASVSGSPGQSITISCTGTSSDVGGYNYVSWYQQH PGKAPKLMIYDVSNRPSGVSNRFSGSKSGNTASLTISGLQAEDEAD YYCSSYTSSSTLYVFGSGTKVTVLTTTPAPRPPTPAPTIASQPLSLRP EACRPAAGGAVHTRGLDFACDIYIWAPLAGTCGVLLLSLVITLYCK RGRKKLLYIFKQPFMRPVQTTQEEDGCSCRFPEEEEGGCELRVKFSR SADAPAYQQGQNQLYNELNLGRREEYDVLDKRRGRDPEMGGKPR RKNPQEGLYNELQKDKMAEAYSEIGMKGERRRGKGHDGLYQGLS TATKDTYDALHMQALPPR |
| SEQ ID NO: 108 | Full CAR DNA sequence | CAAGTGCAGCTGCAGGAATCCGGTGGCGGAGTCGTGCAGCCTGG AAGGAGCCTGAGACTCTCATGCGCCGCGTCAGGGTTCACCTTTT CCTCCTACGGGATGCATTGGGTCAGACAGGCCCCCGGAAAGGGA CTCGAATGGGTGGCTGTGATCAGCTACGACGGCTCCAACAAGTA CTACGCCGACTCCGTGAAAGGCCGGTTCACTATCTCCCGGGACA ACTCCAAGAACACGCTGTATCTGCAAATGAATTCACTGCGCGCG GAGGATACCGCTGTGTACTACTGCGGTGGCTCCGGTTACGCCCT GCACGATGACTATTACGGCCTTGACGTCTGGGGCCAGGGAACCC TCGTGACTGTGTCCAGCGGTGGAGGAGGTTCGGGCGGAGGAGG ATCAGGAGGGGGTGGATCGCAGAGCGCACTGACTCAGCCGGCA TCCGTGTCCGGTAGCCCCGGACAGTCGATTACCATCTCCTGTACC GGCACCTCCTCCGACGTGGGAGGGTACAACTACGTGTCGTGGTA CCAGCAGCACCCAGGAAAGGCCCCTAAGTTGATGATCTACGATG TGTCAAACCGCCCGTCTGGAGTCTCCAACCGGTTCTCCGGCTCCA AGTCCGGCAACACCGCCAGCCTGACCATTAGCGGGCTGCAAGCC GAGGATGAGGCCGACTACTACTGCTCGAGCTACACATCCTCGAG CACCCTCTACGTGTTCGGCTCGGGGACTAAGGTCACCGTGCTGA CCACTACCCCAGCACCGAGGCCACCCACCCCGGCTCCTACCATC GCCTCCCAGCCTCTGTCCCTGCGTCCGGAGGCATGTAGACCCGC AGCTGGTGGGGCCGTGCATACCCGGGGTCTTGACTTCGCCTGCG ATATCTACATTTGGGCCCCTCTGGCTGGTACTTGCGGGGTCCTGC TGCTTTCACTCGTGATCACTCTTTACTGTAAGCGCGGTCGGAAGA AGCTGCTGTACATCTTTAAGCAACCCTTCATGAGGCCTGTGCAG ACTACTCAAGAGGAGGACGGCTGTTCATGCCGGTTCCCAGAGGA GGAGGAAGGCGGCTGCGAACTGCGCGTGAAATTCAGCCGCAGC |

TABLE 6-continued

Amino acid and nucleic acid sequences of exemplary B cell-derived anti-BCMA molecules

| SEQ ID NO | Name/ Description | Sequence |
|---|---|---|
| | | GCAGATGCTCCAGCCTACCAGCAGGGGCAGAACCAGCTCTACAA CGAACTCAATCTTGGTCGGAGAGAGGAGTACGACGTGCTGGACA AGCGGAGAGGACGGGACCCAGAAATGGGCGGGAAGCCGCGCAG AAAGAATCCCCAAGAGGGCCTGTACAACGAGCTCCAAAAGGAT AAGATGGCAGAAGCCTATAGCGAGATTGGTATGAAAGGGGAAC GCAGAAGAGGCAAAGGCCACGACGGACTGTACCAGGGACTCAG CACCGCCACCAAGGACACCTATGACGCTCTTCACATGCAGGCCC TGCCGCCTCGG |
| B61-02 | | |
| SEQ ID NO: 86 | HCDR1 (Kabat) | SYGMH |
| SEQ ID NO: 109 | HCDR2 (Kabat) | VISYKGSNKYYADSVKG |
| SEQ ID NO: 88 | HCDR3 (Kabat) | SGYALHDDYYGLDV |
| SEQ ID NO: 47 | HCDR1 (Chothia) | GFTFSSY |
| SEQ ID NO: 110 | HCDR2 (Chothia) | SYKGSN |
| SEQ ID NO: 88 | HCDR3 (Chothia) | SGYALHDDYYGLDV |
| SEQ ID NO: 90 | HCDR1 (IMGT) | GFTFSSYG |
| SEQ ID NO: 111 | HCDR2 (IMGT) | ISYKGSNK |
| SEQ ID NO: 92 | HCDR3 (IMGT) | GGSGYALHDDYYGLDV |
| SEQ ID NO: 112 | VH | QVQLVESGGGVVQPGRSLRLSCAASGFTFSSYGMHWVRQAPGKGL EWVAVISYKGSNKYYADSVKGRFTISRDNSKNTLYLQMNSLRAED TAVYYCGGSGYALHDDYYGLDVWGQGTLVTVSS |
| SEQ ID NO: 113 | DNA VH | CAAGTGCAGCTTGTCGAATCGGGAGGCGGAGTGGTGCAGCCTGG ACGATCGCTCCGGCTCTCATGTGCCGCGAGCGGATTCACCTTCTC GAGCTACGGCATGCACTGGGTCAGACAAGCCCCAGGAAAGGGC CTGGAATGGGTGGCTGTCATCTCGTACAAGGGCTCAAACAAGTA CTACGCCGACTCCGTGAAGGGCCGGTTCACCATCTCCCGCGATA ACTCCAAGAATACCCTCTATCTGCAAATGAACAGCCTGAGGGCC GAGGATACTGCAGTGTACTACTGCGGGGGTTCAGGCTACGCGCT GCACGACGACTACTACGGATTGGACGTCTGGGGCCAAGGAACTC TTGTGACCGTGTCCTCT |
| SEQ ID NO: 95 | LCDR1 (Kabat) | TGTSSDVGGYNYVS |
| SEQ ID NO: 114 | LCDR2 (Kabat) | EVSNRLR |
| SEQ ID NO: 115 | LCDR3 (Kabat) | SSYTSSSALYV |
| SEQ ID NO: 98 | LCDR1 (Chothia) | TSSDVGGYNY |
| SEQ ID NO: 116 | LCDR2 (Chothia) | EVS |
| SEQ ID NO: 117 | LCDR3 (Chothia) | YTSSSALY |
| SEQ ID NO: 101 | LCDR1 (IMGT) | SSDVGGYNY |

TABLE 6-continued

Amino acid and nucleic acid sequences of exemplary B cell-derived anti-BCMA molecules

| SEQ ID NO | Name/ Description | Sequence |
|---|---|---|
| SEQ ID NO: 116 | LCDR2 (IMGT) | EVS |
| SEQ ID NO: 115 | LCDR3 (IMGT) | SSYTSSSALYV |
| SEQ ID NO: 118 | VL | QSALTQPASVSGSPGQSITISCTGTSSDVGGYNYVSWYQQHPGKAP KLMIYEVSNRLRGVSNRFSGSKSGNTASLTISGLQAEDEADYYCSS YTSSSALYVFGSGTKVTVL |
| SEQ ID NO: 119 | DNA VL | CAGAGCGCGCTGACTCAGCCTGCCTCCGTGAGCGGTTCGCCGGG ACAGTCCATTACCATTTCGTGCACCGGGACCTCCTCCGACGTGG GAGGCTACAACTACGTGTCCTGGTACCAGCAGCATCCCGGAAAG GCCCCGAAGCTGATGATCTACGAAGTGTCGAACAGACTGCGGGG AGTCTCCAACCGCTTTTCCGGGTCCAAGTCCGGCAACACCGCCA GCCTGACCATCAGCGGGCTCCAGGCAGAAGATGAGGCTGACTAT TACTGCTCCTCCTACACGTCAAGCTCCGCCCTCTACGTGTTCGGG TCCGGGACCAAAGTCACTGTGCTG |
| SEQ ID NO: 63 | Linker | GGGGSGGGGSGGGGSGGGGS |
| SEQ ID NO: 120 | scFv (VH-linker-VL) | QVQLVESGGGVVQPGRSLRLSCAASGFTFSSYGMHWVRQAPGKGL EWVAVISYKGSNKYYADSVKGRFTISRDNSKNTLYLQMNSLRAED TAVYYCGGSGYALHDDYYGLDVWGQGTLVTVSSGGGGSGGGGS GGGGSGGGGSQSALTQPASVSGSPGQSITISCTGTSSDVGGYNYVS WYQQHPGKAPKLMIYEVSNRLRGVSNRFSGSKSGNTASLTISGLQA EDEADYYCSSYTSSSALYVFGSGTKVTVL |
| SEQ ID NO: 121 | DNA scFv | CAAGTGCAGCTTGTCGAATCGGGAGGCGGAGTGGTGCAGCCTGG ACGATCGCTCCGGCTCTCATGTGCCGCGAGCGGATTCACCTTCTC GAGCTACGGCATGCACTGGGTCAGACAAGCCCCAGGAAAGGGC CTGGAATGGGTGGCTGTCATCTCGTACAAGGGCTCAAACAAGTA CTACGCCGACTCCGTGAAGGGCCGGTTCACCATCTCCCGCGATA ACTCCAAGAATACCCTCTATCTGCAAATGAACAGCCTGAGGGCC GAGGATACTGCAGTGTACTACTGCGGGGGTTCAGGCTACGCGCT GCACGACGACTACTACGGATTGGACGTCTGGGGCCAAGGAACTC TTGTGACCGTGTCCTCTGGTGGAGGCGGATCAGGGGGTGGCGGA TCTGGGGGTGGTGGTTCCGGGGGAGGAGGATCGCAGAGCGCGC TGACTCAGCCTGCCTCCGTGAGCGGTTCGCCGGGACAGTCCATT ACCATTTCGTGCACCGGGACCTCCTCCGACGTGGGAGGCTACAA CTACGTGTCCTGGTACCAGCAGCATCCCGGAAAGGCCCCGAAGC TGATGATCTACGAAGTGTCGAACAGACTGCGGGGAGTCTCCAAC CGCTTTTCCGGGTCCAAGTCCGGCAACACCGCCAGCCTGACCAT CAGCGGGCTCCAGGCAGAAGATGAGGCTGACTATTACTGCTCCT CCTACACGTCAAGCTCCGCCCTCTACGTGTTCGGGTCCGGGACC AAAGTCACTGTGCTG |
| SEQ ID NO: 122 | Full CAR amino acid sequence | QVQLVESGGGVVQPGRSLRLSCAASGFTFSSYGMHWVRQAPGKGL EWVAVISYKGSNKYYADSVKGRFTISRDNSKNTLYLQMNSLRAED TAVYYCGGSGYALHDDYYGLDVWGQGTLVTVSSGGGGSGGGGS GGGGSGGGGSQSALTQPASVSGSPGQSITISCTGTSSDVGGYNYVS WYQQHPGKAPKLMIYEVSNRLRGVSNRFSGSKSGNTASLTISGLQA EDEADYYCSSYTSSSALYVFGSGTKVTVLTTTPAPRPPTPAPTIASQP LSLRPEACRPAAGGAVHTRGLDFACDIYIWAPLAGTCGVLLLSLVIT LYCKRGRKKLLYIFKQPFMRPVQTTQEEDGCSCRFPEEEEGGCELR VKFSRSADAPAYQQGQNQLYNELNLGRREEYDVLDKRRGRDPEM GGKPRRKNPQEGLYNELQKDKMAEAYSEIGMKGERRRGKGHDGL YQGLSTATKDTYDALHMQALPPR |
| SEQ ID NO: 123 | Full CAR DNA sequence | CAAGTGCAGCTTGTCGAATCGGGAGGCGGAGTGGTGCAGCCTGG ACGATCGCTCCGGCTCTCATGTGCCGCGAGCGGATTCACCTTCTC GAGCTACGGCATGCACTGGGTCAGACAAGCCCCAGGAAAGGGC CTGGAATGGGTGGCTGTCATCTCGTACAAGGGCTCAAACAAGTA CTACGCCGACTCCGTGAAGGGCCGGTTCACCATCTCCCGCGATA ACTCCAAGAATACCCTCTATCTGCAAATGAACAGCCTGAGGGCC GAGGATACTGCAGTGTACTACTGCGGGGGTTCAGGCTACGCGCT GCACGACGACTACTACGGATTGGACGTCTGGGGCCAAGGAACTC TTGTGACCGTGTCCTCTGGTGGAGGCGGATCAGGGGGTGGCGGA TCTGGGGGTGGTGGTTCCGGGGGAGGAGGATCGCAGAGCGCGC TGACTCAGCCTGCCTCCGTGAGCGGTTCGCCGGGACAGTCCATT ACCATTTCGTGCACCGGGACCTCCTCCGACGTGGGAGGCTACAA CTACGTGTCCTGGTACCAGCAGCATCCCGGAAAGGCCCCGAAGC TGATGATCTACGAAGTGTCGAACAGACTGCGGGGAGTCTCCAAC |

TABLE 6-continued

Amino acid and nucleic acid sequences of exemplary B cell-derived anti-BCMA molecules

| SEQ ID NO | Name/ Description | Sequence |
|---|---|---|
| | | CGCTTTTCCGGGTCCAAGTCCGGCAACACCGCCAGCCTGACCAT CAGCGGGCTCCAGGCAGAAGATGAGGCTGACTATTACTGCTCCT CCTACACGTCAAGCTCCGCCCTCTACGTGTTCGGGTCCGGGACC AAAGTCACTGTGCTGACCACTACCCCAGCACCGAGGCCACCCAC CCCGGCTCCTACCATCGCCTCCCAGCCTCTGTCCCTGCGTCCGGA GGCATGTAGACCCGCAGCTGGTGGGGCCGTGCATACCCGGGGTC TTGACTTCGCCTGCGATATCTACATTTGGGCCCCTCTGGCTGGTA CTTGCGGGGTCCTGCTGCTTTCACTCGTGATCACTCTTTACTGTA AGCGCGGTCGGAAGAAGCTGCTGTACATCTTTAAGCAACCCTTC ATGAGGCCTGTGCAGACTACTCAAGAGGAGGACGGCTGTTCATG CCGGTTCCCAGAGGAGGAGGAAGGCGGCTGCGAACTGCGCGTG AAATTCAGCCGCAGCGCAGATGCTCCAGCCTACCAGCAGGGGCA GAACCAGCTCTACAACGAACTCAATCTTGGTCGGAGAGAGGAGT ACGACGTGCTGGACAAGCGGAGAGGACGGGACCCAGAAATGGG CGGGAAGCCGCGCAGAAAGAATCCCCAAGAGGGCCTGTACAAC GAGCTCCAAAAGGATAAGATGGCAGAAGCCTATAGCGAGATTG GTATGAAAGGGGAACGCAGAAGAGGCAAAGGCCACGACGGACT GTACCAGGGACTCAGCACCGCCACCAAGGACACCTATGACGCTC TTCACATGCAGGCCCTGCCGCCTCGG |
| B61-10 | | |
| SEQ ID NO: 86 | HCDR1 (Kabat) | SYGMH |
| SEQ ID NO: 109 | HCDR2 (Kabat) | VISYKGSNKYYADSVKG |
| SEQ ID NO: 88 | HCDR3 (Kabat) | SGYALHDDYYGLDV |
| SEQ ID NO: 47 | HCDR1 (Chothia) | GFTFSSY |
| SEQ ID NO: 110 | HCDR2 (Chothia) | SYKGSN |
| SEQ ID NO: 88 | HCDR3 (Chothia) | SGYALHDDYYGLDV |
| SEQ ID NO: 90 | HCDR1 (IMGT) | GFTFSSYG |
| SEQ ID NO: 111 | HCDR2 (IMGT) | ISYKGSNK |
| SEQ ID NO: 92 | HCDR3 (IMGT) | GGSGYALHDDYYGLDV |
| SEQ ID NO: 112 | VH | QVQLVESGGGVVQPGRSLRLSCAASGFTFSSYGMHWVRQAPGKGL EWVAVISYKGSNKYYADSVKGRFTISRDNSKNTLYLQMNSLRAED TAVYYCGGSGYALHDDYYGLDVWGQGTLVTVSS |
| SEQ ID NO: 113 | DNA VH | CAAGTGCAGCTTGTCGAATCGGGAGGCGGAGTGGTGCAGCCTGG ACGATCGCTCCGGCTCTCATGTGCCGCGAGCGGATTCACCTTCTC GAGCTACGGCATGCACTGGGTCAGACAAGCCCCAGGAAAGGGC CTGGAATGGGTGGCTGTCATCTCGTACAAGGGCTCAAACAAGTA CTACGCCGACTCCGTGAAGGGCCGGTTCACCATCTCCCGCGATA ACTCCAAGAATACCCTCTATCTGCAAATGAACAGCCTGAGGGCC GAGGATACTGCAGTGTACTACTGCGGGGGTTCAGGCTACGCGCT GCACGACGACTACTACGGATTGGACGTCTGGGGCCAAGGAACTC TTGTGACCGTGTCCTCT |
| SEQ ID NO: 95 | LCDR1 (Kabat) | TGTSSDVGGYNYVS |
| SEQ ID NO: 114 | LCDR2 (Kabat) | EVSNRLR |
| SEQ ID NO: 97 | LCDR3 (Kabat) | SSYTSSSTLYV |
| SEQ ID NO: 98 | LCDR1 (Chothia) | TSSDVGGYNY |

TABLE 6-continued

Amino acid and nucleic acid sequences of exemplary B cell-derived anti-BCMA molecules

| SEQ ID NO | Name/ Description | Sequence |
|---|---|---|
| SEQ ID NO: 116 | LCDR2 (Chothia) | EVS |
| SEQ ID NO: 100 | LCDR3 (Chothia) | YTSSSTLY |
| SEQ ID NO: 101 | LCDR1 (IMGT) | SSDVGGYNY |
| SEQ ID NO: 116 | LCDR2 (IMGT) | EVS |
| SEQ ID NO: 97 | LCDR3 (IMGT) | SSYTSSSTLYV |
| SEQ ID NO: 124 | VL | QSALTQPASVSGSPGQSITISCTGTSSDVGGYNYVSWYQQHPGKAP KLMIYEVSNRLRGVSNRFSGSKSGNTASLTISGLQAEDEADYYCSS YTSSSTLYVFGSGTKVTVL |
| SEQ ID NO: 125 | DNA VL | CAGAGCGCGCTGACTCAGCCTGCCTCCGTGAGCGGTTCGCCGGG ACAGTCCATTACCATTTCGTGCACCGGGACCTCCTCCGACGTGG GAGGCTACAACTACGTGTCCTGGTACCAGCAGCATCCCGGAAAG GCCCCGAAGCTGATGATCTACGAAGTGTCGAACAGACTGCGGGG AGTCTCCAACCGCTTTTCCGGGTCCAAGTCCGGCAACACCGCCA GCCTGACCATCAGCGGGCTCCAGGCAGAAGATGAGGCTGACTAT TACTGCTCCTCCTACACGTCAAGCTCCACCCTCTACGTGTTCGGG TCCGGGACCAAAGTCACTGTGCTG |
| SEQ ID NO: 63 | Linker | GGGGSGGGGSGGGGSGGGGS |
| SEQ ID NO: 126 | scFv (VH-linker-VL) | QVQLVESGGGVVQPGRSLRLSCAASGFTFSSYGMHWVRQAPGKGL EWVAVISYKGSNKYYADSVKGRFTISRDNSKNTLYLQMNSLRAED TAVYYCGGSGYALHDDYYGLDVWGQGTLVTVSSGGGGSGGGGS GGGGSGGGGSQSALTQPASVSGSPGQSITISCTGTSSDVGGYNYVS WYQQHPGKAPKLMIYEVSNRLRGVSNRFSGSKSGNTASLTISGLQA EDEADYYCSSYTSSSTLYVFGSGTKVTVL |
| SEQ ID NO: 127 | DNA scFv | CAAGTGCAGCTTGTCGAATCGGGAGGCGGAGTGGTGCAGCCTGG ACGATCGCTCCGGCTCTCATGTGCCGCGAGCGGATTCACCTTCTC GAGCTACGGCATGCACTGGGTCAGACAAGCCCCAGGAAAGGGC CTGGAATGGGTGGCTGTCATCTCGTACAAGGGCTCAAACAAGTA CTACGCCGACTCCGTGAAGGGCCGGTTCACCATCTCCCGCGATA ACTCCAAGAATACCCTCTATCTGCAAATGAACAGCCTGAGGGCC GAGGATACTGCAGTGTACTACTGCGGGGGTTCAGGCTACGCGCT GCACGACGACTACTACGGATTGGACGTCTGGGGCCAAGGAACTC TTGTGACCGTGTCCTCTGGTGGAGGCGGATCAGGGGGTGGCGGA TCTGGGGGTGGTGGTTCCGGGGGAGGAGGATCGCAGAGCGCGC TGACTCAGCCTGCCTCCGTGAGCGGTTCGCCGGGACAGTCCATT ACCATTTCGTGCACCGGGACCTCCTCCGACGTGGGAGGCTACAA CTACGTGTCCTGGTACCAGCAGCATCCCGGAAAGGCCCCGAAGC TGATGATCTACGAAGTGTCGAACAGACTGCGGGGAGTCTCCAAC CGCTTTTCCGGGTCCAAGTCCGGCAACACCGCCAGCCTGACCAT CAGCGGGCTCCAGGCAGAAGATGAGGCTGACTATTACTGCTCCT CCTACACGTCAAGCTCCACCCTCTACGTGTTCGGGTCCGGGACC AAAGTCACTGTGCTG |
| SEQ ID NO: 128 | Full CAR amino acid sequence | QVQLVESGGGVVQPGRSLRLSCAASGFTFSSYGMHWVRQAPGKGL EWVAVISYKGSNKYYADSVKGRFTISRDNSKNTLYLQMNSLRAED TAVYYCGGSGYALHDDYYGLDVWGQGTLVTVSSGGGGSGGGGS GGGGSGGGGSQSALTQPASVSGSPGQSITISCTGTSSDVGGYNYVS WYQQHPGKAPKLMIYEVSNRLRGVSNRFSGSKSGNTASLTISGLQA EDEADYYCSSYTSSSTLYVFGSGTKVTVLTTTPAPRPPTPAPTIASQP LSLRPEACRPAAGGAVHTRGLDFACDIYIWAPLAGTCGVLLLSLVIT LYCKRGRKKLLYIFKQPFMRPVQTTQEEDGCSCRFPEEEEGGCELR VKFSRSADAPAYQQGQNQLYNELNLGRREEYDVLDKRRGRDPEM GGKPRRKNPQEGLYNELQKDKMAEAYSEIGMKGERRRGKGHDGL YQGLSTATKDTYDALHMQALPPR |
| SEQ ID NO: 129 | Full CAR DNA sequence | CAAGTGCAGCTTGTCGAATCGGGAGGCGGAGTGGTGCAGCCTGG ACGATCGCTCCGGCTCTCATGTGCCGCGAGCGGATTCACCTTCTC GAGCTACGGCATGCACTGGGTCAGACAAGCCCCAGGAAAGGGC CTGGAATGGGTGGCTGTCATCTCGTACAAGGGCTCAAACAAGTA |

TABLE 6-continued

| Amino acid and nucleic acid sequences of exemplary B cell-derived anti-BCMA molecules | | |
|---|---|---|
| SEQ ID NO | Name/ Description | Sequence |
| | | CTACGCCGACTCCGTGAAGGGCCGGTTCACCATCTCCCGCGATA ACTCCAAGAATACCCTCTATCTGCAAATGAACAGCCTGAGGGCC GAGGATACTGCAGTGTACTACTGCGGGGGTTCAGGCTACGCGCT GCACGACGACTACTACGGATTGGACGTCTGGGGCCAAGGAACTC TTGTGACCGTGTCCTCTGGTGGAGGCGGATCAGGGGGTGGCGGA TCTGGGGGTGGTGGTTCCGGGGGAGGAGGATCGCAGAGCGCGC TGACTCAGCCTGCCTCCGTGAGCGGTTCGCCGGGACAGTCCATT ACCATTTCGTGCACCGGGACCTCCTCCGACGTGGGAGGCTACAA CTACGTGTCCTGGTACCAGCAGCATCCCGGAAAGGCCCCGAAGC TGATGATCTACGAAGTGTCGAACAGACTGCGGGGAGTCTCCAAC CGCTTTTCCGGGTCCAAGTCCGGCAACACCGCCAGCCTGACCAT CAGCGGGCTCCAGGCAGAAGATGAGGCTGACTATTACTGCTCCT CCTACACGTCAAGCTCCACCCTCTACGTGTTCGGGTCCGGGACC AAAGTCACTGTGCTGACCACTACCCCAGCACCGAGGCCACCCAC CCCGGCTCCTACCATCGCCTCCCAGCCTCTGTCCCTGCGTCCGGA GGCATGTAGACCCGCAGCTGGTGGGGCCGTGCATACCCGGGGTC TTGACTTCGCCTGCGATATCTACATTTGGGCCCCTCTGGCTGGTA CTTGCGGGGTCCTGCTGCTTTCACTCGTGATCACTCTTTACTGTA AGCGCGGTCGGAAGAAGCTGCTGTACATCTTTAAGCAACCCTTC ATGAGGCCTGTGCAGACTACTCAAGAGGAGGACGGCTGTTCATG CCGGTTCCCAGAGGAGGAGGAAGGCGGCTGCGAACTGCGCGTG AAATTCAGCCGCAGCGCAGATGCTCCAGCCTACCAGCAGGGGCA GAACCAGCTCTACAACGAACTCAATCTTGGTCGGAGAGAGGAGT ACGACGTGCTGGACAAGCGGAGAGGACGGGACCCAGAAATGGG CGGGAAGCCGCGCAGAAAGAATCCCCAAGAGGGCCTGTACAAC GAGCTCCAAAAGGATAAGATGGCAGAAGCCTATAGCGAGATTG GTATGAAAGGGGAACGCAGAAGAGGCAAAGGCCACGACGGACT GTACCAGGGACTCAGCACCGCCACCAAGGACACCTATGACGCTC TTCACATGCAGGCCCTGCCGCCTCGG |

TABLE 7

| Kabat CDRs of exemplary B cell-derived anti-BCMA molecules | | | | | | |
|---|---|---|---|---|---|---|
| Kabat | HCDR1 | HCDR2 | HCDR3 | LCDR1 | LCDR2 | LCDR3 |
| PI61 | SYGMH (SEQ ID NO: 86) | VISYDGSN KYYADSV KG (SEQ ID NO: 87) | SGYALHDD YYGLDV (SEQ ID NO: 88) | TGTSSDV GGYNYV S (SEQ ID NO: 95) | DVSNRPS (SEQ ID NO: 96) | SSYTSSS TLYV (SEQ ID NO: 97) |
| B61-02 | SYGMH (SEQ ID NO: 86) | VISYKGSN KYYADSV KG (SEQ ID NO: 109) | SGYALHDD YYGLDV (SEQ ID NO: 88) | TGTSSDV GGYNYV S (SEQ ID NO: 95) | EVSNRLR (SEQ ID NO: 114) | SSYTSSS ALYV (SEQ ID NO: 115) |
| B61-10 | SYGMH (SEQ ID NO: 86) | VISYKGSN KYYADSV KG (SEQ ID NO: 109) | SGYALHDD YYGLDV (SEQ ID NO: 88) | TGTSSDV GGYNYV S (SEQ ID NO: 95) | EVSNRLR (SEQ ID NO: 114) | SSYTSSS TLYV (SEQ ID NO: 97) |
| Consensus | SYGMH (SEQ ID NO: 86) | VISYXGSN KYYADSV KG, wherein X is D or K (SEQ ID NO: 130) | SGYALHDD YYGLDV (SEQ ID NO: 88) | TGTSSDV GGYNYV S (SEQ ID NO: 95) | $X_1$VSNR$X_2X_3$, wherein $X_1$ is D or E; $X_2$ is P or L; and $X_3$ is S or R (SEQ ID NO: 131) | SSYTSSS XLYV, wherein X is T or A (SEQ ID NO: 132) |

TABLE 8

Chothia CDRs of exemplary B cell-derived anti-BCMA molecules

| Chothia | HCDR1 | HCDR2 | HCDR3 | LCDR1 | LCDR2 | LCDR3 |
|---|---|---|---|---|---|---|
| PI61 | GFTFSSY (SEQ ID NO: 47) | SYDGSN (SEQ ID NO: 89) | SGYALHDDY YGLDV (SEQ ID NO: 88) | TSSDVGG YNY (SEQ ID NO: 98) | DVS (SEQ ID NO: 99) | YTSSSTLY (SEQ ID NO: 100) |
| B61-02 | GFTFSSY (SEQ ID NO: 47) | SYKGSN (SEQ ID NO: 110) | SGYALHDDY YGLDV (SEQ ID NO: 88) | TSSDVGG YNY (SEQ ID NO: 98) | EVS (SEQ ID NO: 116) | YTSSSAL Y (SEQ ID NO: 117) |
| B61-10 | GFTFSSY (SEQ ID NO: 47) | SYKGSN (SEQ ID NO: 110) | SGYALHDDY YGLDV (SEQ ID NO: 88) | TSSDVGG YNY (SEQ ID NO: 98) | EVS (SEQ ID NO: 116) | YTSSSTLY (SEQ ID NO: 100) |
| Consensus | GFTFSSY (SEQ ID NO: 47) | SYXGSN, wherein X is D or K (SEQ ID NO: 133) | SGYALHDDY YGLDV (SEQ ID NO: 88) | TSSDVGG YNY (SEQ ID NO: 98) | XVS, wherein X is D or E (SEQ ID NO: 134) | YTSSSXL Y, wherein X is T or A (SEQ ID NO: 135) |

TABLE 9

IMGT CDRs of exemplary B cell-derived anti-BCMA molecules

| IMGT | HCDR1 | HCDR2 | HCDR3 | LCDR1 | LCDR2 | LCDR3 |
|---|---|---|---|---|---|---|
| PI61 | GFTFSSYG (SEQ ID NO: 90) | ISYDGSN K (SEQ ID NO: 91) | GGSGYALHDD YYGLDV (SEQ ID NO: 92) | SSDVGGY NY (SEQ ID NO: 101) | DVS (SEQ ID NO: 99) | SSYTSSSTL YV (SEQ ID NO: 97) |
| B61-02 | GFTFSSYG (SEQ ID NO: 90) | ISYKGSN K (SEQ ID NO: 111) | GGSGYALHDD YYGLDV (SEQ ID NO: 92) | SSDVGGY NY (SEQ ID NO: 101) | EVS (SEQ ID NO: 116) | SSYTSSSA LYV (SEQ ID NO: 115) |
| B61-10 | GFTFSSYG (SEQ ID NO: 90) | ISYKGSN K (SEQ ID NO: 111) | GGSGYALHDD YYGLDV (SEQ ID NO: 92) | SSDVGGY NY (SEQ ID NO: 101) | EVS (SEQ ID NO: 116) | SSYTSSSTL YV (SEQ ID NO: 97) |
| Consensus | GFTFSSYG (SEQ ID NO: 90) | ISYXGSN K, wherein X is D or K (SEQ ID NO: 136) | GGSGYALHDD YYGLDV (SEQ ID NO: 92) | SSDVGGY NY (SEQ ID NO: 101) | XVS, wherein X is D or E (SEQ ID NO: 134) | SSYTSSSX LYV, wherein X is T or A (SEQ ID NO: 132) |

TABLE 18

Amino acid and nucleic acid sequences of exemplary anti-BCMA molecules based on PI61

| Identification | Protein sequence | DNA sequence (5′-3′) |
|---|---|---|
| Signal peptide | MALPVTALLLPLALLLHAA RP (SEQ ID NO: 1) | Atggccctccctgtcaccgctctgttgctgccgcttgctctgctg ctccacgcagcgcgaccg (SEQ ID NO: 252) |
| PI61 VH | QVQLQESGGGVVQPGRSLR LSCAASGFTFSSYGMHWVR QAPGKGLEWVAVISYDGSN KYYADSVKGRFTISRDNSK NTLYLQMNSLRAEDTAVYY CGGSGYALHDDYYGLDVW GQGTLVTVSS (SEQ ID NO: 93) | CAGGTACAATTGCAGGAGTCTGGAGG CGGTGTGGTGCAACCCGGTCGCAGCTT GCGCCTGAGTTGTGCTGCGTCTGGATT TACATTTTCATCTTACGGAATGCATTG GGTACGCCAGGCACCGGGGAAAGGCC TTGAATGGGTGGCTGTAATTTCATACG ATGGTTCCAACAAATACTATGCTGACT CAGTCAAGGGTCGATTTACAATTAGTC GGGACAACTCCAAGAACACCCTTTATC TTCAAATGAATTCCCTTAGAGCAGAGG ATACGGCGGTCTATTACTGTGGTGGCA GTGGTTATGCACTTCATGATGATTACT ATGGCTTGGATGTCTGGGGGCAAGGG ACGCTTGTAACTGTATCCTCT (SEQ ID NO: 260) |

TABLE 18-continued

Amino acid and nucleic acid sequences of exemplary anti-BCMA molecules based on PI61

| Identification | Protein sequence | DNA sequence (5′-3′) |
|---|---|---|
| PI61 VL | QSALTQPASVSGSPGQSITIS<br>CTGTSSDVGGYNYVSWYQ<br>QHPGKAPKLMIYDVSNRPS<br>GVSNRFSGSKSGNTASLTIS<br>GLQAEDEADYYCSSYTSSST<br>LYVFGSGTKVTVL (SEQ ID<br>NO: 102) | CAATCTGCTCTGACTCAACCAGCAAGC<br>GTATCAGGGTCACCGGGACAGAGTATT<br>ACCATAAGTTGCACGGGGACCTCTAGC<br>GATGTAGGGGGGTATAATTATGTATCT<br>TGGTATCAACAACACCCCGGGAAAGC<br>CCCTAAATTGATGATCTACGACGTGAG<br>CAATCGACCTAGTGGCGTATCAAATCG<br>CTTCTCTGGTAGCAAGAGTGGGAATAC<br>GGCGTCCCTTACTATTAGCGGATTGCA<br>AGCAGAAGATGAGGCCGATTACTACT<br>GCAGCTCCTATACTAGCTCTTCTACAT<br>TGTACGTCTTTGGGAGCGGAACAAAA<br>GTAACAGTACTC (SEQ ID NO: 261) |
| Linker | GGGGSGGGGSGGGGS (SEQ<br>ID NO: 104) | |
| ScFv PI61 | QVQLQESGGGVVQPGRSLR<br>LSCAASGFTFSSYGMHWVR<br>QAPGKGLEWVAVISYDGSN<br>KYYADSVKGRFTISRDNSK<br>NTLYLQMNSLRAEDTAVYY<br>CGGSGYALHDDYYGLDVW<br>GQGTLVTVSSGGGGSGGGG<br>SGGGGSQSALTQPASVSGSP<br>GQSITISCTGTSSDVGGYNY<br>VSWYQQHPGKAPKLMIYD<br>VSNRPSGVSNRFSGSKSGNT<br>ASLTISGLQAEDEADYYCSS<br>YTSSSTLYVFGSGTKVTVL<br>(SEQ ID NO: 105) | CaggtacaattgcaggagtctggaggcggtgtgGtgcaacc<br>cggtcgcagcttgcgcctgagttgtGctgcgtctggatttacatt<br>ttcatcttacggaAtgcattgggtacgccaggcaccggggaa<br>aggcCttgaatgggtggctgtaatttcatacgatggtTccaac<br>aaatactatgctgactcagtcaagggtCgatttacaattagtcg<br>ggacaactccaagaacAccctttatcttcaaatgaattcccttag<br>agcaGaggatacggcggtctattactgtggtggcagtGgttat<br>gcacttcatgatgattactatggcttgGatgtctgggggcaagg<br>gacgcttgtaactgtaTcctctggtggtggtggtagtggtggg<br>ggaggcTccggcggtggcggctctcaatctgctctgactCaa<br>ccagcaagcgtatcagggtcaccgggacagAgtattaccata<br>agttgcacggggacctctagcGatgtagggggtataattatg<br>tatcttggtatCaacaacaccccgggaaagcccctaaattgatg<br>AtctacgacgtgagcaatcgacctagtggcgtaTcaaatcgc<br>ttctctggtagcaagagtgggaatAcggcgtcccttactattag<br>cggattgcaagcaGaagatgaggccgattactactgcagctc<br>ctatActagctcttctacattgtacgtctttgggagcggaacaaa<br>agtaacagtactc (SEQ ID NO: 253) |
| Transmembrane domain and hinge | TTTPAPRPPTPAPTIASQPLS<br>LRPEACRPAAGGAVHTRGL<br>DFACDIYIWAPLAGTCGVLL<br>LSLVITLYC (SEQ ID NO:<br>202) | AcaacaacacctgccccgagaccgcctacaccaGccccga<br>ctattgccagccagcctctgagcctcAggcctgaggcctgtag<br>gcccgcagcgggcggcGcagttcatacacggggcttggattt<br>cgcttgtGatatttatatttgggctcctttggcggggacaTgtgg<br>cgtgctgcttctgtcacttgttattacactgtactgt (SEQ ID<br>NO: 254) |
| 4-1BB | KRGRKKLLYIFKQPFMRPV<br>QTTQEEDGCSCRFPEEEEGG<br>CEL (SEQ ID NO: 7) | AaacgcgggcgaaaaaaattgctgtatatttttAagcagccat<br>ttatgaggcccgttcagacgacgCaggaggaggacggttgct<br>cttgcaggttcccagaagaggaagaagggggctgtgaattg<br>(SEQ ID NO: 255) |
| CD3zeta | RVKFSRSADAPAYQQGQNQ<br>LYNELNLGRREEYDVLDKR<br>RGRDPEMGGKPRRKNPQEG<br>LYNELQKDKMAEAYSEIGM<br>KGERRRGKGHDGLYQGLST<br>ATKDTYDALHMQALPPR<br>(SEQ ID NO: 10) | CgggttaaattttcaagatccgcagacgctccaGcataccaac<br>agggacaaaaccaactctataacGagctgaatcttggaagaa<br>gggaggaatatgatGtgctggataaacggcgcggtagagatc<br>cggagAtgggcggaaaaccaaggcgaaaaaccctcagG<br>agggactctacaacgaactgcagaaagacaaaAtggcggag<br>gcttattccgaaataggcatgaagGgcgagcggaggcgagg<br>gaaagggcacgacggaCtgtatcaaggcctctcaaccgcga<br>ctaaggatAcgtacgacgccctgcacatgcaggccctgcctc<br>egaga (SEQ ID NO: 256) |
| PI61 full CAR construct | MALPVTALLLPLALLLHAA<br>RPQVQLQESGGGVVQPGRS<br>LRLSCAASGFTFSSYGMHW<br>VRQAPGKGLEWVAVISYDG<br>SNKYYADSVKGRFTISRDNS<br>KNTLYLQMNSLRAEDTAVY<br>YCGGSGYALHDDYYGLDV<br>WGQGTLVTVSSGGGGSGG<br>GGSGGGGSQSALTQPASVS<br>GSPGQSITISCTGTSSDVGGY<br>NYVSWYQQHPGKAPKLMI<br>YDVSNRPSGVSNRFSGSKSG<br>NTASLTISGLQAEDEADYYC<br>SSYTSSSTLYVFGSGTKVTV<br>LTTTPAPRPPTPAPTIASQPL<br>SLRPEACRPAAGGAVHTRG<br>LDFACDIYIWAPLAGTCGVL | ATGGCCCTCCCTGTCACCGCTCTGTTG<br>CTGCCGCTTGCTCTGCTGCTCCACGCA<br>GCGCGACCGCAGGTACAATTGCAGGA<br>GTCTGGAGGCGGTGTGGTGCAACCCG<br>GTCGCAGCTTGCGCCTGAGTTGTGCTG<br>CGTCTGGATTTACATTTTCATCTTACGG<br>AATGCATTGGGTACGCCAGGCACCGG<br>GGAAAGGCCTTGAATGGGTGGCTGTA<br>ATTTCATACGATGGTTCCAACAAATAC<br>TATGCTGACTCAGTCAAGGGTCGATTT<br>ACAATTAGTCGGGACAACTCCAAGAA<br>CACCCTTTATCTTCAAATGAATTCCCTT<br>AGAGCAGAGGATACGGCGGTCTATTA<br>CTGTGGTGGCAGTGGTTATGCACTTCA<br>TGATGATTACTATGGCTTGGATGTCTG<br>GGGGCAAGGGACGCTTGTAACTGTATC<br>CTCTGGTGGTGGTGGTAGTGGTGGGG |

TABLE 18-continued

Amino acid and nucleic acid sequences of exemplary anti-BCMA molecules based on PI61

| Identification | Protein sequence | DNA sequence (5′-3′) |
| --- | --- | --- |
| | LLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 257) | AGGCTCCGGCGGTGGCGGCTCTCAATCTGCTCTGACTCAACCAGCAAGCGTATCAGGGTCACCGGGACAGAGTATTACCATAAGTTGCACGGGGACCTCTAGCGATGTAGGGGGGTATAATTATGTATCTTGGTATCAACAACACCCCGGGAAAGCCCCTAAATTGATGATCTACGACGTGAGCAATCGACCTAGTGGCGTATCAAATCGCTTCTCTGGTAGCAAGAGTGGGAATACGGCGTCCCTTACTATTAGCGGATTGCAAGCAGAAGATGAGGCCGATTACTACTGCAGCTCCTATACTAGCTCTTCTACATTGTACGTCTTTGGGAGCGGAACAAAAGTAACAGTACTCACAACAACACCTGCCCCGAGACCGCCTACACCAGCCCCGACTATTGCCAGCCAGCCTCTGAGCCTCAGGCCTGAGGCCTGTAGGCCCGCAGCGGGCGGCGCAGTTCATACACGGGGCTTGGATTTCGCTTGTGATATTTATATTTGGGCTCCTTTGGCGGGGACATGTGGCGTGCTGCTTCTGTCACTTGTTATTACACTGTACTGTAAACGCGGGCGAAAAAAATTGCTGTATATTTTTAAGCAGCCATTTATGAGGCCCGTTCAGACGACGCAGGAGGAGGACGGTTGCTCTTGCAGGTTCCCAGAAGAGGAAGAAGGGGGCTGTGAATTGCGGGTTAAATTTTCAAGATCCGCAGACGCTCCAGCATACCAACAGGGACAAAACCAACTCTATAACGAGCTGAATCTTGGAAGAAGGGAGGAATATGATGTGCTGGATAAACGGCGCGGTAGAGATCCGGAGATGGGCGGAAAACCAAGGCGAAAAAACCCTCAGGAGGGACTCTACAACGAACTGCAGAAAGACAAAATGGCGGAGGCTTATTCCGAAATAGGCATGAAGGGCGAGCGGAGGCGAGGGAAAGGGCACGACGGACTGTATCAAGGCCTCTCAACCGCGACTAAGGATACGTACGACGCCCTGCACATGCAGGCCCTGCCTCCGAGA (SEQ ID NO: 258) |
| PI61 mature CAR protein | QVQLQESGGGVVQPGRSLRLSCAASGFTFSSYGMHWVRQAPGKGLEWVAVISYDGSNKYYADSVKGRFTISRDNSKNTLYLQMNSLRAEDTAVYYCGGSGYALHDDYYGLDVWGQGTLVTVSSGGGGSGGGGSGGGGSQSALTQPASVSGSPGQSITISCTGTSSDVGGYNYVSWYQQHPGKAPKLMIYDVSNRPSGVSNRFSGSKSGNTASLTISGLQAEDEADYYCSSYTSSSTLYVFGSGTKVTVLTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (SEQ ID NO: 107) | caggtacaattgcaggagtctggaggcggtgtggtgcaacccggtcgcagcttgcgcctgagttgtgctgcgtctggatttacattttcatcttacggaatgcattgggtacgccaggcaccggggaaaggccttgaatgggtggctgtaatttcatacgatggttccaacaaatactatgctgactcagtcaagggtcgatttacaattagtcgggacaactccaagaacaccctttatcttcaaatgaattcccttagagcagaggatacggcggtctattactgtggtggcagtggttatgcactttcatgatgattactatggcttggatgtctgggggcaagggacgcttgtaactgtatcctctggtggtggtggtagtggtgggggaggctccggcggtggcggctctcaatctgctctgactcaaccagcaagcgtatcagggtcaccgggacagagtattaccataagttgcacggggacctctagcgatgtagggggtataattatgtatcttggtatcaacaacaccccgggaaagcccctaaattgatgatctacgacgtgagcaatcgacctagtggcgtatcaaatcgcttctctggtagcaagagtgggaatacggcgtcccttactattagcggattgcaagcagaagatgaggccgattactactgcagctcctatactagctcttctacattgtacgtctttgggagcggaacaaaagtaacagtactcacaacaacacctgccccgagaccgcctacaccagccccgactattgccagccagcctctgagcctcaggcctgaggcctgtaggcccgcagcgggcggcgcagttcatacacggggcttggatttcgcttgtgatatttatatttgggctcctttggcggggacatgtggcgtgctgcttctgtcacttgttattacactgtactgtaaacgcgggcgaaaaaaattgctgtatatttttaagcagccatttatgaggcccgttcagacgacgcaggaggaggacggttgctcttgcaggttcccagaagaggaagaagggggctgtgaattgcgggttaaattttcaagatccgcagacgctccagcataccaacagggacaaaaccaactctataacgagctgaatcttggaagaagggaggaatatgatgtgctggataaacggcgcggtagagatccggagatgggcggaaaaccaaggcgaaaaaaccctcaggagggactctacaacgaactgcagaaagacaaaatggcggaggcttattccgaaataggcatgaagggcgagcggaggcgagggaaagggcacgacggactgtatcaaggcctctcaaccgcgactaaggatacgtacgacgccctgcacatgcaggccctgcctccgaga (SEQ ID NO: 259) |

TABLE 10

| Amino acid and nucleic acid sequences of exemplary hybridoma-derived anti-BCMA molecules | | |
|---|---|---|
| SEQ ID NO | Name/ Description | Sequence |
| Hy03 | | |
| SEQ ID NO: 137 | HCDR1 (Kabat) | GFWMS |
| SEQ ID NO: 138 | HCDR2 (Kabat) | NIKQDGSEKYYVDSVRG |
| SEQ ID NO: 139 | HCDR3 (Kabat) | ALDYYGMDV |
| SEQ ID NO: 140 | HCDR1 (Chothia) | GFTFSGF |
| SEQ ID NO: 141 | HCDR2 (Chothia) | KQDGSE |
| SEQ ID NO: 139 | HCDR3 (Chothia) | ALDYYGMDV |
| SEQ ID NO: 142 | HCDR1 (IMGT) | GFTFSGFW |
| SEQ ID NO: 143 | HCDR2 (IMGT) | IKQDGSEK |
| SEQ ID NO: 144 | HCDR3 (IMGT) | ARALDYYGMDV |
| SEQ ID NO: 145 | VH | EVQLVESGGGLVQPGGSLRLSCAASGFTFSGFWMSWVRQAPGKGL EWVANIKQDGSEKYYVDSVRGRFTISRDNAKNSLYLQMNSLRAED TAVYYCARALDYYGMDVWGQGTTVTVSS |
| SEQ ID NO: 146 | DNA VH | GAAGTGCAACTGGTGGAGAGCGGTGGAGGGCTTGTCCAGCCCG GAGGATCGCTGCGGCTGTCCTGTGCTGCGTCCGGGTTCACCTTCT CCGGCTTCTGGATGTCCTGGGTCAGACAGGCACCGGGAAAGGGC CTCGAATGGGTGGCCAACATCAAGCAGGATGGCTCCGAGAAGT ACTACGTCGACTCCGTGAGAGGCCGCTTCACCATCTCCCGGGAC AACGCCAAGAACTCGCTGTACCTCCAAATGAATAGCCTCAGGGC GGAAGATACTGCTGTGTATTACTGCGCACGCGCCCTTGACTACT ACGGCATGGACGTCTGGGGCCAAGGGACCACTGTGACCGTGTCT AGC |
| SEQ ID NO: 147 | LCDR1 (Kabat) | RSSQSLLDSDDGNTYLD |
| SEQ ID NO: 148 | LCDR2 (Kabat) | TLSYRAS |
| SEQ ID NO: 149 | LCDR3 (Kabat) | TQRLEFPSIT |
| SEQ ID NO: 150 | LCDR1 (Chothia) | SQSLLDSDDGNTY |
| SEQ ID NO: 151 | LCDR2 (Chothia) | TLS |
| SEQ ID NO: 152 | LCDR3 (Chothia) | RLEFPSI |
| SEQ ID NO: 153 | LCDR1 (IMGT) | QSLLDSDDGNTY |
| SEQ ID NO: 151 | LCDR2 (IMGT) | TLS |
| SEQ ID NO: 149 | LCDR3 (IMGT) | TQRLEFPSIT |
| SEQ ID NO: 154 | VL | DIVMTQTPLSLPVTPGEPASISCRSSQSLLDSDDGNTYLDWYLQKPG QSPRLLIYTLSYRASGVPDRFSGSGSGTDFTLKISRVEAEDVGLYYC TQRLEFPSITFGQGTRLEIK |

TABLE 10-continued

Amino acid and nucleic acid sequences of exemplary hybridoma-derived anti-BCMA molecules

| SEQ ID NO | Name/ Description | Sequence |
|---|---|---|
| SEQ ID NO: 155 | DNA VL | GATATCGTGATGACCCAGACTCCCCTGTCCCTGCCTGTGACTCCC GGAGAACCAGCCTCCATTTCCTGCCGGTCCTCCCAGTCCCTGCTG GACAGCGACGACGGCAACACTTACCTGGACTGGTACTTGCAGAA GCCGGGCCAATCGCCTCGCCTGCTGATCTATACCCTGTCATACCG GGCCTCAGGAGTGCCTGACCGCTTCTCGGGATCAGGGAGCGGGA CCGATTTCACCCTGAAAATTTCCCGAGTGGAAGCCGAGGACGTC GGACTGTACTACTGCACCCAGCGCCTCGAATTCCCGTCGATTAC GTTTGGACAGGGTACCCGGCTTGAGATCAAG |
| SEQ ID NO: 63 | Linker | GGGGSGGGGSGGGGSGGGGS |
| SEQ ID NO: 156 | scFv (VH-linker-VL) | EVQLVESGGGLVQPGGSLRLSCAASGFTFSGFWMSWVRQAPGKGL EWVANIKQDGSEKYYVDSVRGRFTISRDNAKNSLYLQMNSLRAED TAVYYCARALDYYGMDVWGQGTTVTVSSGGGGSGGGGSGGGGS GGGGSDIVMTQTPLSLPVTPGEPASISCRSSQSLLDSDDGNTYLDWY LQKPGQSPRLLIYTLSYRASGVPDRFSGSGSGTDFTLKISRVEAEDV GLYYCTQRLEFPSITFGQGTRLEIK |
| SEQ ID NO: 157 | DNA scFv | GAAGTGCAACTGGTGGAGAGCGGTGGAGGGCTTGTCCAGCCCG GAGGATCGCTGCGGCTGTCCTGTGCTGCGTCCGGGTTCACCTTCT CCGGCTTCTGGATGTCCTGGGTCAGACAGGCACCGGGAAAGGGC CTCGAATGGGTGGCCAACATCAAGCAGGATGGCTCCGAGAAGT ACTACGTCGACTCCGTGAGAGGCCGCTTCACCATCTCCCGGGAC AACGCCAAGAACTCGCTGTACCTCCAAATGAATAGCCTCAGGGC GGAAGATACTGCTGTGTATTACTGCGCACGCGCCCTTGACTACT ACGGCATGGACGTCTGGGGCCAAGGGACCACTGTGACCGTGTCT AGCGGAGGCGGAGGTTCAGGGGGCGGTGGATCAGGCGGAGGAG GATCGGGGGGTGGTGGATCGGATATCGTGATGACCCAGACTCCC CTGTCCCTGCCTGTGACTCCCGGAGAACCAGCCTCCATTTCCTGC CGGTCCTCCCAGTCCCTGCTGGACAGCGACGACGGCAACACTTA CCTGGACTGGTACTTGCAGAAGCCGGGCCAATCGCCTCGCCTGC TGATCTATACCCTGTCATACCGGGCCTCAGGAGTGCCTGACCGC TTCTCGGGATCAGGGAGCGGGACCGATTTCACCCTGAAAATTTC CCGAGTGGAAGCCGAGGACGTCGGACTGTACTACTGCACCCAGC GCCTCGAATTCCCGTCGATTACGTTTGGACAGGGTACCCGGCTT GAGATCAAG |
| SEQ ID NO: 158 | Full CAR amino acid sequence | EVQLVESGGGLVQPGGSLRLSCAASGFTFSGFWMSWVRQAPGKGL EWVANIKQDGSEKYYVDSVRGRFTISRDNAKNSLYLQMNSLRAED TAVYYCARALDYYGMDVWGQGTTVTVSSGGGGSGGGGSGGGGS GGGGSDIVMTQTPLSLPVTPGEPASISCRSSQSLLDSDDGNTYLDWY LQKPGQSPRLLIYTLSYRASGVPDRFSGSGSGTDFTLKISRVEAEDV GLYYCTQRLEFPSITFGQGTRLEIKTTTPAPRPPTPAPTIASQPLSLRP EACRPAAGGAVHTRGLDFACDIYIWAPLAGTCGVLLLSLVITLYCK RGRKKLLYIFKQPFMRPVQTTQEEDGCSCRFPEEEEGGCELRVKFSR SADAPAYQQGQNQLYNELNLGRREEYDVLDKRRGRDPEMGGKPR RKNPQEGLYNELQKDKMAEAYSEIGMKGERRRGKGHDGLYQGLS TATKDTYDALHMQALPPR |
| SEQ ID NO: 159 | Full CAR DNA sequence | GAAGTGCAACTGGTGGAGAGCGGTGGAGGGCTTGTCCAGCCCG GAGGATCGCTGCGGCTGTCCTGTGCTGCGTCCGGGTTCACCTTCT CCGGCTTCTGGATGTCCTGGGTCAGACAGGCACCGGGAAAGGGC CTCGAATGGGTGGCCAACATCAAGCAGGATGGCTCCGAGAAGT ACTACGTCGACTCCGTGAGAGGCCGCTTCACCATCTCCCGGGAC AACGCCAAGAACTCGCTGTACCTCCAAATGAATAGCCTCAGGGC GGAAGATACTGCTGTGTATTACTGCGCACGCGCCCTTGACTACT ACGGCATGGACGTCTGGGGCCAAGGGACCACTGTGACCGTGTCT AGCGGAGGCGGAGGTTCAGGGGGCGGTGGATCAGGCGGAGGAG GATCGGGGGGTGGTGGATCGGATATCGTGATGACCCAGACTCCC CTGTCCCTGCCTGTGACTCCCGGAGAACCAGCCTCCATTTCCTGC CGGTCCTCCCAGTCCCTGCTGGACAGCGACGACGGCAACACTTA CCTGGACTGGTACTTGCAGAAGCCGGGCCAATCGCCTCGCCTGC TGATCTATACCCTGTCATACCGGGCCTCAGGAGTGCCTGACCGC TTCTCGGGATCAGGGAGCGGGACCGATTTCACCCTGAAAATTTC CCGAGTGGAAGCCGAGGACGTCGGACTGTACTACTGCACCCAGC GCCTCGAATTCCCGTCGATTACGTTTGGACAGGGTACCCGGCTT GAGATCAAGACCACTACCCCAGCACCGAGGCCACCCACCCCGGC TCCTACCATCGCCTCCCAGCCTCTGTCCCTGCGTCCGGAGGCATG TAGACCCGCAGCTGGTGGGGCCGTGCATACCCGGGGTCTTGACT TCGCCTGCGATATCTACATTTGGGCCCCTCTGGCTGGTACTTGCG GGGTCCTGCTGCTTTCACTCGTGATCACTCTTTACTGTAAGCGCG GTCGGAAGAAGCTGCTGTACATCTTTAAGCAACCCTTCATGAGG CCTGTGCAGACTACTCAAGAGGAGGACGGCTGTTCATGCCGGTT |

TABLE 10-continued

| Amino acid and nucleic acid sequences of exemplary hybridoma-derived anti-BCMA molecules | | |
|---|---|---|
| SEQ ID NO | Name/ Description | Sequence |
| | | CCCAGAGGAGGAGGAAGGCGGCTGCGAACTGCGCGTGAAATTC AGCCGCAGCGCAGATGCTCCAGCCTACCAGCAGGGGCAGAACC AGCTCTACAACGAACTCAATCTTGGTCGGAGAGAGGAGTACGAC GTGCTGGACAAGCGGAGAGGACGGGACCCAGAAATGGGCGGGA AGCCGCGCAGAAAGAATCCCCAAGAGGGCCTGTACAACGAGCT CCAAAAGGATAAGATGGCAGAAGCCTATAGCGAGATTGGTATG AAAGGGGAACGCAGAAGAGGCAAAGGCCACGACGGACTGTACC AGGGACTCAGCACCGCCACCAAGGACACCTATGACGCTCTTCAC ATGCAGGCCCTGCCGCCTCGG |
| Hy52 | | |
| SEQ ID NO: 160 | HCDR1 (Kabat) | SFRMN |
| SEQ ID NO: 161 | HCDR2 (Kabat) | SISSSSSYIYYADSVKG |
| SEQ ID NO: 162 | HCDR3 (Kabat) | WLSYYGMDV |
| SEQ ID NO: 163 | HCDR1 (Chothia) | GFTFSSF |
| SEQ ID NO: 164 | HCDR2 (Chothia) | SSSSSY |
| SEQ ID NO: 162 | HCDR3 (Chothia) | WLSYYGMDV |
| SEQ ID NO: 165 | HCDR1 (IMGT) | GFTFSSFR |
| SEQ ID NO: 166 | HCDR2 (IMGT) | ISSSSSYI |
| SEQ ID NO: 167 | HCDR3 (IMGT) | ARWLSYYGMDV |
| SEQ ID NO: 168 | VH | EVQLVESGGGLVKPGGSLRLSCAASGFTFSSFRMNWVRQAPGKGL EWVSSISSSSSYIYYADSVKGRFTISRDNAKNSLYLQMNSLRAEDTA VYYCARWLSYYGMDVWGQGTTVTVSS |
| SEQ ID NO: 169 | DNA VH | GAAGTGCAACTGGTGGAGAGCGGTGGAGGGCTTGTCAAGCCCG GAGGATCGCTGCGGCTGTCCTGTGCTGCGTCCGGGTTCACCTTCT CCTCGTTCCGCATGAACTGGGTCAGACAGGCACCGGGAAAGGGC CTCGAATGGGTGTCCTCAATCTCATCGTCCTCGTCCTACATCTAC TACGCCGACTCCGTGAAAGGCCGCTTCACCATCTCCCGGGACAA CGCCAAGAACTCGCTGTACCTCCAAATGAATAGCCTCAGGGCGG AAGATACTGCTGTGTATTACTGCGCACGCTGGCTTTCCTACTACG GCATGGACGTCTGGGGCCAAGGGACCACTGTGACCGTGTCTAGC |
| SEQ ID NO: 147 | LCDR1 (Kabat) | RSSQSLLDSDDGNTYLD |
| SEQ ID NO: 170 | LCDR2 (Kabat) | TLSFRAS |
| SEQ ID NO: 171 | LCDR3 (Kabat) | MQRIGFPIT |
| SEQ ID NO: 150 | LCDR1 (Chothia) | SQSLLDSDDGNTY |
| SEQ ID NO: 151 | LCDR2 (Chothia) | TLS |
| SEQ ID NO: 172 | LCDR3 (Chothia) | RIGFPI |
| SEQ ID NO: 153 | LCDR1 (IMGT) | QSLLDSDDGNTY |

TABLE 10-continued

Amino acid and nucleic acid sequences of exemplary hybridoma-derived anti-BCMA molecules

| SEQ ID NO | Name/ Description | Sequence |
|---|---|---|
| SEQ ID NO: 151 | LCDR2 (IMGT) | TLS |
| SEQ ID NO: 171 | LCDR3 (IMGT) | MQRIGFPIT |
| SEQ ID NO: 173 | VL | DIVMTQTPLSLPVTPGEPASISCRSSQSLLDSDDGNTYLDWYLQKPG QSPQLLIYTLSFRASGVPDRFSGSGSGTDFTLKIRRVEAEDVGVYYC MQRIGFPITFGQGTRLEIK |
| SEQ ID NO: 174 | DNA VL | GATATCGTGATGACCCAGACTCCCCTGTCCCTGCCTGTGACTCCC GGAGAACCAGCCTCCATTTCCTGCCGGTCCTCCCAGTCCCTGCTG GACAGCGACGACGGCAACACTTACCTGGACTGGTACTTGCAGAA GCCGGGCCAATCGCCTCAGCTGCTGATCTATACCCTGTCATTCCG GGCCTCAGGAGTGCCTGACCGCTTCTCGGGATCAGGGAGCGGGA CCGATTTCACCCTGAAAATTAGGCGAGTGGAAGCCGAGGACGTC GGAGTGTACTACTGCATGCAGCGCATCGGCTTCCCGATTACGTTT GGACAGGGTACCCGGCTTGAGATCAAG |
| SEQ ID NO: 63 | Linker | GGGGSGGGGSGGGGSGGGGS |
| SEQ ID NO: 175 | scFv (VH-linker-VL) | EVQLVESGGGLVKPGGSLRLSCAASGFTFSSFRMNWVRQAPGKGL EWVSSISSSSSYIYYADSVKGRFTISRDNAKNSLYLQMNSLRAEDTA VYYCARWLSYYGMDVWGQGTTVTVSSGGGGSGGGGSGGGGSGG GGSDIVMTQTPLSLPVTPGEPASISCRSSQSLLDSDDGNTYLDWYLQ KPGQSPQLLIYTLSFRASGVPDRFSGSGSGTDFTLKIRRVEAEDVGV YYCMQRIGFPITFGQGTRLEIK |
| SEQ ID NO: 176 | DNA scFv | GAAGTGCAACTGGTGGAGAGCGGTGGAGGGCTTGTCAAGCCCG GAGGATCGCTGCGGCTGTCCTGTGCTGCGTCCGGGTTCACCTTCT CCTCGTTCCGCATGAACTGGGTCAGACAGGCACCGGGAAAGGGC CTCGAATGGGTGTCCTCAATCTCATCGTCCTCGTCCTACATCTAC TACGCCGACTCCGTGAAAGGCCGCTTCACCATCTCCCGGGACAA CGCCAAGAACTCGCTGTACCTCCAAATGAATAGCCTCAGGGCGG AAGATACTGCTGTGTATTACTGCGCACGCTGGCTTTCCTACTACG GCATGGACGTCTGGGGCCAAGGGACCACTGTGACCGTGTCTAGC GGAGGCGGAGGTTCAGGGGGCGGTGGATCAGGCGGAGGAGGAT CGGGGGGTGGTGGATCGGATATCGTGATGACCCAGACTCCCCTG TCCCTGCCTGTGACTCCCGGAGAACCAGCCTCCATTTCCTGCCGG TCCTCCCAGTCCCTGCTGGACAGCGACGACGGCAACACTTACCT GGACTGGTACTTGCAGAAGCCGGGCCAATCGCCTCAGCTGCTGA TCTATACCCTGTCATTCCGGGCCTCAGGAGTGCCTGACCGCTTCT CGGGATCAGGGAGCGGGACCGATTTCACCCTGAAAATTAGGCG AGTGGAAGCCGAGGACGTCGGAGTGTACTACTGCATGCAGCGC ATCGGCTTCCCGATTACGTTTGGACAGGGTACCCGGCTTGAGAT CAAG |
| SEQ ID NO: 177 | Full CAR amino acid sequence | EVQLVESGGGLVKPGGSLRLSCAASGFTFSSFRMNWVRQAPGKGL EWVSSISSSSSYIYYADSVKGRFTISRDNAKNSLYLQMNSLRAEDTA VYYCARWLSYYGMDVWGQGTTVTVSSGGGGSGGGGSGGGGSGG GGSDIVMTQTPLSLPVTPGEPASISCRSSQSLLDSDDGNTYLDWYLQ KPGQSPQLLIYTLSFRASGVPDRFSGSGSGTDFTLKIRRVEAEDVGV YYCMQRIGFPITFGQGTRLEIKTTTPAPRPPTPAPTIASQPLSLRPEAC RPAAGGAVHTRGLDFACDIYIWAPLAGTCGVLLLSLVITLYCKRGR KKLLYIFKQPFMRPVQTTQEEDGCSCRFPEEEEGGCELRVKFSRSAD APAYQQGQNQLYNELNLGRREEYDVLDKRRGRDPEMGGKPRRKN PQEGLYNELQKDKMAEAYSEIGMKGERRRGKGHDGLYQGLSTAT KDTYDALHMQALPPR |
| SEQ ID NO: 178 | Full CAR DNA sequence | GAAGTGCAACTGGTGGAGAGCGGTGGAGGGCTTGTCAAGCCCG GAGGATCGCTGCGGCTGTCCTGTGCTGCGTCCGGGTTCACCTTCT CCTCGTTCCGCATGAACTGGGTCAGACAGGCACCGGGAAAGGGC CTCGAATGGGTGTCCTCAATCTCATCGTCCTCGTCCTACATCTAC TACGCCGACTCCGTGAAAGGCCGCTTCACCATCTCCCGGGACAA CGCCAAGAACTCGCTGTACCTCCAAATGAATAGCCTCAGGGCGG AAGATACTGCTGTGTATTACTGCGCACGCTGGCTTTCCTACTACG GCATGGACGTCTGGGGCCAAGGGACCACTGTGACCGTGTCTAGC GGAGGCGGAGGTTCAGGGGGCGGTGGATCAGGCGGAGGAGGAT CGGGGGGTGGTGGATCGGATATCGTGATGACCCAGACTCCCCTG TCCCTGCCTGTGACTCCCGGAGAACCAGCCTCCATTTCCTGCCGG TCCTCCCAGTCCCTGCTGGACAGCGACGACGGCAACACTTACCT GGACTGGTACTTGCAGAAGCCGGGCCAATCGCCTCAGCTGCTGA TCTATACCCTGTCATTCCGGGCCTCAGGAGTGCCTGACCGCTTCT |

TABLE 10-continued

| Amino acid and nucleic acid sequences of exemplary hybridoma-derived anti-BCMA molecules | | |
|---|---|---|
| SEQ ID NO | Name/ Description | Sequence |
| | | CGGGATCAGGGAGCGGGACCGATTTCACCCTGAAAATTAGGCG AGTGGAAGCCGAGGACGTCGGAGTGTACTACTGCATGCAGCGC ATCGGCTTCCCGATTACGTTTGGACAGGGTACCCGGCTTGAGAT CAAGACCACTACCCCAGCACCGAGGCCACCCACCCCGGCTCCTA CCATCGCCTCCCAGCCTCTGTCCCTGCGTCCGGAGGCATGTAGA CCCGCAGCTGGTGGGGCCGTGCATACCCGGGGTCTTGACTTCGC CTGCGATATCTACATTTGGGCCCCTCTGGCTGGTACTTGCGGGGT CCTGCTGCTTTCACTCGTGATCACTCTTTACTGTAAGCGCGGTCG GAAGAAGCTGCTGTACATCTTTAAGCAACCCTTCATGAGGCCTG TGCAGACTACTCAAGAGGAGGACGGCTGTTCATGCCGGTTCCCA GAGGAGGAGGAAGGCGGCTGCGAACTGCGCGTGAAATTCAGCC GCAGCGCAGATGCTCCAGCCTACCAGCAGGGGCAGAACCAGCT CTACAACGAACTCAATCTTGGTCGGAGAGAGGAGTACGACGTGC TGGACAAGCGGAGAGGACGGGACCCAGAAATGGGCGGGAAGCC GCGCAGAAAGAATCCCCAAGAGGGCCTGTACAACGAGCTCCAA AAGGATAAGATGGCAGAAGCCTATAGCGAGATTGGTATGAAAG GGGAACGCAGAAGAGGCAAAGGCCACGACGGACTGTACCAGGG ACTCAGCACCGCCACCAAGGACACCTATGACGCTCTTCACATGC AGGCCCTGCCGCCTCGG |

TABLE 11

| Kabat CDRs of exemplary hybridoma-derived anti-BCMA molecules | | | | | | |
|---|---|---|---|---|---|---|
| Kabat | HCDR1 | HCDR2 | HCDR3 | LCDR1 | LCDR2 | LCDR3 |
| Hy03 | GFWMS (SEQ ID NO: 137) | NIKQDGSEK YYVDSVRG (SEQ ID NO: 138) | ALDYYGMD V (SEQ ID NO: 139) | RSSQSLLDS DDGNTYLD (SEQ ID NO: 147) | TLSYRA S (SEQ ID NO: 148) | TQRLEFP SIT (SEQ ID NO: 149) |
| Hy52 | SFRMN (SEQ ID NO: 160) | SISSSSSYIYY ADSVKG (SEQ ID NO: 161) | WLSYYGMD V (SEQ ID NO: 162) | RSSQSLLDS DDGNTYLD (SEQ ID NO: 147) | TLSFRAS (SEQ ID NO: 170) | MQRIGFP IT (SEQ ID NO: 171) |
| Consensus | $X_1FX_2MX_3$, wherein $X_1$ is G or S; $X_2$ is W or R; and $X_3$ is S or N (SEQ ID NO: 179) | $X_1X_2X_3X_4X_5S$ $X_6X_7YYX_8DS$ $VX_9G$, wherein $X_1$ is N or S; $X_2$ is K or S; $X_3$ is Q or S; $X_4$ is D or S; $X_5$ is G or S; $X_6$ is E or Y; $X_7$ is K or I; $X_8$ is V or A; and $X_9$ is R or K (SEQ ID NO: 180) | $X_1LX_2YYGM$ DV, wherein $X_1$ is A or W; and $X_2$ is D or S (SEQ ID NO: 181) | RSSQSLLDS DDGNTYLD (SEQ ID NO: 147) | TLSXRA S, wherein X is Y or F (SEQ ID NO: 182) | $X_1QRX_2X_3$ $FPX_4IT$, wherein $X_1$ is T or M; $X_2$ is L or l; $X_3$ is E or G; and $X_4$ is S or absent (SEQ ID NO: 183) |

TABLE 12

| Chothia CDRs of exemplary hybridoma-derived anti-BCMA molecules | | | | | | |
|---|---|---|---|---|---|---|
| Chothia | HCDR1 | HCDR2 | HCDR3 | LCDRI | LCDR2 | LCDR3 |
| Hy03 | GFTFSGF (SEQ ID NO: 140) | KQDGSE (SEQ ID NO: 141) | ALDYYGMD V (SEQ ID NO: 139) | SQSLLDSD DGNTY (SEQ ID NO: 150) | TLS (SEQ ID NO: 151) | RLEFPSI (SEQ ID NO: 152) |

TABLE 12-continued

Chothia CDRs of exemplary hybridoma-derived anti-BCMA molecules

| Chothia | HCDR1 | HCDR2 | HCDR3 | LCDRI | LCDR2 | LCDR3 |
|---|---|---|---|---|---|---|
| Hy52 | GFTFSSF (SEQ ID NO: 163) | SSSSSY (SEQ ID NO: 164) | WLSYYGMD V (SEQ ID NO: 162) | SQSLLDSD DGNTY (SEQ ID NO: 150) | TLS (SEQ ID NO: 151) | RIGFPI (SEQ ID NO: 172) |
| Consensus | GFTFSXF, wherein X is G or S (SEQ ID NO: 184) | $X_1X_2X_3X_4SX_5$, wherein $X_1$ is K or S; $X_2$ is Q or S; $X_3$ is D or S; $X_4$ is G or S; and $X_5$ is E or Y (SEQ ID NO: 185) | $X_1LX_2YYGM$ DV, wherein $X_1$ is A or W; and $X_2$ is D or S (SEQ ID NO: 181) | SQSLLDSD DGNTY (SEQ ID NO: 150) | TLS (SEQ ID NO: 151) | $RX_1X_2FP$ $X_3I$, wherein $X_1$ is L or 1; $X_2$ is E or G; and $X_3$ is S or absent (SEQ ID NO: 186) |

TABLE 13

IMGT CDRs of exemplary hybridoma-derived anti-BCMA molecules

| IMGT | HCDR1 | HCDR2 | HCDR3 | LCDR1 | LCDR2 | LCDR3 |
|---|---|---|---|---|---|---|
| Hy03 | GFTFSGF W (SEQ ID NO: 142) | IKQDGSEK (SEQ ID NO: 143) | ARALDYYG MDV (SEQ ID NO: 144) | QSLLDSDD GNTY (SEQ ID NO: 153) | TLS (SEQ ID NO: 151) | TQRLEFPS IT (SEQ ID NO: 149) |
| Hy52 | GFTFSSFR (SEQ ID NO: 165) | ISSSSSYI (SEQ ID NO: 166) | ARWLSYYG MDV (SEQ ID NO: 167) | QSLLDSDD GNTY (SEQ ID NO: 153) | TLS (SEQ ID NO: 151) | MQRIGFPI T (SEQ ID NO: 171) |
| Consensus | $GFTFSX_1F$ $X_2$, wherein $X_1$ is G or S; and $X_2$ is W or R (SEQ ID NO: 187) | $IX_1X_2X_3X_4SX_5$ $X_6$, wherein $X_1$ is K or S; $X_2$ is Q or S; $X_3$ is D or S; $X_4$ is G or S; $X_5$ is E or Y; and $X_6$ is K or 1 (SEQ ID NO: 188) | $ARX_1LX_2YY$ GMDV, wherein $X_1$ is A or W; and $X_2$ is D or S (SEQ ID NO: 189) | QSLLDSDD GNTY (SEQ ID NO: 153) | TLS (SEQ ID NO: 151) | $X_1QRX_2X_3$ $FPX_4IT$, wherein $X_1$ is T or M; $X_2$ is L or 1; $X_3$ is E or G; and $X_4$ is S or absent (SEQ ID NO: 183) |

In some embodiments, the human anti-BCMA binding domain comprises a HC CDR1, HC CDR2, HC CDR3, LC CDR1, LC CDR2, and LC CDR3.

In certain embodiments, the CAR molecule described herein or the anti-BCMA binding domain described herein includes:

(1) one, two, or three light chain (LC) CDRs chosen from:

(i) a LC CDR1 of SEQ ID NO: 54, LC CDR2 of SEQ ID NO: 55 and LC CDR3 of SEQ ID NO: 56; and/or (2) one, two, or three heavy chain (HC) CDRs from one of the following:

(i) a HC CDR1 of SEQ ID NO: 44, HC CDR2 of SEQ ID NO: 45 and HC CDR3 of SEQ ID NO: 84;

(ii) a HC CDR1 of SEQ ID NO: 44, HC CDR2 of SEQ ID NO: 45 and HC CDR3 of SEQ ID NO: 46;

(iii) a HC CDR1 of SEQ ID NO: 44, HC CDR2 of SEQ ID NO: 45 and HC CDR3 of SEQ ID NO: 68; or (iv) a HC CDR1 of SEQ ID NO: 44, HC CDR2 of SEQ ID NO: 45 and HC CDR3 of SEQ ID NO: 76.

In certain embodiments, the CAR molecule described herein or the anti-BCMA binding domain described herein includes:

(1) one, two, or three light chain (LC) CDRs from one of the following:

(i) a LC CDR1 of SEQ ID NO: 95, LC CDR2 of SEQ ID NO: 131 and LC CDR3 of SEQ ID NO: 132;

(ii) a LC CDR1 of SEQ ID NO: 95, LC CDR2 of SEQ ID NO: 96 and LC CDR3 of SEQ ID NO: 97;

(iii) a LC CDR1 of SEQ ID NO: 95, LC CDR2 of SEQ ID NO: 114 and LC CDR3 of SEQ ID NO: 115; or (iv) a LC CDR1 of SEQ ID NO: 95, LC CDR2 of SEQ ID NO: 114 and LC CDR3 of SEQ ID NO: 97; and/or (2) one, two, or three heavy chain (HC) CDRs from one of the following:

(i) a HC CDR1 of SEQ ID NO: 86, HC CDR2 of SEQ ID NO: 130 and HC CDR3 of SEQ ID NO: 88;

(ii) a HC CDR1 of SEQ ID NO: 86, HC CDR2 of SEQ ID NO: 87 and HC CDR3 of SEQ ID NO: 88; or (iii) a HC CDR1 of SEQ ID NO: 86, HC CDR2 of SEQ ID NO: 109 and HC CDR3 of SEQ ID NO: 88.

In certain embodiments, the CAR molecule described herein or the anti-BCMA binding domain described herein includes:

(1) one, two, or three light chain (LC) CDRs from one of the following:

(i) a LC CDR1 of SEQ ID NO: 147, LC CDR2 of SEQ ID NO: 182 and LC CDR3 of SEQ ID NO: 183;

(ii) a LC CDR1 of SEQ ID NO: 147, LC CDR2 of SEQ ID NO: 148 and LC CDR3 of SEQ ID NO: 149; or (iii) a LC CDR1 of SEQ ID NO: 147, LC CDR2 of SEQ ID NO: 170 and LC CDR3 of SEQ ID NO: 171; and/or (2) one, two, or three heavy chain (HC) CDRs from one of the following:

(i) a HC CDR1 of SEQ ID NO: 179, HC CDR2 of SEQ ID NO: 180 and HC CDR3 of SEQ ID NO: 181;

(ii) a HC CDR1 of SEQ ID NO: 137, HC CDR2 of SEQ ID NO: 138 and HC CDR3 of SEQ ID NO: 139; or (iii) a HC CDR1 of SEQ ID NO: 160, HC CDR2 of SEQ ID NO: 161 and HC CDR3 of SEQ ID NO: 162.

In some embodiments, the HC CDR1, HC CDR2, HC CDR3, LC CDR1, LC CDR2, and LC CDR3 comprise the amino acid sequences of SEQ ID NOs: 44, 45, 84, 54, 55, and 56, respectively. In some embodiments, the HC CDR1, HC CDR2, HC CDR3, LC CDR1, LC CDR2, and LC CDR3 comprise the amino acid sequences of SEQ ID NOs: 44, 45, 46, 54, 55, and 56, respectively. In some embodiments, the HC CDR1, HC CDR2, HC CDR3, LC CDR1, LC CDR2, and LC CDR3 comprise the amino acid sequences of SEQ ID NOs: 44, 45, 68, 54, 55, and 56, respectively. In some embodiments, the HC CDR1, HC CDR2, HC CDR3, LC CDR1, LC CDR2, and LC CDR3 comprise the amino acid sequences of SEQ ID NOs: 44, 45, 76, 54, 55, and 56, respectively.

In some embodiments, the HC CDR1, HC CDR2, HC CDR3, LC CDR1, LC CDR2, and LC CDR3 comprise the amino acid sequences of SEQ ID NOs: 47, 48, 84, 57, 58, and 59, respectively. In some embodiments, the HC CDR1, HC CDR2, HC CDR3, LC CDR1, LC CDR2, and LC CDR3 comprise the amino acid sequences of SEQ ID NOs: 47, 48, 46, 57, 58, and 59, respectively. In some embodiments, the HC CDR1, HC CDR2, HC CDR3, LC CDR1, LC CDR2, and LC CDR3 comprise the amino acid sequences of SEQ ID NOs: 47, 48, 68, 57, 58, and 59, respectively. In some embodiments, the HC CDR1, HC CDR2, HC CDR3, LC CDR1, LC CDR2, and LC CDR3 comprise the amino acid sequences of SEQ ID NOs: 47, 48, 76, 57, 58, and 59, respectively.

In some embodiments, the HC CDR1, HC CDR2, HC CDR3, LC CDR1, LC CDR2, and LC CDR3 comprise the amino acid sequences of SEQ ID NOs: 49, 50, 85, 60, 58, and 56, respectively. In some embodiments, the HC CDR1, HC CDR2, HC CDR3, LC CDR1, LC CDR2, and LC CDR3 comprise the amino acid sequences of SEQ ID NOs: 49, 50, 51, 60, 58, and 56, respectively. In some embodiments, the HC CDR1, HC CDR2, HC CDR3, LC CDR1, LC CDR2, and LC CDR3 comprise the amino acid sequences of SEQ ID NOs: 49, 50, 69, 60, 58, and 56, respectively. In some embodiments, the HC CDR1, HC CDR2, HC CDR3, LC CDR1, LC CDR2, and LC CDR3 comprise the amino acid sequences of SEQ ID NOs: 49, 50, 77, 60, 58, and 56, respectively.

In some embodiments, the human anti-BCMA binding domain comprises a scFv comprising a VH (e.g., a VH described herein) and VL (e.g., a VL described herein). In some embodiments, the VH is attached to the VL via a linker, e.g., a linker described herein, e.g., a linker described in Table 1. In some embodiments, the human anti-BCMA binding domain comprises a $(Gly_4\text{-}Ser)n$ linker, wherein n is 1, 2, 3, 4, 5, or 6, preferably 3 or 4 (SEQ ID NO: 26). The light chain variable region and heavy chain variable region of a scFv can be, e.g., in any of the following orientations: light chain variable region-linker-heavy chain variable region or heavy chain variable region-linker-light chain variable region.

In one aspect, the anti-BCMA binding domain is a fragment, e.g., a single chain variable fragment (scFv). In one aspect, the anti-BCMA binding domain is a Fv, a Fab, a (Fab')2, or a bifunctional (e.g. bi-specific) hybrid antibody (e.g., Lanzavecchia et al., Eur. J. Immunol. 17, 105 (1987)). In one aspect, the antibodies and fragments thereof of the invention binds a BCMA protein with wild-type or enhanced affinity.

In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)n$, where n is a positive integer equal to or greater than 1 (SEQ ID NO: 25). In some embodiments, the linker can be $(Gly_4Ser)_4$ (SEQ ID NO: 27) or $(Gly_4Ser)_3$ (SEQ ID NO: 28). Variation in the linker length may retain or enhance activity, giving rise to superior efficacy in activity studies.

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the CAR-expressing cell, e.g., CART cell, surface. In a different aspect the amino acid sequence of the transmembrane domain may be modified or substituted so as to minimize interactions with the binding domains of the native binding partner present in the same CAR-expressing cell, e.g., CART.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain of particular use in this invention may include at least the transmembrane region(s) of, e.g., the alpha, beta or zeta chain of T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154. In some embodiments, a transmembrane domain may include at least the transmembrane region(s) of a costimulatory molecule, e.g., MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In some instances, the transmembrane domain can be attached to the extracellular region of the CAR, e.g., the antigen binding domain of the CAR, via a hinge, e.g., a hinge from a human protein. For example, In some embodiments, the hinge can be a human Ig (immunoglobulin) hinge, e.g., an IgG4 hinge, or a CD8a hinge. In some embodiments, the hinge or spacer comprises (e.g., consists of) the amino acid sequence of SEQ ID NO: 2. In one aspect, the transmembrane domain comprises (e.g., consists of) a transmembrane domain of SEQ ID NO: 6.

In one aspect, the hinge or spacer comprises an IgG4 hinge. For example, In some embodiments, the hinge or spacer comprises a hinge of SEQ ID NO: 3. In some embodiments, the hinge or spacer comprises a hinge encoded by the nucleotide sequence of SEQ ID NO: 14.

In one aspect, the hinge or spacer comprises an IgD hinge. For example, In some embodiments, the hinge or spacer comprises a hinge of the amino acid sequence of SEQ ID NO: 4. In some embodiments, the hinge or spacer comprises a hinge encoded by the nucleotide sequence of SEQ ID NO:15.

In one aspect, the transmembrane domain may be recombinant, in which case it will comprise predominantly hydrophobic residues such as leucine and valine. In one aspect a triplet of phenylalanine, tryptophan and valine can be found at each end of a recombinant transmembrane domain.

Optionally, a short oligo- or polypeptide linker, between 2 and 10 amino acids in length may form the linkage between the transmembrane domain and the cytoplasmic region of the CAR. A glycine-serine doublet provides a particularly suitable linker. For example, in one aspect, the linker comprises the amino acid sequence of SEQ ID NO: 5. In some embodiments, the linker is encoded by a nucleotide sequence of SEQ ID NO: 16.

In one aspect, the hinge or spacer comprises a KIR2DS2 hinge.

Cytoplasmic Domain

The cytoplasmic domain or region of a CAR of the present invention includes an intracellular signaling domain. An intracellular signaling domain is generally responsible for activation of at least one of the normal effector functions of the immune cell in which the CAR has been introduced.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of TCR zeta, FcR gamma, FcR beta, CD3 gamma, CD3 delta, CD3 epsilon, CD5, CD22, CD79a, CD79b, CD278 (also known as "ICOS"), FcεRI, DAP10, DAP12, and CD66d. In some embodiments, a CAR of the invention comprises an intracellular signaling domain, e.g., a primary signaling domain of CD3-zeta.

In some embodiments, a primary signaling domain comprises a modified ITAM domain, e.g., a mutated ITAM domain which has altered (e.g., increased or decreased) activity as compared to the native ITAM domain. In some embodiments, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

Further examples of molecules containing a primary intracellular signaling domain that are of particular use in the invention include those of DAP10, DAP12, and CD32.

The intracellular signalling domain of the CAR can comprise the primary signalling domain, e.g., CD3-zeta signaling domain, by itself or it can be combined with any other desired intracellular signaling domain(s) useful in the context of a CAR of the invention. For example, the intracellular signaling domain of the CAR can comprise a primary signalling domain, e.g., CD3 zeta chain portion, and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706). The intracellular signaling sequences within the cytoplasmic portion of the CAR of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In some embodiments, a glycine-serine doublet can be used as a suitable linker. In some embodiments, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In some embodiments, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of 4-1BB is a signaling domain of SEQ ID NO: 7. In one aspect, the signaling domain of CD3-zeta is a signaling domain of SEQ ID NO: 9 (mutant CD3zeta) or SEQ ID NO: 10 (wild type human CD3zeta).

In one aspect, the intracellular signaling domain is designed to comprise the signaling domain of CD3-zeta and the signaling domain of CD27. In one aspect, the signaling domain of CD27 comprises the amino acid sequence of SEQ ID NO: 8. In one aspect, the signalling domain of CD27 is encoded by the nucleic acid sequence of SEQ ID NO: 19.

In one aspect, the intracellular is designed to comprise the signaling domain of CD3-zeta and the signaling domain of CD28. In one aspect, the signaling domain of CD28 comprises the amino acid sequence of SEQ ID NO: 36. In one aspect, the signaling domain of CD28 is encoded by the nucleic acid sequence of SEQ ID NO: 37.

In one aspect, the intracellular is designed to comprise the signaling domain of CD3-zeta and the signaling domain of ICOS. In one aspect, the signaling domain of ICOS comprises the amino acid sequence of SEQ ID NO: 38. In one aspect, the signaling domain of ICOS is encoded by the nucleic acid sequence of SEQ ID NO: 39.

CAR Configurations

Multi-Specific CARs

In an embodiment, a CAR of the invention is a multi-specific CAR. In some embodiments, the multi-specific CAR is a bispecific CAR. In some embodiments, the bispecific CAR comprises an antigen binding domain which is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv, or fragment thereof, have binding specificity for a first epitope and a scFv, or fragment thereof, have binding specificity for a second epitope.

In certain embodiments, a CAR of the invention comprises an antigen binding domain that is a multi-specific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhydryl reactive groups, as described in, e.g., U.S. Pat. No. 5,273, 743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecific, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760-A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

Within each antibody or antibody fragment (e.g., scFv) of a bispecific antibody molecule, the VH can be upstream or downstream of the VL. In some embodiments, the upstream antibody or antibody fragment (e.g., scFv) is arranged with its VH ($VH_1$) upstream of its VL ($VL_1$) and the downstream antibody or antibody fragment (e.g., scFv) is arranged with its VL ($VL_2$) upstream of its VH ($VH_2$), such that the overall bispecific antibody molecule has the arrangement $VH_1$-$VL_1$-$VL_2$-$VH_2$. In other embodiments, the upstream antibody or antibody fragment (e.g., scFv) is arranged with its VL ($VL_1$) upstream of its VH ($VH_1$) and the downstream antibody or antibody fragment (e.g., scFv) is arranged with its VH ($VH_2$) upstream of its VL ($VL_2$), such that the overall bispecific antibody molecule has the arrangement $VL_1$-$VH_1$-$VH_2$-$VL_2$. Optionally, a linker is disposed between the two antibodies or antibody fragments (e.g., scFvs), e.g., between $VL_1$ and $VL_2$ if the construct is arranged as $VH_1$-$VL_1$-$VL_2$-$VH_2$, or between $VH_1$ and $VH_2$ if the construct is arranged as $VL_1$-$VH_1$-$VH_2$-$VL_2$. The linker may be a linker as described herein, e.g., a ($Gly_4$-Ser)n linker, wherein n is 1, 2, 3, 4, 5, or 6, preferably 4 (SEQ ID NO: 26). In general, the linker between the two scFvs should be long enough to avoid mispairing between the domains of the two scFvs. Optionally, a linker is disposed between the VL and VH of the first scFv. Optionally, a linker is disposed between the VL and VH of the second scFv. In constructs that have multiple linkers, any two or more of the linkers can be the same or different. Accordingly, in some embodiments, a bispecific CAR comprises VLs, VHs, and optionally one or more linkers in an arrangement as described herein.

In one aspect, the bispecific antibody molecule is characterized by a first immunoglobulin variable domain sequence, e.g., a scFv, which has binding specificity for BCMA, e.g., comprises a scFv as described herein, e.g., as described in Tables 2, 6, and 10, or comprises the light chain CDRs and/or heavy chain CDRs from a BCMA scFv described herein, and a second immunoglobulin variable domain sequence that has binding specificity for a second epitope on a different antigen. In some aspects the second immunoglobulin variable domain sequence has binding specificity for an antigen expressed on AML cells, e.g., an antigen other than BCMA. For example, the second immunoglobulin variable domain sequence has binding specificity for CD123. As another example, the second immunoglobulin variable domain sequence has binding specificity for CLL-1. As another example, the second immunoglobulin variable domain sequence has binding specificity for CD34. As another example, the second immunoglobulin variable domain sequence has binding specificity for FLT3. For example, the second immunoglobulin variable domain sequence has binding specificity for folate receptor beta. In some aspects, the second immunoglobulin variable domain sequence has binding specificity for an antigen expressed on B-cells, for example, CD10, CD19, CD20, CD22, CD34, CD123, FLT-3, ROR1, CD79b, CD179b, or CD79a.

Chimeric TCR

In one aspect, the anti-BCMA antibodies and antibody fragments of the present invention (for example, those disclosed in Tables 2, 6, and 10) can be grafted to one or more constant domain of a T cell receptor ("TCR") chain, for example, a TCR alpha or TCR beta chain, to create a chimeric TCR that binds specifically to BCMA. Without being bound by theory, it is believed that chimeric TCRs will signal through the TCR complex upon antigen binding. For example, a BCMA scFv as disclosed herein, can be grafted to the constant domain, e.g., at least a portion of the extracellular constant domain, the transmembrane domain and the cytoplasmic domain, of a TCR chain, for example, the TCR alpha chain and/or the TCR beta chain. As another example, a BCMA antibody fragment, for example a VL domain as described herein, can be grafted to the constant domain of a TCR alpha chain, and a BCMA antibody fragment, for example a VH domain as described herein, can be grafted to the constant domain of a TCR beta chain (or alternatively, a VL domain may be grafted to the constant domain of the TCR beta chain and a VH domain may be grafted to a TCR alpha chain). As another example, the CDRs of an anti-BCMA antibody or antibody fragment, e.g., the CDRs of an anti-BCMA antibody or antibody fragment as described in Tables 2-13 may be grafted into a TCR alpha and/or beta chain to create a chimeric TCR that binds specifically to BCMA. For example, the LCDRs disclosed herein may be grafted into the variable domain of a TCR alpha chain and the HCDRs disclosed herein may be grafted to the variable domain of a TCR beta chain, or vice versa. Such chimeric TCRs may be produced by methods known in the art (For example, Willemsen R A et al, Gene Therapy 2000; 7: 1369-1377; Zhang T et al, Cancer Gene Ther 2004; 11: 487-496; Aggen et al, Gene Ther. 2012 April; 19(4): 365-74).

Additional Embodiments

In one aspect, the CAR-expressing cell described herein can further comprise a second CAR, e.g., a second CAR that includes a different antigen binding domain, e.g., to the same target (BCMA) or a different target (e.g., CD19, CD20, or CS-1, or other multiple myeloma targets, e.g., kappa light chain, CD138, Lewis Y antigen, or CD38 (Garfall et al., Discovery Medicine, 2014, 17(91):37-46)). In some embodiments, the CAR-expressing cell comprises a first CAR that targets a first antigen and includes an intracellular signaling domain having a costimulatory signaling domain but not a primary signaling domain, and a second CAR that targets a second, different, antigen and includes an intracellular signaling domain having a primary signaling domain but not a costimulatory signaling domain. While not wishing to be bound by theory, placement of a costimulatory signaling domain, e.g., 4-1BB, CD28, CD27 ICOS, or OX-40, onto the first CAR, and the primary signaling domain, e.g., CD3 zeta, on the second CAR can limit the CAR activity to cells where both targets are expressed. In some embodiments, the CAR expressing cell comprises a first BCMA CAR that includes a BCMA binding domain, a transmembrane domain and a costimulatory domain and a second CAR that targets an antigen other than BCMA (e.g., an antigen expressed on leukemia or lymphoma cells, e.g., CD19, CD20, CS-1, kappa light chain, CD139, Lewis Y antigen, or CD38) and includes an antigen binding domain, a transmembrane domain and a primary signaling domain. In another embodiment, the CAR expressing cell comprises a first BCMA CAR that includes a BCMA binding domain, a transmembrane domain and a primary signaling domain and a second CAR that targets an antigen other than BCMA (e.g., an antigen expressed on leukemia or lymphoma cells, e.g., CD19, CD20, CS-1, kappa light chain, CD139, Lewis Y antigen, or CD38) and includes an antigen binding domain to the antigen, a transmembrane domain and a costimulatory signaling domain. In some embodiments, the CAR-expressing cell comprises a BCMA CAR described herein and a CAR that targets CD19 (CD19 CAR).

In some embodiments, the CAR-expressing cell comprises a BCMA CAR described herein and an inhibitory CAR. In some embodiments, the inhibitory CAR comprises an antigen binding domain that binds an antigen found on normal cells but not cancer cells. In some embodiments, the inhibitory CAR comprises the antigen binding domain, a transmembrane domain and an intracellular domain of an inhibitory molecule. For example, the intracellular domain of the inhibitory CAR can be an intracellular domain of PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta.

In some embodiments, when the CAR-expressing cell comprises two or more different CARs, the antigen binding domains of the different CARs can be such that the antigen binding domains do not interact with one another. For example, a cell expressing a first and second CAR can have an antigen binding domain of the first CAR, e.g., as a fragment, e.g., an scFv, that does not form an association with the antigen binding domain of the second CAR, e.g., the antigen binding domain of the second CAR is a VHH.

In some embodiments, the antigen binding domain comprises a single domain antigen binding (SDAB) molecules include molecules whose complementarity determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules. SDAB molecules may be derived from any species including, but not limited to mouse, human, camel, llama, lamprey, fish, shark, goat, rabbit, and bovine. This term also includes naturally occurring single domain antibody molecules from species other than Camelidae and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

According to another aspect, an SDAB molecule is a naturally occurring single domain antigen binding molecule known as heavy chain devoid of light chains. Such single domain molecules are disclosed in WO 9404678 and Hamers-Casterman, C. et al. (1993) Nature 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

The SDAB molecules can be recombinant, CDR-grafted, humanized, camelized, de-immunized and/or in vitro generated (e.g., selected by phage display).

It has also been discovered, that cells having a plurality of chimeric membrane embedded receptors comprising an antigen binding domain that interactions between the antigen binding domain of the receptors can be undesirable, e.g., because it inhibits the ability of one or more of the antigen binding domains to bind its cognate antigen. Accordingly, disclosed herein are cells having a first and a second non-naturally occurring chimeric membrane embedded receptor comprising antigen binding domains that minimize such interactions. Also disclosed herein are nucleic acids encoding a first and a second non-naturally occurring chimeric membrane embedded receptor comprising antigen binding domains that minimize such interactions, as well as methods of making and using such cells and nucleic acids. In an embodiment the antigen binding domain of one of said first said second non-naturally occurring chimeric membrane embedded receptor, comprises an scFv, and the other comprises a single VH domain, e.g., a camelid, shark, or lamprey single VH domain, or a single VH domain derived from a human or mouse sequence.

In some embodiments, the claimed invention comprises a first and second CAR, wherein the antigen binding domain of one of said first CAR said second CAR does not comprise a variable light domain and a variable heavy domain. In some embodiments, the antigen binding domain of one of said first CAR said second CAR is an scFv, and the other is not an scFv. In some embodiments, the antigen binding domain of one of said first CAR said second CAR comprises a single VH domain, e.g., a camelid, shark, or lamprey single VH domain, or a single VH domain derived from a human or mouse sequence. In some embodiments, the antigen binding domain of one of said first CAR said second CAR comprises a nanobody. In some embodiments, the antigen binding domain of one of said first CAR said second CAR comprises a camelid VHH domain.

In some embodiments, the antigen binding domain of one of said first CAR said second CAR comprises an scFv, and the other comprises a single VH domain, e.g., a camelid, shark, or lamprey single VH domain, or a single VH domain derived from a human or mouse sequence. In some embodiments, the antigen binding domain of one of said first CAR said second CAR comprises an scFv, and the other comprises a nanobody. In some embodiments, the antigen binding domain of one of said first CAR said second CAR comprises an scFv, and the other comprises a camelid VHH domain.

In some embodiments, when present on the surface of a cell, binding of the antigen binding domain of said first CAR to its cognate antigen is not substantially reduced by the presence of said second CAR. In some embodiments, binding of the antigen binding domain of said first CAR to its cognate antigen in the presence of said second CAR is 85%, 90%, 95%, 96%, 97%, 98% or 99% of binding of the antigen binding domain of said first CAR to its cognate antigen in the absence of said second CAR.

In some embodiments, when present on the surface of a cell, the antigen binding domains of said first CAR said second CAR, associate with one another less than if both were scFv antigen binding domains. In some embodiments, the antigen binding domains of said first CAR said second CAR, associate with one another 85%, 90%, 95%, 96%, 97%, 98% or 99% less than if both were scFv antigen binding domains.

In another aspect, the CAR-expressing cell described herein can further express another agent, e.g., an agent which enhances the activity of a CAR-expressing cell. For example, In some embodiments, the agent can be an agent which inhibits an inhibitory molecule, e.g., an agent described herein. Inhibitory molecules, e.g., PD1, can, in some embodiments, decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In some embodiments, the agent which inhibits an inhibitory molecule comprises a first polypeptide, e.g., an inhibitory molecule, associated with a second polypeptide that provides a positive signal to the cell, e.g., an intracellular signaling domain described herein. In some embodiments, the agent comprises a first polypeptide, e.g., of an inhibitory molecule such as PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27 ICOS, or CD28, e.g., as described herein) and/or a primary signaling domain (e.g., a CD3 zeta signaling domain described herein). In some embodiments, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). In embodiments, the CAR-expressing cell described herein comprises a switch costimulatory receptor, e.g., as described in WO 2013/019615, which is incorporated herein by reference in its entirety. PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In some embodiments, the agent comprises the extracellular domain (ECD) of an inhibitory molecule, e.g., Programmed Death 1 (PD1), can be fused to a transmembrane domain and intracellular signaling domains such as 41BB and CD3 zeta (also referred to herein as a PD1 CAR). In some embodiments, the PD1 CAR, when used in combinations with a BCMA CAR described herein, improves the persistence of the CAR-expressing cell, e.g., T cell or NK cell. In some embodiments, the CAR is a PD1 CAR comprising the extracellular domain of PD1 indicated as underlined in SEQ ID NO: 24. In some embodiments, the PD1 CAR comprises the amino acid sequence of SEQ ID NO: 24.

In some embodiments, the PD1 CAR comprises the amino acid sequence provided below (SEQ ID NO: 22).

In some embodiments, the agent comprises a nucleic acid sequence encoding the PD1 CAR, e.g., the PD1 CAR described herein. In some embodiments, the nucleic acid sequence for the PD1 CAR is provided as SEQ ID NO: 23, with the PD1 ECD underlined.

In another aspect, the present invention provides a population of CAR-expressing cells, e.g., CART cells or CAR-expressing NK cells. In some embodiments, the population of CAR-expressing cells comprises a mixture of cells expressing different CARs. For example, In some embodiments, the population of CAR-expressing cells (e.g., CART cells or CAR-expressing NK cells) can include a first cell expressing a CAR having an anti-BCMA binding domain described herein, and a second cell expressing a CAR having a different anti-BCMA binding domain, e.g., an anti-BCMA binding domain described herein that differs from the anti-BCMA binding domain in the CAR expressed by the first cell. As another example, the population of CAR-expressing cells can include a first cell expressing a CAR that includes an anti-BCMA binding domain, e.g., as described herein, and a second cell expressing a CAR that includes an antigen binding domain to a target other than BCMA (e.g., CD19, CD20, CS-1, kappa light chain, CD139, Lewis Y antigen, or CD38). In some embodiments, the population of CAR-expressing cells includes a first cell expressing a CAR comprising an anti-BCMA binding domain, e.g., as described herein, and a second cell expressing a CAR comprising an antigen binding domain that targets CD19 (CD19 CAR). In some embodiments, the population of CAR-expressing cells includes, e.g., a first cell expressing a CAR that includes a primary intracellular signaling domain, and a second cell expressing a CAR that includes a secondary signaling domain.

In another aspect, the present invention provides a population of cells wherein at least one cell in the population expresses a CAR having an anti-BCMA domain described herein, and a second cell expressing another agent, e.g., an agent which enhances the activity of a CAR-expressing cell. For example, In some embodiments, the agent can be an agent which inhibits an inhibitory molecule. Inhibitory molecules, e.g., can, in some embodiments, decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In some embodiments, the agent which inhibits an inhibitory molecule comprises a first polypeptide, e.g., an inhibitory molecule, associated with a second polypeptide that provides a positive signal to the cell, e.g., an intracellular signaling domain described herein. In some embodiments, the agent comprises a first polypeptide, e.g., of an inhibitory molecule such as PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta, or a fragment of any of these (e.g., at least a portion of an extracellular domain of any of these), and a second polypeptide which is an intracellular signaling domain described herein (e.g., comprising a costimulatory domain (e.g., 41BB, CD27, ICOS, or CD28, e.g., as described herein) and/or a primary signaling domain (e.g., a CD3 zeta signaling domain described herein). In some embodiments, the agent comprises a first polypeptide of PD1 or a fragment thereof (e.g., at least a portion of the extracellular domain of PD1), and a second polypeptide of an intracellular signaling domain described herein (e.g., a CD28 signaling domain described herein and/or a CD3 zeta signaling domain described herein).

In one aspect, the present invention provides methods comprising administering a population of CAR-expressing cells (e.g., CART cells or CAR-expressing NK cells), e.g., a mixture of cells expressing different CARs, in combination with another agent, e.g., a kinase inhibitor, such as a kinase inhibitor described herein. In another aspect, the present invention provides methods comprising administering a population of cells wherein at least one cell in the population expresses a CAR having an anti-cancer associated antigen binding domain as described herein, and a second cell expressing another agent, e.g., an agent which enhances the activity of a CAR-expressing cell, in combination with another agent, e.g., a kinase inhibitor, such as a kinase inhibitor described herein.

Natural Killer Cell Receptor (NKR) CARs

In an embodiment, the CAR molecule described herein comprises one or more components of a natural killer cell receptor (NKR), thereby forming an NKR-CAR. The NKR component can be a transmembrane domain, a hinge domain, or a cytoplasmic domain from any of the following natural killer cell receptors: killer cell immunoglobulin-like receptor (KIR), e.g., KIR2DL1, KIR2DL2/L3, KIR2DL4, KIR2DL5A, KIR2DL5B, KIR2DS1, KIR2DS2, KIR2DS3, KIR2DS4, DIR2DS5, KIR3DL1/S1, KIR3DL2, KIR3DL3, KIR2DP1, and KIR3DP1; natural cytotoxicity receptor (NCR), e.g., NKp30, NKp44, NKp46; signaling lymphocyte activation molecule (SLAM) family of immune cell receptors, e.g., CD48, CD229, 2B4, CD84, NTB-A, CRACC, BLAME, and CD2F-10; Fc receptor (FcR), e.g., CD16, and CD64; and Ly49 receptors, e.g., LY49A, LY49C. The NKR-CAR molecules described herein may interact with an adaptor molecule or intracellular signaling domain, e.g., DAP12. Exemplary configurations and sequences of CAR molecules comprising NKR components are described in International Publication No. WO2014/145252, the contents of which are hereby incorporated by reference.

Strategies for Regulating Chimeric Antigen Receptors

There are many ways CAR activities can be regulated. In some embodiments, a regulatable CAR (RCAR) where the CAR activity can be controlled is desirable to optimize the safety and efficacy of a CAR therapy. For example, inducing apoptosis using, e.g., a caspase fused to a dimerization domain (see, e.g., Di et al., N Engl. J. Med. 2011 Nov. 3; 365(18):1673-1683), can be used as a safety switch in the CAR therapy of the instant invention. In another example, CAR-expressing cells can also express an inducible Caspase-9 (iCaspase-9) molecule that, upon administration of a dimerizer drug (e.g., rimiducid (also called AP1903 (Bellicum Pharmaceuticals) or AP20187 (Ariad)) leads to activation of the Caspase-9 and apoptosis of the cells. The iCaspase-9 molecule contains a chemical inducer of dimerization (CID) binding domain that mediates dimerization in the presence of a CID. This results in inducible and selective depletion of CAR-expressing cells. In some cases, the iCaspase-9 molecule is encoded by a nucleic acid molecule separate from the CAR-encoding vector(s). In some cases, the iCaspase-9 molecule is encoded by the same nucleic acid molecule as the CAR-encoding vector. The iCaspase-9 can provide a safety switch to avoid any toxicity of CAR-expressing cells. See, e.g., Song et al. Cancer Gene Ther. 2008; 15(10):667-75; Clinical Trial Id. No. NCT02107963; and Di Stasi et al. N. Engl. J. Med. 2011; 365:1673-83.

Alternative strategies for regulating the CAR therapy of the instant invention include utilizing small molecules or antibodies that deactivate or turn off CAR activity, e.g., by deleting CAR-expressing cells, e.g., by inducing antibody dependent cell-mediated cytotoxicity (ADCC). For example, CAR-expressing cells described herein may also express an antigen that is recognized by molecules capable of inducing cell death, e.g., ADCC or compliment-induced cell death. For example, CAR expressing cells described herein may also express a receptor capable of being targeted by an antibody or antibody fragment. Examples of such receptors include EpCAM, VEGFR, integrins (e.g., integrins αvβ3, α4, αI¾β3, α4β7, α5β1, αvβ3, αv), members of the TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/lgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof (e.g., versions preserving one or more extracellular epitopes but lacking one or more regions within the cytoplasmic domain). For example, CAR-expressing cells described herein may also express a truncated epidermal growth factor receptor (EGFR) which lacks signaling capacity but retains the epitope that is recognized by molecules capable of inducing ADCC, e.g., cetuximab (ERBITUX®), such that administration of cetuximab induces ADCC and subsequent depletion of the CAR-expressing cells (see, e.g., WO2011/056894, and Jonnalagadda et al., Gene Ther. 2013; 20(8)853-860). Another strategy includes expressing a highly compact marker/suicide gene that combines target epitopes from both CD32 and CD20 antigens in the CAR-expressing cells described herein, which binds rituximab, resulting in selective depletion of the CAR-expressing cells, e.g., by ADCC (see, e.g., Philip et al., Blood. 2014; 124(8)1277-1287). Other methods for depleting CAR-expressing cells described herein include administration of CAMPATH®, a monoclonal anti-CD52 antibody that selectively binds and targets mature lymphocytes, e.g., CAR-expressing cells, for destruction, e.g., by inducing ADCC. In other embodiments, CAR-expressing cells can be selectively targeted using a CAR ligand, e.g., an anti-idiotypic antibody. In some embodiments, the anti-idiotypic antibody can cause effector cell activity, e.g, ADCC or ADC activities, thereby reducing the number of CAR-expressing cells. In other embodiments, the CAR ligand, e.g., the anti-idiotypic antibody, can be coupled to an agent that induces cell killing, e.g., a toxin, thereby reducing the number of CAR-expressing cells. Alternatively, the CAR molecules themselves can be configured such that the activity can be regulated, e.g., turned on and off, as described below.

In some embodiments, a RCAR comprises a set of polypeptides, typically two in the simplest embodiments, in which the components of a standard CAR described herein, e.g., an antigen binding domain and an intracellular signaling domain, are partitioned on separate polypeptides or members. In some embodiments, the set of polypeptides include a dimerization switch that, upon the presence of a dimerization molecule, can couple the polypeptides to one another, e.g., can couple an antigen binding domain to an intracellular signaling domain. Additional description and exemplary configurations of such regulatable CARs are provided herein and in International Publication No. WO 2015/090229, hereby incorporated by reference in its entirety.

In an embodiment, an RCAR comprises two polypeptides or members: 1) an intracellular signaling member comprising an intracellular signaling domain, e.g., a primary intracellular signaling domain described herein, and a first switch domain; 2) an antigen binding member comprising an antigen binding domain, e.g., that targets a tumor antigen described herein, as described herein and a second switch domain. Optionally, the RCAR comprises a transmembrane domain described herein. In an embodiment, a transmembrane domain can be disposed on the intracellular signaling member, on the antigen binding member, or on both. (Unless otherwise indicated, when members or elements of an RCAR are described herein, the order can be as provided, but other orders are included as well. In other words, in an embodiment, the order is as set out in the text, but in other embodiments, the order can be different. E.g., the order of elements on one side of a transmembrane region can be different from the example, e.g., the placement of a switch domain relative to a intracellular signaling domain can be different, e.g., reversed).

In an embodiment, the first and second switch domains can form an intracellular or an extracellular dimerization switch. In an embodiment, the dimerization switch can be a homodimerization switch, e.g., where the first and second switch domain are the same, or a heterodimerization switch, e.g., where the first and second switch domain are different from one another.

In embodiments, an RCAR can comprise a "multi switch." A multi switch can comprise heterodimerization switch domains or homodimerization switch domains. A multi switch comprises a plurality of, e.g., 2, 3, 4, 5, 6, 7, 8, 9, or 10, switch domains, independently, on a first member, e.g., an antigen binding member, and a second member, e.g., an intracellular signaling member. In an embodiment, the first member can comprise a plurality of first switch domains, e.g., FKBP-based switch domains, and the second member can comprise a plurality of second switch domains, e.g., FRB-based switch domains. In an embodiment, the first member can comprise a first and a second switch domain, e.g., a FKBP-based switch domain and a FRB-based switch domain, and the second member can comprise a first and a second switch domain, e.g., a FKBP-based switch domain and a FRB-based switch domain.

In an embodiment, the intracellular signaling member comprises one or more intracellular signaling domains, e.g., a primary intracellular signaling domain and one or more costimulatory signaling domains.

In an embodiment, the antigen binding member may comprise one or more intracellular signaling domains, e.g., one or more costimulatory signaling domains. In an embodiment, the antigen binding member comprises a plurality, e.g., 2 or 3 costimulatory signaling domains described herein, e.g., selected from 4-1BB, CD28, CD27, ICOS, and OX40, and in embodiments, no primary intracellular signaling domain. In an embodiment, the antigen binding member comprises the following costimulatory signaling domains, from the extracellular to intracellular direction: 4-1BB-CD27; 4-1BB-CD27; CD27-4-1BB; 4-1BB-CD28; CD28-4-1BB; OX40-CD28; CD28-OX40; CD28-4-1BB; or 4-1BB-CD28. In such embodiments, the intracellular binding member comprises a CD3zeta domain. In one such embodiment the RCAR comprises (1) an antigen binding member comprising, an antigen binding domain, a transmembrane domain, and two costimulatory domains and a first switch domain; and (2) an intracellular signaling domain comprising a transmembrane domain or membrane tethering domain and at least one primary intracellular signaling domain, and a second switch domain.

An embodiment provides RCARs wherein the antigen binding member is not tethered to the surface of the CAR cell. This allows a cell having an intracellular signaling member to be conveniently paired with one or more antigen binding domains, without transforming the cell with a sequence that encodes the antigen binding member. In such embodiments, the RCAR comprises: 1) an intracellular signaling member comprising: a first switch domain, a transmembrane domain, an intracellular signaling domain, e.g., a primary intracellular signaling domain, and a first switch domain; and 2) an antigen binding member comprising: an antigen binding domain, and a second switch domain, wherein the antigen binding member does not comprise a transmembrane domain or membrane tethering domain, and, optionally, does not comprise an intracellular signaling domain. In some embodiments, the RCAR may further comprise 3) a second antigen binding member comprising: a second antigen binding domain, e.g., a second antigen binding domain that binds a different antigen than is bound by the antigen binding domain; and a second switch domain.

Also provided herein are RCARs wherein the antigen binding member comprises bispecific activation and targeting capacity. In this embodiment, the antigen binding member can comprise a plurality, e.g., 2, 3, 4, or 5 antigen binding domains, e.g., scFvs, wherein each antigen binding domain binds to a target antigen, e.g. different antigens or the same antigen, e.g., the same or different epitopes on the same antigen. In an embodiment, the plurality of antigen binding domains are in tandem, and optionally, a linker or hinge region is disposed between each of the antigen binding domains. Suitable linkers and hinge regions are described herein.

An embodiment provides RCARs having a configuration that allows switching of proliferation. In this embodiment, the RCAR comprises: 1) an intracellular signaling member comprising: optionally, a transmembrane domain or membrane tethering domain; one or more co-stimulatory signaling domain, e.g., selected from 4-1BB, CD28, CD27, ICOS, and OX40, and a switch domain; and 2) an antigen binding member comprising: an antigen binding domain, a transmembrane domain, and a primary intracellular signaling domain, e.g., a CD3zeta domain, wherein the antigen binding member does not comprise a switch domain, or does not comprise a switch domain that dimerizes with a switch domain on the intracellular signaling member. In an embodiment, the antigen binding member does not comprise a co-stimulatory signaling domain. In an embodiment, the intracellular signaling member comprises a switch domain from a homodimerization switch. In an embodiment, the intracellular signaling member comprises a first switch domain of a heterodimerization switch and the RCAR comprises a second intracellular signaling member which comprises a second switch domain of the heterodimerization switch. In such embodiments, the second intracellular signaling member comprises the same intracellular signaling domains as the intracellular signaling member. In an embodiment, the dimerization switch is intracellular. In an embodiment, the dimerization switch is extracellular.

In any of the RCAR configurations described here, the first and second switch domains comprise a FKBP-FRB based switch as described herein.

Also provided herein are cells comprising an RCAR described herein. Any cell that is engineered to express a RCAR can be used as a RCARX cell. In an embodiment the RCARX cell is a T cell, and is referred to as a RCART cell. In an embodiment the RCARX cell is an NK cell, and is referred to as a RCARN cell.

Also provided herein are nucleic acids and vectors comprising RCAR encoding sequences. Sequence encoding various elements of an RCAR can be disposed on the same nucleic acid molecule, e.g., the same plasmid or vector, e.g., viral vector, e.g., lentiviral vector. In an embodiment, (i) sequence encoding an antigen binding member and (ii) sequence encoding an intracellular signaling member, can be present on the same nucleic acid, e.g., vector. Production of the corresponding proteins can be achieved, e.g., by the use of separate promoters, or by the use of a bicistronic transcription product (which can result in the production of two proteins by cleavage of a single translation product or by the translation of two separate protein products). In an embodiment, a sequence encoding a cleavable peptide, e.g., a P2A or F2A sequence, is disposed between (i) and (ii). In an embodiment, a sequence encoding an IRES, e.g., an EMCV or EV71 IRES, is disposed between (i) and (ii). In these embodiments, (i) and (ii) are transcribed as a single RNA. In an embodiment, a first promoter is operably linked to (i) and a second promoter is operably linked to (ii), such that (i) and (ii) are transcribed as separate mRNAs.

Alternatively, the sequence encoding various elements of an RCAR can be disposed on the different nucleic acid molecules, e.g., different plasmids or vectors, e.g., viral vector, e.g., lentiviral vector. E.g., the (i) sequence encoding an antigen binding member can be present on a first nucleic acid, e.g., a first vector, and the (ii) sequence encoding an intracellular signaling member can be present on the second nucleic acid, e.g., the second vector.

Dimerization Switches

Dimerization switches can be non-covalent or covalent. In a non-covalent dimerization switch, the dimerization molecule promotes a non-covalent interaction between the switch domains. In a covalent dimerization switch, the dimerization molecule promotes a covalent interaction between the switch domains.

In an embodiment, the RCAR comprises a FKBP/FRAP, or FKBP/FRB-based dimerization switch. FKBP12 (FKBP, or FK506 binding protein) is an abundant cytoplasmic protein that serves as the initial intracellular target for the natural product immunosuppressive drug, rapamycin. Rapamycin binds to FKBP and to the large PI3K homolog FRAP (RAFT, mTOR). FRB is a 93 amino acid portion of FRAP, that is sufficient for binding the FKBP-rapamycin complex (Chen, J., Zheng, X. F., Brown, E. J. & Schreiber, S. L. (1995) *Identification of an 11-kDa FKBP12-rapamycin-binding domain within the 289-kDa FKBP12-rapamycin-associated protein and characterization of a critical serine residue*. Proc Natl Acad Sci USA 92: 4947-51.)

In embodiments, an FKBP/FRAP, e.g., an FKBP/FRB, based switch can use a dimerization molecule, e.g., rapamycin or a rapamycin analog.

An exemplary amino acid sequence of FKBP is as follows:

(SEQ ID NO: 275)
DVPDYASLGGPSSPKKKRKVSRGVQVETISPGDGRTFPKRGQT

CVVHYTGMLEDGKKFDSSRDRNKPFKFMLGKQEVIRGWEEGVAQM

SVGQRAKLTISPDYAYGATGHPGIIPPHATLVFDVELLKLETSY

In embodiments, an FKBP switch domain can comprise a fragment of FKBP having the ability to bind with FRB, or a fragment or analog thereof, in the presence of rapamycin or a rapalog. In some embodiments, the FKBP switch domain comprises the amino acid sequence of:

(SEQ ID NO: 276)
VQVETISPGDGRTFPKRGQTCVVHYTGMLEDGKKFDSSRDRN

KPFKFMLGKQEVIRGWEEGVAQMSVGQRAKLTISPDYAYGATGHP

GIIPPHATLVFDVELLKLETS

The amino acid sequence of FRB is as follows:

(SEQ ID NO: 277)
ILWHEMWHEG LEEASRLYFG ERNVKGMFEV LEPLHAMMER

GPQTLKETSF NQAYGRDLME AQEWCRKYMK SGNVKDLTQA

WDLYYHVFRR ISK

"FKBP/FRAP, e.g., an FKBP/FRB, based switch" as that term is used herein, refers to a dimerization switch comprising: a first switch domain, which comprises an FKBP fragment or analog thereof having the ability to bind with FRB, or a fragment or analog thereof, in the presence of rapamycin or a rapalog, e.g., RAD001, and has at least 70, 75, 80, 85, 90, 95, 96, 97, 98, or 99% identity with, or differs by no more than 30, 25, 20, 15, 10, 5, 4, 3, 2, or 1 amino acid residues from, the FKBP sequence of SEQ ID NO: 275 or 276; and a second switch domain, which comprises an FRB fragment or analog thereof having the ability to bind with FRB, or a fragment or analog thereof, in the presence of rapamycin or a rapalog, and has at least 70, 75, 80, 85, 90, 95, 96, 97, 98, or 99% identity with, or differs by no more than 30, 25, 20, 15, 10, 5, 4, 3, 2, or 1 amino acid residues from, the FRB sequence of SEQ ID NO: 277. In an embodiment, a RCAR described herein comprises one switch domain comprises amino acid residues disclosed in SEQ ID NO: 275 (or SEQ ID NO: 276), and one switch domain comprises amino acid residues disclosed in SEQ ID NO: 277.

In embodiments, the FKBP/FRB dimerization switch comprises a modified FRB switch domain that exhibits altered, e.g., enhanced, complex formation between an FRB-based switch domain, e.g., the modified FRB switch domain, a FKBP-based switch domain, and the dimerization molecule, e.g., rapamycin or a rapalogue, e.g., RAD001. In an embodiment, the modified FRB switch domain comprises one or more mutations, e.g., 2, 3, 4, 5, 6, 7, 8, 9, 10 or more, selected from mutations at amino acid position(s) L2031, E2032, S2035, R2036, F2039, G2040, T2098, W2101, D2102, Y2105, and F2108, where the wild-type amino acid is mutated to any other naturally-occurring amino acid. In an embodiment, a mutant FRB comprises a mutation at E2032, where E2032 is mutated to phenylalanine (E2032F), methionine (E2032M), arginine (E2032R), valine (E2032V), tyrosine (E2032Y), isoleucine (E2032I), e.g., SEQ ID NO: 278, or leucine (E2032L), e.g., SEQ ID NO: 279. In an embodiment, a mutant FRB comprises a mutation at T2098, where T2098 is mutated to phenylalanine (T2098F) or leucine (T2098L), e.g., SEQ ID NO: 280. In an embodiment, a mutant FRB comprises a mutation at E2032 and at T2098, where E2032 is mutated to any amino acid, and where T2098 is mutated to any amino acid, e.g., SEQ ID NO: 281. In an embodiment, a mutant FRB comprises an E2032I and a T2098L mutation, e.g., SEQ ID NO: 282. In an embodiment, a mutant FRB comprises an E2032L and a T2098L mutation, e.g., SEQ ID NO: 283.

TABLE 14

Exemplary mutant FRB having increased affinity for a dimerization molecule.

| FRB mutant | Amino Acid Sequence | SEQ ID NO: |
|---|---|---|
| E2032I mutant | ILWHEMWHEGLIEASRLYFGERNVKGMFEVLEPLHAMMERGPQTLKE TSFNQAYGRDLMEAQEWCRKYMKSGNVKDLTQAWDLYYHVFRRISKTS | 278 |
| E2032L mutant | ILWHEMWHEGLLEASRLYFGERNVKGMFEVLEPLHAMMERGPQTLKE TSFNQAYGRDLMEAQEWCRKYMKSGNVKDLTQAWDLYYHVFRRISKTS | 279 |
| T2098L mutant | ILWHEMWHEGLEEASRLYFGERNVKGMFEVLEPLHAMMERGPQTLKE TSFNQAYGRDLMEAQEWCRKYMKSGNVKDLLQAWDLYYHVFRRISKTS | 280 |
| E2032, T2098 mutant | ILWHEMWHEGLXEASRLYFGERNVKGMFEVLEPLHAMMERGPQTLKE TSFNQAYGRDLMEAQEWCRKYMKSGNVKDLXQAWDLYYHVFRRISKTS, wherein X is any amino acid residue | 281 |
| E2032I, T2098L mutant | ILWHEMWHEGLIEASRLYFGERNVKGMFEVLEPLHAMMERGPQTLKE TSFNQAYGRDLMEAQEWCRKYMKSGNVKDLLQAWDLYYHVFRRISKTS | 282 |
| E2032L, T2098L mutant | ILWHEMWHEGLLEASRLYFGERNVKGMFEVLEPLHAMMERGPQTLKE TSFNQAYGRDLMEAQEWCRKYMKSGNVKDLLQAWDLYYHVFRRISKTS | 283 |

Other suitable dimerization switches include a GyrB-GyrB based dimerization switch, a Gibberellin-based dimerization switch, a tag/binder dimerization switch, and a halo-tag/snap-tag dimerization switch. Following the guidance provided herein, such switches and relevant dimerization molecules will be apparent to one of ordinary skill.

Dimerization Molecule

Association between the switch domains is promoted by the dimerization molecule. In the presence of dimerization molecule interaction or association between switch domains allows for signal transduction between a polypeptide associated with, e.g., fused to, a first switch domain, and a polypeptide associated with, e.g., fused to, a second switch domain. In the presence of non-limiting levels of dimerization molecule signal transduction is increased by 1.1, 1.2, 1.3, 1.4, 1.5, 1.6, 1.7, 1.8, 1.9, 2, 5, 10, 50, 100 fold, e.g., as measured in a system described herein.

Rapamycin and rapamycin analogs (sometimes referred to as rapalogues), e.g., RAD001, can be used as dimerization molecules in a FKBP/FRB-based dimerization switch described herein. In an embodiment the dimerization molecule can be selected from rapamycin (sirolimus), RAD001 (everolimus), zotarolimus, temsirolimus, AP-23573 (ridaforolimus), biolimus and AP21967. Additional rapamycin analogs suitable for use with FKBP/FRB-based dimerization switches are further described in the section entitled "Combination Therapies", or in the subsection entitled "Combination with a Low, Immune Enhancing, Dose of an mTOR inhibitor".

Split CAR

In some embodiments, the CAR-expressing cell uses a split CAR. The split CAR approach is described in more detail in publications WO2014/055442 and WO2014/055657, incorporated herein by reference. Briefly, a split CAR system comprises a cell expressing a first CAR having a first antigen binding domain and a costimulatory domain (e.g., 41BB), and the cell also expresses a second CAR having a second antigen binding domain and an intracellular signaling domain (e.g., CD3 zeta). When the cell encounters the first antigen, the costimulatory domain is activated, and the cell proliferates. When the cell encounters the second antigen, the intracellular signaling domain is activated and cell-killing activity begins. Thus, the CAR-expressing cell is only fully activated in the presence of both antigens. In embodiments the first antigen binding domain recognizes BCMA, e.g., comprises an antigen binding domain described herein, and the second antigen binding domain recognizes an antigen expressed on acute myeloid leukemia cells, e.g., CD123, CLL-1, CD34, FLT3, or folate receptor beta. In embodiments the first antigen binding domain recognizes BCMA, e.g., comprises an antigen binding domain described herein, and the second antigen binding domain recognizes an antigen expressed on B-cells, e.g., CD10, CD19, CD20, CD22, CD34, CD123, FLT-3, ROR1, CD79b, CD179b, or CD79a.

Stability and Mutations

The stability of an anti-BCMA binding domain, e.g., scFv molecules (e.g., soluble scFv) can be evaluated in reference to the biophysical properties (e.g., thermal stability) of a conventional control scFv molecule or a full length antibody.

The improved thermal stability of the anti-BCMA binding domain, e.g., scFv is subsequently conferred to the entire CART-BCMA construct, leading to improved therapeutic properties of the CART-BCMA construct. The thermal stability of the anti-BCMA binding domain, e.g., scFv can be improved by at least about 2° C. or 3° C. as compared to a conventional antibody. In some embodiments, the anti-BCMA binding domain, e.g., scFv has a 1° C. improved thermal stability as compared to a conventional antibody. In another embodiment, the anti-BCMA binding domain, e.g., scFv has a 2° C. improved thermal stability as compared to a conventional antibody. In another embodiment, the scFv has a 4, 5, 6, 7, 8, 9, 10, 11, 12, 13, 14, 15° C. improved thermal stability as compared to a conventional antibody. Comparisons can be made, for example, between the scFv molecules disclosed herein and scFv molecules or Fab fragments of an antibody from which the scFv VH and VL were derived. Thermal stability can be measured using methods known in the art. For example, In some embodiments, Tm can be measured. Methods for measuring Tm and other methods of determining protein stability are described in more detail below.

Mutations in scFv (arising through humanization or direct mutagenesis of the soluble scFv) alter the stability of the scFv and improve the overall stability of the scFv and the CART33 construct. Stability of the human scFv can be compared against the murine scFv using measurements such as Tm, temperature denaturation and temperature aggregation.

The binding capacity of the mutant scFvs can be determined using assays described in the Examples.

In some embodiments, the anti-BCMA binding domain, e.g., scFv comprises at least one mutation arising from the humanization process such that the mutated scFv confers improved stability to the CART-BCMA construct. In another embodiment, the anti-BCMA binding domain, e.g., scFv comprises at least 1, 2, 3, 4, 5, 6, 7, 8, 9, 10 mutations arising from the humanization process such that the mutated scFv confers improved stability to the CART-BCMA construct.

Methods of Evaluating Protein Stability

The stability of an antigen binding domain may be assessed using, e.g., the methods described below. Such methods allow for the determination of multiple thermal unfolding transitions where the least stable domain either unfolds first or limits the overall stability threshold of a multidomain unit that unfolds cooperatively (e.g., a multidomain protein which exhibits a single unfolding transition). The least stable domain can be identified in a number of additional ways. Mutagenesis can be performed to probe which domain limits the overall stability. Additionally, protease resistance of a multidomain protein can be performed under conditions where the least stable domain is known to be intrinsically unfolded via DSC or other spectroscopic methods (Fontana, et al., (1997) Fold. Des., 2: R17-26; Dimasi et al. (2009) J. Mol. Biol. 393: 672-692). Once the least stable domain is identified, the sequence encoding this domain (or a portion thereof) may be employed as a test sequence in the methods.

a) Thermal Stability

The thermal stability of the compositions may be analyzed using a number of non-limiting biophysical or biochemical techniques known in the art. In certain embodiments, thermal stability is evaluated by analytical spectroscopy.

An exemplary analytical spectroscopy method is Differential Scanning Calorimetry (DSC). DSC employs a calorimeter which is sensitive to the heat absorbances that accompany the unfolding of most proteins or protein domains (see, e.g. Sanchez-Ruiz, et al., Biochemistry, 27: 1648-52, 1988). To determine the thermal stability of a protein, a sample of the protein is inserted into the calorimeter and the temperature is raised until the Fab or scFv unfolds. The temperature at which the protein unfolds is indicative of overall protein stability.

Another exemplary analytical spectroscopy method is Circular Dichroism (CD) spectroscopy. CD spectrometry measures the optical activity of a composition as a function of increasing temperature. Circular dichroism (CD) spectroscopy measures differences in the absorption of left-handed polarized light versus right-handed polarized light which arise due to structural asymmetry. A disordered or unfolded structure results in a CD spectrum very different from that of an ordered or folded structure. The CD spectrum reflects the sensitivity of the proteins to the denaturing effects of increasing temperature and is therefore indicative of a protein's thermal stability (see van Mierlo and Steemsma, J. Biotechnol., 79(3):281-98, 2000).

Another exemplary analytical spectroscopy method for measuring thermal stability is Fluorescence Emission Spectroscopy (see van Mierlo and Steemsma, supra). Yet another exemplary analytical spectroscopy method for measuring thermal stability is Nuclear Magnetic Resonance (NMR) spectroscopy (see, e.g. van Mierlo and Steemsma, supra).

The thermal stability of a composition can be measured biochemically. An exemplary biochemical method for assessing thermal stability is a thermal challenge assay. In a "thermal challenge assay", a composition is subjected to a range of elevated temperatures for a set period of time. For example, In some embodiments, test scFv molecules or molecules comprising scFv molecules are subject to a range of increasing temperatures, e.g., for 1-1.5 hours. The activity of the protein is then assayed by a relevant biochemical assay. For example, if the protein is a binding protein (e.g. an scFv or scFv-containing polypeptide) the binding activity of the binding protein may be determined by a functional or quantitative ELISA.

Such an assay may be done in a high-throughput format and those disclosed in the Examples using *E. coli* and high throughput screening. A library of anti-BCMA binding domain, e.g., scFv variants may be created using methods known in the art. Anti-BCMA binding domain, e.g., scFv expression may be induced and the anti-BCMA binding domain, e.g., scFv may be subjected to thermal challenge. The challenged test samples may be assayed for binding and those anti-BCMA binding domain, e.g., scFvs which are stable may be scaled up and further characterized.

Thermal stability is evaluated by measuring the melting temperature (Tm) of a composition using any of the above techniques (e.g. analytical spectroscopy techniques). The melting temperature is the temperature at the midpoint of a thermal transition curve wherein 50% of molecules of a composition are in a folded state (See e.g., Dimasi et al. (2009) J. Mol Biol. 393: 672-692). In some embodiments, Tm values for an anti-BCMA binding domain, e.g., scFv are about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In some embodiments, Tm values for an IgG is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In some embodiments, Tm values for an multivalent antibody is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C.

Thermal stability is also evaluated by measuring the specific heat or heat capacity (Cp) of a composition using an analytical calorimetric technique (e.g. DSC). The specific heat of a composition is the energy (e.g. in kcal/mol) is required to rise by 1° C., the temperature of 1 mol of water. As large Cp is a hallmark of a denatured or inactive protein composition. The change in heat capacity (ΔCp) of a composition is measured by determining the specific heat of a composition before and after its thermal transition. Thermal stability may also be evaluated by measuring or determining other parameters of thermodynamic stability including Gibbs free energy of unfolding (ΔG), enthalpy of unfolding (ΔH), or entropy of unfolding (ΔS). One or more of the above biochemical assays (e.g. a thermal challenge assay) are used to determine the temperature (i.e. the Tc value) at which 50% of the composition retains its activity (e.g. binding activity).

In addition, mutations to the anti-BCMA binding domain, e.g., scFv alter the thermal stability of the anti-BCMA binding domain, e.g., scFv compared with the unmutated anti-BCMA binding domain, e.g., scFv. When the human or humanized anti-BCMA binding domain, e.g., scFv is incorporated into a BCMA construct, the anti-BCMA binding domain, e.g., humanized scFv confers thermal stability to the overall anti-BCMA CART construct. In some embodiments, the anti-BCMA binding domain, e.g., scFv comprises a single mutation that confers thermal stability to the anti-BCMA binding domain, e.g., scFv. In another embodiment, the anti-BCMA binding domain, e.g., scFv comprises multiple mutations that confer thermal stability to the anti-BCMA binding domain, e.g., scFv. In some embodiments, the multiple mutations in the anti-BCMA binding domain, e.g., scFv have an additive effect on thermal stability of the anti-BCMA binding domain, e.g., scFv.

b) % Aggregation

The stability of a composition can be determined by measuring its propensity to aggregate. Aggregation can be measured by a number of non-limiting biochemical or biophysical techniques. For example, the aggregation of a composition may be evaluated using chromatography, e.g. Size-Exclusion Chromatography (SEC). SEC separates molecules on the basis of size. A column is filled with semi-solid beads of a polymeric gel that will admit ions and small molecules into their interior but not large ones. When a protein composition is applied to the top of the column, the compact folded proteins (i.e. non-aggregated proteins) are distributed through a larger volume of solvent than is available to the large protein aggregates. Consequently, the large aggregates move more rapidly through the column, and in this way the mixture can be separated or fractionated into its components. Each fraction can be separately quantified (e.g. by light scattering) as it elutes from the gel. Accordingly, the % aggregation of a composition can be determined by comparing the concentration of a fraction with the total concentration of protein applied to the gel. Stable compositions elute from the column as essentially a single fraction and appear as essentially a single peak in the elution profile or chromatogram.

c) Binding Affinity

The stability of a composition can be assessed by determining its target binding affinity. A wide variety of methods for determining binding affinity are known in the art. An exemplary method for determining binding affinity employs surface plasmon resonance. Surface plasmon resonance is an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., i (1991) Biotechniques 11:620-627; Johnsson, B., et al. (1995) J. Mol. Recognit. 8:125-131; and Johnnson, B., et al. (1991) Anal. Biochem. 198:268-277.

In one aspect, the antigen binding domain of the CAR comprises an amino acid sequence that is homologous to an antigen binding domain amino acid sequence described herein, and the antigen binding domain retains the desired functional properties of the anti-BCMA antibody fragments described herein. In one specific aspect, the CAR composition of the invention comprises an antibody fragment. In a further aspect, that antibody fragment comprises an scFv.

In various aspects, the antigen binding domain of the CAR is engineered by modifying one or more amino acids within one or both variable regions (e.g., VH and/or VL), for example within one or more CDR regions and/or within one or more framework regions. In one specific aspect, the CAR composition of the invention comprises an antibody fragment. In a further aspect, that antibody fragment comprises a scFv.

It will be understood by one of ordinary skill in the art that the antibody or antibody fragment of the invention may further be modified such that they vary in amino acid sequence (e.g., from wild-type), but not in desired activity. For example, additional nucleotide substitutions, e.g., conservative substitutions leading to amino acid substitutions, e.g., conservative substitutions at "non-essential" amino acid residues may be made to the protein For example, a nonessential amino acid residue in a molecule may be replaced with another amino acid residue from the same side chain family. In another embodiment, a string of amino acids can be replaced with a structurally similar string that differs in order and/or composition of side chain family members, e.g., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences, refers to two or more sequences that are the same. Two sequences are "substantially identical" if two sequences have a specified percentage of amino acid residues or nucleotides that are the same (e.g., 60% identity, optionally 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

In one aspect, the present invention contemplates modifications of the starting antibody or fragment (e.g., scFv) amino acid sequence that generate functionally equivalent molecules. For example, the VH or VL of an anti-BCMA binding domain, e.g., scFv, comprised in the CAR can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting VH or VL framework region of the anti-BCMA binding domain, e.g., scFv. The present invention contemplates modifications of the entire CAR construct, e.g., modifications in one or more amino acid sequences of the various domains of the CAR construct in order to generate functionally equivalent molecules. The CAR construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting CAR construct.

Nucleic Acid Constructs Encoding a CAR

The present invention also provides nucleic acid molecules encoding one or more CAR constructs described herein. In one aspect, the nucleic acid molecule is provided as a messenger RNA transcript. In one aspect, the nucleic acid molecule is provided as a DNA construct.

Accordingly, in one aspect, the invention pertains to an isolated nucleic acid molecule encoding a chimeric antigen receptor (CAR), wherein the CAR comprises an anti-BCMA binding domain (e.g., a human anti-BCMA binding domain), a transmembrane domain, and an intracellular signaling domain comprising a stimulatory domain, e.g., a costimulatory signaling domain and/or a primary signaling domain, e.g., zeta chain. In some embodiments, the anti-BCMA binding domain is an anti-BCMA binding domain described herein, or a sequence with 95-99% identify thereof. In some embodiments, the transmembrane domain is transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In some embodiments, the anti-BCMA binding domain is connected to the transmembrane domain by a hinge region, e.g., a hinge described herein. In some embodiments, the isolated nucleic acid molecule further comprises a sequence encoding a primary signaling domain. In some embodiments, the primary signaling domain comprises a functional signaling domain derived from CD3 zeta, TCR zeta, FcR gamma, FcR beta, CD3 gamma, CD3 delta, CD3 epsilon, CD5, CD22, CD79a, CD79b, CD278 (ICOS), FcεRI, DAP10, DAP12, or CD66d. In some embodiments, the isolated nucleic acid molecule further comprises a sequence encoding a costimulatory domain. In some embodiments, the costimulatory domain is a functional signaling domain of a protein selected from the group consisting of MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In another aspect, the invention pertains to an isolated nucleic acid molecule encoding a CAR construct comprising a leader sequence of SEQ ID NO: 1.

In another aspect, the invention pertains to an isolated polypeptide molecule encoded by the nucleic acid molecule.

The nucleic acid sequences encoding the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. A retroviral vector may also be, e.g., a gammaretroviral vector. A gammaretroviral vector may include, e.g., a promoter, a packaging signal (ψ), a primer binding site (PBS), one or more (e.g., two) long terminal repeats (LTR), and a transgene of interest, e.g., a gene encoding a CAR. A gammaretroviral vector may lack viral structural gens such as gag, pol, and env. Exemplary gammaretroviral vectors include Murine Leukemia Virus (MLV), Spleen-Focus Forming Virus (SFFV), and Myeloproliferative Sarcoma Virus (MPSV), and vectors derived therefrom. Other gammaretroviral vectors are described, e.g., in Tobias Maetzig et al., "Gammaretroviral Vectors: Biology, Technology and Application" Viruses. 2011 June; 3(6): 677-713.

In another embodiment, the vector comprising the nucleic acid encoding the desired CAR of the invention is an adenoviral vector (A5/35). In another embodiment, the expression of nucleic acids encoding CARs can be accomplished using of transposons such as sleeping beauty, CRISPR, CAS9, and zinc finger nucleases. See below June et al. 2009 *Nature Reviews Immunology* 9.10: 704-716, is incorporated herein by reference.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter that is capable of expressing a CAR transgene in a mammalian T cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving CAR expression from transgenes cloned into a lentiviral vector. See, e.g., Milone et al., Mol. Ther. 17(8): 1453-1464 (2009). In one aspect, the EF1a promoter comprises the sequence provided as SEQ ID NO: 11.

Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1α promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Another example of a promoter is the phosphoglycerate kinase (PGK) promoter. In embodiments, a truncated PGK promoter (e.g., a PGK promoter with one or more, e.g., 1, 2, 5, 10, 100, 200, 300, or 400, nucleotide deletions when compared to the wild-type PGK promoter sequence) may be desired. The nucleotide sequences of exemplary PGK promoters are provided below.

```
WT PGK Promoter
                                                     (SEQ ID NO: 190)
ACCCCTCTCTCCAGCCACTAAGCCAGTTGCTCCCTCGGCTGACGGCTGCACGCGAGGCCTCCGAACG

TCTTACGCCTTGTGGCGCGCCCGTCCTTGTCCCGGGTGTGATGGCGGGGTGTGGGGCGGAGGGCGTG

GCGGGGAAGGGCCGGCGACGAGAGCCGCGCGGGACGACTCGTCGGCGATAACCGGTGTCGGGTAGCG

CCAGCCGCGCGACGGTAACGAGGGACCGCGACAGGCAGACGCTCCCATGATCACTCTGCACGCCGAA

GGCAAATAGTGCAGGCCGTGCGGCGCTTGGCGTTCCTTGGAAGGGCTGAATCCCCGCCTCGTCCTTC

GCAGCGGCCCCCCGGGTGTTCCCATCGCCGCTTCTAGGCCCACTGCGACGCTTGCCTGCACTTCTTA

CACGCTCTGGGTCCCAGCCGCGGCGACGCAAAGGGCCTTGGTGCGGGTCTCGTCGGCGCAGGGACGC

GTTTGGGTCCCGACGGAACCTTTTCCGCGTTGGGGTTGGGGCACCATAAGCT

Exemplary truncated PGK Promoters:
PGK 100:
                                                     (SEQ ID NO: 198)
ACCCCTCTCTCCAGCCACTAAGCCAGTTGCTCCCTCGGCTGACGGCTGCACGCGAGGCCTCCGAACG

TCTTACGCCTTGTGGCGCGCCCGTCCTTGTCCCGGGTGTGATGGCGGGGTG

PGK200:
                                                     (SEQ ID NO: 191)
ACCCCTCTCTCCAGCCACTAAGCCAGTTGCTCCCTCGGCTGACGGCTGCACGCGAGGCCTCCGAACG

TCTTACGCCTTGTGGCGCGCCCGTCCTTGTCCCGGGTGTGATGGCGGGGTGTGGGGCGGAGGGCGTG

GCGGGGAAGGGCCGGCGACGAGAGCCGCGCGGGACGACTCGTCGGCGATAACCGGTGTCGGGTAGCG

CCAGCCGCGCGACGGTAACG
```

-continued

PGK300:

(SEQ ID NO: 192)

ACCCCTCTCTCCAGCCACTAAGCCAGTTGCTCCCTCGGCTGACGGCTGCACGCGAGGCCTCCGAACG

TCTTACGCCTTGTGGCGCGCCCGTCCTTGTCCCGGGTGTGATGGCGGGGTGTGGGGCGGAGGGCGTG

GCGGGGAAGGGCCGGCGACGAGAGCCGCGCGGGACGACTCGTCGGCGATAACCGGTGTCGGGTAGCG

CCAGCCGCGCGACGGTAACGAGGGACCGCGACAGGCAGACGCTCCCATGATCACTCTGCACGCCGAA

GGCAAATAGTGCAGGCCGTGCGGCGCTTGGCGTTCCTTGGAAGGGCTGAATCCCCG

PGK400:

(SEQ ID NO: 193)

ACCCCTCTCTCCAGCCACTAAGCCAGTTGCTCCCTCGGCTGACGGCTGCACGCGAGGCCTCCGAACG

TCTTACGCCTTGTGGCGCGCCCGTCCTTGTCCCGGGTGTGATGGCGGGGTGTGGGGCGGAGGGCGTG

GCGGGGAAGGGCCGGCGACGAGAGCCGCGCGGGACGACTCGTCGGCGATAACCGGTGTCGGGTAGCG

CCAGCCGCGCGACGGTAACGAGGGACCGCGACAGGCAGACGCTCCCATGATCACTCTGCACGCCGAA

GGCAAATAGTGCAGGCCGTGCGGCGCTTGGCGTTCCTTGGAAGGGCTGAATCCCCGCCTCGTCCTTC

GCAGCGGCCCCCCGGGTGTTCCCATCGCCGCTTCTAGGCCCACTGCGACGCTTGCCTGCACTTCTTA

CACGCTCTGGGTCCCAGCCG

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection (e.g., ampicillin resistance gene and/or zeocin marker).

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, the vector can further comprise a nucleic acid encoding a second CAR. In some embodiments, the second CAR includes an antigen binding domain to a target expressed on acute myeloid leukemia cells, such as, e.g., CD123, CD34, CLL-1, folate receptor beta, or FLT3; or a target expressed on a B cell, e.g., CD10, CD19, CD20, CD22, CD34, CD123, FLT-3, ROR1, CD79b, CD179b, or CD79a. In some embodiments, the vector comprises a nucleic acid sequence encoding a first CAR that specifically binds a first antigen and includes an intracellular signaling domain having a costimulatory signaling domain but not a primary signaling domain, and a nucleic acid encoding a second CAR that specifically binds a second, different, antigen and includes an intracellular signaling domain having a primary signaling domain but not a costimulatory signaling domain. In some embodiments, the vector comprises a nucleic acid encoding a first BCMA CAR that includes a BCMA binding domain, a transmembrane domain and a costimulatory domain and a nucleic acid encoding a second CAR that targets an antigen other than BCMA (e.g., an antigen expressed on AML cells, e.g., CD123, CD34, CLL-1, folate receptor beta, or FLT3; or an antigen expressed on a B cell, e.g., CD10, CD19, CD20, CD22, CD34, CD123, FLT-3, ROR1, CD79b, CD179b, or CD79a) and includes an antigen binding domain, a transmembrane domain and a primary signaling domain. In another embodiment, the vector comprises a nucleic acid encoding a first BCMA CAR that includes a BCMA binding domain, a transmembrane domain and a primary signaling domain and a nucleic acid encoding a second CAR that specifically binds an antigen other than BCMA (e.g., an antigen expressed on AML cells, e.g., CD123, CD34, CLL-1, folate receptor beta, or FLT3; or an antigen expressed on a B cell, e.g., CD10, CD19, CD20, CD22, CD34, CD123, FLT-3, ROR1, CD79b, CD179b, or CD79a) and includes an antigen binding domain to the antigen, a transmembrane domain and a costimulatory signaling domain.

In some embodiments, the vector comprises a nucleic acid encoding a BCMA CAR described herein and a nucleic acid encoding an inhibitory CAR. In some embodiments, the inhibitory CAR comprises an antigen binding domain that binds an antigen found on normal cells but not cancer cells, e.g., normal cells that also express BCMA. In some embodiments, the inhibitory CAR comprises the antigen binding domain, a transmembrane domain and an intracellular domain of an inhibitory molecule. For example, the intracellular domain of the inhibitory CAR can be an intracellular domain of PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta.

In embodiments, the vector may comprise two or more nucleic acid sequences encoding a CAR, e.g., a BCMA CAR described herein and a second CAR, e.g., an inhibitory CAR or a CAR that specifically binds to an antigen other than BCMA (e.g., an antigen expressed on AML cells, e.g., CD123, CLL-1, CD34, FLT3, or folate receptor beta; or antigen expression B cells, e.g., CD10, CD19, CD20, CD22, CD34, CD123, FLT-3, ROR1, CD79b, CD179b, or CD79a). In such embodiments, the two or more nucleic acid sequences encoding the CAR are encoded by a single nucleic molecule in the same frame and as a single polypeptide chain. In this aspect, the two or more CARs, can, e.g., be separated by one or more peptide cleavage sites. (e.g., an auto-cleavage site or a substrate for an intracellular protease). Examples of peptide cleavage sites include the following, wherein the GSG residues are optional:

```
T2A:
                                     (SEQ ID NO: 194)
(GSG)EGRGSLLTCGDVEENPGP

P2A:
                                     (SEQ ID NO: 195)
(GSG)ATNFSLLKQAGDVEENPGP

E2A:
                                     (SEQ ID NO: 196)
(GSG)QCTNYALLKLAGDVESNPGP

F2A:
                                     (SEQ ID NO: 197)
(GSG)VKQTLNFDLLKLAGDVESNPGP
```

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). A preferred method for the introduction of a polynucleotide into a host cell is calcium phosphate transfection Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable sub-micron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a CAR encoding nucleic acid molecule. In one aspect, a CAR vector can be directly transduced into a cell, e.g., a T cell or NK cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells or NK cells. In one aspect, the mammalian T cell is a human T cell. In one aspect, the mammalian NK cell is a human NK cell.

RNA Transfection

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO: 35). RNA so produced can efficiently transfect different kinds of cells. In one aspect, the template includes sequences for the CAR.

In one aspect the anti-BCMA CAR is encoded by a messenger RNA (mRNA). In one aspect the mRNA encoding the anti-BCMA CAR is introduced into an immune effector cell, e.g., a T cell or a NK cell, for production of a CAR-expressing cell (e.g., CART cell or CAR-expressing NK cell).

In some embodiments, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3-zeta and the signaling domain of 4-1BB.

In some embodiments, the DNA to be used for PCR contains an open reading frame. The DNA can be from a naturally occurring DNA sequence from the genome of an organism. In some embodiments, the nucleic acid can include some or all of the 5' and/or 3' untranslated regions (UTRs). The nucleic acid can include exons and introns. In some embodiments, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In some embodiments, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In some embodiments, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In some embodiments, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (SEQ ID NO: 31) (size can be 50-5000 T (SEQ ID NO: 32)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In some embodiments, the poly(A) tail is between 100 and 5000 adenosines (SEQ ID NO: 33).

Poly(A) tails of RNAs can be further extended following in vitro transcription with the use of a poly(A) polymerase, such as *E. coli* polyA polymerase (E-PAP). In some embodiments, increasing the length of a poly(A) tail from 100 nucleotides to between 300 and 400 nucleotides (SEQ ID NO: 34) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Non-Viral Delivery Methods

In some aspects, non-viral methods can be used to deliver a nucleic acid encoding a CAR described herein into a cell or tissue or a subject.

In some embodiments, the non-viral method includes the use of a transposon (also called a transposable element). In some embodiments, a transposon is a piece of DNA that can insert itself at a location in a genome, for example, a piece of DNA that is capable of self-replicating and inserting its copy into a genome, or a piece of DNA that can be spliced out of a longer nucleic acid and inserted into another place in a genome. For example, a transposon comprises a DNA sequence made up of inverted repeats flanking genes for transposition.

Exemplary methods of nucleic acid delivery using a transposon include a Sleeping Beauty transposon system (SBTS) and a piggyBac (PB) transposon system. See, e.g., Aronovich et al. Hum. Mol. Genet. 20.R1(2011):R14-20; Singh et al. Cancer Res. 15(2008):2961-2971; Huang et al. Mol. Ther. 16(2008):580-589; Grabundzija et al. Mol. Ther. 18(2010):1200-1209; Kebriaei et al. Blood. 122.21(2013): 166; Williams. Molecular Therapy 16.9(2008):1515-16; Bell et al. Nat. Protoc. 2.12(2007):3153-65; and Ding et al. Cell. 122.3(2005):473-83, all of which are incorporated herein by reference.

The SBTS includes two components: 1) a transposon containing a transgene and 2) a source of transposase enzyme. The transposase can transpose the transposon from a carrier plasmid (or other donor DNA) to a target DNA, such as a host cell chromosome/genome. For example, the transposase binds to the carrier plasmid/donor DNA, cuts the transposon (including transgene(s)) out of the plasmid, and inserts it into the genome of the host cell. See, e.g., Aronovich et al. supra.

Exemplary transposons include a pT2-based transposon. See, e.g., Grabundzija et al. Nucleic Acids Res. 41.3(2013): 1829-47; and Singh et al. Cancer Res. 68.8(2008): 2961-2971, all of which are incorporated herein by reference. Exemplary transposases include a Tc1/mariner-type transposase, e.g., the SB10 transposase or the SB11 transposase (a hyperactive transposase which can be expressed, e.g., from a cytomegalovirus promoter). See, e.g., Aronovich et al.; Kebriaei et al.; and Grabundzija et al., all of which are incorporated herein by reference.

Use of the SBTS permits efficient integration and expression of a transgene, e.g., a nucleic acid encoding a CAR described herein. Provided herein are methods of generating a cell, e.g., T cell or NK cell, that stably expresses a CAR described herein, e.g., using a transposon system such as SBTS.

In accordance with methods described herein, in some embodiments, one or more nucleic acids, e.g., plasmids, containing the SBTS components are delivered to a cell (e.g., T or NK cell). For example, the nucleic acid(s) are delivered by standard methods of nucleic acid (e.g., plasmid DNA) delivery, e.g., methods described herein, e.g., electroporation, transfection, or lipofection. In some embodiments, the nucleic acid contains a transposon comprising a transgene, e.g., a nucleic acid encoding a CAR described herein. In some embodiments, the nucleic acid contains a transposon comprising a transgene (e.g., a nucleic acid encoding a CAR described herein) as well as a nucleic acid sequence encoding a transposase enzyme. In other embodiments, a system with two nucleic acids is provided, e.g., a dual-plasmid system, e.g., where a first plasmid contains a transposon comprising a transgene, and a second plasmid contains a nucleic acid sequence encoding a transposase enzyme. For example, the first and the second nucleic acids are co-delivered into a host cell.

In some embodiments, cells, e.g., T or NK cells, are generated that express a CAR described herein by using a combination of gene insertion using the SBTS and genetic editing using a nuclease (e.g., Zinc finger nucleases (ZFNs), Transcription Activator-Like Effector Nucleases (TALENs), the CRISPR/Cas system, or engineered meganuclease re-engineered homing endonucleases).

In some embodiments, use of a non-viral method of delivery permits reprogramming of cells, e.g., T or NK cells, and direct infusion of the cells into a subject. Advantages of non-viral vectors include but are not limited to the ease and relatively low cost of producing sufficient amounts required to meet a patient population, stability during storage, and lack of immunogenicity.

Sources of Cells

Prior to expansion and genetic modification, a source of cells, e.g., immune effector cells (e.g., T cells or NK cells), is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

In certain aspects of the present invention, any number of immune effector cell (e.g., T cell or NK cell) lines available in the art, may be used. In certain aspects of the present invention, T cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations.

Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

It is recognized that the methods of the application can utilize culture media conditions comprising 5% or less, for example 2%, human AB serum, and employ known culture media conditions and compositions, for example those described in Smith et al., "Ex vivo expansion of human T cells for adoptive immunotherapy using the novel Xeno-free CTS Immune Cell Serum Replacement" *Clinical & Translational Immunology* (2015) 4, e31; doi:10.1038/cti.2014.31.

In one aspect, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, in one aspect, T cells are isolated by incubation with anti-CD3/anti-CD28 (e.g., 3×28)-conjugated beads, such as DYNABEADS® M-450 CD3/CD28 T, for a time period sufficient for positive selection of the desired T cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T cells which typically express CD4+, CD25+, CD62Lhi, GITR+, and FoxP3+. Alternatively, in certain aspects, T regulatory cells are depleted by anti-C25 conjugated beads or other similar method of selection.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

In some embodiments, T regulatory cells, e.g., CD25+ T cells, are removed from the population using an anti-CD25 antibody, or fragment thereof, or a CD25-binding ligand, IL-2. In some embodiments, the anti-CD25 antibody, or fragment thereof, or CD25-binding ligand is conjugated to a substrate, e.g., a bead, or is otherwise coated on a substrate, e.g., a bead. In some embodiments, the anti-CD25 antibody, or fragment thereof, is conjugated to a substrate as described herein.

In some embodiments, the T regulatory cells, e.g., CD25+ T cells, are removed from the population using CD25 depletion reagent from Miltenyi®. In some embodiments, the ratio of cells to CD25 depletion reagent is 1e7 cells to 20 uL, or 1e7 cells to 15 uL, or 1e7 cells to 10 uL, or 1e7 cells to 5 uL, or 1e7 cells to 2.5 uL, or 1e7 cells to 1.25 uL. In some embodiments, e.g., for T regulatory cells, e.g., CD25+ depletion, greater than 500 million cells/ml is used. In a further aspect, a concentration of cells of 600, 700, 800, or 900 million cells/ml is used.

In some embodiments, the population of immune effector cells to be depleted includes about $6\times10^9$ CD25+ T cells. In other aspects, the population of immune effector cells to be depleted include about $1\times10^9$ to $1\times10^{10}$ CD25+ T cell, and any integer value in between. In some embodiments, the resulting population T regulatory depleted cells has $2\times10^9$ T regulatory cells, e.g., CD25+ cells, or less (e.g., $1\times10^9$, $5\times10^8$, $1\times10^8$, $5\times10^7$, $1\times10^7$, or less CD25+ cells).

In some embodiments, the T regulatory cells, e.g., CD25+ cells, are removed from the population using the CliniMAC system with a depletion tubing set, such as, e.g., tubing 162-01. In some embodiments, the CliniMAC system is run on a depletion setting such as, e.g., DEPLETION2.1.

Without wishing to be bound by a particular theory, decreasing the level of negative regulators of immune cells (e.g., decreasing the number of unwanted immune cells, e.g., $T_{REG}$ cells), in a subject prior to apheresis or during manufacturing of a CAR-expressing cell product can reduce the risk of subject relapse. For example, methods of depleting $T_{REG}$ cells are known in the art. Methods of decreasing $T_{REG}$ cells include, but are not limited to, cyclophosphamide, anti-GITR antibody (an anti-GITR antibody described herein), CD25-depletion, and combinations thereof.

In some embodiments, the manufacturing methods comprise reducing the number of (e.g., depleting) $T_{REG}$ cells prior to manufacturing of the CAR-expressing cell. For example, manufacturing methods comprise contacting the sample, e.g., the apheresis sample, with an anti-GITR antibody and/or an anti-CD25 antibody (or fragment thereof, or a CD25-binding ligand), e.g., to deplete $T_{REG}$ cells prior to manufacturing of the CAR-expressing cell (e.g., T cell, NK cell) product.

In an embodiment, a subject is pre-treated with one or more therapies that reduce $T_{REG}$ cells prior to collection of cells for CAR-expressing cell product manufacturing, thereby reducing the risk of subject relapse to CAR-expressing cell treatment. In an embodiment, methods of decreasing $T_{REG}$ cells include, but are not limited to, administration to the subject of one or more of cyclophosphamide, anti-GITR antibody, CD25-depletion, or a combination thereof. Administration of one or more of cyclophosphamide, anti-GITR antibody, CD25-depletion, or a combination thereof, can occur before, during or after an infusion of the CAR-expressing cell product.

In an embodiment, a subject is pre-treated with cyclophosphamide prior to collection of cells for CAR-expressing cell product manufacturing, thereby reducing the risk of subject relapse to CAR-expressing cell treatment. In an embodiment, a subject is pre-treated with an anti-GITR antibody prior to collection of cells for CAR-expressing cell product manufacturing, thereby reducing the risk of subject relapse to CAR-expressing cell treatment.

In some embodiments, the population of cells to be removed are neither the regulatory T cells or tumor cells, but cells that otherwise negatively affect the expansion and/or function of CART cells, e.g. cells expressing CD14, CD11b, CD33, CD15, or other markers expressed by potentially immune suppressive cells. In some embodiments, such cells are envisioned to be removed concurrently with regulatory T cells and/or tumor cells, or following said depletion, or in another order.

The methods described herein can include more than one selection step, e.g., more than one depletion step. Enrichment of a T cell population by negative selection can be accomplished, e.g., with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail can include antibodies to CD14, CD20, CD11b, CD16, HLA-DR, and CD8.

The methods described herein can further include removing cells from the population which express a tumor antigen, e.g., a tumor antigen that does not comprise CD25, e.g., CD19, CD30, CD38, CD123, CD20, CD14 or CD11b, to thereby provide a population of T regulatory depleted, e.g., CD25+ depleted, and tumor antigen depleted cells that are suitable for expression of a CAR, e.g., a CAR described herein. In some embodiments, tumor antigen expressing cells are removed simultaneously with the T regulatory, e.g., CD25+ cells. For example, an anti-CD25 antibody, or fragment thereof, and an anti-tumor antigen antibody, or fragment thereof, can be attached to the same substrate, e.g., bead, which can be used to remove the cells or an anti-CD25 antibody, or fragment thereof, or the anti-tumor antigen antibody, or fragment thereof, can be attached to separate beads, a mixture of which can be used to remove the cells. In other embodiments, the removal of T regulatory cells, e.g., CD25+ cells, and the removal of the tumor antigen expressing cells is sequential, and can occur, e.g., in either order.

Also provided are methods that include removing cells from the population which express a check point inhibitor, e.g., a check point inhibitor described herein, e.g., one or more of PD1+ cells, LAG3+ cells, and TIM3+ cells, to thereby provide a population of T regulatory depleted, e.g., CD25+ depleted cells, and check point inhibitor depleted cells, e.g., PD1+, LAG3+ and/or TIM3+ depleted cells. Exemplary check point inhibitors include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. In embodiments, the checkpoint inhibitor is PD1 or PD-L1. In some embodiments, check point inhibitor expressing cells are removed simultaneously with the T regulatory, e.g., CD25+ cells. For example, an anti-CD25 antibody, or fragment thereof, and an anti-check point inhibitor antibody, or fragment thereof, can be attached to the same bead which can be used to remove the cells, or an anti-CD25 antibody, or fragment thereof, and the anti-check point inhibitor antibody, or fragment there, can be attached to separate beads, a mixture of which can be used to remove the cells. In other embodiments, the removal of T regulatory cells, e.g., CD25+ cells, and the removal of the check point inhibitor expressing cells is sequential, and can occur, e.g., in either order.

In some embodiments, a T cell population can be selected that expresses one or more of IFN-γ, TNFα, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/ml is used. In one aspect, a concentration of 1 billion cells/ml is used. In a further aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one aspect, the concentration of cells used is 5×10e6/ml. In other aspects, the concentration used can be from about $1\times10^5$/ml to $1\times10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as immune effector cells, e.g., T cells or NK cells, isolated and frozen for later use in cell therapy, e.g., T cell therapy, for any number of diseases or conditions that would benefit from cell therapy, e.g., T cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the immune effector cells (e.g., T cells or NK cells) may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In some embodiments, the immune effector cells expressing a CAR molecule, e.g., a CAR molecule described herein, are obtained from a subject that has received a low, immune enhancing dose of an mTOR inhibitor. In an embodiment, the population of immune effector cells, e.g., T cells, to be engineered to express a CAR, are harvested after a sufficient time, or after sufficient dosing of the low, immune enhancing, dose of an mTOR inhibitor, such that the level of PD1 negative immune effector cells, e.g., T cells, or the ratio of PD1 negative immune effector cells, e.g., T cells/PD1 positive immune effector cells, e.g., T cells, in the subject or harvested from the subject has been, at least transiently, increased.

In other embodiments, population of immune effector cells, e.g., T cells, which have, or will be engineered to express a CAR, can be treated ex vivo by contact with an amount of an mTOR inhibitor that increases the number of PD1 negative immune effector cells, e.g., T cells or increases the ratio of PD1 negative immune effector cells, e.g., T cells/PD1 positive immune effector cells, e.g., T cells.

In some embodiments, a T cell population is diaglycerol kinase (DGK)-deficient. DGK-deficient cells include cells that do not express DGK RNA or protein, or have reduced or inhibited DGK activity. DGK-deficient cells can be generated by genetic approaches, e.g., administering RNA-interfering agents, e.g., siRNA, shRNA, miRNA, to reduce or prevent DGK expression. Alternatively, DGK-deficient cells can be generated by treatment with DGK inhibitors described herein.

In some embodiments, a T cell population is Ikaros-deficient. Ikaros-deficient cells include cells that do not express Ikaros RNA or protein, or have reduced or inhibited Ikaros activity, Ikaros-deficient cells can be generated by genetic approaches, e.g., administering RNA-interfering agents, e.g., siRNA, shRNA, miRNA, to reduce or prevent Ikaros expression. Alternatively, Ikaros-deficient cells can be generated by treatment with Ikaros inhibitors, e.g., lenalidomide.

In embodiments, a T cell population is DGK-deficient and Ikaros-deficient, e.g., does not express DGK and Ikaros, or has reduced or inhibited DGK and Ikaros activity. Such DGK and Ikaros-deficient cells can be generated by any of the methods described herein.

In an embodiment, the NK cells are obtained from the subject. In another embodiment, the NK cells are an NK cell line, e.g., NK-92 cell line (Conkwest).

Allogeneic CAR

In embodiments described herein, the immune effector cell can be an allogeneic immune effector cell, e.g., T cell or NK cell. For example, the cell can be an allogeneic T cell, e.g., an allogeneic T cell lacking expression of a functional T cell receptor (TCR) and/or human leukocyte antigen (HLA), e.g., HLA class I and/or HLA class II.

A T cell lacking a functional TCR can be, e.g., engineered such that it does not express any functional TCR on its surface, engineered such that it does not express one or more subunits that comprise a functional TCR (e.g., engineered such that it does not express (or exhibits reduced expression) of TCR alpha, TCR beta, TCR gamma, TCR delta, TCR epsilon, and/or TCR zeta) or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

A T cell described herein can be, e.g., engineered such that it does not express a functional HLA on its surface. For example, a T cell described herein, can be engineered such that cell surface expression HLA, e.g., HLA class 1 and/or HLA class II, is downregulated. In some aspects, downregulation of HLA may be accomplished by reducing or eliminating expression of beta-2 microglobulin (B2M). In some embodiments, the T cell can lack a functional TCR and a functional HLA, e.g., HLA class I and/or HLA class II.

Modified T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, clustered regularly interspaced short palindromic repeats (CRISPR) transcription-activator like effector nuclease (TALEN), or zinc finger endonuclease (ZFN).

In some embodiments, the allogeneic cell can be a cell which does not expresses or expresses at low levels an inhibitory molecule, e.g. a cell engineered by any method described herein. For example, the cell can be a cell that does not express or expresses at low levels an inhibitory molecule, e.g., that can decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used.

siRNA and shRNA to Inhibit TCR or HLA

In some embodiments, TCR expression and/or HLA expression can be inhibited using siRNA or shRNA that targets a nucleic acid encoding a TCR, and/or HLA, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta), in a cell, e.g., T cell.

Expression of siRNA and shRNAs in T cells can be achieved using any conventional expression system, e.g., such as a lentiviral expression system.

Exemplary shRNAs that downregulate expression of components of the TCR are described, e.g., in US Publication No.: 2012/0321667. Exemplary siRNA and shRNA that downregulate expression of HLA class I and/or HLA class II genes are described, e.g., in U.S. publication No.: US 2007/0036773.

CRISPR to Inhibit TCR or HLA

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta).

Naturally-occurring CRISPR/Cas systems are found in approximately 40% of sequenced eubacteria genomes and 90% of sequenced archaea. Grissa et al. (2007) *BMC Bioinformatics* 8: 172. This system is a type of prokaryotic immune system that confers resistance to foreign genetic elements such as plasmids and phages and provides a form of acquired immunity. Barrangou et al. (2007) *Science* 315: 1709-1712; Marragini et al. (2008) *Science* 322: 1843-1845.

The CRISPR/Cas system has been modified for use in gene editing (silencing, enhancing or changing specific genes) in eukaryotes such as mice or primates. Wiedenheft et al. (2012) *Nature* 482: 331-8. This is accomplished by introducing into the eukaryotic cell a plasmid containing a specifically designed CRISPR and one or more appropriate Cas.

The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the TCR and/or HLA CRISPR/Cas system, the spacers are derived from the TCR or HLA gene sequence.

RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. (2010) *Science* 327: 167-170; Makarova et al. (2006) *Biology Direct* 1: 7. The spacers thus serve as templates for RNA molecules, analogously to siRNAs. Pennisi (2013) *Science* 341: 833-836.

As these naturally occur in many different types of bacteria, the exact arrangements of the CRISPR and structure, function and number of Cas genes and their product differ somewhat from species to species. Haft et al. (2005) *PLoS Comput. Biol.* 1: e60; Kunin et al. (2007) *Genome Biol.* 8: R61; Mojica et al. (2005) *J. Mol. Evol.* 60: 174-182; Bolotin et al. (2005) *Microbiol.* 151: 2551-2561; Pourcel et al. (2005) *Microbiol.* 151: 653-663; and Stern et al. (2010) *Trends. Genet.* 28: 335-340. For example, the Cse (Cas subtype, *E. coli*) proteins (e.g., CasA) form a functional complex, Cascade, that processes CRISPR RNA transcripts into spacer-repeat units that Cascade retains. Brouns et al. (2008) *Science* 321: 960-964. In other prokaryotes, Cas6 processes the CRISPR transcript. The CRISPR-based phage inactivation in *E. coli* requires Cascade and Cas3, but not Cas1 or Cas2. The Cmr (Cas RAMP module) proteins in *Pyrococcus furiosus* and other prokaryotes form a functional complex with small CRISPR RNAs that recognizes and cleaves complementary target RNAs. A simpler CRISPR system relies on the protein Cas9, which is a nuclease with two active cutting sites, one for each strand of the double helix. Combining Cas9 and modified CRISPR locus RNA can be used in a system for gene editing. Pennisi (2013) *Science* 341: 833-836.

The CRISPR/Cas system can thus be used to edit a TCR and/or HLA gene (adding or deleting a basepair), or introducing a premature stop which thus decreases expression of a TCR and/or HLA. The CRISPR/Cas system can alternatively be used like RNA interference, turning off TCR and/or HLA gene in a reversible fashion. In a mammalian cell, for example, the RNA can guide the Cas protein to a TCR and/or HLA promoter, sterically blocking RNA polymerases.

Artificial CRISPR/Cas systems can be generated which inhibit TCR and/or HLA, using technology known in the art, e.g., that described in U.S. Publication No. 20140068797, and Cong (2013) Science 339: 819-823. Other artificial CRISPR/Cas systems that are known in the art may also be generated which inhibit TCR and/or HLA, e.g., that described in Tsai (2014) Nature Biotechnol., 32:6 569-576, U.S. Pat. Nos. 8,871,445; 8,865,406; 8,795,965; 8,771,945; and 8,697,359.

TALEN to Inhibit TCR and/or HLA

"TALEN" or "TALEN to HLA and/or TCR" or "TALEN to inhibit HLA and/or TCR" refers to a transcription activator-like effector nuclease, an artificial nuclease which can be used to edit the HLA, and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta).

TALENs are produced artificially by fusing a TAL effector DNA binding domain to a DNA cleavage domain. Transcription activator-like effects (TALEs) can be engineered to bind any desired DNA sequence, including a portion of the HLA or TCR gene. By combining an engineered TALE with a DNA cleavage domain, a restriction enzyme can be produced which is specific to any desired DNA sequence, including a HLA or TCR sequence. These can then be introduced into a cell, wherein they can be used for genome editing. Boch (2011) *Nature Biotech.* 29: 135-6; and Boch et al. (2009) *Science* 326: 1509-12; Moscou et al. (2009) *Science* 326: 3501.

TALEs are proteins secreted by *Xanthomonas* bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence.

To produce a TALEN, a TALE protein is fused to a nuclease (N), which is a wild-type or mutated FokI endonuclease. Several mutations to FokI have been made for its use in TALENs; these, for example, improve cleavage specificity or activity. Cermak et al. (2011) *Nucl. Acids Res.* 39: e82; Miller et al. (2011) *Nature Biotech.* 29: 143-8; Hockemeyer et al. (2011) *Nature Biotech.* 29: 731-734; Wood et al. (2011) *Science* 333: 307; Doyon et al. (2010) *Nature Methods* 8: 74-79; Szczepek et al. (2007) *Nature Biotech.* 25: 786-793; and Guo et al. (2010) *J. Mol. Biol.* 200: 96.

The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) *Nature Biotech.* 29: 143-8.

A HLA or TCR TALEN can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN; depending on the sequences of the foreign DNA and chromosomal sequence, this process can be used to correct a defect in the HLA or TCR gene or introduce such a defect into a wt HLA or TCR gene, thus decreasing expression of HLA or TCR.

TALENs specific to sequences in HLA or TCR can be constructed using any method known in the art, including various schemes using modular components. Zhang et al. (2011) *Nature Biotech.* 29: 149-53; Geibler et al. (2011) *PLoS ONE* 6: e19509.

Zinc Finger Nuclease to Inhibit HLA and/or TCR

"ZFN" or "Zinc Finger Nuclease" or "ZFN to HLA and/or TCR" or "ZFN to inhibit HLA and/or TCR" refer to a zinc finger nuclease, an artificial nuclease which can be used to edit the HLA, and/or TCR gene, and/or an inhibitory molecule described herein (e.g., PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta).

Like a TALEN, a ZFN comprises a FokI nuclease domain (or derivative thereof) fused to a DNA-binding domain. In the case of a ZFN, the DNA-binding domain comprises one or more zinc fingers. Carroll et al. (2011) *Genetics Society of America* 188: 773-782; and Kim et al. (1996) *Proc. Natl. Acad. Sci. USA* 93: 1156-1160.

A zinc finger is a small protein structural motif stabilized by one or more zinc ions. A zinc finger can comprise, for example, Cys2His2, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. (1998) *Proc. Natl. Acad. Sci. USA* 95: 10570-5.

Also like a TALEN, a ZFN can create a double-stranded break in the DNA, which can create a frame-shift mutation if improperly repaired, leading to a decrease in the expression and amount of HLA and/or TCR in a cell. ZFNs can also be used with homologous recombination to mutate in the HLA or TCR gene.

ZFNs specific to sequences in HLA AND/OR TCR can be constructed using any method known in the art. See, e.g., Provasi (2011) Nature Med. 18: 807-815; Torikai (2013) Blood 122: 1341-1349; Cathomen et al. (2008) *Mol. Ther.* 16: 1200-7; Guo et al. (2010) *J. Mol. Biol.* 400: 96; U.S. Patent Publication 2011/0158957; and U.S. Patent Publication 2012/0060230.

Telomerase Expression

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117:1466-1476 (2007). Thus, in an embodiment, an immune effector cell, e.g., a T cell, ectopically expresses a telomerase subunit, e.g., the catalytic subunit of telomerase, e.g., TERT, e.g., hTERT. In some aspects, this disclosure provides a method of producing a CAR-expressing cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

In one aspect, the disclosure features a method of making a population of immune effector cells (e.g., T cells, NK cells). In an embodiment, the method comprises: providing a population of immune effector cells (e.g., T cells or NK cells), contacting the population of immune effector cells with a nucleic acid encoding a CAR; and contacting the population of immune effector cells with a nucleic acid encoding a telomerase subunit, e.g., hTERT, under conditions that allow for CAR and telomerase expression.

In an embodiment, the nucleic acid encoding the telomerase subunit is DNA. In an embodiment, the nucleic acid encoding the telomerase subunit comprises a promoter capable of driving expression of the telomerase subunit.

In an embodiment, hTERT has the amino acid sequence of GenBank Protein ID AAC51724.1 (Meyerson et al., "hEST2, the Putative Human Telomerase Catalytic Subunit Gene, Is Up-Regulated in Tumor Cells and during Immortalization" Cell Volume 90, Issue 4, 22 Aug. 1997, Pages 785-795) as follows:

```
                                       (SEQ ID NO: 284)
MPRAPRCRAVRSLLRSHYREVLPLATFVRRLGPQGWRLVQRGDPAAFRALV

AQCLVCVPWDARPPPAAPSFRQVSCLKELVARVLQRLCERGAKNVLAFGFA

LLDGARGGPPEAFTTSVRSYLPNTVTDALRGSGAWGLLLRRVGDDVLVHLL
```

-continued

ARCALFVLVAPSCAYQVCGPPLYQLGAATQARPPPHASGPRRRLGCERAWN
HSVREAGVPLGLPAPGARRRGGSASRSLPLPKRPRRGAAPEPERTPVGQGS
WAHPGRTRGPSDRGFCVVSPARPAEEATSLEGALSGTRHSHPSVGRQHHAG
PPSTSRPPRPWDTPCPPVYAETKHFLYSSGDKEQLRPSFLLSSLRPSLTGA
RRLVETIFLGSRPWMPGTPRRLPRLPQRYWQMRPLFLELLGNHAQCPYGVL
LKTHCPLRAAVTPAAGVCAREKPQGSVAAPEEEDTDPRRLVQLLRQHSSPW
QVYGFVRACLRRLVPPGLWGSRHNERRFLRNTKKFISLGKHAKLSLQELTW
KMSVRGCAWLRRSPGVGCVPAAEHRLREEILAKFLHWLMSVYVVELLRSFF
YVTETTFQKNRLFFYRKSVWSKLQSIGIRQHLKRVQLRELSEAEVRQHREA
RPALLTSRLRFIPKPDGLRPIVNMDYVVGARTFRREKRAERLTSRVKALFS
VLNYERARRPGLLGASVLGLDDIHRAWRTFVLRVRAQDPPPELYFVKVDVT
GAYDTIPQDRLTEVIASIIKPQNTYCVRRYAVVQKAAHGHVRKAFKSHVST
LTDLQPYMRQFVAHLQETSPLRDAVVIEQSSSLNEASSGLFDVFLRFMCHH
AVRIRGKSYVQCQGIPQGSILSTLLCSLCYGDMENKLFAGIRRDGLLLRLV
DDFLLVTPHLTHAKTFLRTLVRGVPEYGCVVNLRKTVVNFPVEDEALGGTA
FVQMPAHGLFPWCGLLLDTRTLEVQSDYSSYARTSIRASLTFNRGFKAGRN
MRRKLFGVLRLKCHSLFLDLQVNSLQTVCTNIYKILLLQAYRFHACVLQLP
FHQQVWKNPTFFLRVISDTASLCYSILKAKNAGMSLGAKGAAGPLPSEAVQ
WLCHQAFLLKLTRHRVTYVPLLGSLRTAQTQLSRKLPGTTLTALEAAANPA
LPSDFKTILD

In an embodiment, the hTERT has a sequence at least 80%, 85%, 90%, 95%, 96%, 97%, 98%, or 99% identical to the sequence of SEQ ID NO: 284. In an embodiment, the hTERT has a sequence of SEQ ID NO: 284. In an embodiment, the hTERT comprises a deletion (e.g., of no more than 5, 10, 15, 20, or 30 amino acids) at the N-terminus, the C-terminus, or both. In an embodiment, the hTERT comprises a transgenic amino acid sequence (e.g., of no more than 5, 10, 15, 20, or 30 amino acids) at the N-terminus, the C-terminus, or both.

Activation and Expansion of T Cells

T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention may be expanded by contact with a surface having attached thereto an agent that stimulates a CD3/TCR complex associated signal and a ligand that stimulates a costimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain aspects, the primary stimulatory signal and the costimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the costimulatory signal is bound to a cell surface and the agent providing the primary activation signal is in solution or coupled to a surface. In certain aspects, both agents can be in solution. In one aspect, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the costimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain aspects of the invention, the ratio of anti CD28 antibody to anti CD3 antibody bound to the beads is greater than 2:1. In one particular aspect, a 1:100 CD3:CD28 ratio of antibody bound to beads is used. In one aspect, a 1:75 CD3:CD28 ratio of antibody bound to beads is used. In a further aspect, a 1:50 CD3:CD28 ratio of antibody bound to beads is used. In one aspect, a 1:30 CD3:CD28 ratio of antibody bound to beads is used. In one preferred aspect, a 1:10 CD3:CD28 ratio of antibody bound to beads is used. In one aspect, a 1:3 CD3:CD28 ratio of antibody bound to the beads is used. In yet one aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, a preferred particle:cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In one aspect, particles are added on a daily or every other day basis to a final ratio of 1:1 on the first day, and 1:5 on the third and fifth days of stimulation. In one aspect, the ratio of particles to cells is 2:1 on the first day of stimulation and adjusted to 1:10 on the third and fifth days of stimulation. In one aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are in the neighborhood of 1:1, 2:1 and 3:1 on the first day.

In further aspects of the present invention, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (i.e., increase the concentration of cells), to ensure maximum contact of cells and particles. For example, in one aspect, a concentration of about 10 billion cells/ml, 9 billion/ml, 8 billion/ml, 7 billion/ml, 6 billion/ml, 5 billion/ml, or 2 billion cells/ml is used. In one aspect, greater than 100 million cells/ml is used. In a further aspect, a concentration of cells of 10, 15, 20, 25, 30, 35, 40, 45, or 50 million cells/ml is used. In yet one aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In some embodiments, cells transduced with a nucleic acid encoding a CAR, e.g., a CAR described herein, are expanded, e.g., by a method described herein. In some embodiments, the cells are expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In some embodiments, the cells are expanded for a period of 4 to 9 days. In some embodiments, the cells are expanded for a period of 8 days or less, e.g., 7, 6 or 5 days. In some embodiments, the cells, e.g., a BCMA CAR cell described herein, are expanded in culture for 5 days, and the resulting cells are more potent than the same cells expanded in culture for 9 days under the same culture conditions. Potency can be defined, e.g., by various T cell functions, e.g. proliferation, target cell killing, cytokine production, activation, migration, or combinations thereof. In some embodiments, the cells, e.g., a BCMA CAR cell described herein, expanded for 5 days show at least a one, two, three or four fold increase in cells doublings upon antigen stimulation as compared to the same cells expanded in culture for 9 days under the same culture conditions. In some embodiments, the cells, e.g., the cells expressing a BCMA CAR described herein, are expanded in culture for 5 days, and the resulting cells exhibit higher proinflammatory cytokine production, e.g., IFN-γ and/or GM-CSF levels, as compared to the same cells expanded in culture for 9 days under the same culture conditions. In some embodiments, the cells, e.g., a BCMA CAR cell described herein, expanded for 5 days show at least a one, two, three, four, five, ten fold or more increase in pg/ml of proinflammatory cytokine production, e.g., IFN-γ and/or GM-CSF levels, as compared to the same cells expanded in culture for 9 days under the same culture conditions.

In one aspect of the present invention, the mixture may be cultured for several hours (about 3 hours) to about 14 days or any hourly integer value in between. In one aspect, the mixture may be cultured for 21 days. In one aspect of the invention the beads and the T cells are cultured together for about eight days. In one aspect, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In some embodiments, the cells are expanded in an appropriate media (e.g., media described herein) that includes one or more interleukin that result in at least a 200-fold (e.g., 200-fold, 250-fold, 300-fold, 350-fold) increase in cells over a 14 day expansion period, e.g., as measured by a method described herein such as flow cytometry. In some embodiments, the cells are expanded in the presence of IL-15 and/or IL-7 (e.g., IL-15 and IL-7).

In embodiments, methods described herein, e.g., CAR-expressing cell manufacturing methods, comprise removing T regulatory cells, e.g., CD25+ T cells, from a cell population, e.g., using an anti-CD25 antibody, or fragment thereof, or a CD25-binding ligand, IL-2. Methods of removing T regulatory cells, e.g., CD25+ T cells, from a cell population are described herein. In embodiments, the methods, e.g., manufacturing methods, further comprise contacting a cell population (e.g., a cell population in which T regulatory cells, such as CD25+ T cells, have been depleted; or a cell population that has previously contacted an anti-CD25 antibody, fragment thereof, or CD25-binding ligand) with IL-15 and/or IL-7. For example, the cell population (e.g., that has previously contacted an anti-CD25 antibody, fragment thereof, or CD25-binding ligand) is expanded in the presence of IL-15 and/or IL-7.

In some embodiments a CAR-expressing cell described herein is contacted with a composition comprising a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15, during the manufacturing of the CAR-expressing cell, e.g., ex vivo. In embodiments, a CAR-expressing cell described herein is contacted with a composition comprising a IL-15 polypeptide during the manufacturing of the CAR-expressing cell, e.g., ex vivo. In embodiments, a CAR-expressing cell described herein is contacted with a composition comprising a combination of both a IL-15 polypeptide and a IL-15 Ra polypeptide during the manufacturing of the CAR-expressing cell, e.g., ex vivo. In embodiments, a CAR-expressing cell described herein is contacted with a composition comprising hetIL-15 during the manufacturing of the CAR-expressing cell, e.g., ex vivo.

In some embodiments the CAR-expressing cell described herein is contacted with a composition comprising hetIL-15 during ex vivo expansion. In an embodiment, the CAR-expressing cell described herein is contacted with a composition comprising an IL-15 polypeptide during ex vivo expansion. In an embodiment, the CAR-expressing cell described herein is contacted with a composition comprising both an IL-15 polypeptide and an IL-15Ra polypeptide during ex vivo expansion. In some embodiments the contacting results in the survival and proliferation of a lymphocyte subpopulation, e.g., CD8+ T cells.

T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8+). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once a BCMA CAR is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models. Assays to evaluate the effects of a BCMA CAR are described in further detail below Western blot analysis of CAR expression in primary T cells can be used to detect the presence of monomers and dimers. See, e.g., Milone et al., Molecular Therapy 17(8): 1453-1464 (2009). Very briefly, T cells (1:1 mixture of $CD4^+$ and $CD8^+$ T cells) expressing the CARs are expanded in vitro for more than 10 days followed by lysis and SDS-PAGE under reducing conditions. CARs containing the full length TCR-ζ cytoplasmic domain and the endogenous TCR-ζ chain are detected by western blotting using an antibody to the TCR-ζ chain. The same T cell subsets are used for SDS-PAGE analysis under non-reducing conditions to permit evaluation of covalent dimer formation.

In vitro expansion of $CAR^+$ T cells following antigen stimulation can be measured by flow cytometry. For example, a mixture of $CD4^+$ and $CD8^+$ T cells are stimulated with αCD3/αCD28 aAPCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the $CD4^+$ and/or $CD8^+$ T cell subsets by flow cytometry. See, e.g., Milone et al., Molecular Therapy 17(8): 1453-1464 (2009). Alternatively, a mixture of $CD4^+$ and $CD8^+$ T cells are stimulated with αCD3/αCD28 coated magnetic beads on day 0, and transduced with CAR on day 1 using a bicistronic lentiviral vector expressing CAR along with eGFP using a 2 A ribosomal skipping sequence. Cultures are re-stimulated with BCMA-expressing cells, such as multiple myeloma cell lines or K562-BCMA, following washing. Exogenous IL-2 is added to the cultures every other day at 100 IU/ml. $GFP^+$ T cells are enumerated by flow cytometry using bead-based counting. See, e.g., Milone et al., Molecular Therapy 17(8): 1453-1464 (2009).

Sustained $CAR^+$ T cell expansion in the absence of re-stimulation can also be measured. See, e.g., Milone et al., Molecular Therapy 17(8): 1453-1464 (2009). Briefly, mean T cell volume (fl) is measured on day 8 of culture using a Coulter Multisizer III particle counter, a Nexcelom Cellometer Vision or Millipore Scepter, following stimulation with αCD3/αCD28 coated magnetic beads on day 0, and transduction with the indicated CAR on day 1.

Animal models can also be used to measure a CART activity. For example, xenograft model using human BCMA-specific $CAR^+$ T cells to treat a primary human multiple myeloma in immunodeficient mice can be used. See, e.g., Milone et al., Molecular Therapy 17(8): 1453-1464 (2009). Very briefly, after establishment of MM, mice are randomized as to treatment groups. Different numbers of BCMA CART cells can be injected into immunodeficient mice bearing MM. Animals are assessed for disease progression and tumor burden at weekly intervals. Survival curves for the groups are compared using the log-rank test. In addition, absolute peripheral blood $CD4^+$ and $CD8^+$ T cell counts 4 weeks following T cell injection in the immunodeficient mice can also be analyzed. Mice are injected with multiple myeloma cells and 3 weeks later are injected with T cells engineered to express BCMA CAR, e.g., by a bicistronic lentiviral vector that encodes the CAR linked to eGFP. T cells are normalized to 45-50% input $GFP^+$ T cells by mixing with mock-transduced cells prior to injection, and confirmed by flow cytometry. Animals are assessed for leukemia at 1-week intervals. Survival curves for the $CAR^+$ T cell groups are compared using the log-rank test.

Assessment of cell proliferation and cytokine production has been previously described, e.g., at Milone et al., Molecular Therapy 17(8): 1453-1464 (2009). Briefly, assessment of CAR-mediated proliferation is performed in microtiter plates by mixing washed T cells with K562 cells expressing BCMA or other BCMA-expressing myeloma cells are irradiated with gamma-radiation prior to use. Anti-CD3 (clone OKT3) and anti-CD28 (clone 9.3) monoclonal antibodies are added to cultures with KT32-BBL cells to serve as a positive control for stimulating T-cell proliferation since these signals support long-term $CD8^+$ T cell expansion ex vivo. T cells are enumerated in cultures using CountBright™ fluorescent beads (Invitrogen, Carlsbad, Calif.) and flow cytometry as described by the manufacturer. $CAR^+$ T cells are identified by GFP expression using T cells that are engineered with eGFP-2A linked CAR-expressing lentiviral vectors. For CAR+ T cells not expressing GFP, the CAR+ T cells are detected with biotinylated recombinant BCMA protein and a secondary avidin-PE conjugate. CD4+ and $CD8^+$ expression on T cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences, San Diego, Calif.) according the manufacturer's instructions. Fluorescence is assessed using a FACScalibur flow cytometer, and data is analyzed according to the manufacturer's instructions.

Cytotoxicity can be assessed by a standard 51Cr-release assay. See, e.g., Milone et al., Molecular Therapy 17(8): 1453-1464 (2009). Briefly, target cells (e.g., K562 lines expressing BCMA and primary multiple myeloma cells) are loaded with 51Cr (as NaCrO4, New England Nuclear, Boston, Mass.) at 37° C. for 2 hours with frequent agitation, washed twice in complete RPMI and plated into microtiter plates. Effector T cells are mixed with target cells in the wells in complete RPMI at varying ratios of effector cell: target cell (E:T). Additional wells containing media only (spontaneous release, SR) or a 1% solution of triton-X 100 detergent (total release, TR) are also prepared. After 4 hours of incubation at 37° C., supernatant from each well is harvested. Released 51Cr is then measured using a gamma particle counter (Packard Instrument Co., Waltham, Mass.). Each condition is performed in at least triplicate, and the percentage of lysis is calculated using the formula: % Lysis=(ER−SR)/(TR−SR), where ER represents the average 51Cr released for each experimental condition.

Imaging technologies can be used to evaluate specific trafficking and proliferation of CARs in tumor-bearing animal models. Such assays have been described, for example, in Barrett et al., Human Gene Therapy 22:1575-1586 (2011).

Briefly, NOD/SCID/$\gamma c^{-/-}$ (NSG) mice or other immunodeficient are injected IV with multiple myeloma cells followed 7 days later with BCMA CART cells 4 hour after electroporation with the CAR constructs. The T cells are stably transfected with a lentiviral construct to express firefly luciferase, and mice are imaged for bioluminescence. Alternatively, therapeutic efficacy and specificity of a single injection of $CAR^+$ T cells in a multiple myeloma xenograft model can be measured as the following: NSG mice are injected with multiple myeloma cells transduced to stably express firefly luciferase, followed by a single tail-vein injection of T cells electroporated with BCMA CAR construct days later. Animals are imaged at various time points post injection. For example, photon-density heat maps of firefly luciferase positive tumors in representative mice at day 5 (2 days before treatment) and day 8 (24 hr post $CAR^+$ PBLs) can be generated.

Alternatively, or in combination to the methods disclosed herein, methods and compositions for one or more of: detection and/or quantification of CAR-expressing cells (e.g., in vitro or in vivo (e.g., clinical monitoring)); immune cell expansion and/or activation; and/or CAR-specific selection, that involve the use of a CAR ligand, are disclosed. In one exemplary embodiment, the CAR ligand is an antibody that binds to the CAR molecule, e.g., binds to the extracellular antigen binding domain of CAR (e.g., an antibody that binds to the antigen binding domain, e.g., an anti-idiotypic antibody; or an antibody that binds to a constant region of the extracellular binding domain). In other embodiments, the CAR ligand is a CAR antigen molecule (e.g., a CAR antigen molecule as described herein).

In one aspect, a method for detecting and/or quantifying CAR-expressing cells is disclosed. For example, the CAR ligand can be used to detect and/or quantify CAR-expressing cells in vitro or in vivo (e.g., clinical monitoring of CAR-expressing cells in a patient, or dosing a patient). The method includes:

providing the CAR ligand (optionally, a labelled CAR ligand, e.g., a CAR ligand that includes a tag, a bead, a radioactive or fluorescent label);

acquiring the CAR-expressing cell (e.g., acquiring a sample containing CAR-expressing cells, such as a manufacturing sample or a clinical sample);

contacting the CAR-expressing cell with the CAR ligand under conditions where binding occurs, thereby detecting the level (e.g., amount) of the CAR-expressing cells present. Binding of the CAR-expressing cell with the CAR ligand can be detected using standard techniques such as FACS, ELISA and the like.

In another aspect, a method of expanding and/or activating cells (e.g., immune effector cells) is disclosed. The method includes:

providing a CAR-expressing cell (e.g., a first CAR-expressing cell or a transiently expressing CAR cell);

contacting said CAR-expressing cell with a CAR ligand, e.g., a CAR ligand as described herein), under conditions where immune cell expansion and/or proliferation occurs, thereby producing the activated and/or expanded cell population.

In certain embodiments, the CAR ligand is present on (e.g., is immobilized or attached to a substrate, e.g., a non-naturally occurring substrate). In some embodiments, the substrate is a non-cellular substrate. The non-cellular substrate can be a solid support chosen from, e.g., a plate (e.g., a microtiter plate), a membrane (e.g., a nitrocellulose membrane), a matrix, a chip or a bead. In embodiments, the CAR ligand is present in the substrate (e.g., on the substrate surface). The CAR ligand can be immobilized, attached, or associated covalently or non-covalently (e.g., cross-linked) to the substrate. In some embodiments, the CAR ligand is attached (e.g., covalently attached) to a bead.

In the aforesaid embodiments, the immune cell population can be expanded in vitro or ex vivo. The method can further include culturing the population of immune cells in the presence of the ligand of the CAR molecule, e.g., using any of the methods described herein.

In other embodiments, the method of expanding and/or activating the cells further comprises addition of a second stimulatory molecule, e.g., CD28. For example, the CAR ligand and the second stimulatory molecule can be immobilized to a substrate, e.g., one or more beads, thereby providing increased cell expansion and/or activation.

In yet another aspect, a method for selecting or enriching for a CAR expressing cell is provided. The method includes contacting the CAR expressing cell with a CAR ligand as described herein; and selecting the cell on the basis of binding of the CAR ligand.

In yet other embodiments, a method for depleting, reducing and/or killing a CAR expressing cell is provided. The method includes contacting the CAR expressing cell with a CAR ligand as described herein; and targeting the cell on the basis of binding of the CAR ligand, thereby reducing the number, and/or killing, the CAR-expressing cell. In some embodiments, the CAR ligand is coupled to a toxic agent (e.g., a toxin or a cell ablative drug). In another embodiment, the anti-idiotypic antibody can cause effector cell activity, e.g., ADCC or ADC activities.

Exemplary anti-CAR antibodies that can be used in the methods disclosed herein are described, e.g., in WO 2014/190273 and by Jena et al., "Chimeric Antigen Receptor (CAR)-Specific Monoclonal Antibody to Detect CD19-Specific T cells in Clinical Trials", PLOS March 2013 8:3 e57838, the contents of which are incorporated by reference. In some embodiments, the anti-idiotypic antibody molecule recognizes an anti-CD19 antibody molecule, e.g., an anti-CD19 scFv. For instance, the anti-idiotypic antibody molecule can compete for binding with the CD19-specific CAR mAb clone no. 136.20.1 described in Jena et al., PLOS March 2013 8:3 e57838; may have the same CDRs (e.g., one or more of, e.g., all of, VH CDR1, VH CDR2, CH CDR3, VL CDR1, VL CDR2, and VL CDR3, using the Kabat definition, the Chothia definition, or a combination of the Kabat and Chothia definitions) as the CD19-specific CAR mAb clone no. 136.20.1; may have one or more (e.g., 2) variable regions as the CD19-specific CAR mAb clone no. 136.20.1, or may comprise the CD19-specific CAR mAb clone no. 136.20.1. In some embodiments, the anti-idiotypic antibody was made according to a method described in Jena et al. In another embodiment, the anti-idiotypic antibody molecule is an anti-idiotypic antibody molecule described in WO 2014/190273. In some embodiments, the anti-idiotypic antibody molecule has the same CDRs (e.g., one or more of, e.g., all of, VH CDR1, VH CDR2, CH CDR3, VL CDR1, VL CDR2, and VL CDR3) as an antibody molecule of WO 2014/190273 such as 136.20.1; may have one or more (e.g., 2) variable regions of an antibody molecule of WO 2014/190273, or may comprise an antibody molecule of WO 2014/190273 such as 136.20.1. In other embodiments, the anti-CAR antibody binds to a constant region of the extracellular binding domain of the CAR molecule, e.g., as described in WO 2014/190273. In some embodiments, the anti-CAR antibody binds to a constant region of the extracellular binding domain of the CAR molecule, e.g., a heavy chain constant region (e.g., a CH2-CH3 hinge region) or light chain constant region. For instance, in some embodiments the anti-CAR antibody competes for binding with the 2D3 monoclonal antibody described in WO 2014/190273, has the same CDRs (e.g., one or more of, e.g., all of, VH CDR1, VH CDR2, CH CDR3, VL CDR1, VL CDR2, and VL CDR3) as 2D3, or has one or more (e.g., 2) variable regions of 2D3, or comprises 2D3 as described in WO 2014/190273.

In some aspects and embodiments, the compositions and methods herein are optimized for a specific subset of T cells, e.g., as described in U.S. Ser. No. 62/031,699 filed Jul. 31, 2014, the contents of which are incorporated herein by reference in their entirety. In some embodiments, the optimized subsets of T cells display an enhanced persistence compared to a control T cell, e.g., a T cell of a different type (e.g., $CD8^+$ or $CD4^+$) expressing the same construct.

In some embodiments, a $CD4^+$ T cell comprises a CAR described herein, which CAR comprises an intracellular signaling domain suitable for (e.g., optimized for, e.g., leading to enhanced persistence in) a $CD4^+$ T cell, e.g., an ICOS domain. In some embodiments, a $CD8^+$ T cell comprises a CAR described herein, which CAR comprises an intracellular signaling domain suitable for (e.g., optimized for, e.g., leading to enhanced persistence of) a $CD8^+$ T cell, e.g., a 4-1BB domain, a CD28 domain, or another costimulatory domain other than an ICOS domain. In some embodiments, the CAR described herein comprises an antigen binding domain described herein, e.g., a CAR comprising an antigen binding domain that targets BCMA, e.g., a CAR of Table 2, 6, or 10).

In an aspect, described herein is a method of treating a subject, e.g., a subject having cancer. The method includes administering to said subject, an effective amount of:

1) a $CD4^+$ T cell comprising a CAR (the $CAR^{CD4+}$) comprising:

an antigen binding domain, e.g., an antigen binding domain described herein, e.g., an antigen binding domain that targets BCMA, e.g., an antigen-binding domain of Table 2, 6, or 10;

a transmembrane domain; and an intracellular signaling domain, e.g., a first costimulatory domain, e.g., an ICOS domain; and 2) a $CD8^+$ T cell comprising a CAR (the $CAR^{CD8+}$) comprising:

an antigen binding domain, e.g., an antigen binding domain described herein, e.g., an antigen binding domain that targets BCMA, e.g., an antigen-binding domain of Table 2, 6, or 10;

a transmembrane domain; and an intracellular signaling domain, e.g., a second costimulatory domain, e.g., a 4-1BB domain, a CD28 domain, or another costimulatory domain other than an ICOS domain;

wherein the $CAR^{CD4+}$ and the $CAR^{CD8+}$ differ from one another.

Optionally, the method further includes administering:

3) a second CD8+ T cell comprising a CAR (the second $CAR^{CD8+}$) comprising:

an antigen binding domain, e.g., an antigen binding domain described herein, e.g., an antigen binding domain that specifically binds BCMA, e.g., an antigen-binding domain of Table 2, 6, or 10;

a transmembrane domain; and an intracellular signaling domain, wherein the second $CAR^{CD8+}$ comprises an intracellular signaling domain, e.g., a costimulatory signaling domain, not present on the $CAR^{CD8+}$ and, optionally, does not comprise an ICOS signaling domain.

Other assays, including those described in the Example section herein as well as those that are known in the art can also be used to evaluate the BCMA CAR constructs of the invention.

Therapeutic Application

BCMA Associated Diseases and/or Disorders

In one aspect, the invention provides methods for treating a disease associated with BCMA expression. In one aspect, the invention provides methods for treating a disease wherein part of the tumor is negative for BCMA and part of the tumor is positive for BCMA For example, the CAR of the invention is useful for treating subjects that have undergone treatment for a disease associated with elevated expression of BCMA, wherein the subject that has undergone treatment for elevated levels of BCMA exhibits a disease associated with elevated levels of BCMA. In embodiments, the CAR of the invention is useful for treating subjects that have undergone treatment for a disease associated with expression of BCMA, wherein the subject that has undergone treatment related to expression of BCMA exhibits a disease associated with expression of BCMA.

In some embodiments, the invention provides methods for treating a disease wherein BCMA is expressed on both normal cells and cancers cells, but is expressed at lower levels on normal cells. In some embodiments, the method further comprises selecting a CAR that binds of the invention with an affinity that allows the BCMA CAR to bind and kill the cancer cells expressing BCMA but less than 30%, 25%, 20%, 15%, 10%, 5% or less of the normal cells expressing BCMA are killed, e.g., as determined by an assay described herein. For example, a killing assay such as flow cytometry based on Cr51 CTL can be used. In some embodiments, the BCMA CAR has an antigen binding domain that has a binding affinity KD of $10^{-4}$ M to $10^{-8}$ M, e.g., $10^{-5}$ M to $10^{-7}$ M, e.g., $10^{-6}$ M or $10^{-7}$ M, for the target antigen. In some embodiments, the BCMA antigen binding domain has a binding affinity that is at least five-fold, 10-fold, 20-fold, 30-fold, 50-fold, 100-fold or 1,000-fold less than a reference antibody, e.g., an antibody described herein.

In one aspect, the invention pertains to a vector comprising BCMA CAR operably linked to promoter for expression in mammalian immune effector cells, e.g., T cells or NK cells. In one aspect, the invention provides a recombinant immune effector cell, e.g., T cell or NK cell, expressing the BCMA CAR for use in treating BCMA-expressing tumors, wherein the recombinant immune effector cell (e.g., T cell or NK cell) expressing the BCMA CAR is termed a BCMA CAR-expressing cell (e.g., BCMA CART or BCMA CAR-expressing NK cell). In one aspect, the BCMA CAR-expressing cell (e.g., BCMA CART or BCMA CAR-expressing NK cell) of the invention is capable of contacting a tumor cell with at least one BCMA CAR of the invention expressed on its surface such that the BCMA CAR-expressing cell (e.g., BCMA CART or BCMA CAR-expressing NK cell) targets the tumor cell and growth of the tumor is inhibited.

In one aspect, the invention pertains to a method of inhibiting growth of a BCMA-expressing tumor cell, comprising contacting the tumor cell with a BCMA CAR-expressing cell (e.g., BCMA CART or BCMA CAR-expressing NK cell) of the present invention such that the BCMA CAR-expressing cell (e.g., BCMA CART or BCMA CAR-expressing NK cell) is activated in response to the antigen and targets the cancer cell, wherein the growth of the tumor is inhibited.

In one aspect, the invention pertains to a method of treating cancer in a subject. The method comprises administering to the subject a BCMA CAR-expressing cell (e.g., BCMA CART or BCMA CAR-expressing NK cell) of the present invention such that the cancer is treated in the subject. An example of a cancer that is treatable by the BCMA CAR-expressing cell (e.g., BCMA CART or BCMA CAR-expressing NK cell) of the invention is a cancer associated with expression of BCMA.

The invention includes a type of cellular therapy where immune effector cells (e.g., T cells or NK cells) are genetically modified to express a chimeric antigen receptor (CAR) and the BCMA CAR-expressing cell (e.g., BCMA CART or BCMA CAR-expressing NK cell) is infused to a recipient in need thereof. The infused cell is able to kill tumor cells in the recipient. Unlike antibody therapies, CAR-modified cells, e.g., T cells or NK cells, are able to replicate in vivo resulting in long-term persistence that can lead to sustained tumor control. In various aspects, the cells (e.g., T cells or NK cells) administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the cell (e.g., T cell or NK cell) to the patient.

The invention also includes a type of cellular therapy where immune effector cells (e.g., T cells or NK cells) are modified, e.g., by in vitro transcribed RNA, to transiently express a chimeric antigen receptor (CAR) and the immune effector cell (e.g., T cell or NK cell) is infused to a recipient in need thereof. The infused cell is able to kill tumor cells in the recipient. Thus, in various aspects, the immune effector cells (e.g., T cells or NK cells) administered to the patient, is present for less than one month, e.g., three weeks, two weeks, one week, after administration of the immune effector cell (e.g., T cell or NK cell) to the patient.

Without wishing to be bound by any particular theory, the anti-tumor immunity response elicited by the CAR-modified immune effector cells (e.g., T cells or NK cells) may be an active or a passive immune response, or alternatively may be due to a direct vs indirect immune response. In one aspect, the CAR transduced immune effector cells (e.g., T cells or NK cells) exhibit specific proinflammatory cytokine secretion and potent cytolytic activity in response to human cancer cells expressing the BCMA, resist soluble BCMA inhibition, mediate bystander killing and mediate regression of an established human tumor. For example, antigen-less tumor cells within a heterogeneous field of BCMA-expressing tumor may be susceptible to indirect destruction by BCMA-redirected immune effector cells (e.g., T cells or NK cells) that has previously reacted against adjacent antigen-positive cancer cells.

In one aspect, the fully-human CAR-modified immune effector cells (e.g., T cells or NK cells) of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified immune effector cells (e.g., T cells or NK cells) of the invention are used in the treatment of diseases, disorders and conditions associated with expression of BCMA. In certain aspects, the cells of the invention are used in the treatment of patients at risk for developing diseases, disorders and conditions associated with expression of BCMA. Thus, the present invention provides methods for the treatment or prevention of diseases, disorders and conditions associated with expression of BCMA comprising administering to a subject in need thereof, a therapeutically effective amount of the CAR-modified immune effector cells (e.g., T cells or NK cells) of the invention.

In one aspect the CAR-expressing cells (e.g., CART cells or CAR-expressing NK cells) of the inventions may be used to treat a proliferative disease such as a cancer or malignancy or is a precancerous condition such as a myelodysplasia, a myelodysplastic syndrome or a preleukemia. In one aspect, the cancer is a hematolical cancer. Hematological cancer conditions are the types of cancer such as leukemia and malignant lymphoproliferative conditions that affect blood, bone marrow and the lymphatic system. In one aspect, the hematological cancer is a leukemia or a hematological. An example of a disease or disorder associated with BCMA is multiple myeloma (also known as MM) (See Claudio et al., *Blood.* 2002, 100(6):2175-86; and Novak et al., *Blood.* 2004, 103(2):689-94). Multiple myeloma, also known as plasma cell myeloma or Kahler's disease, is a cancer characterized by an accumulation of abnormal or malignant plasma B-cells in the bone marrow. Frequently, the cancer cells invade adjacent bone, destroying skeletal structures and resulting in bone pain and fractures. Most cases of myeloma also features the production of a paraprotein (also known as M proteins or myeloma proteins), which is an abnormal immunoglobulin produced in excess by the clonal proliferation of the malignant plasma cells. Blood serum paraprotein levels of more than 30 g/L is diagnostic of multiple myeloma, according to the diagnostic criteria of the International Myeloma Working Group (IMWG) (See Kyle et al. (2009), Leukemia. 23:3-9). Other symptoms or signs of multiple myeloma include reduced kidney function or renal failure, bone lesions, anemia, hypercalcemia, and neurological symptoms.

Criteria for distinguishing multiple myeloma from other plasma cell proliferative disorders have been established by the International Myeloma Working Group (See Kyle et al. (2009), Leukemia. 23:3-9). All three of the following criteria must be met:

- Clonal bone marrow plasma cells ≥10%
- Present of serum and/or urinary monoclonal protein (except in patients with true non-secretory multiple myeloma)
- Evidence of end-organ damage attributable to the underlying plasma cell proliferative disorder, specifically:
  - Hypercalcemia: serum calcium ≥11.5 mg/100 ml
  - Renal insufficiency: serum creatinine >1.73 mmol/l
  - Anemia: normochromic, normocytic with a hemoglobin value of >2 g/100 ml below the lower limit of normal, or a hemoglobin value <10 g/100 ml
  - Bone lesions: lytic lesions, severe osteopenia, or pathologic fractures.

Other plasma cell proliferative disorders that can be treated by the compositions and methods described herein include, but are not limited to, asymptomatic myeloma (smoldering multiple myeloma or indolent myeloma), monoclonal gammapathy of undetermined significance (MGUS), Waldenstrom's macroglobulinemia, plasmacytomas (e.g., plasma cell dyscrasia, solitary myeloma, solitary plasmacytoma, extramedullary plasmacytoma, and multiple plasmacytoma), systemic amyloid light chain amyloidosis, and POEMS syndrome (also known as Crow-Fukase syndrome, Takatsuki disease, and PEP syndrome).

Two staging systems are used in the staging of multiple myeloma: the International Staging System (ISS) (See Greipp et al. (2005), J. Clin. Oncol. 23 (15):3412-3420) and the Durie-Salmon Staging system (DSS) (See Durie et al. (1975), Cancer 36 (3): 842-854). The two staging systems are summarized in the table below:

TABLE 15

Staging systems for the staging of multiple myeloma

| | International Staging System | | Durie-Salmon Staging System | |
|---|---|---|---|---|
| Stage | Criteria | Median survival | Criteria | Median survival* |
| I | $\beta_2$M <3.5 mg/l and serum albumin ≥3.5 g/dL | 62 months | All of the following:<br>Hemoglobin level >10 g/dL<br>Serum calcium, normal or <12 mg/dL<br>Bone x-ray, normal or 1 plasmacytoma only | IA: 62 months<br>IB: 22 months |

TABLE 15-continued

| Staging systems for the staging of multiple myeloma | | | | |
|---|---|---|---|---|
| | International Staging System | | Durie-Salmon Staging System | |
| Stage | Criteria | Median survival | Criteria | Median survival* |
| | | | Low monoclonal protein production (IgG <5 g/dL, IgA <3 g/dL, Bence Jones protein <4 g/dL per 24 hours | |
| II | Neither stage I or stage III | 44 months | Neither stage I or stage III | IIA: 58 months<br>IIB: 354 months |
| III | $\beta_2$M ≥5.5 mg/l | 29 months | One or more of the following:<br>Hemoglobin level <8.5 g/dL<br>Serum calcium, normal or >12 mg/dL<br>Advanced osteolytic lesions<br>High monoclonal protein production (IgG >7 g/dL, IgA >5 g/dL, Bence Jones protein >12 g/dL per 24 hours | IIIA: 45 months<br>IIIB: 24 months |

*The Durie-Salmon Staging system also includes a subclassification that designates the status of renal function. The designation of "A" or "B" is added after the stage number, wherein "A" indicates relatively normal renal function (serum creatinine value <2.0 mg/dL), and B indicates abnormal renal function (serum creatinine value >2.0 mg/dL).

A third staging system for multiple myeloma is referred to as Revised International Staging System (R-ISS) (see Palumbo A, Avet-Loiseau H, Oliva S, et al. Journal of clinical oncology: official journal of the American Society of Clinical Oncology 2015; 33:2863-9, herein incorporated by reference in its entirety). R-ISS stage I includes ISS stage I (serum β2-microglobulin level <3.5 mg/L and serum albumin level ≥3.5 g/dL), no high-risk CA [del(17p) and/or t(4;14) and/or t(14;16)], and normal LDH level (less than the upper limit of normal range). R-ISS stage III includes ISS stage III (serum β2-microglobulin level >5.5 mg/L) and high-risk CA or high LDH level. R-ISS stage II includes all the other possible combinations.

The response of patients can be determined based on IMWG 2016 criteria, as disclosed in Kumar S, Paiva B, Anderson K C, et al. International Myeloma Working Group consensus criteria for response and minimal residual disease assessment in multiple myeloma. The Lancet Oncology; 17(8):e28-e46, herein incorporated by reference in its entirety. Table 16 provides IMWG 2016 criteria for response assessment.

TABLE 16

| IMWG criteria for response assessment including criteria for minimal residual disease (MRD) | |
|---|---|
| | Response criteria* |
| IMWG MRD criteria (requires a complete response as defined below) | |
| Sustained MRD-negative | MRD negativity in the marrow (NGF or NGS, or both) and by imaging as defined below, confirmed minimum of 1 year apart. Subsequent evaluations can be used to further specify the duration of negativity (e.g., MRD-negative at 5 years)† |
| Flow MRD-negative | Absence of phenotypically aberrant clonal plasma cells by NGF‡ on bone marrow aspirates using the EuroFlow standard operation procedure for MRD detection in multiple myeloma (or validated equivalent method) with a minimum sensitivity of 1 in $10^5$ nucleated cells or higher |
| Sequencing MRD-negative | Absence of clonal plasma cells by NGS on bone marrow aspirate in which presence of a clone is defined as less than two identical sequencing reads obtained after DNA sequencing of bone marrow aspirates using the LymphoSIGHT platform (or validated equivalent method) with a minimum sensitivity of 1 in $10^5$ nucleated cells§ or higher |
| Imaging plus MRD-negative | MRD negativity as defined by NGF or NGS plus disappearance of every area of increased tracer uptake found at baseline or a preceding PET/CT or decrease to less mediastinal blood pool SUV or decrease to less than that of surrounding normal tissue¶ |
| Standard IMWG response criteria‖ | |
| Stringent complete response | Complete response as defined below plus normal FLC ratio** and absence of clonal cells in bone marrow biopsy by immunohistochemistry (κ/λ ratio ≤4:1 or ≥1:2 for κ and λ patients, respectively, after counting ≥100 plasma cells)†† |
| Complete response | Negative immunofixation on the serum and urine and disappearance of any soft tissue plasmacytomas and <5% plasma cells in bone marrow aspirates |

TABLE 16-continued

| IMWG criteria for response assessment including criteria for minimal residual disease (MRD) | |
|---|---|
| | Response criteria* |
| Very good partial response | Serum and urine M-protein detectable by immunofixation but not on electrophoresis or ≥90% reduction in serum M-protein plus urine M-protein level <100 mg per 24 h |
| Partial response | ≥50% reduction of serum M-protein plus reduction in 24 h urinary M-protein by ≥90% or to <200 mg per 24 h;<br>If the serum and urine M-protein are unmeasurable, a ≥50% decrease in the difference between involved and uninvolved FLC levels is required in place of the M-protein criteria;<br>If serum and urine M-protein are unmeasurable, and serum-free light assay is also unmeasurable, ≥50% reduction in plasma cells is required in place of M-protein, provided baseline bone marrow plasma-cell percentage was ≥30%. In addition to these criteria, if present at baseline, a ≥50% reduction in the size (SPD)§§ of soft tissue plasmacytomas is also required |
| Minimal response | ≥25% but ≤49% reduction of serum M-protein and reduction in 24-h urine M-protein by 50-89%. In addition to the above listed criteria, if present at baseline, a ≥50% reduction in the size (SPD)§§ of soft tissue plasmacytomas is also required |
| Stable disease | Not recommended for use as an indicator of response; stability of disease is best described by providing the time-to-progression estimates. Not meeting criteria for complete response, very good partial response, partial response, minimal response, or progressive disease |
| Progressive disease ¶¶, \|\|\|\| | Any one or more of the following criteria:<br>Increase of 25% from lowest confirmed response value in one or more of the following criteria:<br>Serum M-protein (absolute increase must be ≥0.5 g/dL);<br>Serum M-protein increase ≥1 g/dL, if the lowest M component was ≥5 g/dL;<br>Urine M-protein (absolute increase must be ≥200 mg/24 h);<br>In patients without measurable serum and urine M-protein levels, the difference between involved and uninvolved FLC levels (absolute increase must be >10 mg/dL);<br>In patients without measurable serum and urine M-protein levels and without measurable involved FLC levels, bone marrow plasma-cell percentage irrespective of baseline status (absolute increase must be ≥10%);<br>Appearance of a new lesion(s), ≥50% increase from nadir in SPD§§ of >1 lesion, or ≥50% increase in the longest diameter of a previous lesion >1 cm in short axis; ≥50% increase in circulating plasma cells (minimum of 200 cells per μL) if this is the only measure of disease |
| Clinical relapse | Clinical relapse requires one or more of the following criteria:<br>Direct indicators of increasing disease and/or end organ dysfunction (CRAB features) related to the underlying clonal plasma-cell proliferative disorder. It is not used in calculation of time to progression or progression-free survival but is listed as something that can be reported optionally or for use in clinical practice;<br>Development of new soft tissue plasmacytomas or bone lesions (osteoporotic fractures do not constitute progression);<br>Definite increase in the size of existing plasmacytomas or bone lesions. A definite increase is defined as a 50% (and ≥1 cm) increase as measured serially by the SPD§§ of the measurable lesion;<br>Hypercalcaemia (>11 mg/dL);<br>Decrease in haemoglobin of ≥2 g/dL not related to therapy or other non-myeloma-related conditions;<br>Rise in serum creatinine by 2 mg/dL or more from the start of the therapy and attributable to myeloma;<br>Hyperviscosity related to serum paraprotein |
| Relapse from complete response (to be used only if the end point is disease-free survival) | Any one or more of the following criteria:<br>Reappearance of serum or urine M-protein by immunofixation or electrophoresis;<br>Development of ≥5% plasma cells in the bone marrow;<br>Appearance of any other sign of progression (i.e., new plasmacytoma, lytic bone lesion, or hypercalcaemia see above) |
| Relapse from MRD negative (to be used only if the end point is disease-free survival) | Any one or more of the following criteria:<br>Loss of MRD negative state (evidence of clonal plasma cells on NGF or NGS, or positive imaging study for recurrence of myeloma);<br>Reappearance of serum or urine M-protein by immunofixation or electrophoresis; |

TABLE 16-continued

| IMWG criteria for response assessment including criteria for minimal residual disease (MRD) | |
|---|---|
| | Response criteria* |
| | Development of ≥5% clonal plasma cells in the bone marrow; Appearance of any other sign of progression (i.e., new plasmacytoma, lytic bone lesion, or hypercalcaemia) |

For MRD assessment, the first bone marrow aspirate should be sent to MRD (not for morphology) and this sample should be taken in one draw with a volume of minimally 2 mL (to obtain sufficient cells), but maximally 4-5 mL to avoid haemodilution. IMWG = International Myeloma Working Group. MRD = minimal residual disease. NGF = next-generation flow. NGS = next-generation sequencing. FLC = free light chain. M-protein = myeloma protein. SPD = sum of the products of the maximal perpendicular diameters of measured lesions. CRAB features = calcium elevation, renal failure, anaemia, lytic bone lesions. FCM = fl ow cytometry. SUVmax = maximum standardised uptake value. MFC = multiparameter flow cytometry. $^{18}$F-FDG PET = $^{18}$F-fluorodeoxyglucose PET. ASCT = autologous stem cell transplantation.

*All response categories require two consecutive assessments made any time before starting any new therapy; for MRD there is no need for two consecutive assessments, but information on MRD after each treatment stage is recommended (eg, after induction, high-dose therapy/ASCT, consolidation, maintenance). MRD tests should be initiated only at the time of suspected complete response.

All categories of response and MRD require no known evidence of progressive or new bone lesions if radiographic studies were performed. However, radiographic studies are not required to satisfy these response requirements except for the requirement of FDG PET if imaging MRD-negative status is reported.

†Sustained MRD negativity when reported should also annotate the method used (eg, sustained flow MRD-negative, sustained sequencing MRD-negative).

‡Bone marrow MFC should follow NGF guidelines (Paiva B, Gutierrez N C, Rosinol L, et al, Blood 2012; 119: 687-91). The reference NGF method is an eight-colour two-tube approach, which has been extensively validated. The two-tube approach improves reliability, consistency, and sensitivity because of the acquisition of a greater number of cells. The eight-colour technology is widely available globally and the NGF method has already been adopted in many flow laboratories worldwide. The complete eight-colour method is most efficient using a lyophilised mixture of antibodies which reduces errors, time, and costs. 5 million cells should be assessed. The FCM method employed should have a sensitivity of detection of at least 1 in $10^5$ plasma cells.

§DNA sequencing assay on bone marrow aspirate should use a validated assay such as LymphoSIGHT (Sequenta).

¶Criteria used by Zamagni and colleagues (Zamagni E, Nanni C, Mancuso K, et al. Clin Cancer Res 2015; 21: 4384-90), and expert panel (IMPetUs; Italian Myeloma criteria for PET Use) (Usmani S Z, Mitchell A, Waheed S, et al. Blood 2013; 121: 1819-23; Nanni C, Zamagni E, Versari A, et al. Eur J Nucl Med Mol Imaging 2015; 43: 414-21.). Baseline positive lesions were identified by presence of focal areas of increased uptake within bones, with or without any underlying lesion identified by CT and present on at least two consecutive slices. Alternatively, an SUVmax = 2.5 within osteolytic CT areas >1 cm in size, or SUVmax = 1.5 within osteolytic CT areas ≤1 cm in size were considered positive. Imaging should be performed once MRD negativity is determined by MFC or NGS.

||Derived from international uniform response criteria for multiple myeloma (Durie B G, Harousseau J L, Miguel J S, et al, Leukemia 2006; 20: 1467-73). Minor response definition and clarifications derived from Rajkumar and colleagues (Rajkumar S V, Harousseau J L, Durie B, et al, Blood 2011; 117: 4691-95). When the only method to measure disease is by serum FLC levels: complete response can be defined as a normal FLC ratio of 0.26 to 1.65 in addition to the complete response criteria listed previously. Very good partial response in such patients requires a ≥90% decrease in the difference between involved and uninvolved FLC levels. All response categories require two consecutive assessments made at any time before the institution of any new therapy; all categories also require no known evidence of progressive or new bone lesions or extramedullary plasmacytomas if radiographic studies were performed. Radiographic studies are not required to satisfy these response requirements. Bone marrow assessments do not need to be confirmed. Each category, except for stable disease, will be considered unconfirmed until the confirmatory test is performed. The date of the initial test is considered as the date of response for evaluation of time dependent outcomes such as duration of response.

**All recommendations regarding clinical uses relating to serum FLC levels or FLC ratio are based on results obtained with the validated Freelite test (Binding Site, Birmingham, UK).

††Presence/absence of clonal cells on immunohistochemistry is based upon the κ/λ/L ratio. An abnormal κ/λ ratio by immunohistochemistry requires a minimum of 100 plasma cells for analysis. An abnormal ratio reflecting presence of an abnormal clone is κ/λ of >4:1 or <1:2.

‡‡Special attention should be given to the emergence of a different monoclonal protein following treatment, especially in the setting of patients having achieved a conventional complete response, often related to oligoclonal reconstitution of the immune system. These bands typically disappear over time and in some studies have been associated with a better outcome. Also, appearance of monoclonal IgG κ in patients receiving monoclonal antibodies should be diff erentiated from the therapeutic antibody.

§§Plasmacytoma measurements should be taken from the CT portion of the PET/CT, or MRI scans, or dedicated CT scans where applicable. For patients with only skin involvement, skin lesions should be measured with a ruler. Measurement of tumour size will be determined by the SPD.

¶¶ Positive immunofi xation alone in a patient previously classifi ed as achieving a complete response will not be considered progression. For purposes of calculating time to progression and progression-free survival, patients who have achieved a complete response and are MRD-negative should be evaluated using criteria listed for progressive disease. Criteria for relapse from a complete response or relapse from MRD should be used only when calculating disease-free survival.

|||| In the case where a value is felt to be a spurious result per physician discretion (eg, a possible laboratory error), that value will not be considered when determining the lowest value.

Standard treatment for multiple myeloma and associated diseases includes chemotherapy, stem cell transplant (autologous or allogeneic), radiation therapy, and other drug therapies. Frequently used anti-myeloma drugs include alkylating agents (e.g., bendamustine, cyclophosphamide and melphalan), proteasome inhibitors (e.g., bortezomib), corticosteroids (e.g., dexamethasone and prednisone), and immunomodulators (e.g., thalidomide and lenalidomide or Revlimid®), or any combination thereof. Biphosphonate drugs are also frequently administered in combination with the standard anti-MM treatments to prevent bone loss. Patients older than 65-70 years of age are unlikely candidates for stem cell transplant. In some cases, double-autologous stem cell transplants are options for patients less than 60 years of age with suboptimal response to the first transplant. The compositions and methods of the present invention may be administered in combination with any of the currently prescribed treatments for multiple myeloma.

Another example of a disease or disorder associated with BCMA is Hodgkin's lymphoma and non-Hodgkin's lymphoma (See Chiu et al., *Blood.* 2007, 109(2):729-39; He et al., *J Immunol.* 2004, 172(5):3268-79).

Hodgkin's lymphoma (HL), also known as Hodgkin's disease, is a cancer of the lymphatic system that originates from white blood cells, or lymphocytes. The abnormal cells that comprise the lymphoma are called Reed-Sternberg cells. In Hodgkin's lymphoma, the cancer spreads from one lymph node group to another. Hodgkin's lymphoma can be subclassified into four pathologic subtypes based upon Reed-Sternberg cell morphology and the cell composition around the Reed-Sternberg cells (as determined through lymph node biopsy): nodular sclerosing HL, mixed-cellularity subtype, lymphocyte-rich or lymphocytic predominance, lymphocyte depleted. Some Hodgkin's lymphoma can also be nodular lymphocyte predominant Hodgkin's lymphoma, or can be unspecified. Symptoms and signs of Hodgkin's lymphoma include painless swelling in the lymph nodes in the neck, armpits, or groin, fever, night sweats, weight loss, fatigue, itching, or abdominal pain.

Non-Hodgkin's lymphoma (NHL) comprises a diverse group of blood cancers that include any kind of lymphoma other than Hodgkin's lymphoma. Subtypes of non-Hodgkin's lymphoma are classified primarily by cell morphology, chromosomal aberrations, and surface markers. NHL subtypes (or NHL-associated cancers) include B cell lymphomas such as, but not limited to, Burkitt's lymphoma, B-cell chronic lymphocytic leukemia (B-CLL), B-cell prolymphocytic leukemia (B-PLL), chronic lymphocytic leukemia (CLL), diffuse large B-cell lymphoma (DLBCL) (e.g., intravascular large B-cell lymphoma and primary mediastinal B-cell lymphoma), follicular lymphoma (e.g., follicle center lymphoma, follicular small cleaved cell), hairy cell leukemia, high grade B-cell lymphoma (Burkitt's like), lymphoplasmacytic lymphoma (Waldenstrom's macroglublinemia), mantle cell lymphoma, marginal zone B-cell lymphomas (e.g., extranodal marginal zone B-cell lymphoma or mucosa-associated lymphoid tissue (MALT) lymphoma, nodal marginal zone B-cell lymphoma, and splenic marginal zone B-cell lymphoma), plasmacytoma/myeloma, precursor B-lymphoblastic leukemia/lymphoma (PB-LBL/L), primary central nervous system (CNS) lymphoma, primary intraocular lymphoma, small lymphocytic lymphoma (SLL); and T cell lymphomas, such as, but not limited to, anaplastic large cell lymphoma (ALCL), adult T-cell lymphoma/leukemia (e.g., smoldering, chronic, acute and lymphomatous), angiocentric lymphoma, angioimmunoblastic T-cell lymphoma, cutaneous T-cell lymphomas (e.g., mycosis fungoides, Sezary syndrome, etc.), extranodal natural killer/T-cell lymphoma (nasal-type), enteropathy type intestinal T-cell lymphoma, large granular lymphocyte leukemia, precursor T-lymphoblastic lymphoma/leukemia (T-LBL/L), T-cell chronic lymphocytic leukemia/prolymphocytic leukemia (T-CLL/PLL), and unspecified peripheral T-cell lymphoma. Symptoms and signs of Hodgkin's lymphoma include painless swelling in the lymph nodes in the neck, armpits, or groin, fever, night sweats, weight loss, fatigue, itching, abdominal pain, coughing, or chest pain.

The staging is the same for both Hodgkin's and non-Hodgkin's lymphoma, and refers to the extent of spread of the cancer cells within the body. In stage I, the lymphoma cells are in one lymph node group. In stage II, lymphoma cells are present in at least two lymph node groups, but both groups are on the same side of the diaphragm, or in one part of a tissue or organ and the lymph nodes near that organ on the same side of the diaphragm. In stage III, lymphoma cells are in lymph nodes on both sides of the diaphragm, or in one part of a tissue or organ near these lymph node groups or in the spleen. In stage IV, lymphoma cells are found in several parts of at least one organ or tissue, or lymphoma cells are in an organ and in lymph nodes on the other side of the diaphragm. In addition to the Roman numeral staging designation, the stages of can also be described by letters A, B, E, and S, wherein A refers to patients without symptoms, B refers to patients with symptoms, E refers to patients in which lymphoma is found in tissues outside the lymph system, and S refers to patients in which lymphoma is found in the spleen.

Hodgkin's lymphoma is commonly treated with radiation therapy, chemotherapy, or hematopoietic stem cell transplantation. The most common therapy for non-Hodgkin's lymphoma is R-CHOP, which consists of four different chemotherapies (cyclophosphamide, doxorubicin, vincristine, and prenisolone) and rituximab (Rituxan®). Other therapies commonly used to treat NHL include other chemotherapeutic agents, radiation therapy, stem cell transplantation (autologous or allogeneic bone marrow transplantation), or biological therapy, such as immunotherapy. Other examples of biological therapeutic agents include, but are not limited to, rituximab (Rituxan®), tositumomab (Bexxar®), epratuzumab (LymphoCide®), and alemtuzumab (MabCampath®). The compositions and methods of the present invention may be administered in combination with any of the currently prescribed treatments for Hodgkin's lymphoma or non-Hodgkin's lymphoma.

BCMA expression has also been associated Waldenstrom's macroglobulinemia (WM), also known as lymphoplasmacytic lymphoma (LPL). (See Elsawa et al., *Blood.* 2006, 107(7):2882-8). Waldenstrom's macroglobulinemia was previously considered to be related to multiple myeloma, but has more recently been classified as a subtype of non-Hodgkin's lymphoma. WM is characterized by uncontrolled B-cell lymphocyte proliferation, resulting in anemia and production of excess amounts of paraprotein, or immunoglobulin M (IgM), which thickens the blood and results in hyperviscosity syndrome. Other symptoms or signs of WM include fever, night sweats, fatigue, anemia, weight loss, lymphadenopathy or splenomegaly, blurred vision, dizziness, nose bleeds, bleeding gums, unusual bruises, renal impairment or failure, amyloidosis, or peripheral neuropathy.

Standard treatment for WM consists of chemotherapy, specifically with rituximab (Rituxan®). Other chemotherapeutic drugs can be used in combination, such as chlorambucil (Leukeran®), cyclophosphamide (Neosar®), fludarabine (Fludara®), cladribine (Leustatin®), vincristine, and/or thalidomide. Corticosteriods, such as prednisone, can also be administered in combination with the chemotherapy. Plasmapheresis, or plasma exchange, is commonly used throughout treatment of the patient to alleviate some symptoms by removing the paraprotein from the blood. In some cases, stem cell transplantation is an option for some patients.

Another example of a disease or disorder associated with BCMA is brain cancer. Specifically, expression of BCMA has been associated with astrocytoma or glioblastoma (See Deshayes et al, *Oncogene.* 2004, 23(17):3005-12, Pelekanou et al., *PLoS One.* 2013, 8(12):e83250). Astrocytomas are tumors that arise from astrocytes, which are a type of glial cell in the brain. Glioblastoma (also known as glioblastoma multiforme or GBM) is the most malignant form of astrocytoma, and is considered the most advanced stage of brain cancer (stage IV). There are two variants of glioblastoma: giant cell glioblastoma and gliosarcoma. Other astrocytomas include juvenile pilocytic astrocytoma (JPA), fibrillary astrocytoma, pleomorphic xantroastrocytoma (PXA), desembryoplastic neuroepithelial tumor (DNET), and anaplastic astrocytoma (AA).

Symptoms or signs associated with glioblastoma or astrocytoma include increased pressure in the brain, headaches, seizures, memory loss, changes in behavior, loss in movement or sensation on one side of the body, language dysfunction, cognitive impairments, visual impairment, nausea, vomiting, and weakness in the arms or legs.

Surgical removal of the tumor (or resection) is the standard treatment for removal of as much of the glioma as possible without damaging or with minimal damage to the normal, surrounding brain. Radiation therapy and/or chemotherapy are often used after surgery to suppress and slow recurrent disease from any remaining cancer cells or satellite lesions. Radiation therapy includes whole brain radiotherapy (conventional external beam radiation), targeted three-dimensional conformal radiotherapy, and targeted radionuclides. Chemotherapeutic agents commonly used to treat glioblastoma include temozolomide, gefitinib or erlotinib, and cisplatin. Angiogenesis inhibitors, such as Bevacizumab (Avastin®), are also commonly used in combination with chemotherapy and/or radiotherapy.

Supportive treatment is also frequently used to relieve neurological symptoms and improve neurologic function, and is administered in combination any of the cancer therapies described herein. The primary supportive agents include anticonvulsants and corticosteroids. Thus, the compositions and methods of the present invention may be used in combination with any of the standard or supportive treatments to treat a glioblastoma or astrocytoma.

Non-cancer related diseases and disorders associated with BCMA expression can also be treated by the compositions and methods disclosed herein. Examples of non-cancer related diseases and disorders associated with BCMA expression include, but are not limited to: viral infections; e.g., HIV, fungal infections, e.g., *C. neoformans*; irritable bowel disease; ulcerative colitis, and disorders related to mucosal immunity.

The CAR-modified immune effector cells (e.g., T cells or NK cells) of the present invention may be administered either alone, or as a pharmaceutical composition in combination with diluents and/or with other components such as IL-2 or other cytokines or cell populations.

The present invention provides for compositions and methods for treating cancer. In one aspect, the cancer is a hematologic cancer including but is not limited to a leukemia or a lymphoma. In one aspect, the CAR-expressing cells (e.g., CART cells or CAR-expressing NK cells) of the invention may be used to treat cancers and malignancies such as, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like. Further a disease associated with BCMA expression includes, but not limited to, e.g., atypical and/or non-classical cancers, malignancies, precancerous conditions or proliferative diseases expressing BCMA.

In embodiments, a composition described herein can be used to treat a disease including but not limited to a plasma cell proliferative disorder, e.g., asymptomatic myeloma (smoldering multiple myeloma or indolent myeloma), monoclonal gammapathy of undetermined significance (MGUS), Waldenstrom's macroglobulinemia, plasmacytomas (e.g., plasma cell dyscrasia, solitary myeloma, solitary plasmacytoma, extramedullary plasmacytoma, and multiple plasmacytoma), systemic amyloid light chain amyloidosis, and POEMS syndrome (also known as Crow-Fukase syndrome, Takatsuki disease, and PEP syndrome).

In embodiments, a composition described herein can be used to treat a disease including but not limited to a cancer, e.g., a cancer described herein, e.g., a prostate cancer (e.g., castrate-resistant or therapy-resistant prostate cancer, or metastatic prostate cancer), pancreatic cancer, or lung cancer.

The present invention also provides methods for inhibiting the proliferation or reducing a BCMA-expressing cell population, the methods comprising contacting a population of cells comprising a BCMA-expressing cell with an anti-BCMA CAR-expressing cell (e.g., BCMA CART cell or BCMA CAR-expressing NK cell) of the invention that binds to the BCMA-expressing cell. In a specific aspect, the present invention provides methods for inhibiting the proliferation or reducing the population of cancer cells expressing BCMA, the methods comprising contacting the BCMA-expressing cancer cell population with an anti-BCMA CAR-expressing cell (e.g., BCMA CART cell or BCMA CAR-expressing NK cell) of the invention that binds to the BCMA-expressing cell. In one aspect, the present invention provides methods for inhibiting the proliferation or reducing the population of cancer cells expressing BCMA, the methods comprising contacting the BCMA-expressing cancer cell population with an anti-BCMA CAR-expressing cell (e.g., BCMA CART cell or BCMA CAR-expressing NK cell) of the invention that binds to the BCMA-expressing cell. In certain aspects, the anti-BCMA CAR-expressing cell (e.g., BCMA CART cell or BCMA CAR-expressing NK cell) of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for myeloid leukemia or another cancer associated with BCMA-expressing cells relative to a negative control. In one aspect, the subject is a human.

The present invention also provides methods for preventing, treating and/or managing a disease associated with BCMA-expressing cells (e.g., a hematologic cancer or atypical cancer expressing BCMA), the methods comprising administering to a subject in need an anti-BCMA CAR-expressing cell (e.g., BCMA CART cell or BCMA CAR-expressing NK cell) of the invention that binds to the BCMA-expressing cell. In one aspect, the subject is a human. Non-limiting examples of disorders associated with BCMA-expressing cells include viral or fungal infections, and disorders related to mucosal immunity.

The present invention also provides methods for preventing, treating and/or managing a disease associated with BCMA-expressing cells, the methods comprising administering to a subject in need an anti-BCMA CAR-expressing cell (e.g., BCMA CART cell or BCMA CAR-expressing NK cell) of the invention that binds to the BCMA-expressing cell. In one aspect, the subject is a human.

The present invention provides methods for preventing relapse of cancer associated with BCMA-expressing cells, the methods comprising administering to a subject in need thereof an anti-BCMA CAR-expressing cell (e.g., BCMA CART cell or BCMA CAR-expressing NK cell) of the invention that binds to the BCMA-expressing cell. In one aspect, the methods comprise administering to the subject in need thereof an effective amount of an anti-BCMA CAR-expressing cell (e.g., BCMA CART cell or BCMA CAR-expressing NK cell) described herein that binds to the BCMA-expressing cell in combination with an effective amount of another therapy.

Combination Therapies

A CAR-expressing cell described herein may be used in combination with other known agents and therapies.

A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

The CAR therapy and/or other therapeutic agents, procedures or modalities can be administered during periods of active disorder, or during a period of remission or less active disease. The CAR therapy can be administered before the other treatment, concurrently with the treatment, post-treatment, or during remission of the disorder.

When administered in combination, the CAR therapy and the additional agent (e.g., second or third agent), or all, can be administered in an amount or dose that is higher, lower or the same than the amount or dosage of each agent used individually, e.g., as a monotherapy. In certain embodiments, the administered amount or dosage of the CAR therapy, the additional agent (e.g., second or third agent), or all, is lower (e.g., at least 20%, at least 30%, at least 40%, or at least 50%) than the amount or dosage of each agent used individually, e.g., as a monotherapy. In other embodiments, the amount or dosage of the CAR therapy, the additional agent (e.g., second or third agent), or all, that results in a desired effect (e.g., treatment of cancer) is lower (e.g., at least 20%, at least 30%, at least 40%, or at least 50% lower) than the amount or dosage of each agent used individually, e.g., as a monotherapy, required to achieve the same therapeutic effect.

In further aspects, a CAR-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Izumoto et al. 2008 J Neurosurg 108:963-971.

In certain instances, compounds of the present invention are combined with other therapeutic agents, such as other anti-cancer agents, anti-allergic agents, anti-nausea agents (or anti-emetics), pain relievers, cytoprotective agents, and combinations thereof.

In some embodiments, a first CAR-expressing cell described herein, e.g., a BCMA CAR-expressing cell described herein, may be used in combination with a second CAR-expressing cell. In some embodiments, the second CAR-expressing cell expresses a CAR comprising a different anti-BCMA binding domain, e.g., an anti-BCMA binding domain described herein that differs from the anti-BCMA binding domain in the CAR expressed by the first CAR-expressing cell. In some embodiments, the second CAR-expressing cell expresses a CAR comprising an antigen-binding domain that targets an antigen other than BCMA (e.g., CD19, CD20, CS-1, kappa light chain, CD139, Lewis Y antigen, or CD38). In some embodiments, a first CAR-expressing cell described herein, e.g., a BCMA CAR-expressing cell described herein, is used in combination with a second CAR-expressing cell comprising a CD19 CAR. In some embodiments, a BCMA CAR-expressing cell described herein is used in combination with a CD19 CAR-expressing cell to treat a BCMA-associated cancer described herein, e.g., multiple myeloma. In some embodiments, the multiple myeloma is CD19-negative, e.g., having a vast majority (e.g., at least 98%, 99%, 99.5%, 99.9%, or 99.95%) of the neoplastic plasma cells with a CD19-negative phenotype, e.g., as detected flow cytometry, RT-PCR, or both flow cytometry and RT-PCR. A CD19 CAR can be effective even against a CD19-negative multiple myeloma. While not wishing to be bound by theory, the CD19 CAR may act on a small but important CD19-positive population of neoplastic cells, by targeting a cell that expresses levels of CD19 that fall below the detection threshold of the assays described herein, or by targeting a non-neoplastic cell that supports the neoplastic cells. In embodiments, a CD19 CAR can remove B cells, e.g., B regulatory B cells.

For example, In some embodiments, the first CAR-expressing cell described herein, e.g., a BCMA CAR-expressing cell, and the second CAR-expressing cell described herein, e.g., a CD19 CAR-expressing cell, are prepared in the same composition and are administered simultaneously. In another embodiment, the first CAR-expressing cell described herein, e.g., a BCMA CAR-expressing cell, and the second CAR-expressing cell described herein, e.g., a CD19 CAR-expressing cell, are prepared in separate compositions, and the separate compositions are administered simultaneously or sequentially. When the BCMA CAR-expressing cell and the second CAR-expressing cell are prepared in separate compositions, the BCMA CAR-expressing cell can be administered first, and the second CAR-expressing cell can be administered second, or the order of administration can be reversed.

In some embodiments, a CD19 CAR is a CD19 CAR, e.g., a humanized CD19 CAR, described in WO2014/153270, filed Mar. 15, 2014 (which is incorporated by reference herein in its entirety) or a sequence at least 95%, e.g., 95-99%, identical thereto. In some embodiments, the CD19 CAR construct is a CAR19 construct provided in PCT publication WO2012/079000 (which is incorporated by reference herein in its entirety) or a sequence at least 95%, e.g., 95-99%, identical thereto. In some embodiments, the anti-CD19 binding domain is a scFv described in WO2012/079000, or a sequence at least 95%, e.g., 95-99%, identical thereto.

In embodiments, a first CAR-expressing cell is administered to a subject, and a second CAR-expressing cell is administered to the subject. In embodiments, the first CAR-expressing cell comprises a CAR (e.g., BCMA or CD19 CAR) comprising a CD27 costimulatory domain and a CD3zeta (mutant or wild type) primary signaling domain. In embodiments, the second CAR-expressing cell comprises a CAR (e.g., BCMA CAR) comprising a 4-1BB costimulatory domain and a CD3zeta (mutant or wild type) primary signaling domain. Without wishing to be bound by theory, in embodiments, the first CAR-expressing cell can be less toxic than the second CAR-expressing cell and be used to debulk a tumor.

In some embodiments, a CAR-expressing cell described herein can be used in combination with a chemotherapeutic agent. Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with the compounds of the present invention include: anthracyclines; alkylating agents; antimetabolites; drugs that inhibit either the calcium dependent phosphatase calcineurin or the p70S6 kinase FK506) or inhibit the p70S6 kinase; mTOR inhibitors; immunomodulators; anthracyclines; vinca alkaloids; proteosome inhibitors; GITR agonists; protein tyrosine phosphatase inhibitors; a CDK4 kinase inhibitor; a BTK inhibitor; a MKN kinase inhibitor; a DGK kinase inhibitor; or an oncolytic virus.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary mTOR inhibitors include, e.g., temsirolimus; ridaforolimus (formally known as deferolimus, (1R,2R,4S)-4-[(2R)-2 [(1R,9S,12S,15R,16E,18R,19R,21R, 23S,24E, 26E,28Z,30S,32S,35R)-1,18-dihydroxy-19,30-dimethoxy-15,17,21,23, 29,35-hexamethyl-2,3,10,14,20-pentaoxo-11, 36-dioxa-4-azatricyclo[30.3.1.$0^{4,9}$] hexatriaconta-16,24,26, 28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7 (8H)-one (PF04691502, CAS 1013101-36-4); and $N^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine- (SEQ ID NO: 285), inner salt (SF1126, CAS 936487-67-1), and XL765.

Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors include bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In embodiments, a CAR-expressing cell described herein is administered to a subject in combination with fludarabine, cyclophosphamide, and/or rituximab. In embodiments, a CAR-expressing cell described herein is administered to a subject in combination with fludarabine, cyclophosphamide, and rituximab (FCR). In embodiments, the subject has CLL. For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region ($IgV_H$) gene. In other embodiments, the subject does not comprise a leukemic cell comprising a mutation in the immunoglobulin heavy-chain variable-region ($IgV_H$) gene. In embodiments, the fludarabine is administered at a dosage of about 10-50 mg/$m^2$ (e.g., about 10-15, 15-20, 20-25, 25-30, 30-35, 35-40, 40-45, or 45-50 mg/$m^2$), e.g., intravenously. In embodiments, the cyclophosphamide is administered at a dosage of about 200-300 mg/$m^2$ (e.g., about 200-225, 225-250, 250-275, or 275-300 mg/$m^2$), e.g., intravenously. In embodiments, the rituximab is administered at a dosage of about 400-600 mg/m2 (e.g., 400-450, 450-500, 500-550, or 550-600 mg/$m^2$), e.g., intravenously.

In embodiments, a CAR-expressing cell described herein is administered to a subject in combination with bendamustine and rituximab. In embodiments, the subject has CLL. For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region ($IgV_H$) gene. In other embodiments, the subject does not comprise a leukemic cell comprising a mutation in the immunoglobulin heavy-chain variable-region ($IgV_H$) gene. In embodiments, the bendamustine is administered at a dosage of about 70-110 mg/m2 (e.g., 70-80, 80-90, 90-100, or 100-110 mg/m2), e.g., intravenously. In embodiments, the rituximab is administered at a dosage of about 400-600 mg/m2 (e.g., 400-450, 450-500, 500-550, or 550-600 mg/$m^2$), e.g., intravenously.

In embodiments, a CAR-expressing cell described herein is administered to a subject in combination with rituximab, cyclophosphamide, doxorubicine, vincristine, and/or a corticosteroid (e.g., prednisone). In embodiments, a CAR-expressing cell described herein is administered to a subject in combination with rituximab, cyclophosphamide, doxorubicine, vincristine, and prednisone (R-CHOP). In embodiments, the subject has diffuse large B-cell lymphoma (DLBCL). In embodiments, the subject has nonbulky limited-stage DLBCL (e.g., comprises a tumor having a size/diameter of less than 7 cm). In embodiments, the subject is treated with radiation in combination with the R-CHOP. For example, the subject is administered R-CHOP (e.g., 1-6 cycles, e.g., 1, 2, 3, 4, 5, or 6 cycles of R-CHOP), followed by radiation. In some cases, the subject is administered R-CHOP (e.g., 1-6 cycles, e.g., 1, 2, 3, 4, 5, or 6 cycles of R-CHOP) following radiation.

In embodiments, a CAR-expressing cell described herein is administered to a subject in combination with etoposide, prednisone, vincristine, cyclophosphamide, doxorubicin, and/or rituximab. In embodiments, a CAR-expressing cell described herein is administered to a subject in combination with etoposide, prednisone, vincristine, cyclophosphamide, doxorubicin, and rituximab (EPOCH-R). In embodiments, a CAR-expressing cell described herein is administered to a subject in combination with dose-adjusted EPOCH-R (DA-EPOCH-R). In embodiments, the subject has a B cell lymphoma, e.g., a Myc-rearranged aggressive B cell lymphoma.

In embodiments, a CAR-expressing cell described herein is administered to a subject in combination with rituximab and/or lenalidomide. Lenalidomide ((RS)-3-(4-Amino-1-oxo 1,3-dihydro-2H-isoindol-2-yl)piperidine-2,6-dione) is an immunomodulator. In embodiments, a CAR-expressing cell described herein is administered to a subject in combination with rituximab and lenalidomide. In embodiments, the subject has follicular lymphoma (FL) or mantle cell lymphoma (MCL). In embodiments, the subject has FL and has not previously been treated with a cancer therapy. In embodiments, lenalidomide is administered at a dosage of about 10-20 mg (e.g., 10-15 or 15-20 mg), e.g., daily. In embodiments, rituximab is administered at a dosage of about 350-550 mg/$m^2$ (e.g., 350-375, 375-400, 400-425, 425-450, 450-475, or 475-500 mg/$m^2$), e.g., intravenously.

In embodiments, a CAR-expressing cell described herein is administered to a subject in combination with brentuximab. Brentuximab is an antibody-drug conjugate of anti-CD30 antibody and monomethyl auristatin E. In embodiments, the subject has Hodgkin's lymphoma (HL), e.g., relapsed or refractory HL. In embodiments, the subject comprises CD30+ HL. In embodiments, the subject has undergone an autologous stem cell transplant (ASCT). In embodiments, the subject has not undergone an ASCT. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In embodiments, a CAR-expressing cell described herein is administered to a subject in combination with brentuximab and dacarbazine or in combination with brentuximab and bendamustine. Dacarbazine is an alkylating agent with a chemical name of 5-(3,3-Dimethyl-1-triazenyl)imidazole-4-carboxamide. Bendamustine is an alkylating agent with a chemical name of 4-[5-[Bis(2-chloroethyl)amino]-1-methylbenzimidazol-2-yl]butanoic acid. In embodiments, the subject has Hodgkin's lymphoma (HL). In embodiments, the subject has not previously been treated with a cancer therapy. In embodiments, the subject is at least 60 years of age, e.g., 60, 65, 70, 75, 80, 85, or older. In embodiments, dacarbazine is administered at a dosage of about 300-450 mg/$m^2$ (e.g., about 300-325, 325-350, 350-375, 375-400, 400-425, or 425-450 mg/$m^2$), e.g., intravenously. In embodiments, bendamustine is administered at a dosage of about 75-125 mg/m2 (e.g., 75-100 or 100-125 mg/$m^2$, e.g., about 90 mg/$m^2$), e.g., intravenously. In embodiments, brentuximab is administered at a dosage of about 1-3 mg/kg (e.g., about 1-1.5, 1.5-2, 2-2.5, or 2.5-3 mg/kg), e.g., intravenously, e.g., every 3 weeks.

In some embodiments, a CAR-expressing cell described herein is administered to a subject in combination with a CD20 inhibitor, e.g., an anti-CD20 antibody (e.g., an anti-CD20 mono- or bispecific antibody) or a fragment thereof. Exemplary anti-CD20 antibodies include but are not limited to rituximab, ofatumumab, ocrelizumab, veltuzumab, obinutuzumab, TRU-015 (Trubion Pharmaceuticals), ocaratuzumab, and Pro131921 (Genentech). See, e.g., Lim et al. Haematologica. 95.1(2010):135-43.

In some embodiments, the anti-CD20 antibody comprises rituximab. Rituximab is a chimeric mouse/human monoclonal antibody IgG1 kappa that binds to CD20 and causes cytolysis of a CD20 expressing cell, e.g., as described in www.accessdata.fda.gov/drugsatfda_docs/label/2010/103705s5311lbl.pdf. In embodiments, a CAR-expressing cell described herein is administered to a subject in combination with rituximab. In embodiments, the subject has CLL or SLL.

In some embodiments, rituximab is administered intravenously, e.g., as an intravenous infusion. For example, each infusion provides about 500-2000 mg (e.g., about 500-550, 550-600, 600-650, 650-700, 700-750, 750-800, 800-850, 850-900, 900-950, 950-1000, 1000-1100, 1100-1200, 1200-1300, 1300-1400, 1400-1500, 1500-1600, 1600-1700, 1700-

1800, 1800-1900, or 1900-2000 mg) of rituximab. In some embodiments, rituximab is administered at a dose of 150 $mg/m^2$ to 750 $mg/m^2$, e.g., about 150-175 $mg/m^2$, 175-200 $mg/m^2$, 200-225 $mg/m^2$, 225-250 $mg/m^2$, 250-300 $mg/m^2$, 300-325 $mg/m^2$, 325-350 $mg/m^2$, 350-375 $mg/m^2$, 375-400 $mg/m^2$, 400-425 $mg/m^2$, 425-450 $mg/m^2$, 450-475 $mg/m^2$, 475-500 $mg/m^2$, 500-525 $mg/m^2$, 525-550 $mg/m^2$, 550-575 $mg/m^2$, 575-600 $mg/m^2$, 600-625 mg/m2, 625-650 $mg/m^2$, 650-675 $mg/m^2$, or 675-700 $mg/m^2$, where $m^2$ indicates the body surface area of the subject. In some embodiments, rituximab is administered at a dosing interval of at least 4 days, e.g., 4, 7, 14, 21, 28, 35 days, or more. For example, rituximab is administered at a dosing interval of at least 0.5 weeks, e.g., 0.5, 1, 2, 3, 4, 5, 6, 7, 8 weeks, or more. In some embodiments, rituximab is administered at a dose and dosing interval described herein for a period of time, e.g., at least 2 weeks, e.g., at least 2, 3, 4, 5, 6, 7, 8, 9, 10, 11, 12, 13, 14, 15, 16, 17, 18, 19, 20 weeks, or greater. For example, rituximab is administered at a dose and dosing interval described herein for a total of at least 4 doses per treatment cycle (e.g., at least 4, 5, 6, 7, 8, 9, 10, 11, 12, 13, 14, 15, 16, or more doses per treatment cycle).

In some embodiments, the anti-CD20 antibody comprises ofatumumab. Ofatumumab is an anti-CD20 IgG1κ human monoclonal antibody with a molecular weight of approximately 149 kDa. For example, ofatumumab is generated using transgenic mouse and hybridoma technology and is expressed and purified from a recombinant murine cell line (NS0). See, e.g., www.accessdata.fda.gov/drugsatfda_docs/label/2009/125326lbl.pdf; and Clinical Trial Identifier number NCT01363128, NCT01515176, NCT01626352, and NCT01397591. In embodiments, a CAR-expressing cell described herein is administered to a subject in combination with ofatumumab. In embodiments, the subject has CLL or SLL.

In some embodiments, ofatumumab is administered as an intravenous infusion. For example, each infusion provides about 150-3000 mg (e.g., about 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1200, 1200-1400, 1400-1600, 1600-1800, 1800-2000, 2000-2200, 2200-2400, 2400-2600, 2600-2800, or 2800-3000 mg) of ofatumumab. In embodiments, ofatumumab is administered at a starting dosage of about 300 mg, followed by 2000 mg, e.g., for about 11 doses, e.g., for 24 weeks. In some embodiments, ofatumumab is administered at a dosing interval of at least 4 days, e.g., 4, 7, 14, 21, 28, 35 days, or more. For example, ofatumumab is administered at a dosing interval of at least 1 week, e.g., 1, 2, 3, 4, 5, 6, 7, 8, 9, 10, 11, 12, 24, 26, 28, 20, 22, 24, 26, 28, 30 weeks, or more. In some embodiments, ofatumumab is administered at a dose and dosing interval described herein for a period of time, e.g., at least 1 week, e.g., 1, 2, 3, 4, 5, 6, 7, 8, 9, 10, 11, 12, 13, 14, 15, 16, 17, 18, 19, 20, 22, 24, 26, 28, 30, 40, 50, 60 weeks or greater, or 1, 2, 3, 4, 5, 6, 7, 8, 9, 10, 11, 12 months or greater, or 1, 2, 3, 4, 5 years or greater. For example, ofatumumab is administered at a dose and dosing interval described herein for a total of at least 2 doses per treatment cycle (e.g., at least 2, 3, 4, 5, 6, 7, 8, 9, 10, 11, 12, 13, 14, 15, 16, 18, 20, or more doses per treatment cycle).

In some cases, the anti-CD20 antibody comprises ocrelizumab. Ocrelizumab is a humanized anti-CD20 monoclonal antibody, e.g., as described in Clinical Trials Identifier Nos. NCT00077870, NCT01412333, NCT00779220, NCT00673920, NCT01194570, and Kappos et al. Lancet. 19.378(2011):1779-87.

In some cases, the anti-CD20 antibody comprises veltuzumab. Veltuzumab is a humanized monoclonal antibody against CD20. See, e.g., Clinical Trial Identifier No. NCT00547066, NCT00546793, NCT01101581, and Goldenberg et al. Leuk Lymphoma. 51(5)(2010):747-55.

In some cases, the anti-CD20 antibody comprises GA101. GA101 (also called obinutuzumab or RO5072759) is a humanized and glyco-engineered anti-CD20 monoclonal antibody. See, e.g., Robak. Curr. Opin. Investig. Drugs. 10.6(2009):588-96; Clinical Trial Identifier Numbers: NCT01995669, NCT01889797, NCT02229422, and NCT01414205; and www.accessdata.fda.gov/drugsatfda_docs/label/2013/125486s000lbl.pdf.

In some cases, the anti-CD20 antibody comprises AME-133v. AME-133v (also called LY2469298 or ocaratuzumab) is a humanized IgG1 monoclonal antibody against CD20 with increased affinity for the FcγRIIIa receptor and an enhanced antibody dependent cellular cytotoxicity (ADCC) activity compared with rituximab. See, e.g., Robak et al. BioDrugs 25.1(2011):13-25; and Forero-Torres et al. Clin Cancer Res. 18.5(2012):1395-403.

In some cases, the anti-CD20 antibody comprises PRO131921. PRO131921 is a humanized anti-CD20 monoclonal antibody engineered to have better binding to FcγRIIIa and enhanced ADCC compared with rituximab. See, e.g., Robak et al. BioDrugs 25.1(2011):13-25; and Casulo et al. Clin Immunol. 154.1(2014):37-46; and Clinical Trial Identifier No. NCT00452127.

In some cases, the anti-CD20 antibody comprises TRU-015. TRU-015 is an anti-CD20 fusion protein derived from domains of an antibody against CD20. TRU-015 is smaller than monoclonal antibodies, but retains Fc-mediated effector functions. See, e.g., Robak et al. BioDrugs 25.1(2011):13-25. TRU-015 contains an anti-CD20 single-chain variable fragment (scFv) linked to human IgG1 hinge, CH2, and CH3 domains but lacks CH1 and CL domains.

In some embodiments, an anti-CD20 antibody described herein is conjugated or otherwise bound to a therapeutic agent, e.g., a chemotherapeutic agent (e.g., cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or anti-emetic), pain reliever, or cytoprotective agent described herein.

In embodiments, a CAR-expressing cell described herein is administered to a subject in combination with a B-cell lymphoma 2 (BCL-2) inhibitor (e.g., venetoclax, also called ABT-199 or GDC-0199) and/or rituximab. In embodiments, a CAR-expressing cell described herein is administered to a subject in combination with venetoclax and rituximab. Venetoclax is a small molecule that inhibits the anti-apoptotic protein, BCL-2. The structure of venetoclax (4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) is shown below.

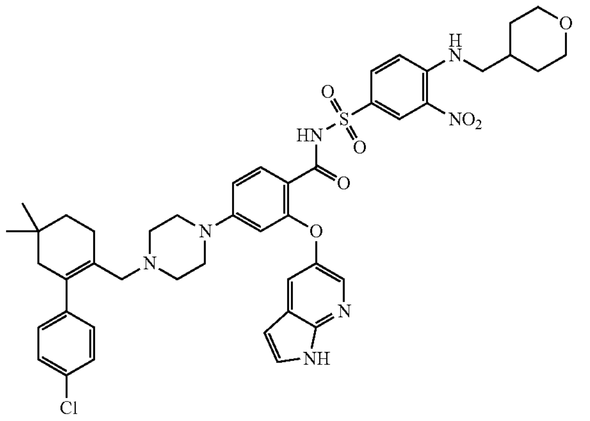 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

In embodiments, the subject has CLL. In embodiments, the subject has relapsed CLL, e.g., the subject has previously been administered a cancer therapy. In embodiments, venetoclax is administered at a dosage of about 15-600 mg (e.g., 15-20, 20-50, 50-75, 75-100, 100-200, 200-300, 300-400, 400-500, or 500-600 mg), e.g., daily. In embodiments, rituximab is administered at a dosage of about 350-550 mg/m2 (e.g., 350-375, 375-400, 400-425, 425-450, 450-475, or 475-500 mg/$m^2$), e.g., intravenously, e.g., monthly.

Without being bound by theory, it is believed that in some cancers, B cells (e.g., B regulatory cells) can suppress T cells. Further, it is believed that a combination of oxiplatin and the B cell depleting agent may reduce tumor size and/or eliminate tumors in a subject. In some embodiments, a CAR-expressing cell described herein (e.g., BCMA CAR) is administered in combination with a B cell depleting agent (e.g., a CD19 CAR-expressing cell, a CD20 CAR-expressing cell, rituximab, ocrelizumab, epratuzumab, or belimumab) and oxiplatin. In embodiments, the cancer cell can be CD19 negative or CD19 positive; or BCMA negative or BCMA positive. In embodiments, a CAR-expressing cell described herein (e.g., BCMA CAR) is administered in combination with a B cell depleting agent and oxiplatin to treat a cancer, e.g., a cancer described herein, e.g., solid cancer, e.g., prostate cancer, pancreatic cancer, or lung cancer.

In embodiments, a CAR-expressing cell described herein (e.g., BCMA CAR) may deplete B cells (e.g., B cells having a plasma cell-like phenotype, e.g., that express BCMA, CD19, and/or CD20) in a subject. In embodiments, the B cell can be CD19 negative or CD19 positive; or BCMA negative or BCMA positive. In some embodiments, a CAR-expressing cell described herein (e.g., BCMA CAR) is administered in combination with oxiplatin. In embodiments, a CAR-expressing cell described herein is administered in combination with oxiplatin is used to treat a cancer, e.g., solid cancer, e.g., prostate cancer, pancreatic cancer, or lung cancer. In some embodiments, a CAR-expressing cell described herein is administered in combination with an oncolytic virus. In embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

In some embodiments, the oncolytic virus is a virus, e.g., recombinant oncolytic virus, described in US2010/0178684 A1, which is incorporated herein by reference in its entirety. In some embodiments, a recombinant oncolytic virus comprises a nucleic acid sequence (e.g., heterologous nucleic acid sequence) encoding an inhibitor of an immune or inflammatory response, e.g., as described in US2010/0178684 A1, incorporated herein by reference in its entirety. In embodiments, the recombinant oncolytic virus, e.g., oncolytic NDV, comprises a pro-apoptotic protein (e.g., apoptin), a cytokine (e.g., GM-CSF, interferon-gamma, interleukin-2 (IL-2), tumor necrosis factor-alpha), an immunoglobulin (e.g., an antibody against ED-B firbonectin), tumor associated antigen, a bispecific adapter protein (e.g., bispecific antibody or antibody fragment directed against NDV HN protein and a T cell co-stimulatory receptor, such as CD3 or CD28; or fusion protein between human IL-2 and single chain antibody directed against NDV HN protein). See, e.g., Zamarin et al. Future Microbiol. 7.3(2012):347-67, incorporated herein by reference in its entirety. In some embodiments, the oncolytic virus is a chimeric oncolytic NDV described in U.S. Pat. No. 8,591,881 B2, US 2012/0122185 A1, or US 2014/0271677 A1, each of which is incorporated herein by reference in their entireties.

In some embodiments, the oncolytic virus comprises a conditionally replicative adenovirus (CRAd), which is designed to replicate exclusively in cancer cells. See, e.g., Alemany et al. Nature Biotechnol. 18(2000):723-27. In some embodiments, an oncolytic adenovirus comprises one described in Table 1 on page 725 of Alemany et al., incorporated herein by reference in its entirety.

Exemplary oncolytic viruses include but are not limited to the following:

Group B Oncolytic Adenovirus (ColoAd1) (PsiOxus Therapeutics Ltd.) (see, e.g., Clinical Trial Identifier: NCT02053220);

ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129);

VCN-01, which is a genetically modified oncolytic human adenovirus encoding human PH20 hyaluronidase (VCN Biosciences, S.L.) (see, e.g., Clinical Trial Identifiers: NCT02045602 and NCT02045589);

Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Català d'Oncologia) (see, e.g., Clinical Trial Identifier: NCT01864759);

Celyvir, which comprises bone marrow-derived autologous mesenchymal stem cells (MSCs) infected with ICOVIR5, an oncolytic adenovirus (Hospital Infantil Universitario Niño Jesús, Madrid, Spain/Ramon Alemany) (see, e.g., Clinical Trial Identifier: NCT01844661);

CG0070, which is a conditionally replicating oncolytic serotype 5 adenovirus (Ad5) in which human E2F-1 promoter drives expression of the essential E1a viral genes, thereby restricting viral replication and cytotoxicity to Rb pathway-defective tumor cells (Cold Genesys, Inc.) (see, e.g., Clinical Trial Identifier: NCT02143804); or DNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, an oncolytic virus described herein is administering by injection, e.g., subcutaneous, intraarterial, intravenous, intramuscular, intrathecal, or intraperitoneal injection. In embodiments, an oncolytic virus described herein is administered intratumorally, transdermally, transmucosally, orally, intranasally, or via pulmonary administration.

In an embodiment, cells expressing a CAR described herein are administered to a subject in combination with a molecule that decreases the Treg cell population. Methods that decrease the number of (e.g., deplete) Treg cells are known in the art and include, e.g., CD25 depletion, cyclophosphamide administration, modulating GITR function. Without wishing to be bound by theory, it is believed that reducing the number of Treg cells in a subject prior to apheresis or prior to administration of a CAR-expressing cell described herein reduces the number of unwanted immune cells (e.g., Tregs) in the tumor microenvironment and reduces the subject's risk of relapse. In some embodiments, a CAR expressing cell described herein is administered to a subject in combination with a molecule targeting GITR and/or modulating GITR functions, such as a GITR agonist and/or a GITR antibody that depletes regulatory T cells (Tregs). In embodiments, cells expressing a CAR described herein are administered to a subject in combination with cyclophosphamide. In some embodiments, the GITR binding molecules and/or molecules modulating GITR functions (e.g., GITR agonist and/or Treg depleting GITR antibodies) are administered prior to administration of the CAR-expressing cell. For example, in some embodiments, the GITR agonist can be administered prior to apheresis of the cells. In embodiments, cyclophosphamide is administered to the subject prior to administration (e.g., infusion or re-infusion) of the CAR-expressing cell or prior to apheresis of the cells. In embodiments, cyclophosphamide and an anti-GITR antibody are administered to the subject prior to administration (e.g., infusion or re-infusion) of the CAR-expressing cell or prior to apheresis of the cells. In some embodiments, the subject has cancer (e.g., a solid cancer or a hematological cancer such as multiple myeloma, ALL or CLL). In an embodiment, the subject has CLL. In embodiments, the subject has multiple myeloma. In embodiments, the subject has a solid cancer, e.g., a solid cancer described herein. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

In some embodiments, a CAR expressing cell described herein is administered to a subject in combination with an mTOR inhibitor, e.g., an mTOR inhibitor described herein, e.g., a rapalog such as everolimus. In some embodiments, the mTOR inhibitor is administered prior to the CAR-expressing cell. For example, in some embodiments, the mTOR inhibitor can be administered prior to apheresis of the cells.

In some embodiments, a CAR expressing cell described herein is administered to a subject in combination with a GITR agonist, e.g., a GITR agonist described herein. In some embodiments, the GITR agonist is administered prior to the CAR-expressing cell. For example, in some embodiments, the GITR agonist can be administered prior to apheresis of the cells.

In some embodiments, a CAR expressing cell described herein is administered to a subject in combination with a protein tyrosine phosphatase inhibitor, e.g., a protein tyrosine phosphatase inhibitor described herein. In some embodiments, the protein tyrosine phosphatase inhibitor is an SHP-1 inhibitor, e.g., an SHP-1 inhibitor described herein, such as, e.g., sodium stibogluconate. In some embodiments, the protein tyrosine phosphatase inhibitor is an SHP-2 inhibitor.

In some embodiments, a CAR-expressing cell described herein can be used in combination with a kinase inhibitor. In some embodiments, the kinase inhibitor is a CDK4 inhibitor, e.g., a CDK4 inhibitor described herein, e.g., a CDK4/6 inhibitor, such as, e.g., 6-Acetyl-8-cyclopentyl-5-methyl-2-(5-piperazin-1-yl-pyridin-2-ylamino)-8H-pyrido[2,3-d]pyrimidin-7-one, hydrochloride (also referred to as palbociclib or PD0332991). In some embodiments, the kinase inhibitor is a BTK inhibitor, e.g., a BTK inhibitor described herein, such as, e.g., ibrutinib. In some embodiments, the kinase inhibitor is an mTOR inhibitor, e.g., an mTOR inhibitor described herein, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor described herein. In some embodiments, the kinase inhibitor is a MNK inhibitor, e.g., a MNK inhibitor described herein, such as, e.g., 4-amino-5-(4-fluoroanilino)-pyrazolo [3,4-d] pyrimidine. The MNK inhibitor can be, e.g., a MNK1a, MNK1b, MNK2a and/or MNK2b inhibitor. In some embodiments, the kinase inhibitor is a dual PI3K/mTOR inhibitor described herein, such as, e.g., PF-04695102. In some embodiments, the kinase inhibitor is a DGK inhibitor, e.g., a DGK inhibitor described herein, such as, e.g., DGKinh1 (D5919) or DGKinh2 (D5794).

In some embodiments, the kinase inhibitor is a CDK4 inhibitor selected from aloisine A; flavopiridol or HMR-1275, 2-(2-chlorophenyl)-5,7-dihydroxy-8-[(3S,4R)-3-hydroxy-1-methyl-4-piperidinyl]-4-chromenone; crizotinib (PF-02341066; 2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride (P276-00); 1-methyl-5-[[2-[5-(trifluoromethyl)-1H-imidazol-2-yl]-4-pyridinyl]oxy]-N-[4-(trifluoromethyl)phenyl]-1H-benzimidazol-2-amine (RAF265); indisulam (E7070); roscovitine (CYC202); palbociclib (PD0332991); dinaciclib (SCH727965); N-[5-[[(5-tert-butyloxazol-2-yl)methyl]thio]thiazol-2-yl]piperidine-4-carboxamide (BMS 387032); 4-[[9-chloro-7-(2,6-difluorophenyl)-5H-pyrimido[5,4-d][2]benzazepin-2-yl]amino]-benzoic acid (MLN8054); 5-[3-(4,6-difluoro-1H-benzimidazol-2-yl)-1H-indazol-5-yl]-N-ethyl-4-methyl-3-pyridinemethanamine (AG-024322); 4-(2,6-dichlorobenzoylamino)-1H-pyrazole-3-carboxylic acid N-(piperidin-4-yl) amide (AT7519); 4-[2-methyl-1-(1-methylethyl)-1H-imidazol-5-yl]-N-[4-(methylsulfonyl)phenyl]-2-pyrimidinamine (AZD5438); and XL281 (BMS908662).

In some embodiments, the kinase inhibitor is a CDK4 inhibitor, e.g., palbociclib (PD0332991), and the palbociclib is administered at a dose of about 50 mg, 60 mg, 70 mg, 75 mg, 80 mg, 90 mg, 100 mg, 105 mg, 110 mg, 115 mg, 120 mg, 125 mg, 130 mg, 135 mg (e.g., 75 mg, 100 mg or 125 mg) daily for a period of time, e.g., daily for 14-21 days of a 28 day cycle, or daily for 7-12 days of a 21 day cycle. In some embodiments, 1, 2, 3, 4, 5, 6, 7, 8, 9, 10, 11, 12 or more cycles of palbociclib are administered.

In embodiments, a CAR-expressing cell described herein is administered to a subject in combination with a cyclin-dependent kinase (CDK) 4 or 6 inhibitor, e.g., a CDK4 inhibitor or a CDK6 inhibitor described herein. In embodiments, a CAR-expressing cell described herein is administered to a subject in combination with a CDK4/6 inhibitor (e.g., an inhibitor that targets both CDK4 and CDK6), e.g., a CDK4/6 inhibitor described herein. In an embodiment, the subject has MCL. MCL is an aggressive cancer that is poorly responsive to currently available therapies, i.e., essentially incurable. In many cases of MCL, cyclin D1 (a regulator of CDK4/6) is expressed (e.g., due to chromosomal translocation involving immunoglobulin and Cyclin D1 genes) in MCL cells. Thus, without being bound by theory, it is thought that MCL cells are highly sensitive to CDK4/6 inhibition with high specificity (i.e., minimal effect on normal immune cells). CDK4/6 inhibitors alone have had some efficacy in treating MCL, but have only achieved partial remission with a high relapse rate. An exemplary CDK4/6 inhibitor is LEE011 (also called ribociclib), the structure of which is shown below.

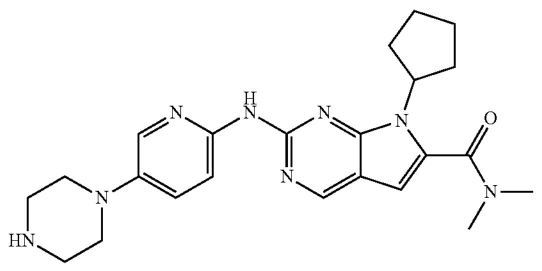 [SMILES: CN(C)C(=O)c1cc2cnc(Nc3ccc(N4CCNCC4)cn3)nc2n1C1CCCC1]

Without being bound by theory, it is believed that administration of a CAR-expressing cell described herein with a CDK4/6 inhibitor (e.g., LEE011 or other CDK4/6 inhibitor described herein) can achieve higher responsiveness, e.g., with higher remission rates and/or lower relapse rates, e.g., compared to a CDK4/6 inhibitor alone.

In some embodiments, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In a preferred embodiment, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In some embodiments, the kinase inhibitor is a BTK inhibitor, e.g., ibrutinib (PCI-32765). In embodiments, a CAR-expressing cell described herein is administered to a subject in combination with a BTK inhibitor (e.g., ibrutinib). In embodiments, a CAR-expressing cell described herein is administered to a subject in combination with ibrutinib (also called PCI-32765). The structure of ibrutinib (1-[(3R)-3-[4-Amino-3-(4-phenoxyphenyl)-1H-pyrazolo[3,4-d]pyrimidin-1-yl]piperidin-1-yl]prop-2-en-1-one) is shown below.

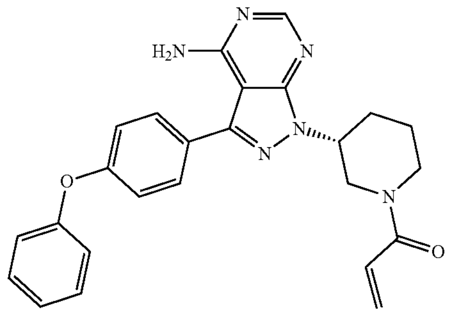 [SMILES: C=CC(=O)N1CCC[C@@H](n2nc(-c3ccc(Oc4ccccc4)cc3)c3c(N)ncnc32)C1]

In embodiments, the subject has CLL, mantle cell lymphoma (MCL), or small lymphocytic lymphoma (SLL). For example, the subject has a deletion in the short arm of chromosome 17 (del(17p), e.g., in a leukemic cell). In other examples, the subject does not have a del(17p). In embodiments, the subject has relapsed CLL or SLL, e.g., the subject has previously been administered a cancer therapy (e.g., previously been administered one, two, three, or four prior cancer therapies). In embodiments, the subject has refractory CLL or SLL. In other embodiments, the subject has follicular lymphoma, e.g., relapse or refractory follicular lymphoma. In some embodiments, ibrutinib is administered at a dosage of about 300-600 mg/day (e.g., about 300-350, 350-400, 400-450, 450-500, 500-550, or 550-600 mg/day, e.g., about 420 mg/day or about 560 mg/day), e.g., orally. In embodiments, the ibrutinib is administered at a dose of about 250 mg, 300 mg, 350 mg, 400 mg, 420 mg, 440 mg, 460 mg, 480 mg, 500 mg, 520 mg, 540 mg, 560 mg, 580 mg, 600 mg (e.g., 250 mg, 420 mg or 560 mg) daily for a period of time, e.g., daily for 21 day cycle cycle, or daily for 28 day cycle. In some embodiments, 1, 2, 3, 4, 5, 6, 7, 8, 9, 10, 11, 12 or more cycles of ibrutinib are administered. In some embodiments, ibrutinib is administered in combination with rituximab. See, e.g., Burger et al. (2013) Ibrutinib In Combination With Rituximab (iR) Is Well Tolerated and Induces a High Rate Of Durable Remissions In Patients With High-Risk Chronic Lymphocytic Leukemia (CLL): New, Updated Results Of a Phase II Trial In 40 Patients, Abstract 675 presented at 55$^{th}$ ASH Annual Meeting and Exposition, New Orleans, LA 7-10 Dec. Without being bound by theory, it is thought that the addition of ibrutinib enhances the T cell proliferative response and may shift T cells from a T-helper-2 (Th2) to T-helper-1 (Th1) phenotype. Th1 and Th2 are phenotypes of helper T cells, with Th1 versus Th2 directing different immune response pathways. A Th1 phenotype is associated with proinflammatory responses, e.g., for killing cells, such as intracellular pathogens/viruses or cancerous cells, or perpetuating autoimmune responses. A Th2 phenotype is associated with eosinophil accumulation and anti-inflammatory responses.

In some embodiments of the methods, uses, and compositions herein, the BTK inhibitor is a BTK inhibitor described in International Application WO/2015/079417, which is herein incorporated by reference in its entirety. For instance, in some embodiments, the BTK inhibitor is a compound of formula (I) or a pharmaceutically acceptable salt thereof;

(I)

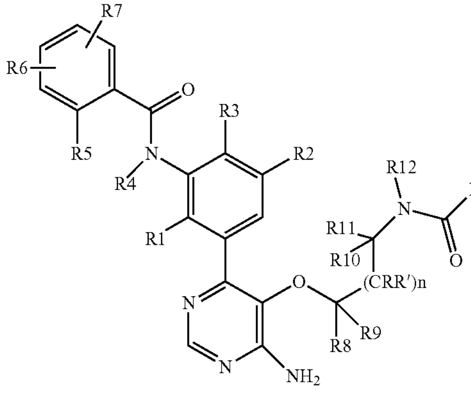

wherein,

R1 is hydrogen, C1-C6 alkyl optionally substituted by hydroxy;

R2 is hydrogen or halogen;

R3 is hydrogen or halogen;

R4 is hydrogen;

R5 is hydrogen or halogen;

or R4 and R5 are attached to each other and stand for a bond, —CH2-, —CH2-CH2-, —CH═CH—, —CH═CH—CH2-; —CH2-CH═CH—; or —CH2-CH2-CH2-;

R6 and R7 stand independently from each other for H, C1-C6 alkyl optionally substituted by hydroxyl, C3-C6 cycloalkyl optionally substituted by halogen or hydroxy, or halogen;

R8, R9, R, R', R10 and R11 independently from each other stand for H, or C1-C6 alkyl optionally substituted by C1-C6 alkoxy; or any two of R8, R9, R, R', R10 and R11 together with the carbon atom to which they are bound may form a 3-6 membered saturated carbocyclic ring;

R12 is hydrogen or C1-C6 alkyl optionally substituted by halogen or C1-C6 alkoxy;

or R12 and any one of R8, R9, R, R', R10 or R11 together with the atoms to which they are bound may form a 4, 5, 6 or 7 membered azacyclic ring, which ring may optionally be substituted by halogen, cyano, hydroxyl, C1-C6 alkyl or C1-C6 alkoxy;

n is 0 or 1; and

R13 is C2-C6 alkenyl optionally substituted by C1-C6 alkyl, C1-C6 alkoxy or N,N-di-C1-C6 alkyl amino; C2-C6 alkynyl optionally substituted by C1-C6 alkyl or C1-C6 alkoxy; or C2-C6 alkylenyl oxide optionally substituted by C1-C6 alkyl.

In some embodiments, the BTK inhibitor of Formula I is chosen from: N-(3-(5-((1-Acryloylazetidin-3-yl)oxy)-6-aminopyrimidin-4-yl)-5-fluoro-2-methylphenyl)-4-cyclopropyl-2-fluorobenzamide; (E)-N-(3-(6-Amino-5-((1-(but-2-enoyl)azetidin-3-yl)oxy)pyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-((1-(but-2-ynoyl)azetidin-3-yl)oxy)pyrimidin-4-yl)-5-fluoro-2-methylphenyl)-4-cyclopropyl-2-fluorobenzamide; N-(3-(5-((1-Acryloylpiperidin-4-yl)oxy)-6-aminopyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; (E)-N-(3-(6-Amino-5-(2-(N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; (E)-N-(3-(6-Amino-5-(2-(4-methoxy-N-methylbut-2-enamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(2-((4-Amino-6-(3-(4-cyclopropyl-2-fluorobenzamido)-5-fluoro-2-methylphenyl)pyrimidin-5-yl)oxy)ethyl)-N-methyloxirane-2-carboxamide; N-(2-((4-Amino-6-(3-(6-cyclopropyl-8-fluoro-1-oxoisoquinolin-2(1H)-yl)phenyl)pyrimidin-5-yl)oxy)ethyl)-N-methylacrylamide; N-(3-(5-(2-Acrylamidoethoxy)-6-aminopyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; N-(3-(5-((1-Acrylamidocyclopropyl)methoxy)-6-aminopyrimidin-4-yl)-5-fluoro-2-methylphenyl)-4-cyclopropyl-2-fluorobenzamide; (S)—N-(3-(5-(2-Acrylamidopropoxy)-6-aminopyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylacrylamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide; N-(3-(6-Amino-5-(3-(N-methylacrylamido)propoxy)pyrimidin-4-yl)-5-fluoro-2-methylphenyl)-4-cyclopropyl-2-fluorobenzamide; (S)—N-(3-(5-((1-Acryloylpyrrolidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-(but-2-ynoyl)pyrrolidin-2-yl)methoxy)pyrimidin-4-yl)-5-fluoro-2-methylphenyl)-4-cyclopropyl-2-fluorobenzamide; (S)-2-(3-(5-((1-Acryloylpyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(2-((4-Amino-6-(3-(6-cyclopropyl-1-oxo-3,4-dihydroisoquinolin-2(1H)-yl)-5-fluoro-2-(hydroxymethyl)phenyl)pyrimidin-5-yl)oxy)ethyl)-N-methylacrylamide; N-(3-(5-(((2S,4R)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; 2-(3-(5-(((2S,4R)-1-Acryloyl-4-methoxypyrrolidin-2-yl)methoxy)-6-aminopyrimidin-4-yl)-5-fluoro-2-(hydroxymethyl)phenyl)-6-cyclopropyl-3,4-dihydroisoquinolin-1(2H)-one; N-(3-(5-(((2S,4S)-1-Acryloyl-4-methoxypyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4S)-1-(but-2-ynoyl)-4-methoxypyrrolidin-2-yl)methoxy)pyrimidin-4-yl)-5-fluoro-2-methylphenyl)-4-cyclopropyl-2-fluorobenzamide; N-(3-(5-(((2S,4R)-1-Acryloyl-4-fluoropyrrolidin-2-yl)methoxy)-6-aminopyrimidin-4-yl)-5-fluoro-2-methylphenyl)-4-cyclopropyl-2-fluorobenzamide; N-(3-(6-Amino-5-(((2S,4R)-1-(but-2-ynoyl)-4-fluoropyrrolidin-2-yl)methoxy)pyrimidin-4-yl)-5-fluoro-2-methylphenyl)-4-cyclopropyl-2-fluorobenzamide; (S)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (S)—N-(3-(6-Amino-5-((1-propioloylazetidin-2-yl)methoxy)pyrimidin-4- yl)-5-fluoro-2-methylphenyl)-4-cyclopropyl-2-fluorobenzamide; (S)-2-(3-(5-((1-Acryloylazetidin-2-yl)methoxy)-6-aminopyrimidin-4-yl)-5-fluoro-2-(hydroxymethyl)phenyl)-6-cyclopropyl-3,4-dihydroisoquinolin-1(2H)-one; (R)—N-(3-(5-((1-Acryloylazetidin-2-yl)methoxy)-6-aminopyrimidin-4-yl)-5-fluoro-2-methylphenyl)-4-cyclopropyl-2-fluorobenzamide; (R)—N-(3-(5-((1-Acryloylpiperidin-3-yl)methoxy)-6-aminopyrimidin-4-yl)-5-fluoro-2-methylphenyl)-4-cyclopropyl-2-fluorobenzamide; N-(3-(5-(((2R,3S)-1-Acryloyl-3-methoxypyrrolidin-2-yl)methoxy)-6-aminopyrimidin-4-yl)-5-fluoro-2-methylphenyl)-4-cyclopropyl-2-fluorobenzamide; N-(3-(5-(((2S,4R)-1-Acryloyl-4-cyanopyrrolidin-2-yl)methoxy)-6-aminopyrimidin-4-yl)-5-fluoro-2-methylphenyl)-4-cyclopropyl-2-fluorobenzamide; or N-(3-(5-(((2S,4S)-1-Acryloyl-4-cyanopyrrolidin-2-yl)methoxy)-6-aminopyrimidin-4-yl)-5-fluoro-2-methylphenyl)-4-cyclopropyl-2-fluorobenzamide.

Unless otherwise provided, the chemical terms used above in describing the BTK inhibitor of Formula I are used according to their meanings as set out in International Application WO/2015/079417, which is herein incorporated by reference in its entirety.

In some embodiments, the kinase inhibitor is an mTOR inhibitor selected from temsirolimus; ridaforolimus (1R,2R,4S)-4-[(2R)-2 [(1R,9S,12S,15R,16E,18R,19R,21R, 23S,24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-{2,4-bis[(3S)-3-methylmorpholin-4-yl]pyrido[2,3-d]pyrimidin-7-yl}-2-methoxyphenyl)methanol (AZD8055); 2-amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine- (SEQ ID NO: 285), inner salt (SF1126); and XL765.

In some embodiments, the kinase inhibitor is an mTOR inhibitor, e.g., rapamycin, and the rapamycin is administered at a dose of about 3 mg, 4 mg, 5 mg, 6 mg, 7 mg, 8 mg, 9 mg, 10 mg (e.g., 6 mg) daily for a period of time, e.g., daily for 21 day cycle cycle, or daily for 28 day cycle. In some embodiments, 1, 2, 3, 4, 5, 6, 7, 8, 9, 10, 11, 12 or more cycles of rapamycin are administered. In some embodiments, the kinase inhibitor is an mTOR inhibitor, e.g., everolimus and the everolimus is administered at a dose of about 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg (e.g., 10 mg) daily for a period of time, e.g., daily for 28 day cycle. In some embodiments, 1, 2, 3, 4, 5, 6, 7, 8, 9, 10, 11, 12 or more cycles of everolimus are administered.

In some embodiments, the kinase inhibitor is an MNK inhibitor selected from CGP052088; 4-amino-3-(p-fluorophenylamino)-pyrazolo [3,4-d] pyrimidine (CGP57380); cercosporamide; ETC-1780445-2; and 4-amino-5-(4-fluoroanilino)-pyrazolo [3,4-d] pyrimidine.

In embodiments, a CAR-expressing cell described herein is administered to a subject in combination with a phosphoinositide 3-kinase (PI3K) inhibitor (e.g., a PI3K inhibitor described herein, e.g., idelalisib or duvelisib) and/or rituximab. In embodiments, a CAR-expressing cell described herein is administered to a subject in combination with idelalisib and rituximab. In embodiments, a CAR-expressing cell described herein is administered to a subject in combination with duvelisib and rituximab. Idelalisib (also called GS-1101 or CAL-101; Gilead) is a small molecule that blocks the delta isoform of PI3K. The structure of idelalisib (5-Fluoro-3-phenyl-2-[(1S)-1-(7H-purin-6-ylamino)propyl]-4(3H)-quinazolinone) is shown below.

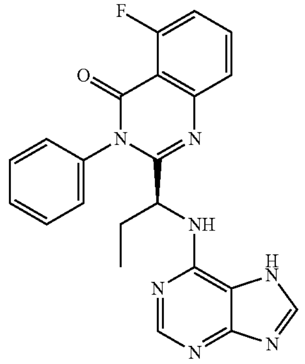 [SMILES: CC[C@H](Nc1ncnc2nc[nH]c12)c1nc2cccc(F)c2c(=O)n1-c1ccccc1]

Duvelisib (also called IPI-145; Infinity Pharmaceuticals and Abbvie) is a small molecule that blocks PI3K-δ,γ. The structure of duvelisib (8-Chloro-2-phenyl-3-[(1S)-1-(9H-purin-6-ylamino)ethyl]-1(2H)-isoquinolinone) is shown below.

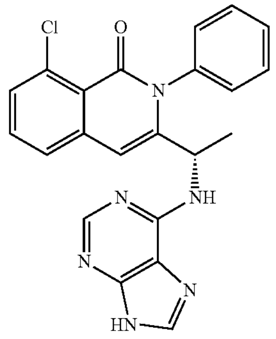 [SMILES: C[C@H](Nc1ncnc2[nH]cnc12)c1cc2cccc(Cl)c2c(=O)n1-c1ccccc1]

In embodiments, the subject has CLL. In embodiments, the subject has relapsed CLL, e.g., the subject has previously been administered a cancer therapy (e.g., previously been administered an anti-CD20 antibody or previously been administered ibrutinib). For example, the subject has a deletion in the short arm of chromosome 17 (del(17p), e.g., in a leukemic cell). In other examples, the subject does not have a del(17p). In embodiments, the subject comprises a leukemic cell comprising a mutation in the immunoglobulin heavy-chain variable-region (IgV$_H$) gene. In other embodiments, the subject does not comprise a leukemic cell comprising a mutation in the immunoglobulin heavy-chain variable-region (IgV$_H$) gene. In embodiments, the subject has a deletion in the long arm of chromosome 11 (del(11q)). In other embodiments, the subject does not have a del(11q). In embodiments, idelalisib is administered at a dosage of about 100-400 mg (e.g., 100-125, 125-150, 150-175, 175-200, 200-225, 225-250, 250-275, 275-300, 325-350, 350-375, or 375-400 mg), e.g., BID. In embodiments, duvelisib is administered at a dosage of about 15-100 mg (e.g., about 15-25, 25-50, 50-75, or 75-100 mg), e.g., twice a day. In embodiments, rituximab is administered at a dosage of about 350-550 mg/m$^2$ (e.g., 350-375, 375-400, 400-425, 425-450, 450-475, or 475-500 mg/m$^2$), e.g., intravenously.

In embodiments, a CAR-expressing cell described herein is administered to a subject in combination with an anaplastic lymphoma kinase (ALK) inhibitor. Exemplary ALK kinases include but are not limited to crizotinib (Pfizer), ceritinib (Novartis), alectinib (Chugai), brigatinib (also called AP26113; Ariad), entrectinib (Ignyta), PF-06463922 (Pfizer), TSR-011 (Tesaro) (see, e.g., Clinical Trial Identifier No. NCT02048488), CEP-37440 (Teva), and X-396 (Xcovery). In some embodiments, the subject has a solid cancer, e.g., a solid cancer described herein, e.g., lung cancer.

The chemical name of crizotinib is 3-[(1R)-1-(2,6-dichloro-3-fluorophenyl)ethoxy]-5-(1-piperidin-4-ylpyrazol-4-yl)pyridin-2-amine. The chemical name of ceritinib is 5-Chloro-$N^2$-[2-isopropoxy-5-methyl-4-(4-piperidinyl)phenyl]-$N^4$-[2-(isopropylsulfonyl)phenyl]-2,4-pyrimidinediamine. The chemical name of alectinib is 9-ethyl-6,6-dimethyl-8-(4-morpholinopiperidin-1-yl)-11-oxo-6,11-dihydro-5H-benzo[b]carbazole-3-carbonitrile. The chemical name of brigatinib is 5-Chloro-$N^2$-{4-[4-(dimethylamino)-1-piperidinyl]-2-methoxyphenyl}-$N^4$-[2-(dimethylphosphoryl) phenyl]-2,4-pyrimidinediamine. The chemical name of entrectinib is N-(5-(3,5-difluorobenzyl)-1H-indazol-3-yl)-4-(4-methylpiperazin-1-yl)-2-((tetrahydro-2H-pyran-4-yl) amino)benzamide. The chemical name of PF-06463922 is (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile. The chemical structure of CEP-37440 is (S)-2-((5-chloro-2-((6-(4-(2-hydroxyethyl)piperazin-1-yl)-1-methoxy-6,7,8,9-tetrahydro-5H-benzo[7]annulen-2-yl)amino)pyrimidin-4-yl)amino)-N-methylbenzamide. The chemical name of X-396 is (R)-6-amino-5-(1-(2,6-dichloro-3-fluorophenyl)ethoxy)-N-(4-(4-methylpiperazine-1-carbonyl)phenyl)pyridazine-3-carboxamide.

In some embodiments, the kinase inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); 2-Methyl-2-{4-[3-methyl-2-oxo-8-(quinolin-3-yl)-2,3-dihydro-1H-imidazo[4,5-c]quinolin-1-yl]phenyl} propanenitrile (BEZ-235); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2 (3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); and N-[2-[(3,5-Dimethoxyphenyl)amino]quinoxalin-3-yl]-4-[(4-methyl-3-methoxyphenyl)carbonyl]aminophenylsulfonamide (XL765).

Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present invention may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present invention are administered following B-cell ablative therapy such as agents that react with CD20, e.g., Rituxan. For example, In some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In some embodiments, a CAR expressing cell described herein is administered to a subject in combination with a biphosphonate, e.g., Pamidronate (Aredia®); Zoledronic acid or Zoledronate (Zometa®, Zomera®, Aclasta®, or Reclast®); Alendronate (Fosamax®); Risedronate (Actonel®); Ibandronate (Boniva®); Clondronate (Bonefos®); Etidronate (Didronel®); Tiludronate (Skelid®); Pamidronate (Aredia®); Neridronate (Nerixia®); Strontiun ranelate (Protelos®, or Protos®); and Teriparatide (Forteo®).

In some embodiments, a CAR expressing cell described herein is administered to a subject in combination with a corticosteroid, e.g., dexamethasone (e.g., Decadron®), beclomethasone (e.g., Beclovent®), hydrocortisone (also known as cortisone, hydrocortisone sodium succinate, hydrocortisone sodium phosphate, and sold under the tradenames Ala-Cort®, hydrocortisone phosphate, Solu-Cortef®, Hydrocort Acetate® and Lanacort®), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-methylprednisolone, methylprednisolone acetate, methylprednisolone sodium succinate, sold under the tradenames Duralone®, Medralone®, Medrol®, M-Prednisol® and Solu-Medrol®); antihistamines, such as diphenhydramine (e.g., Benadryl®), hydroxyzine, and cyproheptadine; and bronchodilators, such as the beta-adrenergic receptor agonists, albuterol (e.g., Proventil®), and terbutaline (Brethine®).

In some embodiments, a CAR expressing cell described herein is administered to a subject in combination with an immunomodulator, e.g., Afutuzumab (available from Roche®); Pegfilgrastim (Neulasta®); Lenalidomide (CC-5013, Revlimid®); Thalidomide (Thalomid®), Actimid (CC4047); and IRX-2 (mixture of human cytokines including interleukin 1, interleukin 2, and interferon γ, CAS 951209-71-5, available from IRX Therapeutics.

In some embodiments, a CAR expressing cell described herein is administered to a subject in combination with a proteasome inhibitor, e.g., Bortezomib (Velcade®); Ixazomib citrate (MLN9708, CAS 1201902-80-8); Danoprevir (RG7227, CAS 850876-88-9); Ixazomib (MLN2238, CAS 1072833-77-2); and (S)—N-[(phenylmethoxy)carbonyl]-L-leucyl-N-(1-formyl-3-methylbutyl)-L-Leucinamide (MG-132, CAS 133407-82-6).

In some embodiments, a CAR expressing cell described herein is administered to a subject in combination with a vascular endothelial growth factor (VEGF) receptor, e.g., Bevacizumab (Avastin®), axitinib (Inlyta®); Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2, 3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl]methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2, 4]triazin-5-yl)methyl)piperidin-3-ol (BMS690514); N-(3,4-Dichloro-2-fluorophenyl)-6-methoxy-7-[[(3aa,5f,6aa)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

In some embodiments, a CAR expressing cell described herein is administered to a subject in combination with a CD20 antibody or a conjugate thereof, e.g., Rituximab (Riuxan® and MabThera®); and Tositumomab (Bexxar®); and Ofatumumab (Arzerra®), Ibritumomab tiuxetan (Zevalin®); and Tositumomab.

In some embodiments, a CAR expressing cell described herein is administered to a subject in combination with an anticonvulsant, e.g., Anticonvulsants (antiepileptic or anti-seizure drugs): aldehydes, e.g., paraldehyde; aromatic allylic alcohols, e.g., stiripentol (Diacomit®); barbiturates, e.g., phenobarbital (Luminal®), methylphenobarbital (Mebaral®), barbexaclone (Maliasin®), benzodiazepines, e.g., clobazam (Onfi®), clonazepam (Klonopin®), clorazepate (Tranxene® and Novo-Clopate®), diazepam (Valium®, Lembrol®, Diastat®), midazolam (Versed®), lorazepam (Ativan® and Orfidal®), nitrazepam (Alodorm®, Arem®, Insoma®), temazepam (Restoril®, Normison®), nimetzepam (Erimin®), bromides, e.g., potassium bromide; carbamates, e.g., felbamate (Felbatol®); carboxamides, e.g., carbamazepine (Tegretol®, Equetro®), oxcarbazepine (Trileptal®, Oxcarb®), eslicarbazepine acetate (Aptiom®); fatty acids, e.g., valproates (valproic acid, sodium valproate, divalproex sodium), vigabatrin (Sabril®), progabide (Gabren®), tiagabine (Gabitril®); fructose derivatives, e.g., topiramate (Topamax®); GABA analogs, e.g., gabapentin (Neurontin®), pregabalin (Lyrica®); hydantoins, e.g., ethotoin (Peganone®), phenytoin (Dilantin®), mephenytoin (Mesantoin®), fosphenytoin (Cerebyx®, Prodilantin®); oxazolidinediones, e.g., paramethadione (Paradione®), trimethadione (Tridione®); propionates, e.g., beclamide (Choracon®, Hibicon®, Posedrine®); pyrimidinediones, e.g., primidone (Mysoline®); pyrrolidines, e.g., brivaracetam, levetiracetam, seletracetam (Keppra®); succinimides, e.g., ethosuximide (Zarontin®), phensuximide (Milontin®), mesuximide (Celontin®, Petinutin®); sulfonamides, e.g., acetazolamide (Diamox®), sultiame (Ospolot®), methazolamide (Neptazane®), zonisamide (Zonegran®); triazines, e.g., lamotrigine (Lamictal®); ureas, e.g., pheneturide, phenacemide (Phenurone®); valproylamides (amide derivatives of valproate), e.g., valpromide (Depamide®), valnoctamide; AMPA receptor antagonist, e.g., perampanel (Fycompa®).

In embodiments, a CAR-expressing cell described herein is administered to a subject in combination with an indoleamine 2,3-dioxygenase (IDO) inhibitor. IDO is an enzyme that catalyzes the degradation of the amino acid, L-tryptophan, to kynurenine. Many cancers overexpress IDO, e.g., prostatic, colorectal, pancreatic, cervical, gastric, ovarian, head, and lung cancer. pDCs, macrophages, and dendritic cells (DCs) can express IDO. Without being bound by theory, it is thought that a decrease in L-tryptophan (e.g., catalyzed by IDO) results in an immunosuppressive milieu by inducing T-cell anergy and apoptosis. Thus, without being bound by theory, it is thought that an IDO inhibitor can enhance the efficacy of a CAR-expressing cell described herein, e.g., by decreasing the suppression or death of a CAR-expressing immune cell. In embodiments, the subject has a solid tumor, e.g., a solid tumor described herein, e.g., prostatic, colorectal, pancreatic, cervical, gastric, ovarian, head, or lung cancer. Exemplary inhibitors of IDO include but are not limited to 1-methyl-tryptophan, indoximod (NewLink Genetics) (see, e.g., Clinical Trial Identifier Nos. NCT01191216; NCT01792050), and INCB024360 (Incyte Corp.) (see, e.g., Clinical Trial Identifier Nos. NCT01604889; NCT01685255).

In embodiments, a CAR-expressing cell described herein is administered to a subject in combination with a modulator of myeloid-derived suppressor cells (MDSCs). MDSCs accumulate in the periphery and at the tumor site of many solid tumors. These cells suppress T cell responses, thereby hindering the efficacy of CAR-expressing cell therapy. Without being bound by theory, it is thought that administration of a MDSC modulator enhances the efficacy of a CAR-expressing cell described herein. In an embodiment, the subject has a solid tumor, e.g., a solid tumor described herein, e.g., glioblastoma. Exemplary modulators of MDSCs include but are not limited to MCS110 and BLZ945. MCS110 is a monoclonal antibody (mAb) against macrophage colony-stimulating factor (M-CSF). See, e.g., Clinical Trial Identifier No. NCT00757757. BLZ945 is a small molecule inhibitor of colony stimulating factor 1 receptor (CSF1R). See, e.g., Pyonteck et al. Nat. Med. 19(2013): 1264-72. The structure of BLZ945 is shown below.

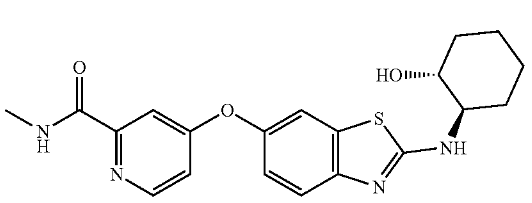 [SMILES: CNC(=O)c1cc(Oc2ccc3nc(N[C@@H]4CCCC[C@H]4O)sc3c2)ccn1]

In embodiments, a CAR-expressing cell described herein is administered to a subject in combination with a CD19 CART cell (e.g., CTL019, e.g., as described in WO2012/079000, incorporated herein by reference). In embodiments, the subject has acute myeloid leukemia (AML), e.g., a CD19 positive AML or a CD19 negative AML. In embodiments, the subject has a CD19+ lymphoma, e.g., a CD19+ Non-Hodgkin's Lymphoma (NHL), a CD19+ FL, or a CD19+ DLBCL. In embodiments, the subject has a relapsed or refractory CD19+ lymphoma. In embodiments, a lymphodepleting chemotherapy is administered to the subject prior to, concurrently with, or after administration (e.g., infusion) of CD19 CART cells. In an example, the lymphodepleting chemotherapy is administered to the subject prior to administration of CD19 CART cells. For example, the lymphodepleting chemotherapy ends 1-4 days (e.g., 1, 2, 3, or 4 days) prior to CD19 CART cell infusion. In embodiments, multiple doses of CD19 CART cells are administered, e.g., as described herein. For example, a single dose comprises about $5\times10^8$ CD19 CART cells. In embodiments, a lymphodepleting chemotherapy is administered to the subject prior to, concurrently with, or after administration (e.g., infusion) of a CAR-expressing cell described herein, e.g., a non-CD19 CAR-expressing cell. In embodiments, a CD19 CART is administered to the subject prior to, concurrently with, or after administration (e.g., infusion) of a non-CD19 CAR-expressing cell, e.g., a non-CD19 CAR-expressing cell described herein.

In some embodiments, a CAR-expressing cell described herein is administered to a subject in combination with a CD19 CAR-expressing cell, e.g., CTL019, e.g., as described in WO2012/079000, incorporated herein by reference, for treatment of a disease associated with the expression of BCMA, e.g., a cancer described herein. Without being bound by theory, it is believed that administering a CD19 CAR-expressing cell in combination with a CAR-expressing cell improves the efficacy of a CAR-expressing cell described herein by targeting early lineage cancer cells, e.g., cancer stem cells, modulating the immune response, depleting regulatory B cells, and/or improving the tumor microenvironment. For example, a CD19 CAR-expressing cell targets cancer cells that express early lineage markers, e.g., cancer stem cells and CD19-expressing cells, while the CAR-expressing cell described herein targets cancer cells that express later lineage markers, e.g., BCMA. This preconditioning approach can improve the efficacy of the CAR-expressing cell described herein. In such embodiments, the CD19 CAR-expressing cell is administered prior to, concurrently with, or after administration (e.g., infusion) of a CAR-expressing cell described herein.

In embodiments, a CAR-expressing cell described herein also expresses a CAR targeting CD19, e.g., a CD19 CAR. In an embodiment, the cell expressing a CAR described herein and a CD19 CAR is administered to a subject for treatment of a cancer described herein, e.g., AML. In an embodiment, the configurations of one or both of the CAR molecules comprise a primary intracellular signaling domain and a costimulatory signaling domain. In another embodiment, the configurations of one or both of the CAR molecules comprise a primary intracellular signaling domain and two or more, e.g., 2, 3, 4, or 5 or more, costimulatory signaling domains. In such embodiments, the CAR molecule described herein and the CD19 CAR may have the same or a different primary intracellular signaling domain, the same or different costimulatory signaling domains, or the same number or a different number of costimulatory signaling domains. Alternatively, the CAR described herein and the CD19 CAR are configured as a split CAR, in which one of the CAR molecules comprises an antigen binding domain and a costimulatory domain (e.g., 4-1BB), while the other CAR molecule comprises an antigen binding domain and a primary intracellular signaling domain (e.g., CD3 zeta).

In some embodiments, a CAR-expressing cell described herein is administered to a subject in combination with a interleukin-15 (IL-15) polypeptide, a interleukin-15 receptor alpha (IL-15Ra) polypeptide, or a combination of both a IL-15 polypeptide and a IL-15Ra polypeptide e.g., hetIL-15 (Admune Therapeutics, LLC). hetIL-15 is a heterodimeric non-covalent complex of IL-15 and IL-15Ra. hetIL-15 is described in, e.g., U.S. Pat. No. 8,124,084, U.S. 2012/0177598, U.S. 2009/0082299, U.S. 2012/0141413, and U.S. 2011/0081311, incorporated herein by reference. In embodiments, het-IL-15 is administered subcutaneously. In embodiments, the subject has a cancer, e.g., solid cancer, e.g., melanoma or colon cancer. In embodiments, the subject has a metastatic cancer.

In some embodiments, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. CRS may include clinical constitutional signs and symptoms such as fever, fatigue, anorexia, myalgias, arthalgias, nausea, vomiting, and headache. CRS may include clinical skin signs and symptoms such as rash. CRS may include clinical gastrointestinal signs and symptoms such as nausea, vomiting and diarrhea. CRS may include clinical respiratory signs and symptoms such as tachypnea and hypoxemia. CRS may include clinical cardiovascular signs and symptoms such as tachycardia, widened pulse pressure, hypotension, increased cardiac output (early) and potentially diminished cardiac output (late). CRS may include clinical coagulation signs and symptoms such as elevated d-dimer, hypofibrinogenemia with or without bleeding. CRS may include clinical renal signs and symptoms such as azotemia. CRS may include clinical hepatic signs and symptoms such as transaminitis and hyperbilirubinemia. CRS may include clinical neurologic signs and symptoms such as headache, mental status changes, confusion, delirium, word finding difficulty or frank aphasia, hallucinations, tremor, dymetria, altered gait, and seizures.

Accordingly, the methods described herein can comprise administering a CAR-expressing cell described herein to a subject and further administering one or more agents to manage elevated levels of a soluble factor resulting from treatment with a CAR-expressing cell. In some embodiments, the soluble factor elevated in the subject is one or more of IFN-γ, TNFα, IL-2 and IL-6. In an embodiment, the factor elevated in the subject is one or more of IL-1, GM-CSF, IL-10, IL-8, IL-5 and fraktalkine. Therefore, an agent administered to treat this side effect can be an agent that neutralizes one or more of these soluble factors. In some embodiments, the agent that neutralizes one or more of these soluble forms is an antibody or antibody fragment. Examples of such agents include, but are not limited to a steroid (e.g., corticosteroid), an inhibitor of TNFα, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitors of TNFα include, but are not limited to, xanthine derivatives (e.g. pentoxifylline) and bupropion. An example of an IL-6 inhibitor is an anti-IL-6 antibody molecule such as tocilizumab (toc), sarilumab, elsilimomab, CNTO 328, ALD518/BMS-945429, CNTO 136, CPSI-2364, CDP6038, VX30, ARGX-109, FE301, and FM101. In some embodiments, the anti-IL-6 antibody molecule is tocilizumab. An example of an IL-1R based inhibitor is anakinra.

In some embodiment, the subject is administered a corticosteroid, such as, e.g., methylprednisolone, hydrocortisone, among others.

In some embodiments, the subject is administered a vasopressor, such as, e.g., norepinephrine, dopamine, phenylephrine, epinephrine, vasopressin, or a combination thereof.

In an embodiment, the subject can be administered an antipyretic agent. In an embodiment, the subject can be administered an analgesic agent.

In some embodiments, the subject can be administered an agent that prevents trafficking of the BCMA CAR-expressing cell to the brain, e.g., natalizumab (TYSABRI®). BCMA expression, e.g., a splice variant thereof, has been detected in some parts of the brain, e.g., the cerebellum or medulla oblongata. Without being bound by any particular theory, prevention of trafficking of the BCMA CAR-expressing cells to the brain is preferred to prevent any BCMA CAR-expressing cells from interacting with or acting on BCMA-expressing brain tissue.

In some embodiments, the subject can be administered an agent which enhances the activity of a CAR-expressing cell. For example, in some embodiments, the agent can be an agent which inhibits an inhibitory molecule, e.g., the agent is a checkpoint inhibitor. Inhibitory molecules, e.g., Programmed Death 1 (PD1), can, in some embodiments, decrease the ability of a CAR-expressing cell to mount an immune effector response. Examples of inhibitory molecules include PD1, PD-L1, PD-L2, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), e.g., as described herein, can be used to inhibit expression of an inhibitory molecule in the CAR-expressing cell. In an embodiment the inhibitor is an shRNA. In an embodiment, the inhibitory molecule is inhibited within a CAR-expressing cell. In these embodiments, a dsRNA molecule that inhibits expression of the inhibitory molecule is linked to the nucleic acid that encodes a component, e.g., all of the components, of the CAR. In embodiments, a CAR-expressing cell described herein is administered in combination with an inhibitor of an inhibitory molecule, e.g., in combination with a checkpoint inhibitor, e.g., in combination with an inhibitor of PD1 and/or PD-L1. In embodiments, a CAR-expressing cell described herein is administered in combination with an inhibitor of PD1. In embodiments, a CAR-expressing cell described herein is administered in combination with an inhibitor of PD-L1.

In an embodiment, a nucleic acid molecule that encodes a dsRNA molecule that inhibits expression of the molecule that modulates or regulates, e.g., inhibits, T-cell function is operably linked to a promoter, e.g., a H1- or a U6-derived promoter such that the dsRNA molecule that inhibits expression of the molecule that modulates or regulates, e.g., inhibits, T-cell function is expressed, e.g., is expressed within a CAR-expressing cell. See e.g., Tiscornia G., "Development of Lentiviral Vectors Expressing siRNA," Chapter 3, in *Gene Transfer: Delivery and Expression of DNA and RNA* (eds. Friedmann and Rossi). Cold Spring Harbor Laboratory Press, Cold Spring Harbor, N.Y., USA, 2007; Brummelkamp T R, et al. (2002) *Science* 296: 550-553; Miyagishi M, et al. (2002) *Nat. Biotechnol.* 19: 497-500. In an embodiment the nucleic acid molecule that encodes a dsRNA molecule that inhibits expression of the molecule that modulates or regulates, e.g., inhibits, T-cell function is present on the same vector, e.g., a lentiviral vector, that comprises a nucleic acid molecule that encodes a component, e.g., all of the components, of the CAR. In such an embodiment, the nucleic acid molecule that encodes a dsRNA molecule that inhibits expression of the molecule that modulates or regulates, e.g., inhibits, T-cell function is located on the vector, e.g., the lentiviral vector, 5'- or 3'- to the nucleic acid that encodes a component, e.g., all of the components, of the CAR. The nucleic acid molecule that encodes a dsRNA molecule that inhibits expression of the molecule that modulates or regulates, e.g., inhibits, T-cell function can be transcribed in the same or different direction as the nucleic acid that encodes a component, e.g., all of the components, of the CAR. In an embodiment the nucleic acid molecule that encodes a dsRNA molecule that inhibits expression of the molecule that modulates or regulates, e.g., inhibits, T-cell function is present on a vector other than the vector that comprises a nucleic acid molecule that encodes a component, e.g., all of the components, of the CAR. In an embodiment, the nucleic acid molecule that encodes a dsRNA molecule that inhibits expression of the molecule that modulates or regulates, e.g., inhibits, T-cell function it transiently expressed within a CAR-expressing cell. In an embodiment, the nucleic acid molecule that encodes a dsRNA molecule that inhibits expression of the molecule that modulates or regulates, e.g., inhibits, T-cell function is stably integrated into the genome of a CAR-expressing cell.

Examples of dsRNA molecules useful for inhibiting expression of a molecule that modulates or regulates, e.g., inhibits, T-cell function, wherein the molecule that modulates or regulates, e.g., inhibits, T-cell function is PD-1 are provided below.

In some embodiments, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy®; Bristol-Myers Squibb; Tremelimumab (IgG2 monoclonal antibody available from Pfizer, formerly known as ticilimumab, CP-675,206)). In an embodiment, the agent is an antibody or antibody fragment that binds to TIM3. In an embodiment, the agent is an antibody or antibody fragment that binds to LAG3. In embodiments, the agent that enhances the activity of a CAR-expressing cell, e.g., inhibitor of an inhibitory molecule, is administered in combination with an allogeneic CAR, e.g., an allogeneic CAR described herein (e.g., described in the Allogeneic CAR section herein).

PD-1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD-1, PD-L1 and PD-L2 have been shown to downregulate T cell activation upon binding to PD-1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD-1 with PD-L1. Antibodies, antibody fragments, and other inhibitors of PD-1, PD-L1 and PD-L2 are available in the art and may be used combination with a cars of the present invention described herein. For example, nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611. Pembrolizumab (formerly known as lambrolizumab, and also referred to as MK03475; Merck) is a humanized IgG4 monoclonal antibody that binds to PD-1. Pembrolizumab and other humanized anti-PD-1 antibodies are disclosed in U.S. Pat. No. 8,354,509 and WO2009/114335. MEDI4736 (Medimmune) is a human monoclonal antibody that binds to PDL1, and inhibits interaction of the ligand with PD1. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906. Other anti-PD-L1 binding agents include YW243.55.570 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, US 2010028330, and/or US 20120114649.

TIM3 (T cell immunoglobulin-3) also negatively regulates T cell function, particularly in IFN-g-secreting CD4+ T helper 1 and CD8+ T cytotoxic 1 cells, and plays a critical role in T cell exhaustion. Inhibition of the interaction between TIM3 and its ligands, e.g., galectin-9 (Gal9), phosphotidylserine (PS), and HMGB1, can increase immune response. Antibodies, antibody fragments, and other inhibitors of TIM3 and its ligands are available in the art and may be used combination with a CD19 or BCMA CAR described herein. For example, antibodies, antibody fragments, small molecules, or peptide inhibitors that target TIM3 binds to the IgV domain of TIM3 to inhibit interaction with its ligands. Antibodies and peptides that inhibit TIM3 are disclosed in WO2013/006490 and US20100247521. Other anti-TIM3 antibodies include humanized versions of RMT3-23 (disclosed in Ngiow et al., 2011, Cancer Res, 71:3540-3551), and clone 8B.2C12 (disclosed in Monney et al., 2002, Nature, 415:536-541). Bi-specific antibodies that inhibit TIM3 and PD-1 are disclosed in US20130156774.

In other embodiments, the agent which enhances the activity of a CAR-expressing cell is a CEACAM inhibitor (e.g., CEACAM-1, CEACAM-3, and/or CEACAM-5 inhibitor). In some embodiments, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. *PLoS One.* 2010 Sep. 2; 5(9). pii: e12529 (DOI:10:1371/journal-.pone.0021146), or crossreacts with CEACAM-1 and CEACAM-5 as described in, e.g., WO 2013/054331 and US 2014/0271618.

Without wishing to be bound by theory, carcinoembryonic antigen cell adhesion molecules (CEACAM), such as CEACAM-1 and CEACAM-5, are believed to mediate, at least in part, inhibition of an anti-tumor immune response (see e.g., Markel et al. *J Immunol.* 2002 Mar. 15; 168(6): 2803-10; Markel et al. *J Immunol.* 2006 Nov. 1; 177(9): 6062-71; Markel et al. *Immunology.* 2009 February; 126(2): 186-200; Markel et al. *Cancer Immunol Immunother.* 2010 February; 59(2):215-30; Ortenberg et al. *Mol Cancer Ther.* 2012 June; 11(6):1300-10; Stern et al. *J Immunol.* 2005 Jun. 1; 174(11):6692-701; Zheng et al. *PLoS One.* 2010 Sep. 2; 5(9). pii: e12529). For example, CEACAM-1 has been described as a heterophilic ligand for TIM-3 and as playing a role in TIM-3-mediated T cell tolerance and exhaustion (see e.g., WO 2014/022332; Huang, et al. (2014) *Nature doi:*10.1038/nature13848). In embodiments, co-blockade of CEACAM-1 and TIM-3 has been shown to enhance an anti-tumor immune response in xenograft colorectal cancer models (see e.g., WO 2014/022332; Huang, et al. (2014), supra). In other embodiments, co-blockade of CEACAM-1 and PD-1 reduce T cell tolerance as described, e.g., in WO 2014/059251. Thus, CEACAM inhibitors can be used with the other immunomodulators described herein (e.g., anti-PD-1 and/or anti-TIM-3 inhibitors) to enhance an immune response against a cancer, e.g., a melanoma, a lung cancer (e.g., NSCLC), a bladder cancer, a colon cancer an ovarian cancer, and other cancers as described herein.

LAG3 (lymphocyte activation gene-3 or CD223) is a cell surface molecule expressed on activated T cells and B cells that has been shown to play a role in CD8+ T cell exhaustion. Antibodies, antibody fragments, and other inhibitors of LAG3 and its ligands are available in the art and may be used combination with a CD19 or BCMA CAR described herein. For example, BMS-986016 (Bristol-Myers Squib) is a monoclonal antibody that targets LAG3. IMP701 (Immutep) is an antagonist LAG3 antibody and IMP731 (Immutep and GlaxoSmithKline) is a depleting LAG3 antibody. Other LAG3 inhibitors include IMP321 (Immutep), which is a recombinant fusion protein of a soluble portion of LAG3 and Ig that binds to MHC class II molecules and activates antigen presenting cells (APC). Other antibodies are disclosed, e.g., in WO2010/019570.

In some embodiments, the agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an intracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In some embodiments, the fusion protein is expressed by the same cell that expressed the CAR. In another embodiment, the fusion protein is expressed by a cell, e.g., a T cell or NK cell that does not express an anti-BCMA CAR.

In some embodiments, the agent which enhances activity of a CAR-expressing cell described herein is miR-17-92.

In some embodiments, the agent which enhances activity of a CAR-described herein is a cytokine. Cytokines have important functions related to T cell expansion, differentiation, survival, and homeostatis. Cytokines that can be administered to the subject receiving a CAR-expressing cell described herein include: IL-2, IL-4, IL-7, IL-9, IL-15, IL-18, and IL-21, or a combination thereof. In preferred embodiments, the cytokine administered is IL-7, IL-15, or IL-21, or a combination thereof. The cytokine can be administered once a day or more than once a day, e.g., twice a day, three times a day, or four times a day. The cytokine can be administered for more than one day, e.g. the cytokine is administered for 2 days, 3 days, 4 days, 5 days, 6 days, 1 week, 2 weeks, 3 weeks, or 4 weeks. For example, the cytokine is administered once a day for 7 days.

In embodiments, the cytokine is administered in combination with CAR-expressing T cells. The cytokine can be administered simultaneously or concurrently with the CAR-expressing T cells, e.g., administered on the same day. The cytokine may be prepared in the same pharmaceutical composition as the CAR-expressing T cells, or may be prepared in a separate pharmaceutical composition. Alternatively, the cytokine can be administered shortly after administration of the CAR-expressing T cells, e.g., 1 day, 2 days, 3 days, 4 days, 5 days, 6 days, or 7 days after administration of the CAR-expressing T cells. In embodiments where the cytokine is administered in a dosing regimen that occurs over more than one day, the first day of the cytokine dosing regimen can be on the same day as administration with the CAR-expressing T cells, or the first day of the cytokine dosing regimen can be 1 day, 2 days, 3 days, 4 days, 5 days, 6 days, or 7 days after administration of the CAR-expressing T cells. In some embodiments, on the first day, the CAR-expressing T cells are administered to the subject, and on the second day, a cytokine is administered once a day for the next 7 days. In a preferred embodiment, the cytokine to be administered in combination with CAR-expressing T cells is IL-7, IL-15, or IL-21.

In other embodiments, the cytokine is administered a period of time after administration of CAR-expressing cells, e.g., at least 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells. In some embodiments, the cytokine is administered after assessment of the subject's response to the CAR-expressing cells. For example, the subject is administered CAR-expressing cells according to the dosage and regimens described herein. The response of the subject to CAR-expressing cell therapy is assessed at 2 weeks, 3 weeks, 4 weeks, 6 weeks, 8 weeks, 10 weeks, 12 weeks, 4 months, 5 months, 6 months, 7 months, 8 months, 9 months, 10 months, 11 months, or 1 year or more after administration of CAR-expressing cells, using any of the methods described herein, including inhibition of tumor growth, reduction of circulating tumor cells, or tumor regression. Subjects that do not exhibit a sufficient response to CAR-expressing cell therapy can be administered a cytokine. Administration of the cytokine to the subject that has sub-optimal response to the CAR-expressing cell therapy improves CAR-expressing cell efficacy or anti-cancer activity. In a preferred embodiment, the cytokine administered after administration of CAR-expressing cells is IL-7.

In some embodiments, the BCMA CAR T cells described herein can be used in combination with a low, immune enhancing, dose of an mTOR inhibitor. Methods described herein use low, immune enhancing, doses of mTOR inhibitors, e.g., allosteric mTOR inhibitors, including rapalogs such as RAD001. Administration of a low, immune enhancing, dose of an mTOR inhibitor (e.g., a dose that is insufficient to completely suppress the immune system, but sufficient to improve immune function) can optimize the performance of immune effector cells, e.g., T cells or CAR-expressing cells, in the subject. Methods for measuring mTOR inhibition, dosages, treatment regimens, and suitable pharmaceutical compositions are described in U.S. Patent Application No. 2015/01240036, hereby incorporated by reference. For methods of combining BCMA CAR T cells with an mTOR inhibitor, see, e.g., paragraphs [0826]-[0861] of US20160046724, herein incorporated by reference in its entirety.

Methods and Biomarkers for Evaluating CAR-Effectiveness or Sample Suitability

In another aspect, the invention features a method of evaluating or monitoring the effectiveness of a CAR-expressing cell therapy (e.g., a BCMACAR therapy), in a subject (e.g., a subject having a cancer, e.g., a hematological cancer), or the suitability of a sample (e.g., an apheresis sample) for a CAR therapy (e.g., a BCMACAR therapy). The method includes acquiring a value of effectiveness to the CAR therapy, or sample suitability, wherein said value is indicative of the effectiveness or suitability of the CAR-expressing cell therapy.

In embodiments, the value of effectiveness to the CAR therapy, or sample suitability, comprises a measure of one, two, three, four, five, six or more (all) of the following:

(i) the level or activity of one, two, three, or more (e.g., all) of resting $T_{EFF}$ cells, resting $T_{REG}$ cells, younger T cells (e.g., younger CD4 or CD8 cells, or gamma/delta T cells), or early memory T cells, or a combination thereof, in a sample (e.g., an apheresis sample or a manufactured CAR-expressing cell product sample);

(ii) the level or activity of one, two, three, or more (e.g., all) of activated $T_{EFF}$ cells, activated $T_{REG}$ cells, older T cells (e.g., older CD4 or CD8 cells), or late memory T cells, or a combination thereof, in a sample (e.g., an apheresis sample or a manufactured CAR-expressing cell product sample);

(iii) the level or activity of an immune cell exhaustion marker, e.g., one, two or more immune checkpoint inhibitors (e.g., PD-1, PD-L1, TIM-3 and/or LAG-3) in a sample (e.g., an apheresis sample or a manufactured CAR-expressing cell product sample). In some embodiments, an immune cell has an exhausted phenotype, e.g., co-expresses at least two exhaustion markers, e.g., co-expresses PD-1 and TIM-3. In other embodiments, an immune cell has an exhausted phenotype, e.g., co-expresses at least two exhaustion markers, e.g., co-expresses PD-1 and LAG-3;

(iv) the level or activity of CD27 and/or CD45RO− (e.g., CD27+ CD45RO−) immune effector cells, e.g., in a CD4+ or a CD8+ T cell population, in a sample (e.g., an apheresis sample or a manufactured CAR-expressing cell product sample);

(v) the level or activity of one, two, three, four, five, ten, twenty or more of the biomarkers chosen from CCL20, IL-17a and/or IL-6, PD-1, PD-L1, LAG-3, TIM-3, CD57, CD27, CD122, CD62L, KLRG1;

(vi) a cytokine level or activity (e.g., quality of cytokine reportoire) in a CAR-expressing cell product sample, e.g., BCMA-expressing cell product sample; or (vii) a transduction efficiency of a CAR-expressing cell in a manufactured CAR-expressing cell product sample.

In some embodiments of any of the methods disclosed herein, the CAR-expressing cell therapy comprises a plurality (e.g., a population) of CAR-expressing immune effector cells, e.g., a plurality (e.g., a population) of T cells or NK cells, or a combination thereof. In some embodiments, the CAR-expressing cell therapy is a BCMACAR therapy.

In some embodiments of any of the methods disclosed herein, the measure of one or more of (i)-(vii) is obtained from an apheresis sample acquired from the subject. The apheresis sample can be evaluated prior to infusion or re-infusion.

In some embodiments of any of the methods disclosed herein, the measure of one or more of (i)-(vii) is obtained from a manufactured CAR-expressing cell product sample, e.g., BCMACAR-expressing cell product sample. The manufactured CAR-expressing cell product can be evaluated prior to infusion or re-infusion.

In some embodiments of any of the methods disclosed herein, the subject is evaluated prior to receiving, during, or after receiving, the CAR-expressing cell therapy.

In some embodiments of any of the methods disclosed herein, the measure of one or more of (i)-(vii) evaluates a profile for one or more of gene expression, flow cytometry or protein expression.

In some embodiments of any of the methods disclosed herein, the method further comprises identifying the subject as a responder, a non-responder, a relapser or a non-relapser, based on a measure of one or more of (i)-(vii).

In some embodiments of any of the methods disclosed herein, a responder (e.g., a complete responder) has, or is identified as having, a greater level or activity of one, two, or more (all) of GZMK, PPF1BP2, or naïve T cells as compared to a non-responder.

In some embodiments of any of the methods disclosed herein, a non-responder has, or is identified as having, a greater level or activity of one, two, three, four, five, six, seven, or more (e.g., all) of IL22, IL-2RA, IL-21, IRF8, IL8, CCL17, CCL22, effector T cells, or regulatory T cells, as compared to a responder.

In an embodiment, a relapser is a patient having, or who is identified as having, an increased level of expression of one or more of (e.g., 2, 3, 4, or all of) the following genes, compared to non relapsers: MIR199A1, MIR1203, uc021ovp, ITM2C, and HLA-DQB1 and/or a decreased levels of expression of one or more of (e.g., 2, 3, 4, 5, 6, 7, 8, 9, 10, 11, or all of) the following genes, compared to non relapsers: PPIAL4D, TTTY10, TXLNG2P, MIR4650-1, KDM5D, USP9Y, PRKY, RPS4Y2, RPS4Y1, NCRNA00185, SULT1E1, and EIF1AY.

In some embodiments of any of the methods disclosed herein, a complete responder has, or is identified as having, a greater, e.g., a statistically significant greater, percentage of CD8+ T cells compared to a reference value, e.g., a non-responder percentage of CD8+ T cells.

In some embodiments of any of the methods disclosed herein, a complete responder has, or is identified as having, a greater percentage of CD27+ CD45RO− immune effector cells, e.g., in the CD8+ population, compared to a reference value, e.g., a non-responder number of CD27+ CD45RO− immune effector cells.

In some embodiments of any of the methods disclosed herein, a complete responder or a partial responder has, or is identified as having, a greater, e.g., a statistically significant greater, percentage of CD4+ T cells compared to a reference value, e.g., a non-responder percentage of CD4+ T cells.

In some embodiments of any of the methods disclosed herein, a complete responder has, or is identified as having, a greater percentage of one, two, three, or more (e.g., all) of resting $T_{EFF}$ cells, resting $T_{REG}$ cells, younger T cells (e.g., younger CD4 or CD8 cells, or gamma/delta T cells), or early memory T cells, or a combination thereof, compared to a reference value, e.g., a non-responder number of resting $T_{EFF}$ cells, resting $T_{REG}$ cells, younger T cells (e.g., younger CD4 or CD8 cells), or early memory T cells.

In some embodiments of any of the methods disclosed herein, a non-responder has, or is identified as having, a greater percentage of one, two, three, or more (e.g., all) of activated $T_{EFF}$ cells, activated $T_{REG}$ cells, older T cells (e.g., older CD4 or CD8 cells), or late memory T cells, or a combination thereof, compared to a reference value, e.g., a responder number of activated $T_{EFF}$ cells, activated $T_{REG}$ cells, older T cells (e.g., older CD4 or CD8 cells), or late memory T cells.

In some embodiments of any of the methods disclosed herein, a non-responder has, or is identified as having, a greater percentage of an immune cell exhaustion marker, e.g., one, two or more immune checkpoint inhibitors (e.g., PD-1, PD-L1, TIM-3 and/or LAG-3). In some embodiments, a non-responder has, or is identified as having, a greater percentage of PD-1, PD-L1, or LAG-3 expressing immune effector cells (e.g., CD4+ T cells and/or CD8+ T cells) (e.g., CAR-expressing CD4+ cells and/or CD8+ T cells) compared to the percentage of PD-1 or LAG-3 expressing immune effector cells from a responder.

In some embodiments, a non-responder has, or is identified as having, a greater percentage of immune cells having an exhausted phenotype, e.g., immune cells that co-express at least two exhaustion markers, e.g., co-expresses PD-1, PD-L1 and/or TIM-3. In other embodiments, a non-responder has, or is identified as having, a greater percentage of immune cells having an exhausted phenotype, e.g., immune cells that co-express at least two exhaustion markers, e.g., co-expresses PD-1 and LAG-3.

In some embodiments of any of the methods disclosed herein, a non-responder has, or is identified as having, a greater percentage of PD-1/PD-L1+/LAG-3+ cells in the CAR-expressing cell population (e.g., a BCMACAR+ cell population) compared to a responder (e.g., a complete responder) to the CAR-expressing cell therapy.

In some embodiments of any of the methods disclosed herein, a partial responder has, or is identified as having, a higher percentages of PD-1/PD-L1+/LAG-3+ cells, than a responder, in the CAR-expressing cell population (e.g., a BCMACAR+ cell population).

In some embodiments of any of the methods disclosed herein, a non-responder has, or is identified as having, an exhausted phenotype of PD1/PD-L1+ CAR+ and co-expression of LAG3 in the CAR-expressing cell population (e.g., a BCMACAR+ cell population).

In some embodiments of any of the methods disclosed herein, a non-responder has, or is identified as having, a greater percentage of PD-1/PD-L1+/TIM-3+ cells in the CAR-expressing cell population (e.g., a BCMACAR+ cell population) compared to the responder (e.g., a complete responder).

In some embodiments of any of the methods disclosed herein, a partial responders has, or is identified as having, a higher percentage of PD-1/PD-L1+/TIM-3+ cells, than responders, in the CAR-expressing cell population (e.g., a BCMACAR+ cell population).

In some embodiments of any of the methods disclosed herein, the presence of CD8+ CD27+ CD45RO− T cells in an apheresis sample is a positive predictor of the subject response to a CAR-expressing cell therapy (e.g., a BCMACAR therapy).

In some embodiments of any of the methods disclosed herein, a high percentage of PD1+ CAR+ and LAG3+ or TIM3+ T cells in an apheresis sample is a poor prognostic predictor of the subject response to a CAR-expressing cell therapy (e.g., a BCMACAR therapy).

In some embodiments of any of the methods disclosed herein, the responder (e.g., the complete or partial responder) has one, two, three or more (or all) of the following profile:

(i) has a greater number of CD27+ immune effector cells compared to a reference value, e.g., a non-responder number of CD27+ immune effector cells;

(ii) (i) has a greater number of CD8+ T cells compared to a reference value, e.g., a non-responder number of CD8+ T cells;

(iii) has a lower number of immune cells expressing one or more checkpoint inhibitors, e.g., a checkpoint inhibitor chosen from PD-1, PD-L1, LAG-3, TIM-3, or KLRG-1, or a combination, compared to a reference value, e.g., a non-responder number of cells expressing one or more checkpoint inhibitors; or (iv) has a greater number of one, two, three, four or more (all) of resting $T_{EFF}$ cells, resting $T_{REG}$ cells, naïve CD4 cells, unstimulated memory cells or early memory T cells, or a combination thereof, compared to a reference value, e.g., a non-responder number of resting $T_{EFF}$ cells, resting $T_{REG}$ cells, naïve CD4 cells, unstimulated memory cells or early memory T cells.

In some embodiments of any of the methods disclosed herein, the cytokine level or activity of (vi) is chosen from one, two, three, four, five, six, seven, eight, or more (or all) of cytokine CCL20/MIP3a, IL17A, IL6, GM-CSF, IFNγ, IL10, IL13, IL2, IL21, IL4, IL5, IL9 or TNFα, or a combination thereof. The cytokine can be chosen from one, two, three, four or more (all) of IL-17a, CCL20, IL2, IL6, or TNFa. In some embodiments, an increased level or activity of a cytokine is chosen from one or both of IL-17a and CCL20, is indicative of increased responsiveness or decreased relapse.

In some embodiments of any of the methods disclosed herein, a transduction efficiency of 15% or higher in (vii) is indicative of increased responsiveness or decreased relapse.

In some embodiments of any of the methods disclosed herein, a transduction efficiency of less than 15% in (vii) is indicative of decreased responsiveness or increased relapse.

In embodiments, the responder, a non-responder, a relapser or a non-relapser identified by the methods herein can be further evaluated according to clinical criteria. For example, a complete responder has, or is identified as, a subject having a disease, e.g., a cancer, who exhibits a complete response, e.g., a complete remission, to a treatment. A complete response may be identified, e.g., using the NCCN Guidelines®, or Cheson et al, J Clin Oncol 17:1244 (1999) and Cheson et al., "Revised Response Criteria for Malignant Lymphoma", J Clin Oncol 25:579-586 (2007) (both of which are incorporated by reference herein in their entireties), as described herein. A partial responder has, or is identified as, a subject having a disease, e.g., a cancer, who exhibits a partial response, e.g., a partial remission, to a treatment. A partial response may be identified, e.g., using the NCCN Guidelines®, or Cheson criteria as described herein. A non-responder has, or is identified as, a subject having a disease, e.g., a cancer, who does not exhibit a response to a treatment, e.g., the patient has stable disease or progressive disease. A non-responder may be identified, e.g., using the NCCN Guidelines®, or Cheson criteria as described herein.

Alternatively, or in combination with the methods disclosed herein, responsive to said value, performing one, two, three four or more of:

administering e.g., to a responder or a non-relapser, a CAR-expressing cell therapy;

administered an altered dosing of a CAR-expressing cell therapy;

altering the schedule or time course of a CAR-expressing cell therapy;

administering, e.g., to a non-responder or a partial responder, an additional agent in combination with a CAR-expressing cell therapy, e.g., a checkpoint inhibitor, e.g., a checkpoint inhibitor described herein;

administering to a non-responder or partial responder a therapy that increases the number of younger T cells in the subject prior to treatment with a CAR-expressing cell therapy;

modifying a manufacturing process of a CAR-expressing cell therapy, e.g., enriching for younger T cells prior to introducing a nucleic acid encoding a CAR, or increasing the transduction efficiency, e.g., for a subject identified as a non-responder or a partial responder;

administering an alternative therapy, e.g., for a non-responder or partial responder or relapser; or if the subject is, or is identified as, a non-responder or a relapser, decreasing the $T_{REG}$ cell population and/or $T_{REG}$ gene signature, e.g., by one or more of CD25 depletion, administration of cyclophosphamide, anti-GITR antibody, or a combination thereof.

In certain embodiments, the subject is pre-treated with an anti-GITR antibody. In certain embodiment, the subject is treated with an anti-GITR antibody prior to infusion or re-infusion.

Biopolymer Delivery Methods

In some embodiments, one or more CAR-expressing cells as disclosed herein can be administered or delivered to the subject via a biopolymer scaffold, e.g., a biopolymer implant. Biopolymer scaffolds can support or enhance the delivery, expansion, and/or dispersion of the CAR-expressing cells described herein. A biopolymer scaffold comprises a biocompatible (e.g., does not substantially induce an inflammatory or immune response) and/or a biodegradable polymer that can be naturally occurring or synthetic.

Examples of suitable biopolymers include, but are not limited to, agar, agarose, alginate, alginate/calcium phosphate cement (CPC), beta-galactosidase (β-GAL), (1,2,3,4,6-pentaacetyl a-D-galactose), cellulose, chitin, chitosan, collagen, elastin, gelatin, hyaluronic acid collagen, hydroxyapatite, poly(3-hydroxybutyrate-co-3-hydroxy-hexanoate) (PHBHHx), poly(lactide), poly(caprolactone) (PCL), poly(lactide-co-glycolide) (PLG), polyethylene oxide (PEO), poly(lactic-co-glycolic acid) (PLGA), polypropylene oxide (PPO), polyvinyl alcohol) (PVA), silk, soy protein, and soy protein isolate, alone or in combination with any other polymer composition, in any concentration and in any ratio. The biopolymer can be augmented or modified with adhesion- or migration-promoting molecules, e.g., collagen-mimetic peptides that bind to the collagen receptor of lymphocytes, and/or stimulatory molecules to enhance the delivery, expansion, or function, e.g., anti-cancer activity, of the cells to be delivered. The biopolymer scaffold can be an injectable, e.g., a gel or a semi-solid, or a solid composition.

In some embodiments, CAR-expressing cells described herein are seeded onto the biopolymer scaffold prior to delivery to the subject. In embodiments, the biopolymer scaffold further comprises one or more additional therapeutic agents described herein (e.g., another CAR-expressing cell, an antibody, or a small molecule) or agents that enhance the activity of a CAR-expressing cell, e.g., incorporated or conjugated to the biopolymers of the scaffold. In embodiments, the biopolymer scaffold is injected, e.g., intratumorally, or surgically implanted at the tumor or within a proximity of the tumor sufficient to mediate an anti-tumor effect. Additional examples of biopolymer compositions and methods for their delivery are described in Stephan et al., *Nature Biotechnology,* 2015, 33:97-101; and WO2014/110591.

Pharmaceutical Compositions and Treatments

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In some embodiments, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In some embodiments, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In one aspect, the CAR-expressing cell (e.g., T cell or NK cell) compositions of the present invention are administered by i.v. injection. The compositions of CAR-expressing cells (e.g., T cells or NK cells) may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., immune effector cells (e.g., T cells or NK cells). These immune effector cell (e.g., T cell or NK cell) isolates may be expanded by methods known in the art and treated such that one or more CAR constructs of the invention may be introduced, thereby creating a CAR-expressing cell (e.g., CAR T cell or CAR-expressing NK cell) of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR-expressing cells (e.g., CAR T cells or NK cells) of the present invention. In an additional aspect, expanded cells are administered before or following surgery.

In embodiments, lymphodepletion is performed on a subject, e.g., prior to administering one or more cells that express a CAR described herein, e.g., a BCMA-binding CAR described herein. In embodiments, the lymphodepletion comprises administering one or more of melphalan, cytoxan, cyclophosphamide, and fludarabine.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In some embodiments, the CAR is introduced into immune effector cells (e.g., T cells or NK cells), e.g., using in vitro transcription, and the subject (e.g., human) receives an initial administration of CAR immune effector cells (e.g., T cells or NK cells) of the invention, and one or more subsequent administrations of the CAR immune effector cells (e.g., T cells or NK cells) of the invention, wherein the one or more subsequent administrations are administered less than 15 days, e.g., 14, 13, 12, 11, 10, 9, 8, 7, 6, 5, 4, 3, or 2 days after the previous administration. In some embodiments, more than one administration of the CAR immune effector cells (e.g., T cells or NK cells) of the invention are administered to the subject (e.g., human) per week, e.g., 2, 3, or 4 administrations of the CAR immune effector cells (e.g., T cells or NK cells) of the invention are administered per week. In some embodiments, the subject (e.g., human subject) receives more than one administration of the CAR immune effector cells (e.g., T cells or NK cells) per week (e.g., 2, 3 or 4 administrations per week) (also referred to herein as a cycle), followed by a week of no CAR immune effector cells (e.g., T cells or NK cells) administrations, and then one or more additional administration of the CAR immune effector cells (e.g., T cells or NK cells) (e.g., more than one administration of the CAR immune effector cells (e.g., T cells or NK cells) per week) is administered to the subject. In another embodiment, the subject (e.g., human subject) receives more than one cycle of CAR immune effector cells (e.g., T cells or NK cells), and the time between each cycle is less than 10, 9, 8, 7, 6, 5, 4, or 3 days. In some embodiments, the CAR immune effector cells (e.g., T cells or NK cells) are administered every other day for 3 administrations per week. In some embodiments, the CAR immune effector cells (e.g., T cells or NK cells) of the invention are administered for at least two, three, four, five, six, seven, eight or more weeks.

In one aspect, BCMA CAR-expressing cells (e.g., BCMA CARTs or BCMA CAR-expressing NK cells) are generated using lentiviral viral vectors, such as lentivirus. CAR-expressing cells (e.g., CARTs or CAR-expressing NK cells) generated that way will have stable CAR expression.

In one aspect, CAR-expressing cells, e.g., CARTs, are generated using a viral vector such as a gammaretroviral vector, e.g., a gammaretroviral vector described herein. CARTs generated using these vectors can have stable CAR expression.

In one aspect, CAR-expressing cells (e.g., CARTs or CAR-expressing NK cells) transiently express CAR vectors for 4, 5, 6, 7, 8, 9, 10, 11, 12, 13, 14, 15 days after transduction. Transient expression of CARs can be effected by RNA CAR vector delivery. In one aspect, the CAR RNA is transduced into the cell, e.g., T cell or NK cell, by electroporation.

A potential issue that can arise in patients being treated using transiently expressing CAR-expressing cells (e.g., CARTs or CAR-expressing NK cells) (particularly with murine scFv bearing CAR-expressing cells (e.g., CARTs or CAR-expressing NK cells)) is anaphylaxis after multiple treatments.

Without being bound by this theory, it is believed that such an anaphylactic response might be caused by a patient developing humoral anti-CAR response, i.e., anti-CAR antibodies having an anti-IgE isotype. It is thought that a patient's antibody producing cells undergo a class switch from IgG isotype (that does not cause anaphylaxis) to IgE isotype when there is a ten to fourteen day break in exposure to antigen.

If a patient is at high risk of generating an anti-CAR antibody response during the course of transient CAR therapy (such as those generated by RNA transductions), CAR-expressing cell (e.g., CART or CAR-expressing NK cell) infusion breaks should not last more than ten to fourteen days.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: In Vitro Characterization of Human BCMA CARs

A set of fully human single chain variable fragments (scFv) was cloned into lentiviral CAR expression vectors with the CD3zeta chain and the 4-1BB stimulatory molecules: R1B6, R1F2, R1G5, PI61, B61-10, B61-02, Hy03, and Hy52. The constructs were initially screened using automated cell reporter assay followed by selection for optimal clones based on expression on primary T cells as well as quantity and quality of effector T cell responses ("BCMA CART" or "BCMA CAR T cells") in response to BCMA expressing ("BCMA+" or "BCMA positive") targets. Effector T cell responses include, but are not limited to, cellular expansion, proliferation, doubling, cytokine production and target cell killing or cytolytic activity (degranulation).

Generation of BCMA CAR Lentivirus

All the above-mentioned scFv encoding lentiviral transfer vectors were used to produce the genomic material packaged into the VSVg pseudotyped lentiviral particles. Lentiviral transfer vector DNA encoding the CAR was mixed with the three packaging components VSVg, gag/pol and rev in combination with lipofectamine reagent to transfect Lenti-X 293T cells (Clontech), followed by medium replacement 12-18 h later. 30 hours after medium change, the media was collected, filtered and stored at −80° C.

BCMA CAR JNL and JNL Screening Reporter Assay Using Automated System

For the reporter assay, lentivirus encoding for BCMA CARs was generated in HEK293 cells at two different cell densities (40,000 cells (1×H293) or 80,000 cells (2×H293)) in an automated, small scale fashion in 96-well plates, where virus-containing supernatant was harvested 48 h after transfection and used fresh, without freezing, for the transduction of a Jurkat T cell reporter cell line. The Jurkat NFAT Luciferase (JNL) reporter cell line is based on the acute T cell leukemia line Jurkat. The line was modified to express luciferase under control of the Nuclear Factor of Activated T cells (NFAT) response element. For the transduction with BCMA CARs, 10,000 JNL cells/well of a 96-well plate were transduced with 50 µl of fresh, 45 µm-filtered virus-containing supernatant. The plates were cultured for 5 days before co-culturing with target cells.

To evaluate the functional ability of BCMA CARs to activate JNL cells, they were co-cultured with target cancer cells at different effector to target cell ratios (E:T ratio) to read out their activation by quantifying luciferase expression. The scFv-based CARs R1B6, R1F2, R1G5, PI61, B61-10, B61-02, Hy03, and Hy52 were assessed. The CD19 JNL CAR cells were used as a target specific control, and media alone without target cells served as a negative control.

Figure 1B:
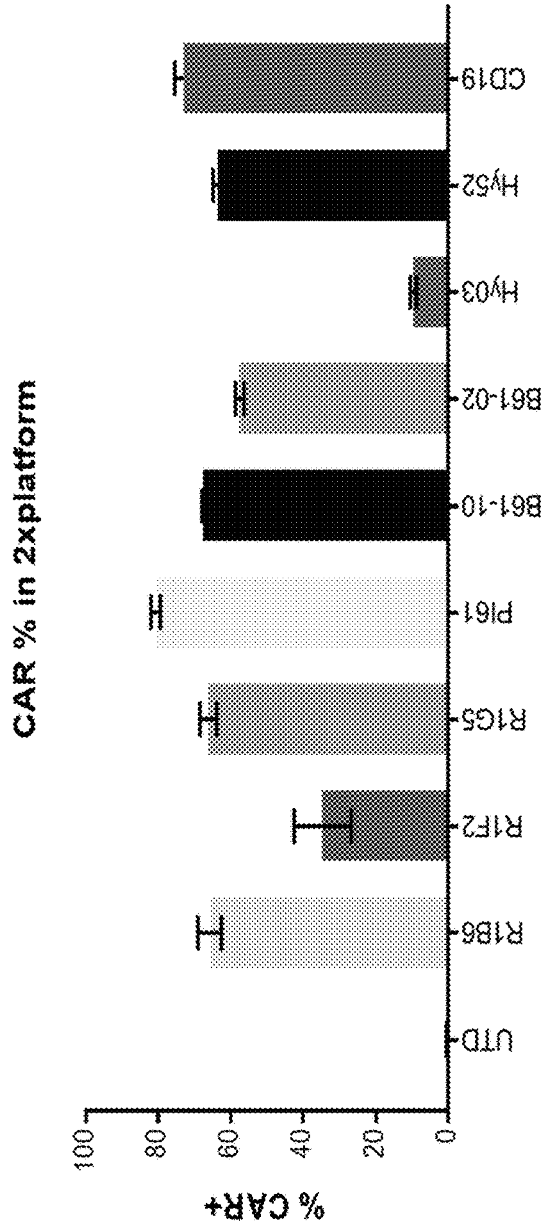
Figure 1C:
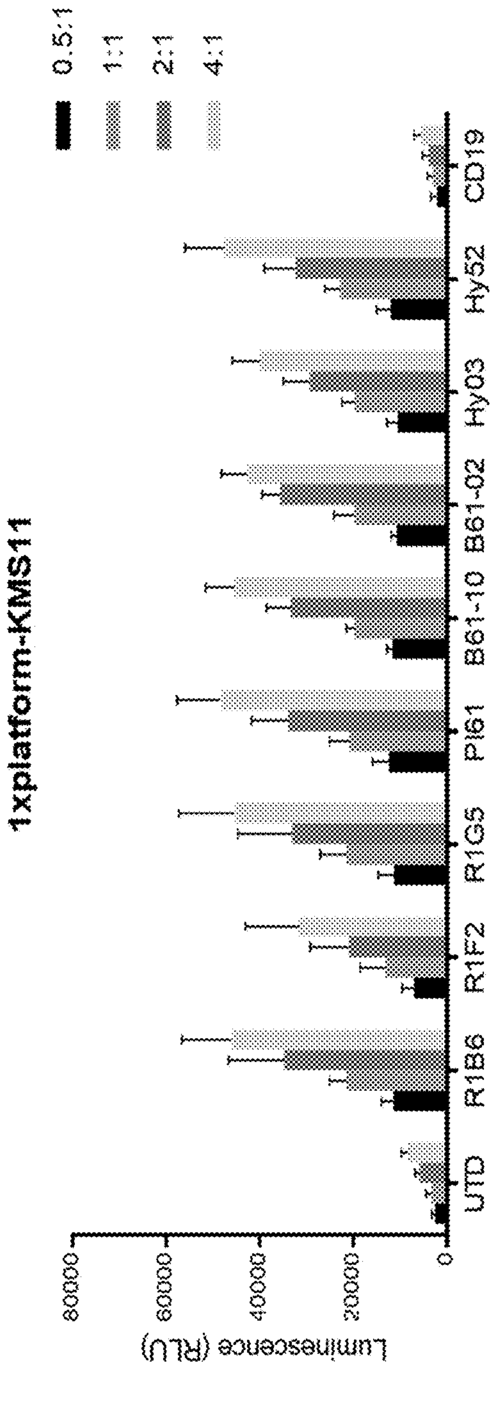
Figure 1D:
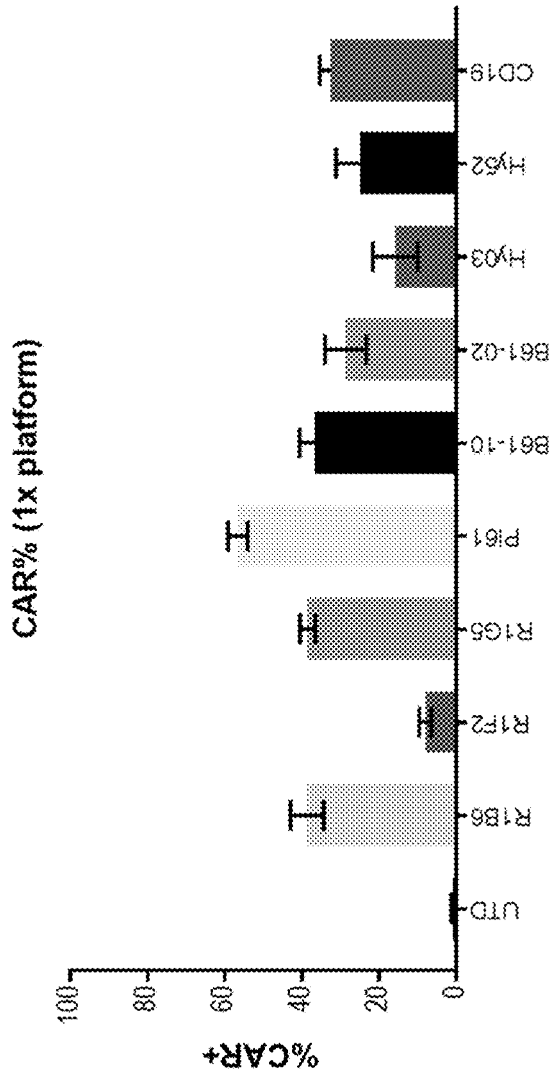
Figure 1E:
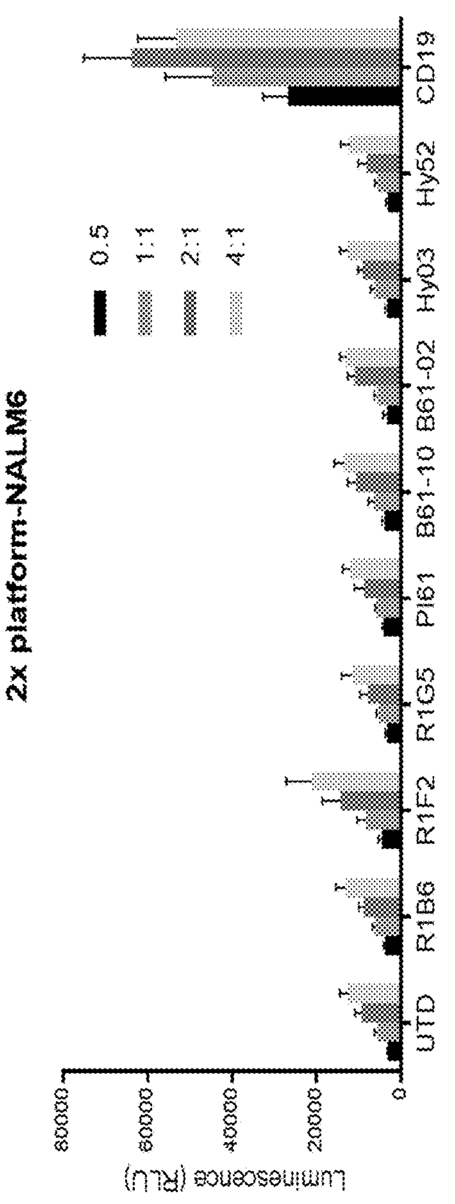
Figure 1F:
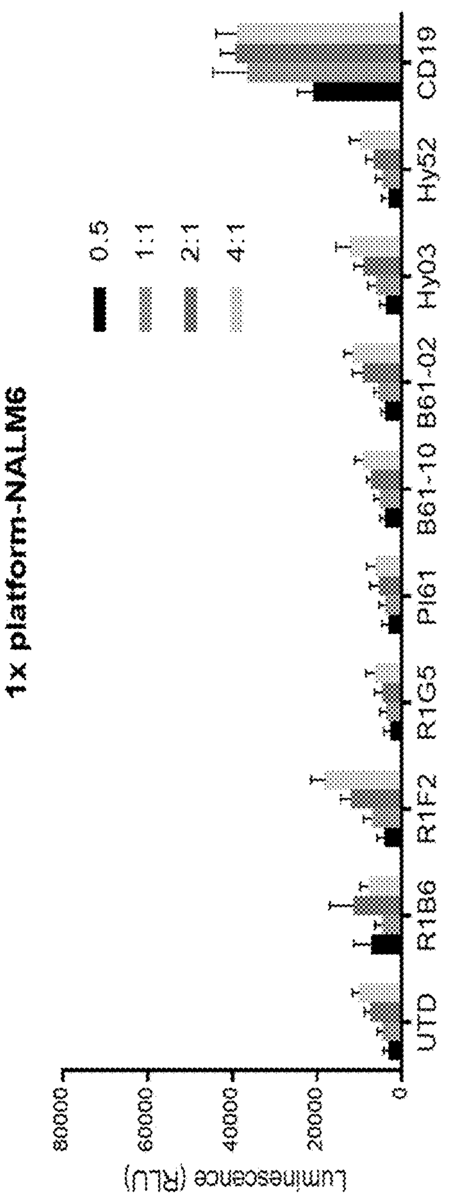
Figure 1G:
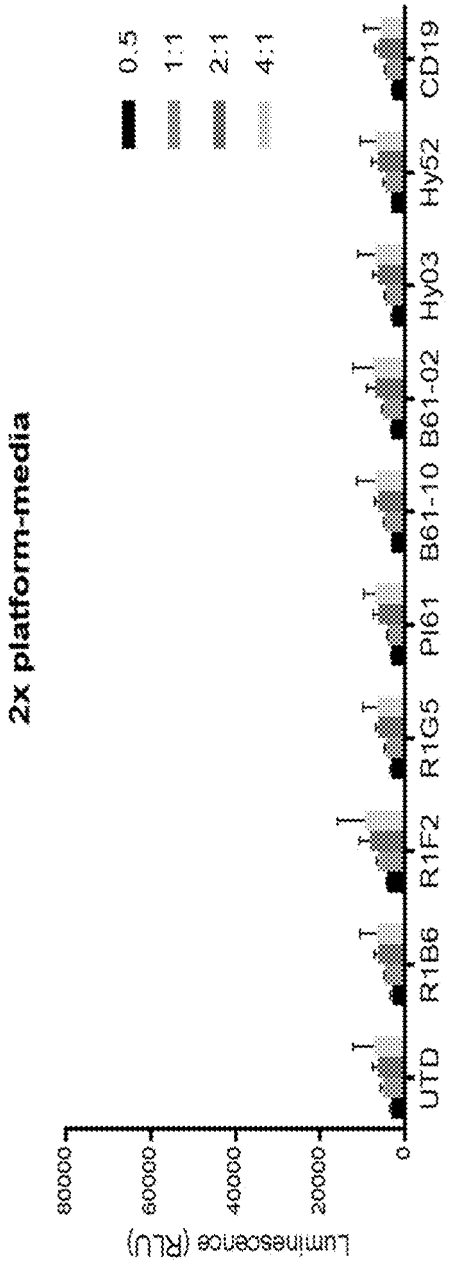
Figure 1H:
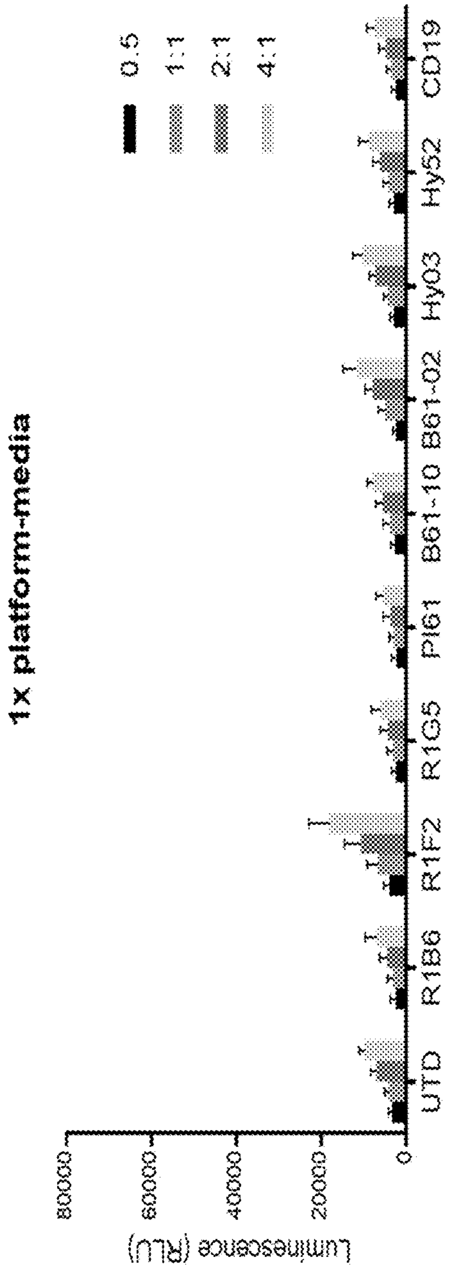

The above mentioned five-day transduced JNL CAR cells were co-cultured with the BCMA-positive multiple myeloma (MM) cell line KMS11, or NALM6, an acute lymphocytic leukemia cell line, served as a BCMA-negative control. Remaining JNL CAR T cells were evaluated for BCMA CAR expression by flow cytometry. Co-cultures were set up in 384-well plates at effector-to-target (E:T) ratios of 4:1, 2:1, 1:1 and 0.5:1 and incubated for 24 h, after which the expression of luciferase by the activated JNL CAR T cells was quantified by Bright-Glo™ Luciferase Assay System (Promega, Madison, Wis.). The amount of light emitted from each well (luminescence) was a direct read-out of JNL activation by the respective CAR. JNL cells were considered to be activated when the level of luminescence was equal or more than twofold of UTD cells. The BCMA+ KMS11 cell line led to activation of the JNL cells expressing R1B6, R1F2, R1G5, PI61, B61-10, B61-02, Hy03, and Hy52 (FIGS. 1A and 1C). None of the BCMA CARs showed activation by the BCMA-negative line NALM6 (FIGS. 1E and 1F). Media alone, without target cells, did not activate any of the CAR transduced JNLs tested (FIGS. 1G and 1H). FACS analyses demonstrated that BCMA-CAR expression in transduced JNLs was detected to different degrees; CAR % is generally positively correlated with JNL activation by KMS11 cells in the most active JNL CARTs (FIGS. 1B and 1D).

Generation of BCMA CAR T Cells

The following 8 CARs were chosen for analysis of CAR expression, stability and efficacy in primary T cells: R1B6, R1F2, R1G5, PI61, B61-10, B61-02, Hy03, and Hy52. BCMA CAR T cells were generated by starting with blood from healthy apheresed donors whose T cells (CD4+ and CD8+ lymphocytes) were obtained by negative selection for CD3+ T cells. These cells were activated by the addition of CD3/CD28 beads (Dynabeads® Human T-Expander CD3/CD28, Thermo Fisher Scientific) at a ratio of 1:3 (T cell to bead) in T cell medium (RPMI1640, 10% heat-inactivated fetal calf serum (FCS), 2 mM L-glutamine, 1× Penicillin/Streptomycin, 100 μM non-essential amino acids, 1 mM Sodium Pyruvate, 10 mM Hepes, and 55 μM 2-mercapto-ethanol). T cells were cultured at $0.5\times10^6$ T cells in 1 mL medium per well of a 24-well plate at 37° C., 5% $CO_2$. After 24 hours, when T cells were blasting, T cells were transduced with BCMA CAR virus at a multiplicity of infection (MOI) of 5. T cells began to divide in a logarithmic growth pattern, which was monitored by measuring the cell counts per mL, and T cells were diluted in fresh medium every two days and de-beaded and harvested for further analyses at day 9. Aliquots of T cells were stained to measure CAR expression by flow cytometry at day 5 and 9 on a FACS Fortessa (BD). All BCMA CAR T cells were produced under research grade (i.e., not clinical grade) manufacturing conditions.

Figure 2:
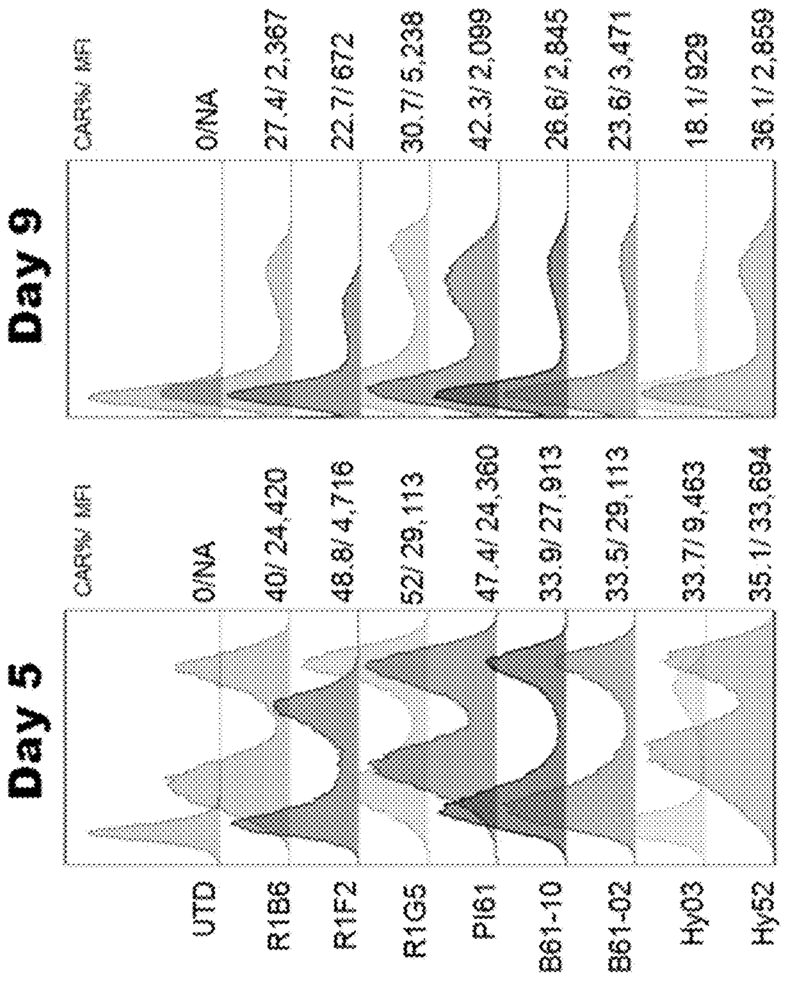
FIG. 2. Expression level of BCMA CARs on primary human T cells. Cells were stained with a human rBCMA_Fc-AF647 reagent and assayed by flow cytometry. The percentage of CAR+ cells and MFI are shown in the graph for day 5 and day 9 of cell culture. Data is summarized in Table 17, which includes the viral titer achieved for the respective CARs.

The BCMA-CAR surface expression and its stability was assessed by measuring CAR % and MFI (mean fluorescence intensity) at day 5 and day 9 using flow cytometry analyses of rBCMA_Fc-AF647 stained cells (FIG. 2 and Table 17). BCMA CAR expression in the final product at day 9 differs from construct to construct, ranging from 18% to 42.4%, and MFI from 672 to 5238. Constructs from PALLAS-derived clones R1F2, R1B6, and R1G5, and the hybridoma clone, Hy03 showed ~30% to 50% CAR loss from day 5 to day 9, while PI61, B61-10 and -02, as well as Hy52 are relatively stable in terms of the percentage of CAR expression, though all the CAR constructs showed a decrease in MFI from day 5 to day 9, which was probably due to the smaller size of T cells at their resting stage on day 9. The cell counts of the CAR T cell cultures indicated that there is no detectable negative effect of the human scFv bearing BCMA CAR on the ability of the cells to expand normally when compared to the untransduced T cells ("UTD").

TABLE 17

Analysis of CAR expression

| CAR Construct | Titer | CAR % on T cells Day 5 | CAR % on T cells Day 9 | CAR MFI on T cells Day 5 | CAR MFI on T cells Day 9 |
|---|---|---|---|---|---|
| R1B6 | 2.68E+08 | 40.0 | 27.4 | 24,420 | 2,367 |
| R1F2 | 3.60E+08 | 48.8 | 22.7 | 4,716 | 672 |
| R1G5 | 2.27E+08 | 52.0 | 30.7 | 29,113 | 5,238 |
| PI61 | 1.71E+08 | 47.4 | 42.3 | 24,360 | 2,099 |
| B61-10 | 7.06E+07 | 41.1 | 30.3 | 27,298 | 3,288 |
| B61-02 | 8.16E+07 | 33.5 | 23.6 | 29,113 | 3,471 |
| Hy03 | 4.96E+07 | 33.7 | 18.1 | 9,463 | 929 |
| Hy52 | 7.03E+07 | 35.1 | 36.1 | 33,694 | 2,859 |

Evaluating Functionality of BCMA CAR-Redirected T Cells

To evaluate the functional abilities of BCMA CAR-T cells, co-cultures were set up with BCMA-positive and -negative cancer lines. CAR-T cells were thawed, counted and co-cultured with target cells to read out their killing capabilities and secretion of cytokines. BCMA CAR-clones R1B6, R1F2, R1G5, B61-02, B61-10, PI61, Hy03, and Hy52 were tested. Non-transduced T cells (UTD) were used as non-targeting T cell controls.

Figure 3A:
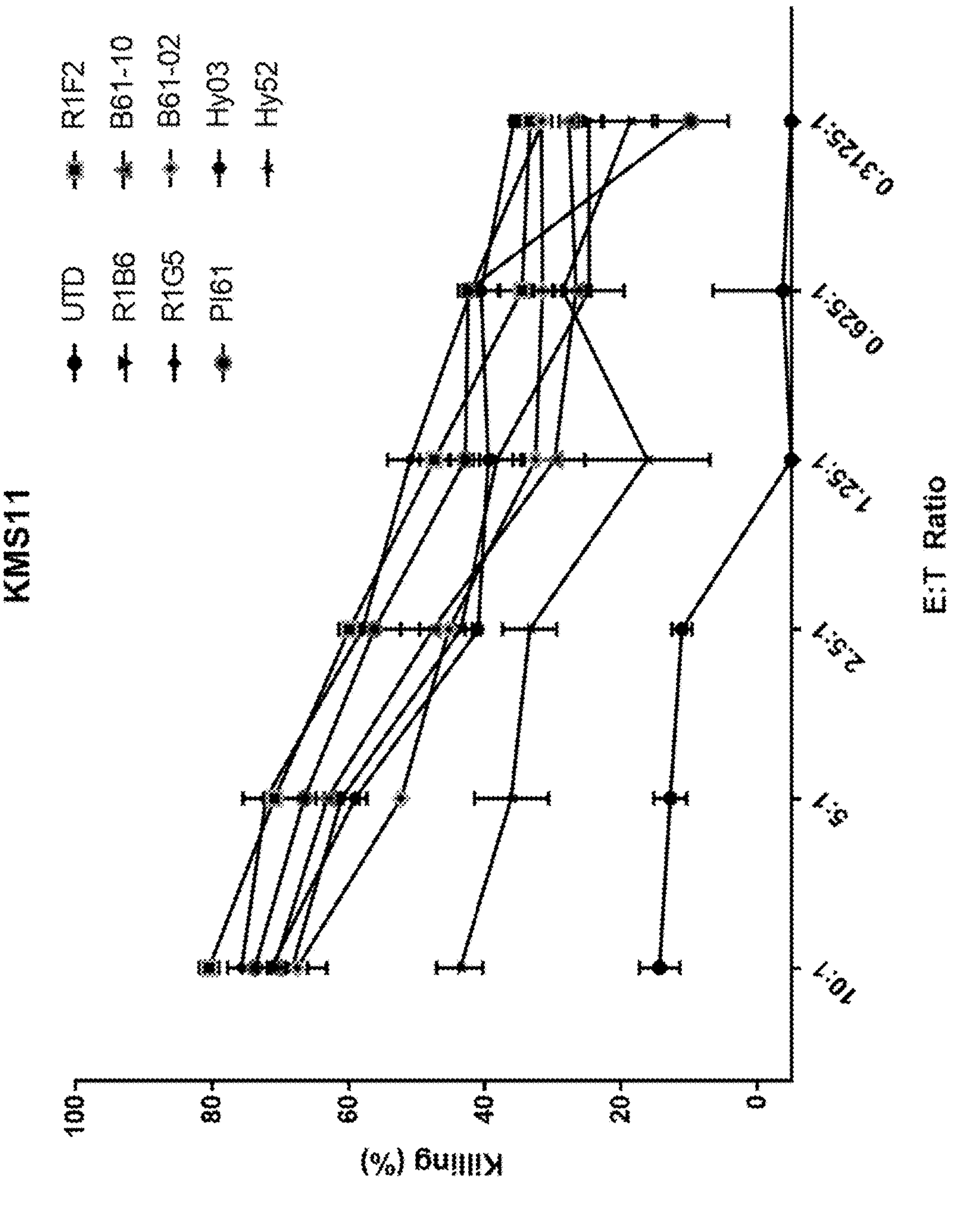
FIGS. 3A-3C. The ability of T cells expressing the indicated CARs to mediate cell lysis and cytokine production were evaluated against the KMS11 target cell line expressing fire fly luciferase (KMS11-luc).
Figure 3B:
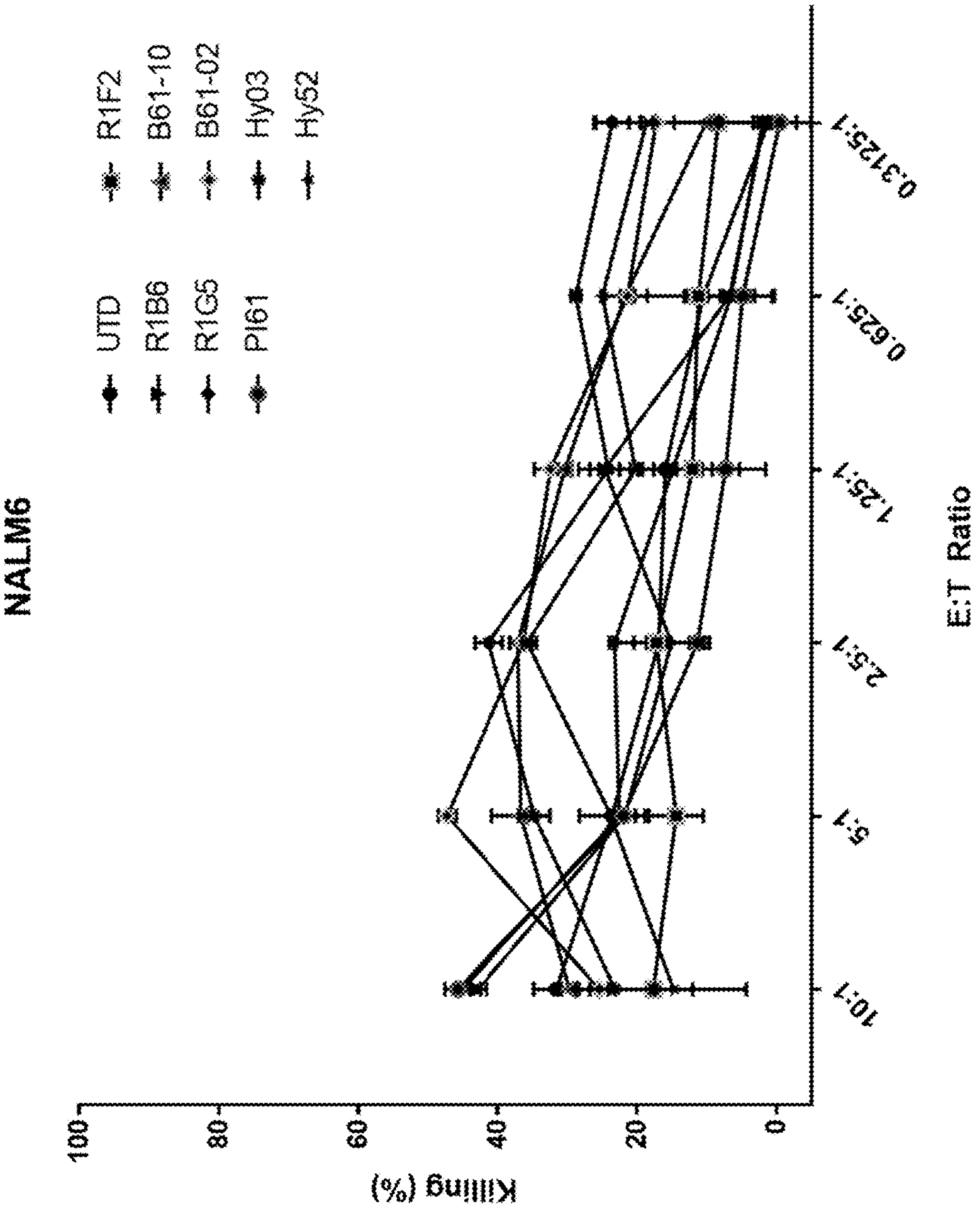
Figure 3C:
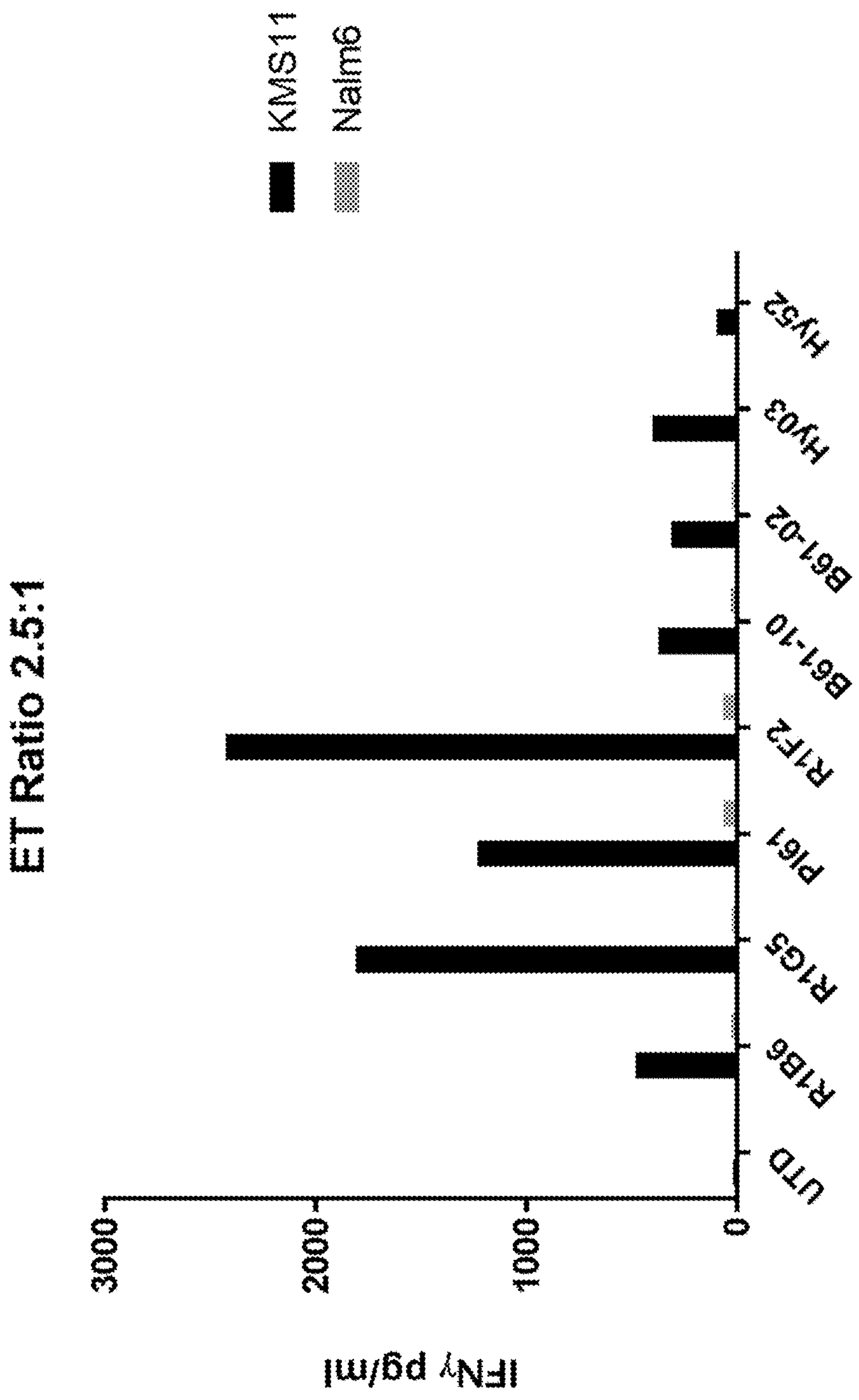

CART cell killing was performed by co-culturing CART cells with KMS11-Luc and NALM6-Luc target cells at different E:T ratios for 20 hours. CAR T cell populations were normalized to equivalent percentages of CAR-positive cells before plating. The cytokine IFNγ was measured in supernatants from 20 hour co-cultures of CAR-T cells with target cells at effector to target ratio of 2.5:1 using the Meso Scale Discovery (MSD; Gaithersburg, Md.) and the results for each cytokine were calculated in pg/ml using known standards. All assays were performed in duplicate from a single source of donor cells. Killing data shows that all the BCMA CAR clones kill KMS11 cancer cells effectively (FIG. 3A). The control target cell NALM6 was not killed by any of these BCMA-specific CARs (FIG. 3B). The ability of these CARs to produce IFN-γ when cultured with KMS11 was also tested (FIG. 3C). BCMA CAR R1F2, R1G5 and PI61 led to the highest amounts of IFN-γ being produced. Levels of cytokine produced by BCMA CARTs after exposure to the control NALM6 cells were low (FIG. 3C), indicating no unspecific activation by BCMA CARs.

CONCLUSIONS

New BCMA-binding scFvs were tested in the context of CAR T cells. Eight CARs were assayed in a JNL reporter assay as well as in primary T cells: R1B6, R1F2, R1G5, B61-02, B61-10, PI61, Hy03, and Hy52. All eight CAR-T cells showed target-specific killing. T cells expressing R1F2, R1G5, or PI61 produced the highest amounts of IFN-γ in the presence of target cells. Overall, the transfer of BCMA CARs to primary T cells induced anti-BCMA CAR reactivity but no off-target function.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

SEQUENCE LISTING

```
Sequence total quantity: 285
SEQ ID NO: 1            moltype = AA  length = 21
FEATURE                 Location/Qualifiers
REGION                  1..21
                        note = source = /note="Description of Artificial Sequence:
                         Synthetic peptide"
source                  1..21
                        mol_type = protein
                        organism = synthetic construct
SEQUENCE: 1
MALPVTALLL PLALLLHAAR P                                            21

SEQ ID NO: 2            moltype = AA  length = 45
FEATURE                 Location/Qualifiers
REGION                  1..45
                        note = source = /note="Description of Artificial Sequence:
                         Synthetic polypeptide"
source                  1..45
                        mol_type = protein
                        organism = synthetic construct
SEQUENCE: 2
TTTPAPRPPT PAPTIASQPL SLRPEACRPA AGGAVHTRGL DFACD                  45

SEQ ID NO: 3            moltype = AA  length = 230
FEATURE                 Location/Qualifiers
REGION                  1..230
                        note = source = /note="Description of Artificial Sequence:
                         Synthetic polypeptide"
source                  1..230
                        mol_type = protein
                        organism = synthetic construct
SEQUENCE: 3
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKM             230

SEQ ID NO: 4            moltype = AA  length = 282
FEATURE                 Location/Qualifiers
REGION                  1..282
                        note = source = /note="Description of Artificial Sequence:
                         Synthetic polypeptide"
source                  1..282
                        mol_type = protein
                        organism = synthetic construct
SEQUENCE: 4
RWPESPKAQA SSVPTAQPQA EGSLAKATTA PATTRNTGRG GEEKKKEKEK EEQEERETKT  60
PECPSHTQPL GVYLLTPAVQ DLWLRDKATF TCFVVGSDLK DAHLTWEVAG KVPTGGVEEG  120
LLERHSNGSQ SQHSRLTLPR SLWNAGTSVT CTLNHPSLPP QRLMALREPA AQAPVKLSLN  180
LLASSDPPEA ASWLLCEVSG FSPPNILLMW LEDQREVNTS GFAPARPPPQ PGSTTFWAWS  240
VLRVPAPPSP QPATYTCVVS HEDSRTLLNA SRSLEVSYVT DH                     282

SEQ ID NO: 5            moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 5
GGGGSGGGGS                                                         10

SEQ ID NO: 6            moltype = AA  length = 24
FEATURE                 Location/Qualifiers
REGION                  1..24
                        note = source = /note="Description of Artificial Sequence:
                         Synthetic peptide"
source                  1..24
                        mol_type = protein
                        organism = synthetic construct
SEQUENCE: 6
IYIWAPLAGT CGVLLLSLVI TLYC                                         24

SEQ ID NO: 7            moltype = AA  length = 42
FEATURE                 Location/Qualifiers
REGION                  1..42
                        note = source = /note="Description of Artificial Sequence:
```

```
                         Synthetic polypeptide"
source                  1..42
                        mol_type = protein
                        organism = synthetic construct
SEQUENCE: 7
KRGRKKLLYI FKQPFMRPVQ TTQEEDGCSC RFPEEEEGGC EL                    42

SEQ ID NO: 8            moltype = AA  length = 48
FEATURE                 Location/Qualifiers
REGION                  1..48
                        note = source = /note="Description of Artificial Sequence:
                         Synthetic polypeptide"
source                  1..48
                        mol_type = protein
                        organism = synthetic construct
SEQUENCE: 8
QRRKYRSNKG ESPVEPAEPC RYSCPREEEG STIPIQEDYR KPEPACSP              48

SEQ ID NO: 9            moltype = AA  length = 112
FEATURE                 Location/Qualifiers
REGION                  1..112
                        note = source = /note="Description of Artificial Sequence:
                         Synthetic polypeptide"
source                  1..112
                        mol_type = protein
                        organism = synthetic construct
SEQUENCE: 9
RVKFSRSADA PAYKQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 10           moltype = AA  length = 112
FEATURE                 Location/Qualifiers
source                  1..112
                        mol_type = protein
                        organism = Homo sapiens
SEQUENCE: 10
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 11           moltype = DNA  length = 1184
FEATURE                 Location/Qualifiers
misc_feature            1..1184
                        note = source = /note="Description of Artificial Sequence:
                         Synthetic polynucleotide"
source                  1..1184
                        mol_type = other DNA
                        organism = synthetic construct
SEQUENCE: 11
cgtgaggctc cggtgcccgt cagtgggcag agcgcacatc gcccacagtc cccgagaagt  60
tggggggagg ggtcggcaat tgaaccggtg cctagagaag gtggcgcggg gtaaactggg  120
aaagtgatgt cgtgtactgg ctccgccttt ttcccgaggg tgggggagaa ccgtatataa  180
gtgcagtagt cgccgtgaac gttctttttc gcaacgggtt tgccgccaga acacaggtaa  240
gtgccgtgtg tggttcccgc gggcctggcc tctttacggg ttatggccct tgcgtgcctt  300
gaattacttc cacctggctg cagtacgtga ttcttgatcc cgagcttcgg gttggaagtg  360
ggtgggagag ttcgaggcct tgcgcttaag gagccccttc gcctcgtgct tgagttgagg  420
cctggcctgg gcgctggggc cgccgcgtgc gaatctggtg gcaccttcgc gcctgtctcg  480
ctgctttcga taagtctcta gccatttaaa atttttgatg acctgctgcg acgctttttt  540
tctggcaaga tagtcttgta aatgcgggcc aagatctgca cactggtatt tcggtttttg  600
gggccgcggg cggcgacggg gcccgtgcgt cccagcgcac atgttcggcg aggcggggcc  660
tgcgagcgcg gccaccgaga atcggacggg ggtagtctca agctggccgg cctgctctgg  720
tgcctggcct cgcgccgccg tgtatcgccc cgccctgggc ggcaaggctg gcccggtcgg  780
caccagttgc gtgagcggaa agatggccgc ttcccggccc tgctgcaggg agctcaaaat  840
ggaggacgcg gcgctcggga gagcgggcgg gtgagtcacc cacacaaagg aaaagggcct  900
ttccgtcctc agccgtcgct tcatgtgact ccacggagta ccgggcgccg tccaggcacc  960
tcgattagtt ctcgagcttt tggagtacgt cgtctttagg ttggggggag gggttttatg  1020
cgatggagtt tccccacact gagtgggtgg agactgaagt taggccagct tggcacttga  1080
tgtaattctc cttggaattt gccctttttg agtttggatc ttggttcatt ctcaagcctc  1140
agacagtggt tcaaagtttt tttcttccat ttcaggtgtc gtga                  1184

SEQ ID NO: 12           moltype = DNA  length = 63
FEATURE                 Location/Qualifiers
misc_feature            1..63
                        note = source = /note="Description of Artificial Sequence:
                         Synthetic oligonucleotide"
source                  1..63
                        mol_type = other DNA
                        organism = synthetic construct
SEQUENCE: 12
atggccctgc ctgtgacagc cctgctgctg cctctggctc tgctgctgca tgccgctaga  60
```

-continued

```
ccc                                                               63

SEQ ID NO: 13          moltype = DNA  length = 135
FEATURE                Location/Qualifiers
misc_feature           1..135
                       note = source = /note="Description of Artificial Sequence:
                        Synthetic polynucleotide"
source                 1..135
                       mol_type = other DNA
                       organism = synthetic construct
SEQUENCE: 13
accacgacgc cagcgccgcg accaccaaca ccggcgccca ccatcgcgtc gcagcccctg  60
tccctgcgcc cagaggcgtg ccggccagcg gcggggggcg cagtgcacac gagggggctg  120
gacttcgcct gtgat                                                   135

SEQ ID NO: 14          moltype = DNA  length = 690
FEATURE                Location/Qualifiers
misc_feature           1..690
                       note = source = /note="Description of Artificial Sequence:
                        Synthetic polynucleotide"
source                 1..690
                       mol_type = other DNA
                       organism = synthetic construct
SEQUENCE: 14
gagagcaagt acggccctcc ctgcccccct tgccctgccc ccgagttcct gggcggaccc  60
agcgtgttcc tgttcccccc caagcccaag gacaccctga tgatcagccg gacccccgag  120
gtgacctgtg tggtggtgga cgtgtcccag gaggaccccg aggtccagtt caactggtac  180
gtggacggcg tggaggtgca caacgccaag accaagcccc gggaggagca gttcaatagc  240
acctaccggg tggtgtccgt gctgaccgtg ctgcaccagg actggctgaa cggcaaggaa  300
tacaagtgta aggtgtccaa caagggcctg cccagcagca tcgagaaaac catcagcaag  360
gccaagggcc agcctcggga gccccaggtg tacaccctgc cccctagcca agaggagatg  420
accaagaacc aggtgtccct gacctgcctg gtgaagggct tctaccccag cgacatcgcc  480
gtggagtggg agagcaacgg ccagcccgag aacaactaca agaccacccc ccctgtgctg  540
gacagcgacg gcagcttctt cctgtacagc cggctgaccg tggacaagag ccggtggcag  600
gagggcaacg tctttagctg ctccgtgatg cacgaggccc tgcacaacca ctacacccag  660
aagagcctga gcctgtccct gggcaagatg                                   690

SEQ ID NO: 15          moltype = DNA  length = 847
FEATURE                Location/Qualifiers
misc_feature           1..847
                       note = source = /note="Description of Artificial Sequence:
                        Synthetic polynucleotide"
source                 1..847
                       mol_type = other DNA
                       organism = synthetic construct
SEQUENCE: 15
aggtggcccg aaagtcccaa ggcccaggca tctagtgttc ctactgcaca gccccaggca  60
gaaggcagcc tagccaaagc tactactgca cctgccacta cgcgcaatac tggccgtggc  120
ggggaggaga agaaaaagga gaaagagaaa gaagaacagg aagagaggga gaccaagacc  180
cctgaatgtc catcccatac ccagccgctg ggcgtctatc tcttgactcc cgcagtacag  240
gacttgtggc ttagagataa ggccaccttt acatgtttcg tcgtgggctc tgacctgaag  300
gatgcccatt tgacttggga ggttgccgga aaggtaccca caggggggt tgaggaaggg  360
ttgctggagc gccattccaa tggctctcag agccagcact caagactcac ccttccgaga  420
tccctgtgga acgccgggac ctctgtcaca tgtactctaa atcatcctag cctgcccccca  480
cagcgtctga tggcccttag agagccagcc gcccaggcac cagttaagct tagcctgaat  540
ctgctcgcca gtagtgatcc cccagaggcc gccagctggc tcttatgcga agtgtccggc  600
tttagcccgc ccaacatctt gctcatgtgg ctggaggacc agcgagaagt gaacaccagc  660
ggcttcgctc cagcccggcc cccaccccag ccgggttcta ccacattctg ggcctggagt  720
gtcttaaggg tcccagcacc acctagcccc cagccagcca catacacctg tgttgtgtcc  780
catgaagata gcaggaccct gctaaatgct tctaggagtc tggaggtttc ctacgtgact  840
gaccatt                                                            847

SEQ ID NO: 16          moltype = DNA  length = 30
FEATURE                Location/Qualifiers
misc_feature           1..30
                       note = source = /note="Description of Artificial Sequence:
                        Synthetic oligonucleotide"
source                 1..30
                       mol_type = other DNA
                       organism = synthetic construct
SEQUENCE: 16
ggtggcggag gttctggagg tggaggttcc                                   30

SEQ ID NO: 17          moltype = DNA  length = 72
FEATURE                Location/Qualifiers
misc_feature           1..72
                       note = source = /note="Description of Artificial Sequence:
                        Synthetic oligonucleotide"
source                 1..72
```

```
                         mol_type = other DNA
                         organism = synthetic construct
SEQUENCE: 17
atctacatct gggcgccctt ggccgggact tgtggggtcc ttctcctgtc actggttatc  60
accctttact gc                                                      72

SEQ ID NO: 18            moltype = DNA  length = 126
FEATURE                  Location/Qualifiers
misc_feature             1..126
                         note = source = /note="Description of Artificial Sequence:
                          Synthetic polynucleotide"
source                   1..126
                         mol_type = other DNA
                         organism = synthetic construct
SEQUENCE: 18
aaacggggca gaaagaaact cctgtatata ttcaaacaac catttatgag accagtacaa  60
actactcaag aggaagatgg ctgtagctgc cgatttccag aagaagaaga aggaggatgt  120
gaactg                                                             126

SEQ ID NO: 19            moltype = DNA  length = 123
FEATURE                  Location/Qualifiers
misc_feature             1..123
                         note = source = /note="Description of Artificial Sequence:
                          Synthetic polynucleotide"
source                   1..123
                         mol_type = other DNA
                         organism = synthetic construct
SEQUENCE: 19
aggagtaaga ggagcaggct cctgcacagt gactacatga acatgactcc ccgccgcccc  60
gggcccaccc gcaagcatta ccagccctat gccccaccac gcgacttcgc agcctatcgc  120
tcc                                                                123

SEQ ID NO: 20            moltype = DNA  length = 336
FEATURE                  Location/Qualifiers
misc_feature             1..336
                         note = source = /note="Description of Artificial Sequence:
                          Synthetic polynucleotide"
source                   1..336
                         mol_type = other DNA
                         organism = synthetic construct
SEQUENCE: 20
agagtgaagt tcagcaggag cgcagacgcc cccgcgtaca agcagggcca gaaccagctc  60
tataacgagc tcaatctagg acgaagagag gagtacgatg ttttggacaa gagacgtggc  120
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggtctca gtacagccac caaggacacc  300
tacgacgccc ttcacatgca ggccctgccc cctcgc                            336

SEQ ID NO: 21            moltype = DNA  length = 336
FEATURE                  Location/Qualifiers
source                   1..336
                         mol_type = unassigned DNA
                         organism = Homo sapiens
SEQUENCE: 21
agagtgaagt tcagcaggag cgcagacgcc cccgcgtacc agcagggcca gaaccagctc  60
tataacgagc tcaatctagg acgaagagag gagtacgatg ttttggacaa gagacgtggc  120
cgggaccctg agatgggggg aaagccgaga aggaagaacc ctcaggaagg cctgtacaat  180
gaactgcaga aagataagat ggcggaggcc tacagtgaga ttgggatgaa aggcgagcgc  240
cggaggggca aggggcacga tggcctttac cagggtctca gtacagccac caaggacacc  300
tacgacgccc ttcacatgca ggccctgccc cctcgc                            336

SEQ ID NO: 22            moltype = AA  length = 373
FEATURE                  Location/Qualifiers
REGION                   1..373
                         note = source = /note="Description of Artificial Sequence:
                          Synthetic polypeptide"
source                   1..373
                         mol_type = protein
                         organism = synthetic construct
SEQUENCE: 22
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV TTTPAPRPPT PAPTIASQPL SLRPEACRPA  180
AGGAVHTRGL DFACDIYIWA PLAGTCGVLL LSLVITLYCK RGRKKLLYIF KQPFMRPVQT  240
TQEEDGCSCR FPEEEEGGCE LRVKFSRSAD APAYKQGQNQ LYNELNLGRR EEYDVLDKRR  300
GRDPEMGGKP RRKNPQEGLY NELQKDKMAE AYSEIGMKGE RRRGKGHDGL YQGLSTATKD  360
TYDALHMQAL PPR                                                     373

SEQ ID NO: 23            moltype = DNA  length = 1182
```

```
FEATURE                 Location/Qualifiers
misc_feature            1..1182
                        note = source = /note="Description of Artificial Sequence:
                         Synthetic polynucleotide"
source                  1..1182
                        mol_type = other DNA
                        organism = synthetic construct
SEQUENCE: 23
atggccctcc ctgtcactgc cctgcttctc cccctcgcac tcctgctcca cgccgctaga  60
ccacccggat ggtttctgga ctctccggat cgcccgtgga atcccccaac cttctcaccg  120
gcactcttgg ttgtgactga gggcgataat gcgaccttca cgtgctcgtt ctccaacacc  180
tccgaatcat tcgtgctgaa ctggtaccgc atgagcccgt caaaccagac cgacaagctc  240
gccgcgtttc cggaagatcg gtcgcaaccg ggacaggatt gtcggttccg cgtgactcaa  300
ctgccgaatg gcagagactt ccacatgagc gtggtccgcg ctaggcgaaa cgactccggg  360
acctacctgt gcggagccat ctcgctggcg cctaaggccc aaatcaaaga gagcttgagg  420
gccgaactga gagtgaccga gcgcagagct gaggtgccaa ctgcacatcc atccccatcg  480
cctcggcctg cggggcagtt tcagaccctg gtcacgacca ctccggcgcc gcgcccaccg  540
actccggccc caactatcgc gagccagccc ctgtcgctga ggccggaagc atgccgccct  600
gccgccggag gtgctgtgca tacccgggga ttggacttcg catgcgacat ctacatttgg  660
gctcctctcg ccggaacttg tggcgtgctc cttctgtccc tggtcatcac cctgtactgc  720
aagcggggtc ggaaaaagct tctgtacatt ttcaagcagc ccttcatgag gcccgtgcaa  780
accacccagg aggaggacgg ttgctcctgc cggttccccg aagaggaaga aggaggttgc  840
gagctgcgcg tgaagttctc ccggagcgcc gacgcccccg cctataagca gggccagaac  900
cagctgtaca acgaactgaa cctgggacgg cgggaagagt acgatgtgct ggacaagcgg  960
cgcggccggg accccgaaat gggcgggaag cctagaagaa agaaccctca ggaaggcctg  1020
tataacgagc tgcagaagga caagatggcc gaggcctact ccgaaattgg gatgaaggga  1080
gagcggcgga ggggaaaggg gcacgacggc ctgtaccaag gactgtccac cgccaccaag  1140
gacacatacg atgccctgca catgcaggcc cttccccctc gc                    1182

SEQ ID NO: 24           moltype = AA  length = 394
FEATURE                 Location/Qualifiers
REGION                  1..394
                        note = source = /note="Description of Artificial Sequence:
                         Synthetic polypeptide"
source                  1..394
                        mol_type = protein
                        organism = synthetic construct
SEQUENCE: 24
MALPVTALLL PLALLLHAAR PPGWFLDSPD RPWNPPTFSP ALLVVTEGDN ATFTCSFSNT  60
SESFVLNWYR MSPSNQTDKL AAFPEDRSQP GQDCRFRVTQ LPNGRDFHMS VVRARRNDSG  120
TYLCGAISLA PKAQIKESLR AELRVTERRA EVPTAHPSPS PRPAGQFQTL VTTTPAPRPP  180
TPAPTIASQP LSLRPEACRP AAGGAVHTRG LDFACDIYIW APLAGTCGVL LLSLVITLYC  240
KRGRKKLLYI FKQPFMRPVQ TTQEEDGCSC RFPEEEEGGC ELRVKFSRSA DAPAYKQGQN  300
QLYNELNLGR REEYDVLDKR RGRDPEMGGK PRRKNPQEGL YNELQKDKMA EAYSEIGMKG  360
ERRRGKGHDG LYQGLSTATK DTYDALHMQA LPPR                              394

SEQ ID NO: 25           moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 25
GGGGS                                                              5

SEQ ID NO: 26           moltype = AA  length = 30
FEATURE                 Location/Qualifiers
SITE                    1..30
                        note = /note="This sequence may encompass 1-6 'Gly Gly Gly
                         Gly Ser' repeating units"
REGION                  1..30
                        note = source = /note="Description of Artificial Sequence:
                         Synthetic polypeptide"
REGION                  1..30
                        note = source = /note="See specification as filed for
                         detailed description of substitutions and preferred
                         embodiments"
source                  1..30
                        mol_type = protein
                        organism = synthetic construct
SEQUENCE: 26
GGGGSGGGGS GGGGSGGGGS GGGGSGGGGS                                   30

SEQ ID NO: 27           moltype = AA  length = 20
FEATURE                 Location/Qualifiers
REGION                  1..20
                        note = source = /note="Description of Artificial Sequence:
```

```
                         Synthetic peptide"
source                   1..20
                         mol_type = protein
                         organism = synthetic construct
SEQUENCE: 27
GGGGSGGGGS GGGGSGGGGS                                                20

SEQ ID NO: 28            moltype = AA  length = 15
FEATURE                  Location/Qualifiers
REGION                   1..15
                         note = source = /note="Description of Artificial Sequence:
                          Synthetic peptide"
source                   1..15
                         mol_type = protein
                         organism = synthetic construct
SEQUENCE: 28
GGGGSGGGGS GGGGS                                                     15

SEQ ID NO: 29            moltype = AA  length = 4
FEATURE                  Location/Qualifiers
REGION                   1..4
                         note = source = /note="Description of Artificial Sequence:
                          Synthetic peptide"
source                   1..4
                         mol_type = protein
                         organism = synthetic construct
SEQUENCE: 29
GGGS                                                                 4

SEQ ID NO: 30            moltype = RNA  length = 5000
FEATURE                  Location/Qualifiers
misc_feature             1..5000
                         note = /note="This sequence may encompass 50-5000
                          nucleotides"
misc_feature             1..5000
                         note = source = /note="Description of Artificial Sequence:
                          Synthetic polynucleotide"
misc_feature             1..5000
                         note = source = /note="See specification as filed for
                          detailed description of substitutions and preferred
                          embodiments"
source                   1..5000
                         mol_type = other RNA
                         organism = synthetic construct
SEQUENCE: 30
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa aaaaaaaaaa aaaaaaaaaa  420
aaaaaaaaaa aaaaaaaaaa aaaaaaaaaa aaaaaaaaaa aaaaaaaaaa aaaaaaaaaa  480
aaaaaaaaaa aaaaaaaaaa aaaaaaaaaa aaaaaaaaaa aaaaaaaaaa aaaaaaaaaa  540
aaaaaaaaaa aaaaaaaaaa aaaaaaaaaa aaaaaaaaaa aaaaaaaaaa aaaaaaaaaa  600
aaaaaaaaaa aaaaaaaaaa aaaaaaaaaa aaaaaaaaaa aaaaaaaaaa aaaaaaaaaa  660
aaaaaaaaaa aaaaaaaaaa aaaaaaaaaa aaaaaaaaaa aaaaaaaaaa aaaaaaaaaa  720
aaaaaaaaaa aaaaaaaaaa aaaaaaaaaa aaaaaaaaaa aaaaaaaaaa aaaaaaaaaa  780
aaaaaaaaaa aaaaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaaaaaaaa  1020
aaaaaaaaaa aaaaaaaaaa aaaaaaaaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaaaaa aaaaaaaaaa aaaaaaaaaa aaaaaaaaaa  1200
aaaaaaaaaa aaaaaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaaaaaaaaa aaaaaaaaaa aaaaaaaaaa aaaaaaaaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa aaaaaaaaaa aaaaaaaaaa aaaaaaaaaa  1500
aaaaaaaaaa aaaaaaaaaa aaaaaaaaaa aaaaaaaaaa aaaaaaaaaa aaaaaaaaaa  1560
aaaaaaaaaa aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaaa aaaaaaaaaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
```

```
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
aaaaaaaaaa aaaaaaaaaa aaaaaaaaaa aaaaaaaaaa aaaaaaaaaa aaaaaaaaaa  2220
aaaaaaaaaa aaaaaaaaaa aaaaaaaaaa aaaaaaaaaa aaaaaaaaaa aaaaaaaaaa  2280
aaaaaaaaaa aaaaaaaaaa aaaaaaaaaa aaaaaaaaaa aaaaaaaaaa aaaaaaaaaa  2340
aaaaaaaaaa aaaaaaaaaa aaaaaaaaaa aaaaaaaaaa aaaaaaaaaa aaaaaaaaaa  2400
aaaaaaaaaa aaaaaaaaaa aaaaaaaaaa aaaaaaaaaa aaaaaaaaaa aaaaaaaaaa  2460
aaaaaaaaaa aaaaaaaaaa aaaaaaaaaa aaaaaaaaaa aaaaaaaaaa aaaaaaaaaa  2520
aaaaaaaaaa aaaaaaaaaa aaaaaaaaaa aaaaaaaaaa aaaaaaaaaa aaaaaaaaaa  2580
aaaaaaaaaa aaaaaaaaaa aaaaaaaaaa aaaaaaaaaa aaaaaaaaaa aaaaaaaaaa  2640
aaaaaaaaaa aaaaaaaaaa aaaaaaaaaa aaaaaaaaaa aaaaaaaaaa aaaaaaaaaa  2700
aaaaaaaaaa aaaaaaaaaa aaaaaaaaaa aaaaaaaaaa aaaaaaaaaa aaaaaaaaaa  2760
aaaaaaaaaa aaaaaaaaaa aaaaaaaaaa aaaaaaaaaa aaaaaaaaaa aaaaaaaaaa  2820
aaaaaaaaaa aaaaaaaaaa aaaaaaaaaa aaaaaaaaaa aaaaaaaaaa aaaaaaaaaa  2880
aaaaaaaaaa aaaaaaaaaa aaaaaaaaaa aaaaaaaaaa aaaaaaaaaa aaaaaaaaaa  2940
aaaaaaaaaa aaaaaaaaaa aaaaaaaaaa aaaaaaaaaa aaaaaaaaaa aaaaaaaaaa  3000
aaaaaaaaaa aaaaaaaaaa aaaaaaaaaa aaaaaaaaaa aaaaaaaaaa aaaaaaaaaa  3060
aaaaaaaaaa aaaaaaaaaa aaaaaaaaaa aaaaaaaaaa aaaaaaaaaa aaaaaaaaaa  3120
aaaaaaaaaa aaaaaaaaaa aaaaaaaaaa aaaaaaaaaa aaaaaaaaaa aaaaaaaaaa  3180
aaaaaaaaaa aaaaaaaaaa aaaaaaaaaa aaaaaaaaaa aaaaaaaaaa aaaaaaaaaa  3240
aaaaaaaaaa aaaaaaaaaa aaaaaaaaaa aaaaaaaaaa aaaaaaaaaa aaaaaaaaaa  3300
aaaaaaaaaa aaaaaaaaaa aaaaaaaaaa aaaaaaaaaa aaaaaaaaaa aaaaaaaaaa  3360
aaaaaaaaaa aaaaaaaaaa aaaaaaaaaa aaaaaaaaaa aaaaaaaaaa aaaaaaaaaa  3420
aaaaaaaaaa aaaaaaaaaa aaaaaaaaaa aaaaaaaaaa aaaaaaaaaa aaaaaaaaaa  3480
aaaaaaaaaa aaaaaaaaaa aaaaaaaaaa aaaaaaaaaa aaaaaaaaaa aaaaaaaaaa  3540
aaaaaaaaaa aaaaaaaaaa aaaaaaaaaa aaaaaaaaaa aaaaaaaaaa aaaaaaaaaa  3600
aaaaaaaaaa aaaaaaaaaa aaaaaaaaaa aaaaaaaaaa aaaaaaaaaa aaaaaaaaaa  3660
aaaaaaaaaa aaaaaaaaaa aaaaaaaaaa aaaaaaaaaa aaaaaaaaaa aaaaaaaaaa  3720
aaaaaaaaaa aaaaaaaaaa aaaaaaaaaa aaaaaaaaaa aaaaaaaaaa aaaaaaaaaa  3780
aaaaaaaaaa aaaaaaaaaa aaaaaaaaaa aaaaaaaaaa aaaaaaaaaa aaaaaaaaaa  3840
aaaaaaaaaa aaaaaaaaaa aaaaaaaaaa aaaaaaaaaa aaaaaaaaaa aaaaaaaaaa  3900
aaaaaaaaaa aaaaaaaaaa aaaaaaaaaa aaaaaaaaaa aaaaaaaaaa aaaaaaaaaa  3960
aaaaaaaaaa aaaaaaaaaa aaaaaaaaaa aaaaaaaaaa aaaaaaaaaa aaaaaaaaaa  4020
aaaaaaaaaa aaaaaaaaaa aaaaaaaaaa aaaaaaaaaa aaaaaaaaaa aaaaaaaaaa  4080
aaaaaaaaaa aaaaaaaaaa aaaaaaaaaa aaaaaaaaaa aaaaaaaaaa aaaaaaaaaa  4140
aaaaaaaaaa aaaaaaaaaa aaaaaaaaaa aaaaaaaaaa aaaaaaaaaa aaaaaaaaaa  4200
aaaaaaaaaa aaaaaaaaaa aaaaaaaaaa aaaaaaaaaa aaaaaaaaaa aaaaaaaaaa  4260
aaaaaaaaaa aaaaaaaaaa aaaaaaaaaa aaaaaaaaaa aaaaaaaaaa aaaaaaaaaa  4320
aaaaaaaaaa aaaaaaaaaa aaaaaaaaaa aaaaaaaaaa aaaaaaaaaa aaaaaaaaaa  4380
aaaaaaaaaa aaaaaaaaaa aaaaaaaaaa aaaaaaaaaa aaaaaaaaaa aaaaaaaaaa  4440
aaaaaaaaaa aaaaaaaaaa aaaaaaaaaa aaaaaaaaaa aaaaaaaaaa aaaaaaaaaa  4500
aaaaaaaaaa aaaaaaaaaa aaaaaaaaaa aaaaaaaaaa aaaaaaaaaa aaaaaaaaaa  4560
aaaaaaaaaa aaaaaaaaaa aaaaaaaaaa aaaaaaaaaa aaaaaaaaaa aaaaaaaaaa  4620
aaaaaaaaaa aaaaaaaaaa aaaaaaaaaa aaaaaaaaaa aaaaaaaaaa aaaaaaaaaa  4680
aaaaaaaaaa aaaaaaaaaa aaaaaaaaaa aaaaaaaaaa aaaaaaaaaa aaaaaaaaaa  4740
aaaaaaaaaa aaaaaaaaaa aaaaaaaaaa aaaaaaaaaa aaaaaaaaaa aaaaaaaaaa  4800
aaaaaaaaaa aaaaaaaaaa aaaaaaaaaa aaaaaaaaaa aaaaaaaaaa aaaaaaaaaa  4860
aaaaaaaaaa aaaaaaaaaa aaaaaaaaaa aaaaaaaaaa aaaaaaaaaa aaaaaaaaaa  4920
aaaaaaaaaa aaaaaaaaaa aaaaaaaaaa aaaaaaaaaa aaaaaaaaaa aaaaaaaaaa  4980
aaaaaaaaaa aaaaaaaaaa                                              5000

SEQ ID NO: 31           moltype = DNA  length = 100
FEATURE                 Location/Qualifiers
misc_feature            1..100
                        note = source = /note="Description of Artificial Sequence:
                         Synthetic polynucleotide"
source                  1..100
                        mol_type = other DNA
                        organism = synthetic construct
SEQUENCE: 31
tttttttttt tttttttttt tttttttttt tttttttttt tttttttttt tttttttttt  60
tttttttttt tttttttttt tttttttttt tttttttttt                        100

SEQ ID NO: 32           moltype = DNA  length = 5000
FEATURE                 Location/Qualifiers
misc_feature            1..5000
                        note = /note="This sequence may encompass 50-5000
                         nucleotides"
misc_feature            1..5000
                        note = source = /note="Description of Artificial Sequence:
                         Synthetic polynucleotide"
source                  1..5000
                        mol_type = other DNA
                        organism = synthetic construct
SEQUENCE: 32
tttttttttt tttttttttt tttttttttt tttttttttt tttttttttt tttttttttt  60
tttttttttt tttttttttt tttttttttt tttttttttt tttttttttt tttttttttt  120
tttttttttt tttttttttt tttttttttt tttttttttt tttttttttt tttttttttt  180
tttttttttt tttttttttt tttttttttt tttttttttt tttttttttt tttttttttt  240
```

-continued

```
tttttttttt tttttttttt tttttttttt tttttttttt tttttttttt tttttttttt  300
tttttttttt tttttttttt tttttttttt tttttttttt tttttttttt tttttttttt  360
tttttttttt tttttttttt tttttttttt tttttttttt tttttttttt tttttttttt  420
tttttttttt tttttttttt tttttttttt tttttttttt tttttttttt tttttttttt  480
tttttttttt tttttttttt tttttttttt tttttttttt tttttttttt tttttttttt  540
tttttttttt tttttttttt tttttttttt tttttttttt tttttttttt tttttttttt  600
tttttttttt tttttttttt tttttttttt tttttttttt tttttttttt tttttttttt  660
tttttttttt tttttttttt tttttttttt tttttttttt tttttttttt tttttttttt  720
tttttttttt tttttttttt tttttttttt tttttttttt tttttttttt tttttttttt  780
tttttttttt tttttttttt tttttttttt tttttttttt tttttttttt tttttttttt  840
tttttttttt tttttttttt tttttttttt tttttttttt tttttttttt tttttttttt  900
tttttttttt tttttttttt tttttttttt tttttttttt tttttttttt tttttttttt  960
tttttttttt tttttttttt tttttttttt tttttttttt tttttttttt tttttttttt  1020
tttttttttt tttttttttt tttttttttt tttttttttt tttttttttt tttttttttt  1080
tttttttttt tttttttttt tttttttttt tttttttttt tttttttttt tttttttttt  1140
tttttttttt tttttttttt tttttttttt tttttttttt tttttttttt tttttttttt  1200
tttttttttt tttttttttt tttttttttt tttttttttt tttttttttt tttttttttt  1260
tttttttttt tttttttttt tttttttttt tttttttttt tttttttttt tttttttttt  1320
tttttttttt tttttttttt tttttttttt tttttttttt tttttttttt tttttttttt  1380
tttttttttt tttttttttt tttttttttt tttttttttt tttttttttt tttttttttt  1440
tttttttttt tttttttttt tttttttttt tttttttttt tttttttttt tttttttttt  1500
tttttttttt tttttttttt tttttttttt tttttttttt tttttttttt tttttttttt  1560
tttttttttt tttttttttt tttttttttt tttttttttt tttttttttt tttttttttt  1620
tttttttttt tttttttttt tttttttttt tttttttttt tttttttttt tttttttttt  1680
tttttttttt tttttttttt tttttttttt tttttttttt tttttttttt tttttttttt  1740
tttttttttt tttttttttt tttttttttt tttttttttt tttttttttt tttttttttt  1800
tttttttttt tttttttttt tttttttttt tttttttttt tttttttttt tttttttttt  1860
tttttttttt tttttttttt tttttttttt tttttttttt tttttttttt tttttttttt  1920
tttttttttt tttttttttt tttttttttt tttttttttt tttttttttt tttttttttt  1980
tttttttttt tttttttttt tttttttttt tttttttttt tttttttttt tttttttttt  2040
tttttttttt tttttttttt tttttttttt tttttttttt tttttttttt tttttttttt  2100
tttttttttt tttttttttt tttttttttt tttttttttt tttttttttt tttttttttt  2160
tttttttttt tttttttttt tttttttttt tttttttttt tttttttttt tttttttttt  2220
tttttttttt tttttttttt tttttttttt tttttttttt tttttttttt tttttttttt  2280
tttttttttt tttttttttt tttttttttt tttttttttt tttttttttt tttttttttt  2340
tttttttttt tttttttttt tttttttttt tttttttttt tttttttttt tttttttttt  2400
tttttttttt tttttttttt tttttttttt tttttttttt tttttttttt tttttttttt  2460
tttttttttt tttttttttt tttttttttt tttttttttt tttttttttt tttttttttt  2520
tttttttttt tttttttttt tttttttttt tttttttttt tttttttttt tttttttttt  2580
tttttttttt tttttttttt tttttttttt tttttttttt tttttttttt tttttttttt  2640
tttttttttt tttttttttt tttttttttt tttttttttt tttttttttt tttttttttt  2700
tttttttttt tttttttttt tttttttttt tttttttttt tttttttttt tttttttttt  2760
tttttttttt tttttttttt tttttttttt tttttttttt tttttttttt tttttttttt  2820
tttttttttt tttttttttt tttttttttt tttttttttt tttttttttt tttttttttt  2880
tttttttttt tttttttttt tttttttttt tttttttttt tttttttttt tttttttttt  2940
tttttttttt tttttttttt tttttttttt tttttttttt tttttttttt tttttttttt  3000
tttttttttt tttttttttt tttttttttt tttttttttt tttttttttt tttttttttt  3060
tttttttttt tttttttttt tttttttttt tttttttttt tttttttttt tttttttttt  3120
tttttttttt tttttttttt tttttttttt tttttttttt tttttttttt tttttttttt  3180
tttttttttt tttttttttt tttttttttt tttttttttt tttttttttt tttttttttt  3240
tttttttttt tttttttttt tttttttttt tttttttttt tttttttttt tttttttttt  3300
tttttttttt tttttttttt tttttttttt tttttttttt tttttttttt tttttttttt  3360
tttttttttt tttttttttt tttttttttt tttttttttt tttttttttt tttttttttt  3420
tttttttttt tttttttttt tttttttttt tttttttttt tttttttttt tttttttttt  3480
tttttttttt tttttttttt tttttttttt tttttttttt tttttttttt tttttttttt  3540
tttttttttt tttttttttt tttttttttt tttttttttt tttttttttt tttttttttt  3600
tttttttttt tttttttttt tttttttttt tttttttttt tttttttttt tttttttttt  3660
tttttttttt tttttttttt tttttttttt tttttttttt tttttttttt tttttttttt  3720
tttttttttt tttttttttt tttttttttt tttttttttt tttttttttt tttttttttt  3780
tttttttttt tttttttttt tttttttttt tttttttttt tttttttttt tttttttttt  3840
tttttttttt tttttttttt tttttttttt tttttttttt tttttttttt tttttttttt  3900
tttttttttt tttttttttt tttttttttt tttttttttt tttttttttt tttttttttt  3960
tttttttttt tttttttttt tttttttttt tttttttttt tttttttttt tttttttttt  4020
tttttttttt tttttttttt tttttttttt tttttttttt tttttttttt tttttttttt  4080
tttttttttt tttttttttt tttttttttt tttttttttt tttttttttt tttttttttt  4140
tttttttttt tttttttttt tttttttttt tttttttttt tttttttttt tttttttttt  4200
tttttttttt tttttttttt tttttttttt tttttttttt tttttttttt tttttttttt  4260
tttttttttt tttttttttt tttttttttt tttttttttt tttttttttt tttttttttt  4320
tttttttttt tttttttttt tttttttttt tttttttttt tttttttttt tttttttttt  4380
tttttttttt tttttttttt tttttttttt tttttttttt tttttttttt tttttttttt  4440
tttttttttt tttttttttt tttttttttt tttttttttt tttttttttt tttttttttt  4500
tttttttttt tttttttttt tttttttttt tttttttttt tttttttttt tttttttttt  4560
tttttttttt tttttttttt tttttttttt tttttttttt tttttttttt tttttttttt  4620
tttttttttt tttttttttt tttttttttt tttttttttt tttttttttt tttttttttt  4680
tttttttttt tttttttttt tttttttttt tttttttttt tttttttttt tttttttttt  4740
tttttttttt tttttttttt tttttttttt tttttttttt tttttttttt tttttttttt  4800
tttttttttt tttttttttt tttttttttt tttttttttt tttttttttt tttttttttt  4860
tttttttttt tttttttttt tttttttttt tttttttttt tttttttttt tttttttttt  4920
tttttttttt tttttttttt tttttttttt tttttttttt tttttttttt tttttttttt  4980
```

```
tttttttttt tttttttttt                                          5000

SEQ ID NO: 33          moltype = RNA  length = 5000
FEATURE                Location/Qualifiers
misc_feature           1..5000
                       note = /note="This sequence may encompass 100-5000
                        nucleotides"
misc_feature           1..5000
                       note = source = /note="Description of Artificial Sequence:
                        Synthetic polynucleotide"
source                 1..5000
                       mol_type = other RNA
                       organism = synthetic construct
SEQUENCE: 33
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa aaaaaaaaaa aaaaaaaaaa  420
aaaaaaaaaa aaaaaaaaaa aaaaaaaaaa aaaaaaaaaa aaaaaaaaaa aaaaaaaaaa  480
aaaaaaaaaa aaaaaaaaaa aaaaaaaaaa aaaaaaaaaa aaaaaaaaaa aaaaaaaaaa  540
aaaaaaaaaa aaaaaaaaaa aaaaaaaaaa aaaaaaaaaa aaaaaaaaaa aaaaaaaaaa  600
aaaaaaaaaa aaaaaaaaaa aaaaaaaaaa aaaaaaaaaa aaaaaaaaaa aaaaaaaaaa  660
aaaaaaaaaa aaaaaaaaaa aaaaaaaaaa aaaaaaaaaa aaaaaaaaaa aaaaaaaaaa  720
aaaaaaaaaa aaaaaaaaaa aaaaaaaaaa aaaaaaaaaa aaaaaaaaaa aaaaaaaaaa  780
aaaaaaaaaa aaaaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaaaaaaaa  1020
aaaaaaaaaa aaaaaaaaaa aaaaaaaaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaaaaa aaaaaaaaaa aaaaaaaaaa aaaaaaaaaa  1200
aaaaaaaaaa aaaaaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaaaaaaaaa aaaaaaaaaa aaaaaaaaaa aaaaaaaaaa  1380
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa aaaaaaaaaa aaaaaaaaaa aaaaaaaaaa  1500
aaaaaaaaaa aaaaaaaaaa aaaaaaaaaa aaaaaaaaaa aaaaaaaaaa aaaaaaaaaa  1560
aaaaaaaaaa aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaaa aaaaaaaaaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaaaaa aaaaaaaaaa aaaaaaaaaa aaaaaaaaaa aaaaaaaaaa  2160
aaaaaaaaaa aaaaaaaaaa aaaaaaaaaa aaaaaaaaaa aaaaaaaaaa aaaaaaaaaa  2220
aaaaaaaaaa aaaaaaaaaa aaaaaaaaaa aaaaaaaaaa aaaaaaaaaa aaaaaaaaaa  2280
aaaaaaaaaa aaaaaaaaaa aaaaaaaaaa aaaaaaaaaa aaaaaaaaaa aaaaaaaaaa  2340
aaaaaaaaaa aaaaaaaaaa aaaaaaaaaa aaaaaaaaaa aaaaaaaaaa aaaaaaaaaa  2400
aaaaaaaaaa aaaaaaaaaa aaaaaaaaaa aaaaaaaaaa aaaaaaaaaa aaaaaaaaaa  2460
aaaaaaaaaa aaaaaaaaaa aaaaaaaaaa aaaaaaaaaa aaaaaaaaaa aaaaaaaaaa  2520
aaaaaaaaaa aaaaaaaaaa aaaaaaaaaa aaaaaaaaaa aaaaaaaaaa aaaaaaaaaa  2580
aaaaaaaaaa aaaaaaaaaa aaaaaaaaaa aaaaaaaaaa aaaaaaaaaa aaaaaaaaaa  2640
aaaaaaaaaa aaaaaaaaaa aaaaaaaaaa aaaaaaaaaa aaaaaaaaaa aaaaaaaaaa  2700
aaaaaaaaaa aaaaaaaaaa aaaaaaaaaa aaaaaaaaaa aaaaaaaaaa aaaaaaaaaa  2760
aaaaaaaaaa aaaaaaaaaa aaaaaaaaaa aaaaaaaaaa aaaaaaaaaa aaaaaaaaaa  2820
aaaaaaaaaa aaaaaaaaaa aaaaaaaaaa aaaaaaaaaa aaaaaaaaaa aaaaaaaaaa  2880
aaaaaaaaaa aaaaaaaaaa aaaaaaaaaa aaaaaaaaaa aaaaaaaaaa aaaaaaaaaa  2940
aaaaaaaaaa aaaaaaaaaa aaaaaaaaaa aaaaaaaaaa aaaaaaaaaa aaaaaaaaaa  3000
aaaaaaaaaa aaaaaaaaaa aaaaaaaaaa aaaaaaaaaa aaaaaaaaaa aaaaaaaaaa  3060
aaaaaaaaaa aaaaaaaaaa aaaaaaaaaa aaaaaaaaaa aaaaaaaaaa aaaaaaaaaa  3120
aaaaaaaaaa aaaaaaaaaa aaaaaaaaaa aaaaaaaaaa aaaaaaaaaa aaaaaaaaaa  3180
aaaaaaaaaa aaaaaaaaaa aaaaaaaaaa aaaaaaaaaa aaaaaaaaaa aaaaaaaaaa  3240
aaaaaaaaaa aaaaaaaaaa aaaaaaaaaa aaaaaaaaaa aaaaaaaaaa aaaaaaaaaa  3300
aaaaaaaaaa aaaaaaaaaa aaaaaaaaaa aaaaaaaaaa aaaaaaaaaa aaaaaaaaaa  3360
aaaaaaaaaa aaaaaaaaaa aaaaaaaaaa aaaaaaaaaa aaaaaaaaaa aaaaaaaaaa  3420
aaaaaaaaaa aaaaaaaaaa aaaaaaaaaa aaaaaaaaaa aaaaaaaaaa aaaaaaaaaa  3480
aaaaaaaaaa aaaaaaaaaa aaaaaaaaaa aaaaaaaaaa aaaaaaaaaa aaaaaaaaaa  3540
aaaaaaaaaa aaaaaaaaaa aaaaaaaaaa aaaaaaaaaa aaaaaaaaaa aaaaaaaaaa  3600
aaaaaaaaaa aaaaaaaaaa aaaaaaaaaa aaaaaaaaaa aaaaaaaaaa aaaaaaaaaa  3660
aaaaaaaaaa aaaaaaaaaa aaaaaaaaaa aaaaaaaaaa aaaaaaaaaa aaaaaaaaaa  3720
aaaaaaaaaa aaaaaaaaaa aaaaaaaaaa aaaaaaaaaa aaaaaaaaaa aaaaaaaaaa  3780
aaaaaaaaaa aaaaaaaaaa aaaaaaaaaa aaaaaaaaaa aaaaaaaaaa aaaaaaaaaa  3840
aaaaaaaaaa aaaaaaaaaa aaaaaaaaaa aaaaaaaaaa aaaaaaaaaa aaaaaaaaaa  3900
```

```
aaaaaaaaaa aaaaaaaaaa aaaaaaaaaa aaaaaaaaaa aaaaaaaaaa aaaaaaaaaa  3960
aaaaaaaaaa aaaaaaaaaa aaaaaaaaaa aaaaaaaaaa aaaaaaaaaa aaaaaaaaaa  4020
aaaaaaaaaa aaaaaaaaaa aaaaaaaaaa aaaaaaaaaa aaaaaaaaaa aaaaaaaaaa  4080
aaaaaaaaaa aaaaaaaaaa aaaaaaaaaa aaaaaaaaaa aaaaaaaaaa aaaaaaaaaa  4140
aaaaaaaaaa aaaaaaaaaa aaaaaaaaaa aaaaaaaaaa aaaaaaaaaa aaaaaaaaaa  4200
aaaaaaaaaa aaaaaaaaaa aaaaaaaaaa aaaaaaaaaa aaaaaaaaaa aaaaaaaaaa  4260
aaaaaaaaaa aaaaaaaaaa aaaaaaaaaa aaaaaaaaaa aaaaaaaaaa aaaaaaaaaa  4320
aaaaaaaaaa aaaaaaaaaa aaaaaaaaaa aaaaaaaaaa aaaaaaaaaa aaaaaaaaaa  4380
aaaaaaaaaa aaaaaaaaaa aaaaaaaaaa aaaaaaaaaa aaaaaaaaaa aaaaaaaaaa  4440
aaaaaaaaaa aaaaaaaaaa aaaaaaaaaa aaaaaaaaaa aaaaaaaaaa aaaaaaaaaa  4500
aaaaaaaaaa aaaaaaaaaa aaaaaaaaaa aaaaaaaaaa aaaaaaaaaa aaaaaaaaaa  4560
aaaaaaaaaa aaaaaaaaaa aaaaaaaaaa aaaaaaaaaa aaaaaaaaaa aaaaaaaaaa  4620
aaaaaaaaaa aaaaaaaaaa aaaaaaaaaa aaaaaaaaaa aaaaaaaaaa aaaaaaaaaa  4680
aaaaaaaaaa aaaaaaaaaa aaaaaaaaaa aaaaaaaaaa aaaaaaaaaa aaaaaaaaaa  4740
aaaaaaaaaa aaaaaaaaaa aaaaaaaaaa aaaaaaaaaa aaaaaaaaaa aaaaaaaaaa  4800
aaaaaaaaaa aaaaaaaaaa aaaaaaaaaa aaaaaaaaaa aaaaaaaaaa aaaaaaaaaa  4860
aaaaaaaaaa aaaaaaaaaa aaaaaaaaaa aaaaaaaaaa aaaaaaaaaa aaaaaaaaaa  4920
aaaaaaaaaa aaaaaaaaaa aaaaaaaaaa aaaaaaaaaa aaaaaaaaaa aaaaaaaaaa  4980
aaaaaaaaaa aaaaaaaaaa                                              5000

SEQ ID NO: 34          moltype = RNA  length = 400
FEATURE                Location/Qualifiers
misc_feature           1..400
                       note = /note="This sequence may encompass 100-400
                        nucleotides"
misc_feature           1..400
                       note = source = /note="Description of Artificial Sequence:
                        Synthetic polynucleotide"
misc_feature           1..400
                       note = source = /note="See specification as filed for
                        detailed description of substitutions and preferred
                        embodiments"
source                 1..400
                       mol_type = other RNA
                       organism = synthetic construct
SEQUENCE: 34
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa                        400

SEQ ID NO: 35          moltype = RNA  length = 2000
FEATURE                Location/Qualifiers
misc_feature           1..2000
                       note = /note="This sequence may encompass 50-2000
                        nucleotides"
misc_feature           1..2000
                       note = source = /note="Description of Artificial Sequence:
                        Synthetic polynucleotide"
source                 1..2000
                       mol_type = other RNA
                       organism = synthetic construct
SEQUENCE: 35
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa aaaaaaaaaa aaaaaaaaaa aaaaaaaaaa aaaaaaaaaa aaaaaaaaaa  180
aaaaaaaaaa aaaaaaaaaa aaaaaaaaaa aaaaaaaaaa aaaaaaaaaa aaaaaaaaaa  240
aaaaaaaaaa aaaaaaaaaa aaaaaaaaaa aaaaaaaaaa aaaaaaaaaa aaaaaaaaaa  300
aaaaaaaaaa aaaaaaaaaa aaaaaaaaaa aaaaaaaaaa aaaaaaaaaa aaaaaaaaaa  360
aaaaaaaaaa aaaaaaaaaa aaaaaaaaaa aaaaaaaaaa aaaaaaaaaa aaaaaaaaaa  420
aaaaaaaaaa aaaaaaaaaa aaaaaaaaaa aaaaaaaaaa aaaaaaaaaa aaaaaaaaaa  480
aaaaaaaaaa aaaaaaaaaa aaaaaaaaaa aaaaaaaaaa aaaaaaaaaa aaaaaaaaaa  540
aaaaaaaaaa aaaaaaaaaa aaaaaaaaaa aaaaaaaaaa aaaaaaaaaa aaaaaaaaaa  600
aaaaaaaaaa aaaaaaaaaa aaaaaaaaaa aaaaaaaaaa aaaaaaaaaa aaaaaaaaaa  660
aaaaaaaaaa aaaaaaaaaa aaaaaaaaaa aaaaaaaaaa aaaaaaaaaa aaaaaaaaaa  720
aaaaaaaaaa aaaaaaaaaa aaaaaaaaaa aaaaaaaaaa aaaaaaaaaa aaaaaaaaaa  780
aaaaaaaaaa aaaaaaaaaa aaaaaaaaaa aaaaaaaaaa aaaaaaaaaa aaaaaaaaaa  840
aaaaaaaaaa aaaaaaaaaa aaaaaaaaaa aaaaaaaaaa aaaaaaaaaa aaaaaaaaaa  900
aaaaaaaaaa aaaaaaaaaa aaaaaaaaaa aaaaaaaaaa aaaaaaaaaa aaaaaaaaaa  960
aaaaaaaaaa aaaaaaaaaa aaaaaaaaaa aaaaaaaaaa aaaaaaaaaa aaaaaaaaaa  1020
aaaaaaaaaa aaaaaaaaaa aaaaaaaaaa aaaaaaaaaa aaaaaaaaaa aaaaaaaaaa  1080
aaaaaaaaaa aaaaaaaaaa aaaaaaaaaa aaaaaaaaaa aaaaaaaaaa aaaaaaaaaa  1140
aaaaaaaaaa aaaaaaaaaa aaaaaaaaaa aaaaaaaaaa aaaaaaaaaa aaaaaaaaaa  1200
aaaaaaaaaa aaaaaaaaaa aaaaaaaaaa aaaaaaaaaa aaaaaaaaaa aaaaaaaaaa  1260
aaaaaaaaaa aaaaaaaaaa aaaaaaaaaa aaaaaaaaaa aaaaaaaaaa aaaaaaaaaa  1320
aaaaaaaaaa aaaaaaaaaa aaaaaaaaaa aaaaaaaaaa aaaaaaaaaa aaaaaaaaaa  1380
```

-continued

```
aaaaaaaaaa aaaaaaaaaa aaaaaaaaaa aaaaaaaaaa aaaaaaaaaa aaaaaaaaaa  1440
aaaaaaaaaa aaaaaaaaaa aaaaaaaaaa aaaaaaaaaa aaaaaaaaaa aaaaaaaaaa  1500
aaaaaaaaaa aaaaaaaaaa aaaaaaaaaa aaaaaaaaaa aaaaaaaaaa aaaaaaaaaa  1560
aaaaaaaaaa aaaaaaaaaa aaaaaaaaaa aaaaaaaaaa aaaaaaaaaa aaaaaaaaaa  1620
aaaaaaaaaa aaaaaaaaaa aaaaaaaaaa aaaaaaaaaa aaaaaaaaaa aaaaaaaaaa  1680
aaaaaaaaaa aaaaaaaaaa aaaaaaaaaa aaaaaaaaaa aaaaaaaaaa aaaaaaaaaa  1740
aaaaaaaaaa aaaaaaaaaa aaaaaaaaaa aaaaaaaaaa aaaaaaaaaa aaaaaaaaaa  1800
aaaaaaaaaa aaaaaaaaaa aaaaaaaaaa aaaaaaaaaa aaaaaaaaaa aaaaaaaaaa  1860
aaaaaaaaaa aaaaaaaaaa aaaaaaaaaa aaaaaaaaaa aaaaaaaaaa aaaaaaaaaa  1920
aaaaaaaaaa aaaaaaaaaa aaaaaaaaaa aaaaaaaaaa aaaaaaaaaa aaaaaaaaaa  1980
aaaaaaaaaa aaaaaaaaaa                                              2000

SEQ ID NO: 36          moltype = AA  length = 41
FEATURE                Location/Qualifiers
REGION                 1..41
                       note = source = /note="Description of Artificial Sequence:
                        Synthetic polypeptide"
source                 1..41
                       mol_type = protein
                       organism = synthetic construct
SEQUENCE: 36
RSKRSRLLHS DYMNMTPRRP GPTRKHYQPY APPRDFAAYR S                      41

SEQ ID NO: 37          moltype = DNA  length = 123
FEATURE                Location/Qualifiers
misc_feature           1..123
                       note = source = /note="Description of Artificial Sequence:
                        Synthetic polynucleotide"
source                 1..123
                       mol_type = other DNA
                       organism = synthetic construct
SEQUENCE: 37
aggagtaaga ggagcaggct cctgcacagt gactacatga acatgactcc ccgccgcccc  60
gggcccaccc gcaagcatta ccagccctat gccccaccac gcgacttcgc agcctatcgc  120
tcc                                                                123

SEQ ID NO: 38          moltype = AA  length = 35
FEATURE                Location/Qualifiers
REGION                 1..35
                       note = source = /note="Description of Artificial Sequence:
                        Synthetic polypeptide"
source                 1..35
                       mol_type = protein
                       organism = synthetic construct
SEQUENCE: 38
TKKKYSSSVH DPNGEYMFMR AVNTAKKSRL TDVTL                             35

SEQ ID NO: 39          moltype = DNA  length = 105
FEATURE                Location/Qualifiers
misc_feature           1..105
                       note = source = /note="Description of Artificial Sequence:
                        Synthetic polynucleotide"
source                 1..105
                       mol_type = other DNA
                       organism = synthetic construct
SEQUENCE: 39
acaaaaaaga agtattcatc cagtgtgcac gaccctaacg gtgaatacat gttcatgaga  60
gcagtgaaca cagccaaaaa atccagactc acagatgtga cccta                  105

SEQ ID NO: 40          moltype = DNA  length = 30
FEATURE                Location/Qualifiers
misc_feature           1..30
                       note = source = /note="Description of Artificial Sequence:
                        Synthetic oligonucleotide"
source                 1..30
                       mol_type = other DNA
                       organism = synthetic construct
SEQUENCE: 40
ggtggcggag gttctggagg tgggggttcc                                   30

SEQ ID NO: 41          moltype = AA  length = 4
FEATURE                Location/Qualifiers
REGION                 1..4
                       note = source = /note="Description of Artificial Sequence:
                        Synthetic peptide"
REGION                 1..4
                       note = source = /note="See specification as filed for
                        detailed description of substitutions and preferred
                        embodiments"
```

-continued

```
source                  1..4
                        mol_type = protein
                        organism = synthetic construct
SEQUENCE: 41
GGGS                                                                        4

SEQ ID NO: 42           moltype = AA  length = 40
FEATURE                 Location/Qualifiers
SITE                    1..40
                        note = /note="This sequence may encompass 1-10 'Gly Gly Gly
                         Ser' repeating units"
REGION                  1..40
                        note = source = /note="Description of Artificial Sequence:
                         Synthetic polypeptide"
REGION                  1..40
                        note = source = /note="See specification as filed for
                         detailed description of substitutions and preferred
                         embodiments"
source                  1..40
                        mol_type = protein
                        organism = synthetic construct
SEQUENCE: 42
GGGSGGGSGG GSGGGSGGGS GGGSGGGSGG GSGGGSGGGS                                 40

SEQ ID NO: 43           moltype = AA  length = 18
FEATURE                 Location/Qualifiers
REGION                  1..18
                        note = source = /note="Description of Artificial Sequence:
                         Synthetic peptide"
source                  1..18
                        mol_type = protein
                        organism = synthetic construct
SEQUENCE: 43
GSTSGSGKPG SGEGSTKG                                                         18

SEQ ID NO: 44           moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 44
SYAMS                                                                       5

SEQ ID NO: 45           moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 45
AISGSGGSTY YADSVKG                                                          17

SEQ ID NO: 46           moltype = AA  length = 14
FEATURE                 Location/Qualifiers
REGION                  1..14
                        note = source = /note="Description of Artificial Sequence:
                         Synthetic peptide"
source                  1..14
                        mol_type = protein
                        organism = synthetic construct
SEQUENCE: 46
REWVPYDVSW YFDY                                                             14

SEQ ID NO: 47           moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 47
GFTFSSY                                                                     7
```

```
SEQ ID NO: 48          moltype = AA  length = 6
FEATURE                Location/Qualifiers
REGION                 1..6
                       note = source = /note="Description of Artificial Sequence:
                        Synthetic peptide"
source                 1..6
                       mol_type = protein
                       organism = synthetic construct
SEQUENCE: 48
SGSGGS                                                             6

SEQ ID NO: 49          moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 49
GFTFSSYA                                                           8

SEQ ID NO: 50          moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 50
ISGSGGST                                                           8

SEQ ID NO: 51          moltype = AA  length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 51
ARREWVPYDV SWYFDY                                                  16

SEQ ID NO: 52          moltype = AA  length = 123
FEATURE                Location/Qualifiers
REGION                 1..123
                       note = source = /note="Description of Artificial Sequence:
                        Synthetic polypeptide"
source                 1..123
                       mol_type = protein
                       organism = synthetic construct
SEQUENCE: 52
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARRE WVPYDVSWYF DYWGQGTLVT  120
VSS                                                                123

SEQ ID NO: 53          moltype = DNA  length = 369
FEATURE                Location/Qualifiers
misc_feature           1..369
                       note = source = /note="Description of Artificial Sequence:
                        Synthetic polynucleotide"
source                 1..369
                       mol_type = other DNA
                       organism = synthetic construct
SEQUENCE: 53
gaagtgcagt tgctggagtc aggcggagga ctggtgcagc ccggaggatc gcttcgcttg  60
agctgcgcag cctcaggctt taccttctcc tcctacgcca tgtcctgggt cagacaggct  120
cccgggaagg gactggaatg ggtgtccgcc attagcggtt ccggcggaag cacttactat  180
gccgactctg tgaagggccg cttcactatc tcccgggaca actccaagaa caccctgtat  240
ctccaaatga attccctgag ggccgaagat accgcggtgt actactgcgc tagacgggag  300
tgggtgccct acgatgtcag ctggtacttc gactactggg gacagggcac tctcgtgact  360
gtgtcctcc                                                          369

SEQ ID NO: 54          moltype = AA  length = 11
FEATURE                Location/Qualifiers
REGION                 1..11
                       note = source = /note="Description of Artificial Sequence:
                        Synthetic peptide"
```

```
source                  1..11
                        mol_type = protein
                        organism = synthetic construct
SEQUENCE: 54
RASQSISSYL N                                                       11

SEQ ID NO: 55           moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 55
AASSLQS                                                            7

SEQ ID NO: 56           moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 56
QQSYSTPLT                                                          9

SEQ ID NO: 57           moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 57
SQSISSY                                                            7

SEQ ID NO: 58           moltype =   length =
SEQUENCE: 58
000

SEQ ID NO: 59           moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 59
SYSTPL                                                             6

SEQ ID NO: 60           moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 60
QSISSY                                                             6

SEQ ID NO: 61           moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 61
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPLTFGQ GTKVEIK                107

SEQ ID NO: 62           moltype = DNA  length = 321
FEATURE                 Location/Qualifiers
```

-continued

```
misc_feature            1..321
                        note = source = /note="Description of Artificial Sequence:
                         Synthetic polynucleotide"
source                  1..321
                        mol_type = other DNA
                        organism = synthetic construct
SEQUENCE: 62
gacattcaaa tgactcagtc cccgtcctcc ctctccgcct ccgtgggaga tcgcgtcacg  60
atcacgtgca gggccagcca gagcatctcc agctacctga actggtacca gcagaagcca  120
gggaaggcac cgaagctcct gatctacgcc gctagctcgc tgcagtccgg cgtcccttca  180
cggttctcgg gatcgggctc aggcaccgac ttcaccctga ccattagcag cctgcagccg  240
gaggacttcg cgacatacta ctgtcagcag tcatactcca cccctctgac cttcggccaa  300
gggaccaaag tggagatcaa g                                          321

SEQ ID NO: 63           moltype = AA  length = 20
FEATURE                 Location/Qualifiers
REGION                  1..20
                        note = source = /note="Description of Artificial Sequence:
                         Synthetic peptide"
source                  1..20
                        mol_type = protein
                        organism = synthetic construct
SEQUENCE: 63
GGGGSGGGGS GGGGSGGGGS                                            20

SEQ ID NO: 64           moltype = AA  length = 250
FEATURE                 Location/Qualifiers
REGION                  1..250
                        note = source = /note="Description of Artificial Sequence:
                         Synthetic polypeptide"
source                  1..250
                        mol_type = protein
                        organism = synthetic construct
SEQUENCE: 64
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARRE WVPYDVSWYF DYWGQGTLVT  120
VSSGGGGSGG GGSGGGGSGG GGSDIQMTQS PSSLSASVGD RVTITCRASQ SISSYLNWYQ  180
QKPGKAPKLL IYAASSLQSG VPSRFSGSGS GTDFTLTISS LQPEDFATYY CQQSYSTPLT  240
FGQGTKVEIK                                                       250

SEQ ID NO: 65           moltype = DNA  length = 750
FEATURE                 Location/Qualifiers
misc_feature            1..750
                        note = source = /note="Description of Artificial Sequence:
                         Synthetic polynucleotide"
source                  1..750
                        mol_type = other DNA
                        organism = synthetic construct
SEQUENCE: 65
gaagtgcagt tgctggagtc aggcggagga ctggtgcagc ccggaggatc gcttcgcttg  60
agctgcgcag cctcaggctt taccttctcc tcctacgcca tgtcctgggt cagacaggct  120
cccgggaagg gactggaatg ggtgtccgcc attagcggtt ccggcggaag cacttactat  180
gccgactctg tgaagggccg cttcactatc tcccgggaca actccaagaa caccctgtat  240
ctccaaatga attccctgag ggccgaagat accgcggtgt actactgcgc tagacgggag  300
tgggtgccct acgatgtcag ctggtacttc gactactggg gacagggcac tctcgtgact  360
gtgtcctccg gtggtggtgg atcggggggt ggtggttcgg gcggaggagg atctggagga  420
ggagggtcgg acattcaaat gactcagtcc ccgtcctccc tctccgcctc cgtgggagat  480
cgcgtcacga tcacgtgcag ggccagccag agcatctcca gctacctgaa ctggtaccag  540
cagaagccag ggaaggcacc gaagctcctg atctacgccg ctagctcgct gcagtccggc  600
gtcccttcac ggttctcggg atcgggctca ggcaccgact tcaccctgac cattagcagc  660
ctgcagccgg aggacttcgc gacatactac tgtcagcagt catactccac ccctctgacc  720
ttcggccaag ggaccaaagt ggagatcaag                                 750

SEQ ID NO: 66           moltype = AA  length = 473
FEATURE                 Location/Qualifiers
REGION                  1..473
                        note = source = /note="Description of Artificial Sequence:
                         Synthetic polypeptide"
source                  1..473
                        mol_type = protein
                        organism = synthetic construct
SEQUENCE: 66
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARRE WVPYDVSWYF DYWGQGTLVT  120
VSSGGGGSGG GGSGGGGSGG GGSDIQMTQS PSSLSASVGD RVTITCRASQ SISSYLNWYQ  180
QKPGKAPKLL IYAASSLQSG VPSRFSGSGS GTDFTLTISS LQPEDFATYY CQQSYSTPLT  240
FGQGTKVEIK TTTPAPRPPT PAPTIASQPL SLRPEACRPA AGGAVHTRGL DFACDIYIWA  300
PLAGTCGVLL LSLVITLYCK RGRKKLLYIF KQPFMRPVQT TQEEDGCSCR FPEEEEGGCE  360
LRVKFSRSAD APAYQQGQNQ LYNELNLGRR EEYDVLDKRR GRDPEMGGKP RRKNPQEGLY  420
```

-continued

```
NELQKDKMAE AYSEIGMKGE RRRGKGHDGL YQGLSTATKD TYDALHMQAL PPR         473

SEQ ID NO: 67          moltype = DNA  length = 1419
FEATURE                Location/Qualifiers
misc_feature           1..1419
                       note = source = /note="Description of Artificial Sequence:
                        Synthetic polynucleotide"
source                 1..1419
                       mol_type = other DNA
                       organism = synthetic construct
SEQUENCE: 67
gaagtgcagt tgctggagtc aggcggagga ctggtgcagc ccggaggatc gcttcgcttg  60
agctgcgcag cctcaggctt taccttctcc tcctacgcca tgtcctgggt cagacaggct  120
cccgggaagg gactggaatg ggtgtccgcc attagcggtt ccggcggaag cacttactat  180
gccgactctg tgaagggccg cttcactatc tcccgggaca actccaagaa caccctgtat  240
ctccaaatga attccctgag ggccgaagat accgcggtgt actactgcgc tagacgggag  300
tgggtgccct acgatgtcag ctggtacttc gactactggg gacagggcac tctcgtgact  360
gtgtcctccg gtggtggtgg atcggggggt ggtggttcgg gcggaggagg atctggagga  420
ggagggtcgg acattcaaat gactcagtcc ccgtcctccc tctccgcctc cgtgggagat  480
cgcgtcacga tcacgtgcag ggccagccag agcatctcca gctacctgaa ctggtaccag  540
cagaagccag ggaaggcacc gaagctcctg atctacgccg ctagctcgct gcagtccggc  600
gtcccttcac ggttctcggg atcgggctca ggcaccgact tcaccctgac cattagcagc  660
ctgcagccgg aggacttcgc gacatactac tgtcagcagt catactccac ccctctgacc  720
ttcggccaag ggaccaaagt ggagatcaag accactaccc cagcaccgag gccacccacc  780
ccggctccta ccatcgcctc ccagcctctg tccctgcgtc cggaggcatg tagacccgca  840
gctggtgggg ccgtgcatac ccggggtctt gacttcgcct gcgatatcta catttgggcc  900
cctctggctg gtacttgcgg ggtcctgctg ctttcactcg tgatcactct ttactgtaag  960
cgcggtcgga agaagctgct gtacatcttt aagcaaccct tcatgaggcc tgtgcagact  1020
actcaagagg aggacggctg ttcatgccgg ttcccagagg aggaggaagg cggctgcgaa  1080
ctgcgcgtga aattcagccg cagcgcagat gctccagcct accagcaggg gcagaaccag  1140
ctctacaacg aactcaatct tggtcggaga gaggagtacg acgtgctgga caagcggaga  1200
ggacgggacc cagaaatggg cgggaagccg cgcagaaaga atccccaaga gggcctgtac  1260
aacgagctcc aaaaggataa gatggcagaa gcctatagcg agattggtat gaaaggggaa  1320
cgcagaagag gcaaaggcca cgacggactg taccagggac tcagcaccgc caccaaggac  1380
acctatgacg ctcttcacat gcaggccctg ccgcctcgg                        1419

SEQ ID NO: 68          moltype = AA  length = 12
FEATURE                Location/Qualifiers
REGION                 1..12
                       note = source = /note="Description of Artificial Sequence:
                        Synthetic peptide"
source                 1..12
                       mol_type = protein
                       organism = synthetic construct
SEQUENCE: 68
REWWYDDWYL DY                                                      12

SEQ ID NO: 69          moltype = AA  length = 14
FEATURE                Location/Qualifiers
REGION                 1..14
                       note = source = /note="Description of Artificial Sequence:
                        Synthetic peptide"
source                 1..14
                       mol_type = protein
                       organism = synthetic construct
SEQUENCE: 69
ARREWWYDDW YLDY                                                    14

SEQ ID NO: 70          moltype = AA  length = 121
FEATURE                Location/Qualifiers
REGION                 1..121
                       note = source = /note="Description of Artificial Sequence:
                        Synthetic polypeptide"
source                 1..121
                       mol_type = protein
                       organism = synthetic construct
SEQUENCE: 70
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARRE WWYDDWYLDY WGQGTLVTVS  120
S                                                                  121

SEQ ID NO: 71          moltype = DNA  length = 363
FEATURE                Location/Qualifiers
misc_feature           1..363
                       note = source = /note="Description of Artificial Sequence:
                        Synthetic polynucleotide"
source                 1..363
                       mol_type = other DNA
                       organism = synthetic construct
```

```
SEQUENCE: 71
gaagtgcagt tgctggagtc aggcggagga ctggtgcagc ccggaggatc gcttcgcttg  60
agctgcgcag cctcaggctt taccttctcc tcctacgcca tgtcctgggt cagacaggct  120
cccgggaagg gactggaatg ggtgtccgcc attagcggtt ccggcggaag cacttactat  180
gccgactctg tgaagggccg cttcactatc tcccgggaca actccaagaa caccctgtat  240
ctccaaatga attccctgag ggccgaagat accgcggtgt actactgcgc tagacgggag  300
tggtggtacg acgattggta cctggactac tggggacagg gcactctcgt gactgtgtcc  360
tcc                                                                363

SEQ ID NO: 72          moltype = AA  length = 248
FEATURE                Location/Qualifiers
REGION                 1..248
                       note = source = /note="Description of Artificial Sequence:
                        Synthetic polypeptide"
source                 1..248
                       mol_type = protein
                       organism = synthetic construct
SEQUENCE: 72
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARRE WWYDDWYLDY WGQGTLVTVS  120
SGGGGSGGGG SGGGGSGGGG SDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
QGTKVEIK                                                           248

SEQ ID NO: 73          moltype = DNA  length = 744
FEATURE                Location/Qualifiers
misc_feature           1..744
                       note = source = /note="Description of Artificial Sequence:
                        Synthetic polynucleotide"
source                 1..744
                       mol_type = other DNA
                       organism = synthetic construct
SEQUENCE: 73
gaagtgcagt tgctggagtc aggcggagga ctggtgcagc ccggaggatc gcttcgcttg  60
agctgcgcag cctcaggctt taccttctcc tcctacgcca tgtcctgggt cagacaggct  120
cccgggaagg gactggaatg ggtgtccgcc attagcggtt ccggcggaag cacttactat  180
gccgactctg tgaagggccg cttcactatc tcccgggaca actccaagaa caccctgtat  240
ctccaaatga attccctgag ggccgaagat accgcggtgt actactgcgc tagacgggag  300
tggtggtacg acgattggta cctggactac tggggacagg gcactctcgt gactgtgtcc  360
tccggtggtg gtggatcggg gggtggtggt tcgggcggag gaggatctgg aggaggaggg  420
tcggacattc aaatgactca gtccccgtcc tccctctccg cctccgtggg agatcgcgtc  480
acgatcacgt gcagggccag ccagagcatc tccagctacc tgaactggta ccagcagaag  540
ccagggaagg caccgaagct cctgatctac gccgctagct cgctgcagtc cggcgtccct  600
tcacggttct cgggatcggg ctcaggcacc gacttcaccc tgaccattag cagcctgcag  660
ccggaggact tcgcgacata ctactgtcag cagtcatact ccacccctct gaccttcggc  720
caagggacca aagtggagat caag                                         744

SEQ ID NO: 74          moltype = AA  length = 471
FEATURE                Location/Qualifiers
REGION                 1..471
                       note = source = /note="Description of Artificial Sequence:
                        Synthetic polypeptide"
source                 1..471
                       mol_type = protein
                       organism = synthetic construct
SEQUENCE: 74
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARRE WWYDDWYLDY WGQGTLVTVS  120
SGGGGSGGGG SGGGGSGGGG SDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
QGTKVEIKTT TPAPRPPTPA PTIASQPLSL RPEACRPAAG GAVHTRGLDF ACDIYIWAPL  300
AGTCGVLLLS LVITLYCKRG RKKLLYIFKQ PFMRPVQTTQ EEDGCSCRFP EEEEGGCELR  360
VKFSRSADAP AYQQGQNQLY NELNLGRREE YDVLDKRRGR DPEMGGKPRR KNPQEGLYNE  420
LQKDKMAEAY SEIGMKGERR RGKGHDGLYQ GLSTATKDTY DALHMQALPP R           471

SEQ ID NO: 75          moltype = DNA  length = 1413
FEATURE                Location/Qualifiers
misc_feature           1..1413
                       note = source = /note="Description of Artificial Sequence:
                        Synthetic polynucleotide"
source                 1..1413
                       mol_type = other DNA
                       organism = synthetic construct
SEQUENCE: 75
gaagtgcagt tgctggagtc aggcggagga ctggtgcagc ccggaggatc gcttcgcttg  60
agctgcgcag cctcaggctt taccttctcc tcctacgcca tgtcctgggt cagacaggct  120
cccgggaagg gactggaatg ggtgtccgcc attagcggtt ccggcggaag cacttactat  180
gccgactctg tgaagggccg cttcactatc tcccgggaca actccaagaa caccctgtat  240
ctccaaatga attccctgag ggccgaagat accgcggtgt actactgcgc tagacgggag  300
```

```
tggtggtacg acgattggta cctggactac tggggacagg gcactctcgt gactgtgtcc  360
tccggtggtg gtggatcggg gggtggtggt tcgggcggag gaggatctgg aggaggaggg  420
tcggacattc aaatgactca gtccccgtcc tccctctccg cctccgtggg agatcgcgtc  480
acgatcacgt gcagggccag ccagagcatc tccagctacc tgaactggta ccagcagaag  540
ccagggaagg caccgaagct cctgatctac gccgctagct cgctgcagtc cggcgtccct  600
tcacggttct cgggatcggg ctcaggcacc gacttcaccc tgaccattag cagcctgcag  660
ccggaggact tcgcgacata ctactgtcag cagtcatact ccacccctct gaccttcggc  720
caagggacca aagtggagat caagaccact accccagcac cgaggccacc cacccccggct  780
cctaccatcg cctcccagcc tctgtccctg cgtccggagg catgtagacc cgcagctggt  840
ggggccgtgc atacccgggg tcttgacttc gcctgcgata tctacatttg ggcccctctg  900
gctggtactt gcggggtcct gctgctttca ctcgtgatca ctctttactg taagcgcggt  960
cggaagaagc tgctgtacat ctttaagcaa cccttcatga ggcctgtgca gactactcaa  1020
gaggaggacg gctgttcatg ccggttccca gaggaggagg aaggcggctg cgaactgcgc  1080
gtgaaattca gccgcagcgc agatgctcca gcctaccagc aggggcagaa ccagctctac  1140
aacgaactca atcttggtcg gagagaggag tacgacgtgc tggacaagcg gagaggacgg  1200
gacccagaaa tgggcgggaa gccgcgcaga aagaatcccc aagagggcct gtacaacgag  1260
ctccaaaagg ataagatggc agaagcctat agcgagattg gtatgaaagg ggaacgcaga  1320
agaggcaaag gccacgacgg actgtaccag ggactcagca ccgccaccaa ggacacctat  1380
gacgctcttc acatgcaggc cctgccgcct cgg                               1413

SEQ ID NO: 76          moltype = AA  length = 12
FEATURE                Location/Qualifiers
REGION                 1..12
                       note = source = /note="Description of Artificial Sequence:
                        Synthetic peptide"
source                 1..12
                       mol_type = protein
                       organism = synthetic construct
SEQUENCE: 76
REWWGESWLF DY                                                      12

SEQ ID NO: 77          moltype = AA  length = 14
FEATURE                Location/Qualifiers
REGION                 1..14
                       note = source = /note="Description of Artificial Sequence:
                        Synthetic peptide"
source                 1..14
                       mol_type = protein
                       organism = synthetic construct
SEQUENCE: 77
ARREWWGESW LFDY                                                    14

SEQ ID NO: 78          moltype = AA  length = 121
FEATURE                Location/Qualifiers
REGION                 1..121
                       note = source = /note="Description of Artificial Sequence:
                        Synthetic polypeptide"
source                 1..121
                       mol_type = protein
                       organism = synthetic construct
SEQUENCE: 78
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARRE WWGESWLFDY WGQGTLVTVS  120
S                                                                  121

SEQ ID NO: 79          moltype = DNA  length = 363
FEATURE                Location/Qualifiers
misc_feature           1..363
                       note = source = /note="Description of Artificial Sequence:
                        Synthetic polynucleotide"
source                 1..363
                       mol_type = other DNA
                       organism = synthetic construct
SEQUENCE: 79
gaagtgcagt tgctggagtc aggcggagga ctggtgcagc ccggaggatc gcttcgcttg  60
agctgcgcag cctcaggctt taccttctcc tcctacgcca tgtcctgggt cagacaggct  120
cccgggaagg gactggaatg ggtgtccgcc attagcggtt ccggcggaag cacttactat  180
gccgactctg tgaagggccg cttcactatc tcccgggaca actccaagaa caccctgtat  240
ctccaaatga attccctgag ggccgaagat accgcggtgt actactgcgc tagacgggag  300
tggtggggag aaagctggct gttcgactac tggggacagg gcactctcgt gactgtgtcc  360
tcc                                                                363

SEQ ID NO: 80          moltype = AA  length = 248
FEATURE                Location/Qualifiers
REGION                 1..248
                       note = source = /note="Description of Artificial Sequence:
                        Synthetic polypeptide"
source                 1..248
                       mol_type = protein
```

```
                         organism = synthetic construct
SEQUENCE: 80
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARRE WWGESWLFDY WGQGTLVTVS  120
SGGGGSGGGG SGGGGSGGGG SDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
QGTKVEIK                                                           248

SEQ ID NO: 81            moltype = DNA  length = 744
FEATURE                  Location/Qualifiers
misc_feature             1..744
                         note = source = /note="Description of Artificial Sequence:
                          Synthetic polynucleotide"
source                   1..744
                         mol_type = other DNA
                         organism = synthetic construct
SEQUENCE: 81
gaagtgcagt tgctggagtc aggcggagga ctggtgcagc ccggaggatc gcttcgcttg  60
agctgcgcag cctcaggctt taccttctcc tcctacgcca tgtcctgggt cagacaggct  120
cccgggaagg gactggaatg ggtgtccgcc attagcggtt ccggcggaag cacttactat  180
gccgactctg tgaagggccg cttcactatc tcccgggaca actccaagaa caccctgtat  240
ctccaaatga attccctgag ggccgaagat accgcggtgt actactgcgc tagacgggag  300
tggtggggag aaagctggct gttcgactac tggggacagg gcactctcgt gactgtgtcc  360
tccggtggtg gtggatcggg gggtggtggt tcgggcggag gaggatctgg aggaggaggg  420
tcggacattc aaatgactca gtccccgtcc tccctctccg cctccgtggg agatcgcgtc  480
acgatcacgt gcagggccag ccagagcatc tccagctacc tgaactggta ccagcagaag  540
ccagggaagg caccgaagct cctgatctac gccgctagct cgctgcagtc cggcgtccct  600
tcacggttct cgggatcggg ctcaggcacc gacttcaccc tgaccattag cagcctgcag  660
ccggaggact tcgcgacata ctactgtcag cagtcatact ccacccctct gaccttcggc  720
caagggacca aagtggagat caag                                         744

SEQ ID NO: 82            moltype = AA  length = 471
FEATURE                  Location/Qualifiers
REGION                   1..471
                         note = source = /note="Description of Artificial Sequence:
                          Synthetic polypeptide"
source                   1..471
                         mol_type = protein
                         organism = synthetic construct
SEQUENCE: 82
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCARRE WWGESWLFDY WGQGTLVTVS  120
SGGGGSGGGG SGGGGSGGGG SDIQMTQSPS SLSASVGDRV TITCRASQSI SSYLNWYQQK  180
PGKAPKLLIY AASSLQSGVP SRFSGSGSGT DFTLTISSLQ PEDFATYYCQ QSYSTPLTFG  240
QGTKVEIKTT TPAPRPPTPA PTIASQPLSL RPEACRPAAG GAVHTRGLDF ACDIYIWAPL  300
AGTCGVLLLS LVITLYCKRG RKKLLYIFKQ PFMRPVQTTQ EEDGCSCRFP EEEEGGCELR  360
VKFSRSADAP AYQQGQNQLY NELNLGRREE YDVLDKRRGR DPEMGGKPRR KNPQEGLYNE  420
LQKDKMAEAY SEIGMKGERR RGKGHDGLYQ GLSTATKDTY DALHMQALPP R           471

SEQ ID NO: 83            moltype = DNA  length = 1413
FEATURE                  Location/Qualifiers
misc_feature             1..1413
                         note = source = /note="Description of Artificial Sequence:
                          Synthetic polynucleotide"
source                   1..1413
                         mol_type = other DNA
                         organism = synthetic construct
SEQUENCE: 83
gaagtgcagt tgctggagtc aggcggagga ctggtgcagc ccggaggatc gcttcgcttg  60
agctgcgcag cctcaggctt taccttctcc tcctacgcca tgtcctgggt cagacaggct  120
cccgggaagg gactggaatg ggtgtccgcc attagcggtt ccggcggaag cacttactat  180
gccgactctg tgaagggccg cttcactatc tcccgggaca actccaagaa caccctgtat  240
ctccaaatga attccctgag ggccgaagat accgcggtgt actactgcgc tagacgggag  300
tggtggggag aaagctggct gttcgactac tggggacagg gcactctcgt gactgtgtcc  360
tccggtggtg gtggatcggg gggtggtggt tcgggcggag gaggatctgg aggaggaggg  420
tcggacattc aaatgactca gtccccgtcc tccctctccg cctccgtggg agatcgcgtc  480
acgatcacgt gcagggccag ccagagcatc tccagctacc tgaactggta ccagcagaag  540
ccagggaagg caccgaagct cctgatctac gccgctagct cgctgcagtc cggcgtccct  600
tcacggttct cgggatcggg ctcaggcacc gacttcaccc tgaccattag cagcctgcag  660
ccggaggact tcgcgacata ctactgtcag cagtcatact ccacccctct gaccttcggc  720
caagggacca aagtggagat caagaccact accccagcac cgaggccacc caccccggct  780
cctaccatcg cctcccagcc tctgtccctg cgtccggagg catgtagacc cgcagctggt  840
ggggccgtgc atacccgggg tcttgacttc gcctgcgata tctacatttg ggcccctctg  900
gctggtactt gcggggtcct gctgctttca ctcgtgatca ctctttactg taagcgcggt  960
cggaagaagc tgctgtacat ctttaagcaa cccttcatga ggcctgtgca gactactcaa  1020
gaggaggacg gctgttcatg ccggttccca gaggaggagg aaggcggctg cgaactgcgc  1080
gtgaaattca gccgcagcgc agatgctcca gcctaccagc aggggcagaa ccagctctac  1140
aacgaactca atcttggtcg gagagaggag tacgacgtgc tggacaagcg gagaggacgg  1200
gacccagaaa tgggcgggaa gccgcgcaga aagaatcccc aagagggcct gtacaacgag  1260
```

```
ctccaaaagg ataagatggc agaagcctat agcgagattg gtatgaaagg ggaacgcaga  1320
agaggcaaag gccacgacgg actgtaccag ggactcagca ccgccaccaa ggacacctat  1380
gacgctcttc acatgcaggc cctgccgcct cgg                               1413

SEQ ID NO: 84           moltype = AA  length = 14
FEATURE                 Location/Qualifiers
VARIANT                 4
                        note = /replace=" "
VARIANT                 5
                        note = /replace=" "
VARIANT                 6
                        note = /replace="Tyr"
VARIANT                 7
                        note = /replace="Tyr" or "Asp"
VARIANT                 8
                        note = /replace="Asp" or "Val"
VARIANT                 9
                        note = /replace="Asp"
VARIANT                 11
                        note = /replace="Tyr"
VARIANT                 12
                        note = /replace="Leu"
SITE                    1..14
                        note = /note="Variant residues given in the sequence have
                         no preference with respect to those in the annotations for
                         variant positions"
REGION                  1..14
                        note = source = /note="Description of Artificial Sequence:
                         Synthetic peptide"
source                  1..14
                        mol_type = protein
                        organism = synthetic construct
SEQUENCE: 84
REWVPWGESW LFDY                                                    14

SEQ ID NO: 85           moltype = AA  length = 16
FEATURE                 Location/Qualifiers
VARIANT                 6
                        note = /replace=" "
VARIANT                 7
                        note = /replace=" "
VARIANT                 8
                        note = /replace="Tyr"
VARIANT                 9
                        note = /replace="Tyr" or "Asp"
VARIANT                 10
                        note = /replace="Asp" or "Val"
VARIANT                 11
                        note = /replace="Asp"
VARIANT                 13
                        note = /replace="Tyr"
VARIANT                 14
                        note = /replace="Leu"
SITE                    1..16
                        note = /note="Variant residues given in the sequence have
                         no preference with respect to those in the annotations for
                         variant positions"
REGION                  1..16
                        note = source = /note="Description of Artificial Sequence:
                         Synthetic peptide"
source                  1..16
                        mol_type = protein
                        organism = synthetic construct
SEQUENCE: 85
ARREWVPWGE SWLFDY                                                  16

SEQ ID NO: 86           moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 86
SYGMH                                                              5

SEQ ID NO: 87           moltype = AA  length = 17
FEATURE                 Location/Qualifiers
```

```
REGION                  1..17
                        note = source = /note="Description of Artificial Sequence:
                         Synthetic peptide"
source                  1..17
                        mol_type = protein
                        organism = synthetic construct
SEQUENCE: 87
VISYDGSNKY YADSVKG                                                  17

SEQ ID NO: 88           moltype = AA  length = 14
FEATURE                 Location/Qualifiers
REGION                  1..14
                        note = source = /note="Description of Artificial Sequence:
                         Synthetic peptide"
source                  1..14
                        mol_type = protein
                        organism = synthetic construct
SEQUENCE: 88
SGYALHDDYY GLDV                                                     14

SEQ ID NO: 89           moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 89
SYDGSN                                                              6

SEQ ID NO: 90           moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 90
GFTFSSYG                                                            8

SEQ ID NO: 91           moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 91
ISYDGSNK                                                            8

SEQ ID NO: 92           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 92
GGSGYALHDD YYGLDV                                                   16

SEQ ID NO: 93           moltype = AA  length = 123
FEATURE                 Location/Qualifiers
REGION                  1..123
                        note = source = /note="Description of Artificial Sequence:
                         Synthetic polypeptide"
source                  1..123
                        mol_type = protein
                        organism = synthetic construct
SEQUENCE: 93
QVQLQESGGG VVQPGRSLRL SCAASGFTFS SYGMHWVRQA PGKGLEWVAV ISYDGSNKYY  60
ADSVKGRFTI SRDNSKNTLY LQMNSLRAED TAVYYCGGSG YALHDDYYGL DVWGQGTLVT  120
VSS                                                                 123

SEQ ID NO: 94           moltype = DNA  length = 369
FEATURE                 Location/Qualifiers
```

```
misc_feature          1..369
                      note = source = /note="Description of Artificial Sequence:
                       Synthetic polynucleotide"
source                1..369
                      mol_type = other DNA
                      organism = synthetic construct
SEQUENCE: 94
caagtgcagc tgcaggaatc cggtggcgga gtcgtgcagc ctggaaggag cctgagactc  60
tcatgcgccg cgtcagggtt caccttttcc tcctacggga tgcattgggt cagacaggcc  120
cccggaaagg gactcgaatg ggtggctgtg atcagctacg acggctccaa caagtactac  180
gccgactccg tgaaaggccg gttcactatc tcccgggaca actccaagaa cacgctgtat  240
ctgcaaatga attcactgcg cgcggaggat accgctgtgt actactgcgg tggctccggt  300
tacgccctgc acgatgacta ttacggcctt gacgtctggg gccagggaac cctcgtgact  360
gtgtccagc                                                           369

SEQ ID NO: 95         moltype = AA  length = 14
FEATURE               Location/Qualifiers
REGION                1..14
                      note = source = /note="Description of Artificial Sequence:
                       Synthetic peptide"
source                1..14
                      mol_type = protein
                      organism = synthetic construct
SEQUENCE: 95
TGTSSDVGGY NYVS                                                     14

SEQ ID NO: 96         moltype = AA  length = 7
FEATURE               Location/Qualifiers
REGION                1..7
                      note = source = /note="Description of Artificial Sequence:
                       Synthetic peptide"
source                1..7
                      mol_type = protein
                      organism = synthetic construct
SEQUENCE: 96
DVSNRPS                                                             7

SEQ ID NO: 97         moltype = AA  length = 11
FEATURE               Location/Qualifiers
REGION                1..11
                      note = source = /note="Description of Artificial Sequence:
                       Synthetic peptide"
source                1..11
                      mol_type = protein
                      organism = synthetic construct
SEQUENCE: 97
SSYTSSSTLY V                                                        11

SEQ ID NO: 98         moltype = AA  length = 10
FEATURE               Location/Qualifiers
REGION                1..10
                      note = source = /note="Description of Artificial Sequence:
                       Synthetic peptide"
source                1..10
                      mol_type = protein
                      organism = synthetic construct
SEQUENCE: 98
TSSDVGGYNY                                                          10

SEQ ID NO: 99         moltype =   length =
SEQUENCE: 99
000

SEQ ID NO: 100        moltype = AA  length = 8
FEATURE               Location/Qualifiers
REGION                1..8
                      note = source = /note="Description of Artificial Sequence:
                       Synthetic peptide"
source                1..8
                      mol_type = protein
                      organism = synthetic construct
SEQUENCE: 100
YTSSSTLY                                                            8

SEQ ID NO: 101        moltype = AA  length = 9
FEATURE               Location/Qualifiers
REGION                1..9
                      note = source = /note="Description of Artificial Sequence:
                       Synthetic peptide"
```

```
source                  1..9
                        mol_type = protein
                        organism = synthetic construct
SEQUENCE: 101
SSDVGGYNY                                                                9

SEQ ID NO: 102          moltype = AA  length = 111
FEATURE                 Location/Qualifiers
REGION                  1..111
                        note = source = /note="Description of Artificial Sequence:
                         Synthetic polypeptide"
source                  1..111
                        mol_type = protein
                        organism = synthetic construct
SEQUENCE: 102
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTLY VFGSGTKVTV L           111

SEQ ID NO: 103          moltype = DNA  length = 333
FEATURE                 Location/Qualifiers
misc_feature            1..333
                        note = source = /note="Description of Artificial Sequence:
                         Synthetic polynucleotide"
source                  1..333
                        mol_type = other DNA
                        organism = synthetic construct
SEQUENCE: 103
cagagcgcac tgactcagcc ggcatccgtg tccggtagcc ccggacagtc gattaccatc  60
tcctgtaccg gcacctcctc cgacgtggga gggtacaact acgtgtcgtg gtaccagcag  120
cacccaggaa aggcccctaa gttgatgatc tacgatgtgt caaaccgccc gtctggagtc  180
tccaaccggt tctccggctc caagtccggc aacaccgcca gcctgaccat tagcgggctg  240
caagccgagg atgaggccga ctactactgc tcgagctaca catcctcgag caccctctac  300
gtgttcggct cggggactaa ggtcaccgtg ctg                                333

SEQ ID NO: 104          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 104
GGGGSGGGGS GGGGS                                                     15

SEQ ID NO: 105          moltype = AA  length = 249
FEATURE                 Location/Qualifiers
REGION                  1..249
                        note = source = /note="Description of Artificial Sequence:
                         Synthetic polypeptide"
source                  1..249
                        mol_type = protein
                        organism = synthetic construct
SEQUENCE: 105
QVQLQESGGG VVQPGRSLRL SCAASGFTFS SYGMHWVRQA PGKGLEWVAV ISYDGSNKYY  60
ADSVKGRFTI SRDNSKNTLY LQMNSLRAED TAVYYCGGSG YALHDDYYGL DVWGQGTLVT  120
VSSGGGGSGG GGSGGGGSQS ALTQPASVSG SPGQSITISC TGTSSDVGGY NYVSWYQQHP  180
GKAPKLMIYD VSNRPSGVSN RFSGSKSGNT ASLTISGLQA EDEADYYCSS YTSSSTLYVF  240
GSGTKVTVL                                                            249

SEQ ID NO: 106          moltype = DNA  length = 747
FEATURE                 Location/Qualifiers
misc_feature            1..747
                        note = source = /note="Description of Artificial Sequence:
                         Synthetic polynucleotide"
source                  1..747
                        mol_type = other DNA
                        organism = synthetic construct
SEQUENCE: 106
caagtgcagc tgcaggaatc cggtggcgga gtcgtgcagc ctggaaggag cctgagactc  60
tcatgcgccg cgtcagggtt caccttttcc tcctacggga tgcattgggt cagacaggcc  120
cccggaaagg gactcgaatg ggtggctgtg atcagctacg acggctccaa caagtactac  180
gccgactccg tgaaaggccg gttcactatc tcccgggaca actccaagaa cacgctgtat  240
ctgcaaatga attcactgcg cgcggaggat accgctgtgt actactgcgg tggctccggt  300
tacgccctgc acgatgacta ttacggcctt gacgtctggg gccagggaac cctcgtgact  360
gtgtccagcg gtggaggagg ttcgggcgga ggaggatcag gagggggtgg atcgcagagc  420
gcactgactc agccggcatc cgtgtccggt agccccggac agtcgattac catctcctgt  480
accggcacct cctccgacgt gggagggtac aactacgtgt cgtggtacca gcagcaccca  540
ggaaaggccc ctaagttgat gatctacgat gtgtcaaacc gcccgtctgg agtctccaac  600
```

```
cggttctccg gctccaagtc cggcaacacc gccagcctga ccattagcgg gctgcaagcc  660
gaggatgagg ccgactacta ctgctcgagc tacacatcct cgagcaccct ctacgtgttc  720
ggctcgggga ctaaggtcac cgtgctg                                      747

SEQ ID NO: 107         moltype = AA  length = 472
FEATURE                Location/Qualifiers
REGION                 1..472
                       note = source = /note="Description of Artificial Sequence:
                        Synthetic polypeptide"
source                 1..472
                       mol_type = protein
                       organism = synthetic construct
SEQUENCE: 107
QVQLQESGGG VVQPGRSLRL SCAASGFTFS SYGMHWVRQA PGKGLEWVAV ISYDGSNKYY  60
ADSVKGRFTI SRDNSKNTLY LQMNSLRAED TAVYYCGGSG YALHDDYYGL DVWGQGTLVT  120
VSSGGGGSGG GGSGGGGSQS ALTQPASVSG SPGQSITISC TGTSSDVGGY NYVSWYQQHP  180
GKAPKLMIYD VSNRPSGVSN RFSGSKSGNT ASLTISGLQA EDEADYYCSS YTSSSTLYVF  240
GSGTKVTVLT TTPAPRPPTP APTIASQPLS LRPEACRPAA GGAVHTRGLD FACDIYIWAP  300
LAGTCGVLLL SLVITLYCKR GRKKLLYIFK QPFMRPVQTT QEEDGCSCRF PEEEEGGCEL  360
RVKFSRSADA PAYQQGQNQL YNELNLGRRE EYDVLDKRRG RDPEMGGKPR RKNPQEGLYN  420
ELQKDKMAEA YSEIGMKGER RRGKGHDGLY QGLSTATKDT YDALHMQALP PR          472

SEQ ID NO: 108         moltype = DNA  length = 1416
FEATURE                Location/Qualifiers
misc_feature           1..1416
                       note = source = /note="Description of Artificial Sequence:
                        Synthetic polynucleotide"
source                 1..1416
                       mol_type = other DNA
                       organism = synthetic construct
SEQUENCE: 108
caagtgcagc tgcaggaatc cggtggcgga gtcgtgcagc ctggaaggag cctgagactc  60
tcatgcgccg cgtcagggtt caccttttcc tcctacggga tgcattgggt cagacaggcc  120
cccggaaagg gactcgaatg ggtggctgtg atcagctacg acggctccaa caagtactac  180
gccgactccg tgaaaggccg gttcactatc tcccgggaca actccaagaa cacgctgtat  240
ctgcaaatga attcactgcg cgcggaggat accgctgtgt actactgcgg tggctccggt  300
tacgccctgc acgatgacta ttacggcctt gacgtctggg gccagggaac cctcgtgact  360
gtgtccagcg gtggaggagg ttcgggcgga ggaggatcag gaggggggtgg atcgcagagc  420
gcactgactc agccggcatc cgtgtccggt agccccggac agtcgattac catctcctgt  480
accggcacct cctccgacgt gggagggtac aactacgtgt cgtggtacca gcagcaccca  540
ggaaaggccc ctaagttgat gatctacgat gtgtcaaacc gcccgtctgg agtctccaac  600
cggttctccg gctccaagtc cggcaacacc gccagcctga ccattagcgg gctgcaagcc  660
gaggatgagg ccgactacta ctgctcgagc tacacatcct cgagcaccct ctacgtgttc  720
ggctcgggga ctaaggtcac cgtgctgacc actaccccag caccgaggcc acccaccccg  780
gctcctacca tcgcctccca gcctctgtcc ctgcgtccgg aggcatgtag acccgcagct  840
ggtggggccg tgcatacccg gggtcttgac ttcgcctgcg atatctacat ttgggcccct  900
ctggctggta cttgcggggt cctgctgctt tcactcgtga tcactcttta ctgtaagcgc  960
ggtcggaaga agctgctgta catctttaag caacccttca tgaggcctgt gcagactact  1020
caagaggagg acggctgttc atgccggttc ccagaggagg aggaaggcgg ctgcgaactg  1080
cgcgtgaaat tcagccgcag cgcagatgct ccagcctacc agcaggggca gaaccagctc  1140
tacaacgaac tcaatcttgg tcggagagag gagtacgacg tgctggacaa gcggagagga  1200
cgggacccag aaatgggcgg gaagccgcgc agaaagaatc cccaagaggg cctgtacaac  1260
gagctccaaa aggataagat ggcagaagcc tatagcgaga ttggtatgaa aggggaacgc  1320
agaagaggca aaggccacga cggactgtac cagggactca gcaccgccac caaggacacc  1380
tatgacgctc ttcacatgca ggccctgccg cctcgg                             1416

SEQ ID NO: 109         moltype = AA  length = 17
FEATURE                Location/Qualifiers
REGION                 1..17
                       note = source = /note="Description of Artificial Sequence:
                        Synthetic peptide"
source                 1..17
                       mol_type = protein
                       organism = synthetic construct
SEQUENCE: 109
VISYKGSNKY YADSVKG                                                 17

SEQ ID NO: 110         moltype = AA  length = 6
FEATURE                Location/Qualifiers
REGION                 1..6
                       note = source = /note="Description of Artificial Sequence:
                        Synthetic peptide"
source                 1..6
                       mol_type = protein
                       organism = synthetic construct
SEQUENCE: 110
SYKGSN                                                             6

SEQ ID NO: 111         moltype = AA  length = 8
```

```
FEATURE               Location/Qualifiers
REGION                1..8
                      note = source = /note="Description of Artificial Sequence:
                       Synthetic peptide"
source                1..8
                      mol_type = protein
                      organism = synthetic construct
SEQUENCE: 111
ISYKGSNK                                                          8

SEQ ID NO: 112        moltype = AA  length = 123
FEATURE               Location/Qualifiers
REGION                1..123
                      note = source = /note="Description of Artificial Sequence:
                       Synthetic polypeptide"
source                1..123
                      mol_type = protein
                      organism = synthetic construct
SEQUENCE: 112
QVQLVESGGG VVQPGRSLRL SCAASGFTFS SYGMHWVRQA PGKGLEWVAV ISYKGSNKYY  60
ADSVKGRFTI SRDNSKNTLY LQMNSLRAED TAVYYCGGSG YALHDDYYGL DVWGQGTLVT  120
VSS                                                               123

SEQ ID NO: 113        moltype = DNA  length = 369
FEATURE               Location/Qualifiers
misc_feature          1..369
                      note = source = /note="Description of Artificial Sequence:
                       Synthetic polynucleotide"
source                1..369
                      mol_type = other DNA
                      organism = synthetic construct
SEQUENCE: 113
caagtgcagc ttgtcgaatc gggaggcgga gtggtgcagc ctggacgatc gctccggctc  60
tcatgtgccg cgagcggatt caccttctcg agctacggca tgcactgggt cagacaagcc  120
ccaggaaagg gcctggaatg ggtggctgtc atctcgtaca agggctcaaa caagtactac  180
gccgactccg tgaagggccg gttcaccatc tcccgcgata actccaagaa taccctctat  240
ctgcaaatga acagcctgag ggccgaggat actgcagtgt actactgcgg gggttcaggc  300
tacgcgctgc acgacgacta ctacggattg gacgtctggg gccaaggaac tcttgtgacc  360
gtgtcctct                                                         369

SEQ ID NO: 114        moltype = AA  length = 7
FEATURE               Location/Qualifiers
REGION                1..7
                      note = source = /note="Description of Artificial Sequence:
                       Synthetic peptide"
source                1..7
                      mol_type = protein
                      organism = synthetic construct
SEQUENCE: 114
EVSNRLR                                                           7

SEQ ID NO: 115        moltype = AA  length = 11
FEATURE               Location/Qualifiers
REGION                1..11
                      note = source = /note="Description of Artificial Sequence:
                       Synthetic peptide"
source                1..11
                      mol_type = protein
                      organism = synthetic construct
SEQUENCE: 115
SSYTSSSALY V                                                      11

SEQ ID NO: 116        moltype =   length =
SEQUENCE: 116
000

SEQ ID NO: 117        moltype = AA  length = 8
FEATURE               Location/Qualifiers
REGION                1..8
                      note = source = /note="Description of Artificial Sequence:
                       Synthetic peptide"
source                1..8
                      mol_type = protein
                      organism = synthetic construct
SEQUENCE: 117
YTSSSALY                                                          8

SEQ ID NO: 118        moltype = AA  length = 111
FEATURE               Location/Qualifiers
```

```
REGION                  1..111
                        note = source = /note="Description of Artificial Sequence:
                         Synthetic polypeptide"
source                  1..111
                        mol_type = protein
                        organism = synthetic construct
SEQUENCE: 118
QSALTQPASV SGSPGQSITI SCTGTSSDVG GYNYVSWYQQ HPGKAPKLMI YEVSNRLRGV  60
SNRFSGSKSG NTASLTISGL QAEDEADYYC SSYTSSSALY VFGSGTKVTV L           111

SEQ ID NO: 119          moltype = DNA  length = 333
FEATURE                 Location/Qualifiers
misc_feature            1..333
                        note = source = /note="Description of Artificial Sequence:
                         Synthetic polynucleotide"
source                  1..333
                        mol_type = other DNA
                        organism = synthetic construct
SEQUENCE: 119
cagagcgcgc tgactcagcc tgcctccgtg agcggttcgc cgggacagtc cattaccatt  60
tcgtgcaccg ggacctcctc cgacgtggga ggctacaact acgtgtcctg gtaccagcag  120
catcccggaa aggccccgaa gctgatgatc tacgaagtgt cgaacagact gcggggagtc  180
tccaaccgct tttccgggtc caagtccggc aacaccgcca gcctgaccat cagcgggctc  240
caggcagaag atgaggctga ctattactgc tcctcctaca cgtcaagctc cgccctctac  300
gtgttcgggt ccgggaccaa agtcactgtg ctg                               333

SEQ ID NO: 120          moltype = AA  length = 254
FEATURE                 Location/Qualifiers
REGION                  1..254
                        note = source = /note="Description of Artificial Sequence:
                         Synthetic polypeptide"
source                  1..254
                        mol_type = protein
                        organism = synthetic construct
SEQUENCE: 120
QVQLVESGGG VVQPGRSLRL SCAASGFTFS SYGMHWVRQA PGKGLEWVAV ISYKGSNKYY  60
ADSVKGRFTI SRDNSKNTLY LQMNSLRAED TAVYYCGGSG YALHDDYYGL DVWGQGTLVT  120
VSSGGGGSGG GGSGGGGSGG GGSQSALTQP ASVSGSPGQS ITISCTGTSS DVGGYNYVSW  180
YQQHPGKAPK LMIYEVSNRL RGVSNRFSGS KSGNTASLTI SGLQAEDEAD YYCSSYTSSS  240
ALYVFGSGTK VTVL                                                    254

SEQ ID NO: 121          moltype = DNA  length = 762
FEATURE                 Location/Qualifiers
misc_feature            1..762
                        note = source = /note="Description of Artificial Sequence:
                         Synthetic polynucleotide"
source                  1..762
                        mol_type = other DNA
                        organism = synthetic construct
SEQUENCE: 121
caagtgcagc ttgtcgaatc gggaggcgga gtggtgcagc ctggacgatc gctccggctc  60
tcatgtgccg cgagcggatt caccttctcg agctacggca tgcactgggt cagacaagcc  120
ccaggaaagg gcctggaatg ggtggctgtc atctcgtaca agggctcaaa caagtactac  180
gccgactccg tgaagggccg gttcaccatc tcccgcgata actccaagaa taccctctat  240
ctgcaaatga acagcctgag ggccgaggat actgcagtgt actactgcgg gggttcaggc  300
tacgcgctgc acgacgacta ctacggattg gacgtctggg gccaaggaac tcttgtgacc  360
gtgtcctctg gtggaggcgg atcagggggt ggcggatctg ggggtggtgg ttccgggggga  420
ggaggatcgc agagcgcgct gactcagcct gcctccgtga gcggttcgcc gggacagtcc  480
attaccattt cgtgcaccgg gacctcctcc gacgtgggag gctacaacta cgtgtcctgg  540
taccagcagc atcccggaaa ggccccgaag ctgatgatct acgaagtgtc gaacagactg  600
cggggagtct ccaaccgctt ttccgggtcc aagtccggca acaccgccag cctgaccatc  660
agcgggctcc aggcagaaga tgaggctgac tattactgct cctcctacac gtcaagctcc  720
gccctctacg tgttcgggtc cgggaccaaa gtcactgtgc tg                     762

SEQ ID NO: 122          moltype = AA  length = 477
FEATURE                 Location/Qualifiers
REGION                  1..477
                        note = source = /note="Description of Artificial Sequence:
                         Synthetic polypeptide"
source                  1..477
                        mol_type = protein
                        organism = synthetic construct
SEQUENCE: 122
QVQLVESGGG VVQPGRSLRL SCAASGFTFS SYGMHWVRQA PGKGLEWVAV ISYKGSNKYY  60
ADSVKGRFTI SRDNSKNTLY LQMNSLRAED TAVYYCGGSG YALHDDYYGL DVWGQGTLVT  120
VSSGGGGSGG GGSGGGGSGG GGSQSALTQP ASVSGSPGQS ITISCTGTSS DVGGYNYVSW  180
YQQHPGKAPK LMIYEVSNRL RGVSNRFSGS KSGNTASLTI SGLQAEDEAD YYCSSYTSSS  240
ALYVFGSGTK VTVLTTTPAP RPPTPAPTIA SQPLSLRPEA CRPAAGGAVH TRGLDFACDI  300
YIWAPLAGTC GVLLLSLVIT LYCKRGRKKL LYIFKQPFMR PVQTTQEEDG CSCRFPEEEE  360
```

-continued

```
GGCELRVKFS RSADAPAYQQ GQNQLYNELN LGRREEYDVL DKRRGRDPEM GGKPRRKNPQ  420
EGLYNELQKD KMAEAYSEIG MKGERRRGKG HDGLYQGLST ATKDTYDALH MQALPPR     477

SEQ ID NO: 123          moltype = DNA  length = 1431
FEATURE                 Location/Qualifiers
misc_feature            1..1431
                        note = source = /note="Description of Artificial Sequence:
                         Synthetic polynucleotide"
source                  1..1431
                        mol_type = other DNA
                        organism = synthetic construct
SEQUENCE: 123
caagtgcagc ttgtcgaatc gggaggcgga gtggtgcagc ctggacgatc gctccggctc  60
tcatgtgccg cgagcggatt caccttctcg agctacggca tgcactgggt cagacaagcc  120
ccaggaaagg gcctggaatg ggtggctgtc atctcgtaca agggctcaaa caagtactac  180
gccgactccg tgaagggccg gttcaccatc tcccgcgata actccaagaa taccctctat  240
ctgcaaatga acagcctgag ggccgaggat actgcagtgt actactgcgg gggttcaggc  300
tacgcgctgc acgacgacta ctacggattg gacgtctggg gccaaggaac tcttgtgacc  360
gtgtcctctg gtggaggcgg atcagggggt ggcggatctg gggtggtgg ttccgggggga  420
ggaggatcgc agagcgcgct gactcagcct gcctccgtga gcggttcgcc gggacagtcc  480
attaccattt cgtgcaccgg gacctcctcc gacgtgggag gctacaacta cgtgtcctgg  540
taccagcagc atcccggaaa ggccccgaag ctgatgatct acgaagtgtc gaacagactg  600
cggggagtct ccaaccgctt ttccgggtcc aagtccggca acaccgccag cctgaccatc  660
agcgggctcc aggcagaaga tgaggctgac tattactgct cctcctacac gtcaagctcc  720
gccctctacg tgttcgggtc cgggaccaaa gtcactgtgc tgaccactac cccagcaccg  780
aggccaccca ccccggctcc taccatcgcc tcccagcctc tgtccctgcg tccggaggca  840
tgtagacccg cagctggtgg ggccgtgcat acccggggtc ttgacttcgc ctgcgatatc  900
tacatttggg cccctctggc tggtacttgc ggggtcctgc tgctttcact cgtgatcact  960
ctttactgta agcgcggtcg gaagaagctg ctgtacatct ttaagcaacc cttcatgagg  1020
cctgtgcaga ctactcaaga ggaggacggc tgttcatgcc ggttcccaga ggaggaggaa  1080
ggcggctgcg aactgcgcgt gaaattcagc cgcagcgcag atgctccagc ctaccagcag  1140
gggcagaacc agctctacaa cgaactcaat cttggtcgga gagaggagta cgacgtgctg  1200
gacaagcgga gaggacggga cccagaaatg ggcgggaagc cgcgcagaaa gaatccccaa  1260
gagggcctgt acaacgagct ccaaaaggat aagatggcag aagcctatag cgagattggt  1320
atgaaagggg aacgcagaag aggcaaaggc cacgacggac tgtaccaggg actcagcacc  1380
gccaccaagg acacctatga cgctcttcac atgcaggccc tgccgcctcg g           1431

SEQ ID NO: 124          moltype = AA  length = 111
FEATURE                 Location/Qualifiers
REGION                  1..111
                        note = source = /note="Description of Artificial Sequence:
                         Synthetic polypeptide"
source                  1..111
                        mol_type = protein
                        organism = synthetic construct
SEQUENCE: 124
QSALTQPASV SGSPGQSITI SCTGTSSDVG GYNYVSWYQQ HPGKAPKLMI YEVSNRLRGV  60
SNRFSGSKSG NTASLTISGL QAEDEADYYC SSYTSSSTLY VFGSGTKVTV L           111

SEQ ID NO: 125          moltype = DNA  length = 333
FEATURE                 Location/Qualifiers
misc_feature            1..333
                        note = source = /note="Description of Artificial Sequence:
                         Synthetic polynucleotide"
source                  1..333
                        mol_type = other DNA
                        organism = synthetic construct
SEQUENCE: 125
cagagcgcgc tgactcagcc tgcctccgtg agcggttcgc cgggacagtc cattaccatt  60
tcgtgcaccg ggacctcctc cgacgtggga ggctacaact acgtgtcctg gtaccagcag  120
catcccggaa aggccccgaa gctgatgatc tacgaagtgt cgaacagact gcggggagtc  180
tccaaccgct tttccgggtc caagtccggc aacaccgcca gcctgaccat cagcgggctc  240
caggcagaag atgaggctga ctattactgc tcctcctaca cgtcaagctc caccctctac  300
gtgttcgggt ccgggaccaa agtcactgtg ctg                                333

SEQ ID NO: 126          moltype = AA  length = 254
FEATURE                 Location/Qualifiers
REGION                  1..254
                        note = source = /note="Description of Artificial Sequence:
                         Synthetic polypeptide"
source                  1..254
                        mol_type = protein
                        organism = synthetic construct
SEQUENCE: 126
QVQLVESGGG VVQPGRSLRL SCAASGFTFS SYGMHWVRQA PGKGLEWVAV ISYKGSNKYY  60
ADSVKGRFTI SRDNSKNTLY LQMNSLRAED TAVYYCGGSG YALHDDYYGL DVWGQGTLVT  120
VSSGGGGSGG GGSGGGGSGG GGSQSALTQP ASVSGSPGQS ITISCTGTSS DVGGYNYVSW  180
YQQHPGKAPK LMIYEVSNRL RGVSNRFSGS KSGNTASLTI SGLQAEDEAD YYCSSYTSSS  240
TLYVFGSGTK VTVL                                                     254
```

```
SEQ ID NO: 127          moltype = DNA  length = 762
FEATURE                 Location/Qualifiers
misc_feature            1..762
                        note = source = /note="Description of Artificial Sequence:
                         Synthetic polynucleotide"
source                  1..762
                        mol_type = other DNA
                        organism = synthetic construct
SEQUENCE: 127
caagtgcagc ttgtcgaatc gggaggcgga gtggtgcagc ctggacgatc gctccggctc  60
tcatgtgccg cgagcggatt caccttctcg agctacggca tgcactgggt cagacaagcc  120
ccaggaaagg gcctggaatg ggtggctgtc atctcgtaca agggctcaaa caagtactac  180
gccgactccg tgaagggccg gttcaccatc tcccgcgata actccaagaa taccctctat  240
ctgcaaatga acagcctgag ggccgaggat actgcagtgt actactgcgg gggttcaggc  300
tacgcgctgc acgacgacta ctacggattg gacgtctggg gccaaggaac tcttgtgacc  360
gtgtcctctg gtggaggcgg atcagggggt ggcggatctg gggggtggtgg ttccggggga  420
ggaggatcgc agagcgcgct gactcagcct gcctccgtga gcggttcgcc gggacagtcc  480
attaccattt cgtgcaccgg gacctcctcc gacgtgggag gctacaacta cgtgtcctgg  540
taccagcagc atcccggaaa ggccccgaag ctgatgatct acgaagtgtc gaacagactg  600
cggggagtct ccaaccgctt ttccgggtcc aagtccggca acaccgccag cctgaccatc  660
agcgggctcc aggcagaaga tgaggctgac tattactgct cctcctacac gtcaagctcc  720
accctctacg tgttcgggtc cgggaccaaa gtcactgtgc tg                    762

SEQ ID NO: 128          moltype = AA  length = 477
FEATURE                 Location/Qualifiers
REGION                  1..477
                        note = source = /note="Description of Artificial Sequence:
                         Synthetic polypeptide"
source                  1..477
                        mol_type = protein
                        organism = synthetic construct
SEQUENCE: 128
QVQLVESGGG VVQPGRSLRL SCAASGFTFS SYGMHWVRQA PGKGLEWVAV ISYKGSNKYY  60
ADSVKGRFTI SRDNSKNTLY LQMNSLRAED TAVYYCGGSG YALHDDYYGL DVWGQGTLVT  120
VSSGGGGSGG GGSGGGGSGG GGSQSALTQP ASVSGSPGQS ITISCTGTSS DVGGYNYVSW  180
YQQHPGKAPK LMIYEVSNRL RGVSNRFSGS KSGNTASLTI SGLQAEDEAD YYCSSYTSSS  240
TLYVFGSGTK VTVLTTTPAP RPPTPAPTIA SQPLSLRPEA CRPAAGGAVH TRGLDFACDI  300
YIWAPLAGTC GVLLLSLVIT LYCKRGRKKL LYIFKQPFMR PVQTTQEEDG CSCRFPEEEE  360
GGCELRVKFS RSADAPAYQQ GQNQLYNELN LGRREEYDVL DKRRGRDPEM GGKPRRKNPQ  420
EGLYNELQKD KMAEAYSEIG MKGERRRGKG HDGLYQGLST ATKDTYDALH MQALPPR     477

SEQ ID NO: 129          moltype = DNA  length = 1431
FEATURE                 Location/Qualifiers
misc_feature            1..1431
                        note = source = /note="Description of Artificial Sequence:
                         Synthetic polynucleotide"
source                  1..1431
                        mol_type = other DNA
                        organism = synthetic construct
SEQUENCE: 129
caagtgcagc ttgtcgaatc gggaggcgga gtggtgcagc ctggacgatc gctccggctc  60
tcatgtgccg cgagcggatt caccttctcg agctacggca tgcactgggt cagacaagcc  120
ccaggaaagg gcctggaatg ggtggctgtc atctcgtaca agggctcaaa caagtactac  180
gccgactccg tgaagggccg gttcaccatc tcccgcgata actccaagaa taccctctat  240
ctgcaaatga acagcctgag ggccgaggat actgcagtgt actactgcgg gggttcaggc  300
tacgcgctgc acgacgacta ctacggattg gacgtctggg gccaaggaac tcttgtgacc  360
gtgtcctctg gtggaggcgg atcagggggt ggcggatctg gggggtggtgg ttccggggga  420
ggaggatcgc agagcgcgct gactcagcct gcctccgtga gcggttcgcc gggacagtcc  480
attaccattt cgtgcaccgg gacctcctcc gacgtgggag gctacaacta cgtgtcctgg  540
taccagcagc atcccggaaa ggccccgaag ctgatgatct acgaagtgtc gaacagactg  600
cggggagtct ccaaccgctt ttccgggtcc aagtccggca acaccgccag cctgaccatc  660
agcgggctcc aggcagaaga tgaggctgac tattactgct cctcctacac gtcaagctcc  720
accctctacg tgttcgggtc cgggaccaaa gtcactgtgc tgaccactac cccagcaccg  780
aggccaccca ccccggctcc taccatcgcc tcccagcctc tgtccctgcg tccggaggca  840
tgtagacccg cagctggtgg ggccgtgcat acccggggtc ttgacttcgc ctgcgatatc  900
tacatttggg cccctctggc tggtacttgc ggggtcctgc tgctttcact cgtgatcact  960
ctttactgta agcgcggtcg gaagaagctg ctgtacatct ttaagcaacc cttcatgagg  1020
cctgtgcaga ctactcaaga ggaggacggc tgttcatgcc ggttcccaga ggaggaggaa  1080
ggcggctgcg aactgcgcgt gaaattcagc cgcagcgcag atgctccagc ctaccagcag  1140
gggcagaacc agctctacaa cgaactcaat cttggtcgga gagaggagta cgacgtgctg  1200
gacaagcgga gaggacggga cccagaaatg ggcgggaagc cgcgcagaaa gaatccccaa  1260
gagggcctgt acaacgagct ccaaaaggat aagatggcag aagcctatag cgagattggt  1320
atgaaagggg aacgcagaag aggcaaaggc cacgacggac tgtaccaggg actcagcacc  1380
gccaccaagg acacctatga cgctcttcac atgcaggccc tgccgcctcg g           1431

SEQ ID NO: 130          moltype = AA  length = 17
FEATURE                 Location/Qualifiers
VARIANT                 5
```

```
                        note = /replace="Lys"
SITE                    1..17
                        note = /note="Variant residues given in the sequence have
                         no preference with respect to those in the annotations for
                         variant positions"
REGION                  1..17
                        note = source = /note="Description of Artificial Sequence:
                         Synthetic peptide"
source                  1..17
                        mol_type = protein
                        organism = synthetic construct
SEQUENCE: 130
VISYDGSNKY YADSVKG                                                          17

SEQ ID NO: 131          moltype = AA  length = 7
FEATURE                 Location/Qualifiers
VARIANT                 1
                        note = /replace="Glu"
VARIANT                 6
                        note = /replace="Leu"
VARIANT                 7
                        note = /replace="Arg"
SITE                    1..7
                        note = /note="Variant residues given in the sequence have
                         no preference with respect to those in the annotations for
                         variant positions"
REGION                  1..7
                        note = source = /note="Description of Artificial Sequence:
                         Synthetic peptide"
source                  1..7
                        mol_type = protein
                        organism = synthetic construct
SEQUENCE: 131
DVSNRPS                                                                     7

SEQ ID NO: 132          moltype = AA  length = 11
FEATURE                 Location/Qualifiers
VARIANT                 8
                        note = /replace="Ala"
SITE                    1..11
                        note = /note="Variant residues given in the sequence have
                         no preference with respect to those in the annotations for
                         variant positions"
REGION                  1..11
                        note = source = /note="Description of Artificial Sequence:
                         Synthetic peptide"
source                  1..11
                        mol_type = protein
                        organism = synthetic construct
SEQUENCE: 132
SSYTSSSTLY V                                                                11

SEQ ID NO: 133          moltype = AA  length = 6
FEATURE                 Location/Qualifiers
VARIANT                 3
                        note = /replace="Lys"
SITE                    1..6
                        note = /note="Variant residues given in the sequence have
                         no preference with respect to those in the annotations for
                         variant positions"
REGION                  1..6
                        note = source = /note="Description of Artificial Sequence:
                         Synthetic peptide"
source                  1..6
                        mol_type = protein
                        organism = synthetic construct
SEQUENCE: 133
SYDGSN                                                                      6

SEQ ID NO: 134          moltype =   length =
SEQUENCE: 134
000

SEQ ID NO: 135          moltype = AA  length = 8
FEATURE                 Location/Qualifiers
VARIANT                 6
                        note = /replace="Ala"
SITE                    1..8
                        note = /note="Variant residues given in the sequence have
```

```
                         no preference with respect to those in the annotations for
                         variant positions"
REGION                  1..8
                        note = source = /note="Description of Artificial Sequence:
                         Synthetic peptide"
source                  1..8
                        mol_type = protein
                        organism = synthetic construct
SEQUENCE: 135
YTSSSTLY                                                                     8

SEQ ID NO: 136          moltype = AA  length = 8
FEATURE                 Location/Qualifiers
VARIANT                 4
                        note = /replace="Lys"
SITE                    1..8
                        note = /note="Variant residues given in the sequence have
                         no preference with respect to those in the annotations for
                         variant positions"
REGION                  1..8
                        note = source = /note="Description of Artificial Sequence:
                         Synthetic peptide"
source                  1..8
                        mol_type = protein
                        organism = synthetic construct
SEQUENCE: 136
ISYDGSNK                                                                     8

SEQ ID NO: 137          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 137
GFWMS                                                                        5

SEQ ID NO: 138          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 138
NIKQDGSEKY YVDSVRG                                                           17

SEQ ID NO: 139          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 139
ALDYYGMDV                                                                    9

SEQ ID NO: 140          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 140
GFTFSGF                                                                      7

SEQ ID NO: 141          moltype = AA  length = 6
FEATURE                 Location/Qualifiers
REGION                  1..6
                        note = source = /note="Description of Artificial Sequence:
                         Synthetic peptide"
source                  1..6
                        mol_type = protein
```

```
                        organism = synthetic construct
SEQUENCE: 141
KQDGSE                                                      6

SEQ ID NO: 142          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 142
GFTFSGFW                                                    8

SEQ ID NO: 143          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 143
IKQDGSEK                                                    8

SEQ ID NO: 144          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 144
ARALDYYGMD V                                                11

SEQ ID NO: 145          moltype = AA  length = 118
FEATURE                 Location/Qualifiers
REGION                  1..118
                        note = source = /note="Description of Artificial Sequence:
                         Synthetic polypeptide"
source                  1..118
                        mol_type = protein
                        organism = synthetic construct
SEQUENCE: 145
EVQLVESGGG LVQPGGSLRL SCAASGFTFS GFWMSWVRQA PGKGLEWVAN IKQDGSEKYY  60
VDSVRGRFTI SRDNAKNSLY LQMNSLRAED TAVYYCARAL DYYGMDVWGQ GTTVTVSS    118

SEQ ID NO: 146          moltype = DNA  length = 354
FEATURE                 Location/Qualifiers
misc_feature            1..354
                        note = source = /note="Description of Artificial Sequence:
                         Synthetic polynucleotide"
source                  1..354
                        mol_type = other DNA
                        organism = synthetic construct
SEQUENCE: 146
gaagtgcaac tggtggagag cggtggaggg cttgtccagc ccggaggatc gctgcggctg  60
tcctgtgctg cgtccgggtt caccttctcc ggcttctgga tgtcctgggt cagacaggca  120
ccgggaaagg gcctcgaatg ggtggccaac atcaagcagg atggctccga gaagtactac  180
gtcgactccg tgagaggccg cttcaccatc tcccgggaca acgccaagaa ctcgctgtac  240
ctccaaatga atagcctcag ggcggaagat actgctgtgt attactgcgc acgcgccctt  300
gactactacg gcatggacgt ctggggccaa gggaccactg tgaccgtgtc tagc        354

SEQ ID NO: 147          moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 147
RSSQSLLDSD DGNTYLD                                          17

SEQ ID NO: 148          moltype = AA  length = 7
FEATURE                 Location/Qualifiers
REGION                  1..7
```

```
                        note = source = /note="Description of Artificial Sequence:
                         Synthetic peptide"
source                  1..7
                        mol_type = protein
                        organism = synthetic construct
SEQUENCE: 148
TLSYRAS                                                                    7

SEQ ID NO: 149          moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 149
TQRLEFPSIT                                                                 10

SEQ ID NO: 150          moltype = AA  length = 13
FEATURE                 Location/Qualifiers
REGION                  1..13
                        note = source = /note="Description of Artificial Sequence:
                         Synthetic peptide"
source                  1..13
                        mol_type = protein
                        organism = synthetic construct
SEQUENCE: 150
SQSLLDSDDG NTY                                                             13

SEQ ID NO: 151          moltype =   length =
SEQUENCE: 151
000

SEQ ID NO: 152          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 152
RLEFPSI                                                                    7

SEQ ID NO: 153          moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 153
QSLLDSDDGN TY                                                              12

SEQ ID NO: 154          moltype = AA  length = 114
FEATURE                 Location/Qualifiers
REGION                  1..114
                        note = source = /note="Description of Artificial Sequence:
                         Synthetic polypeptide"
source                  1..114
                        mol_type = protein
                        organism = synthetic construct
SEQUENCE: 154
DIVMTQTPLS LPVTPGEPAS ISCRSSQSLL DSDDGNTYLD WYLQKPGQSP RLLIYTLSYR  60
ASGVPDRFSG SGSGTDFTLK ISRVEAEDVG LYYCTQRLEF PSITFGQGTR LEIK        114

SEQ ID NO: 155          moltype = DNA  length = 342
FEATURE                 Location/Qualifiers
misc_feature            1..342
                        note = source = /note="Description of Artificial Sequence:
                         Synthetic polynucleotide"
source                  1..342
                        mol_type = other DNA
                        organism = synthetic construct
SEQUENCE: 155
gatatcgtga tgacccagac tcccctgtcc ctgcctgtga ctcccggaga accagcctcc  60
atttcctgcc ggtcctccca gtccctgctg gacagcgacg acggcaacac ttacctggac  120
```

```
tggtacttgc agaagccggg ccaatcgcct cgcctgctga tctataccct gtcataccgg  180
gcctcaggag tgcctgaccg cttctcggga tcagggagcg ggaccgattt caccctgaaa  240
atttcccgag tggaagccga ggacgtcgga ctgtactact gcacccagcg cctcgaattc  300
ccgtcgatta cgtttggaca gggtacccgg cttgagatca ag                     342

SEQ ID NO: 156          moltype = AA  length = 252
FEATURE                 Location/Qualifiers
REGION                  1..252
                        note = source = /note="Description of Artificial Sequence:
                         Synthetic polypeptide"
source                  1..252
                        mol_type = protein
                        organism = synthetic construct
SEQUENCE: 156
EVQLVESGGG LVQPGGSLRL SCAASGFTFS GFWMSWVRQA PGKGLEWVAN IKQDGSEKYY  60
VDSVRGRFTI SRDNAKNSLY LQMNSLRAED TAVYYCARAL DYYGMDVWGQ GTTVTVSSGG  120
GGSGGGGSGG GGSGGGGSDI VMTQTPLSLP VTPGEPASIS CRSSQSLLDS DDGNTYLDWY  180
LQKPGQSPRL LIYTLSYRAS GVPDRFSGSG SGTDFTLKIS RVEAEDVGLY YCTQRLEFPS  240
ITFGQGTRLE IK                                                      252

SEQ ID NO: 157          moltype = DNA  length = 756
FEATURE                 Location/Qualifiers
misc_feature            1..756
                        note = source = /note="Description of Artificial Sequence:
                         Synthetic polynucleotide"
source                  1..756
                        mol_type = other DNA
                        organism = synthetic construct
SEQUENCE: 157
gaagtgcaac tggtggagag cggtggaggg cttgtccagc ccggaggatc gctgcggctg  60
tcctgtgctg cgtccgggtt caccttctcc ggcttctgga tgtcctgggt cagacaggca  120
ccgggaaagg gcctcgaatg ggtggccaac atcaagcagg atggctccga gaagtactac  180
gtcgactccg tgagaggccg cttcaccatc tcccgggaca acgccaagaa ctcgctgtac  240
ctccaaatga atagcctcag ggcggaagat actgctgtgt attactgcgc acgcgccctt  300
gactactacg gcatggacgt ctggggccaa gggaccactg tgaccgtgtc tagcggaggc  360
ggaggttcag gggcggtgg atcaggcgga ggaggatcgg ggggtggtgg atcggatatc  420
gtgatgaccc agactcccct gtccctgcct gtgactcccg gagaaccagc ctccatttcc  480
tgccggtcct cccagtccct gctggacagc gacgacggca acacttacct ggactggtac  540
ttgcagaagc cgggccaatc gcctcgcctg ctgatctata ccctgtcata ccgggcctca  600
ggagtgcctg accgcttctc gggatcaggg agcgggaccg atttcaccct gaaaatttcc  660
cgagtggaag ccgaggacgt cggactgtac tactgcaccc agcgcctcga attcccgtcg  720
attacgtttg gacagggtac ccggcttgag atcaag                            756

SEQ ID NO: 158          moltype = AA  length = 475
FEATURE                 Location/Qualifiers
REGION                  1..475
                        note = source = /note="Description of Artificial Sequence:
                         Synthetic polypeptide"
source                  1..475
                        mol_type = protein
                        organism = synthetic construct
SEQUENCE: 158
EVQLVESGGG LVQPGGSLRL SCAASGFTFS GFWMSWVRQA PGKGLEWVAN IKQDGSEKYY  60
VDSVRGRFTI SRDNAKNSLY LQMNSLRAED TAVYYCARAL DYYGMDVWGQ GTTVTVSSGG  120
GGSGGGGSGG GGSGGGGSDI VMTQTPLSLP VTPGEPASIS CRSSQSLLDS DDGNTYLDWY  180
LQKPGQSPRL LIYTLSYRAS GVPDRFSGSG SGTDFTLKIS RVEAEDVGLY YCTQRLEFPS  240
ITFGQGTRLE IKTTTPAPRP PTPAPTIASQ PLSLRPEACR PAAGGAVHTR GLDFACDIYI  300
WAPLAGTCGV LLLSLVITLY CKRGRKKLLY IFKQPFMRPV QTTQEEDGCS CRFPEEEEGG  360
CELRVKFSRS ADAPAYQQGQ NQLYNELNLG RREEYDVLDK RRGRDPEMGG KPRRKNPQEG  420
LYNELQKDKM AEAYSEIGMK GERRRGKGHD GLYQGLSTAT KDTYDALHMQ ALPPR       475

SEQ ID NO: 159          moltype = DNA  length = 1425
FEATURE                 Location/Qualifiers
misc_feature            1..1425
                        note = source = /note="Description of Artificial Sequence:
                         Synthetic polynucleotide"
source                  1..1425
                        mol_type = other DNA
                        organism = synthetic construct
SEQUENCE: 159
gaagtgcaac tggtggagag cggtggaggg cttgtccagc ccggaggatc gctgcggctg  60
tcctgtgctg cgtccgggtt caccttctcc ggcttctgga tgtcctgggt cagacaggca  120
ccgggaaagg gcctcgaatg ggtggccaac atcaagcagg atggctccga gaagtactac  180
gtcgactccg tgagaggccg cttcaccatc tcccgggaca acgccaagaa ctcgctgtac  240
ctccaaatga atagcctcag ggcggaagat actgctgtgt attactgcgc acgcgccctt  300
gactactacg gcatggacgt ctggggccaa gggaccactg tgaccgtgtc tagcggaggc  360
ggaggttcag gggcggtgg atcaggcgga ggaggatcgg ggggtggtgg atcggatatc  420
gtgatgaccc agactcccct gtccctgcct gtgactcccg gagaaccagc ctccatttcc  480
tgccggtcct cccagtccct gctggacagc gacgacggca acacttacct ggactggtac  540
```

```
ttgcagaagc cgggccaatc gcctcgcctg ctgatctata ccctgtcata ccgggcctca  600
ggagtgcctg accgcttctc gggatcaggg agcgggaccg atttcaccct gaaaatttcc  660
cgagtggaag ccgaggacgt cggactgtac tactgcaccc agcgcctcga attcccgtcg  720
attacgtttg gacagggtac ccggcttgag atcaagacca ctaccccagc accgaggcca  780
cccaccccgg ctcctaccat cgcctcccag cctctgtccc tgcgtccgga ggcatgtaga  840
cccgcagctg gtggggccgt gcatacccgg ggtcttgact tcgcctgcga tatctacatt  900
tgggcccctc tggctggtac ttgcggggtc ctgctgcttt cactcgtgat cactctttac  960
tgtaagcgcg gtcggaagaa gctgctgtac atctttaagc aacccttcat gaggcctgtg  1020
cagactactc aagaggagga cggctgttca tgccggttcc cagaggagga ggaaggcggc  1080
tgcgaactgc gcgtgaaatt cagccgcagc gcagatgctc cagcctacca gcaggggcag  1140
aaccagctct acaacgaact caatcttggt cggagagagg agtacgacgt gctggacaag  1200
cggagaggac gggacccaga aatgggcggg aagccgcgca gaaagaatcc ccaagagggc  1260
ctgtacaacg agctccaaaa ggataagatg gcagaagcct atagcgagat tggtatgaaa  1320
ggggaacgca gaagaggcaa aggccacgac ggactgtacc agggactcag caccgccacc  1380
aaggacacct atgacgctct tcacatgcag gccctgccgc ctcgg                  1425

SEQ ID NO: 160         moltype = AA  length = 5
FEATURE                Location/Qualifiers
REGION                 1..5
                       note = source = /note="Description of Artificial Sequence:
                        Synthetic peptide"
source                 1..5
                       mol_type = protein
                       organism = synthetic construct
SEQUENCE: 160
SFRMN                                                                5

SEQ ID NO: 161         moltype = AA  length = 17
FEATURE                Location/Qualifiers
REGION                 1..17
                       note = source = /note="Description of Artificial Sequence:
                        Synthetic peptide"
source                 1..17
                       mol_type = protein
                       organism = synthetic construct
SEQUENCE: 161
SISSSSSYIY YADSVKG                                                   17

SEQ ID NO: 162         moltype = AA  length = 9
FEATURE                Location/Qualifiers
REGION                 1..9
                       note = source = /note="Description of Artificial Sequence:
                        Synthetic peptide"
source                 1..9
                       mol_type = protein
                       organism = synthetic construct
SEQUENCE: 162
WLSYYGMDV                                                            9

SEQ ID NO: 163         moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 163
GFTFSSF                                                              7

SEQ ID NO: 164         moltype = AA  length = 6
FEATURE                Location/Qualifiers
REGION                 1..6
                       note = source = /note="Description of Artificial Sequence:
                        Synthetic peptide"
source                 1..6
                       mol_type = protein
                       organism = synthetic construct
SEQUENCE: 164
SSSSSY                                                               6

SEQ ID NO: 165         moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
```

```
SEQUENCE: 165
GFTFSSFR                                                        8

SEQ ID NO: 166          moltype = AA  length = 8
FEATURE                 Location/Qualifiers
REGION                  1..8
                        note = source = /note="Description of Artificial Sequence:
                         Synthetic peptide"
source                  1..8
                        mol_type = protein
                        organism = synthetic construct
SEQUENCE: 166
ISSSSSYI                                                        8

SEQ ID NO: 167          moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 167
ARWLSYYGMD V                                                    11

SEQ ID NO: 168          moltype = AA  length = 118
FEATURE                 Location/Qualifiers
REGION                  1..118
                        note = source = /note="Description of Artificial Sequence:
                         Synthetic polypeptide"
source                  1..118
                        mol_type = protein
                        organism = synthetic construct
SEQUENCE: 168
EVQLVESGGG LVKPGGSLRL SCAASGFTFS SFRMNWVRQA PGKGLEWVSS ISSSSSYIYY  60
ADSVKGRFTI SRDNAKNSLY LQMNSLRAED TAVYYCARWL SYYGMDVWGQ GTTVTVSS    118

SEQ ID NO: 169          moltype = DNA  length = 354
FEATURE                 Location/Qualifiers
misc_feature            1..354
                        note = source = /note="Description of Artificial Sequence:
                         Synthetic polynucleotide"
source                  1..354
                        mol_type = other DNA
                        organism = synthetic construct
SEQUENCE: 169
gaagtgcaac tggtggagag cggtggaggg cttgtcaagc ccggaggatc gctgcggctg  60
tcctgtgctg cgtccgggtt caccttctcc tcgttccgca tgaactgggt cagacaggca  120
ccgggaaagg gcctcgaatg ggtgtcctca atctcatcgt cctcgtccta catctactac  180
gccgactccg tgaaaggccg cttcaccatc tcccgggaca acgccaagaa ctcgctgtac  240
ctccaaatga atagcctcag ggcggaagat actgctgtgt attactgcgc acgctggctt  300
tcctactacg gcatggacgt ctggggccaa gggaccactg tgaccgtgtc tagc        354

SEQ ID NO: 170          moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 170
TLSFRAS                                                         7

SEQ ID NO: 171          moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 171
MQRIGFPIT                                                       9

SEQ ID NO: 172          moltype = AA  length = 6
FEATURE                 Location/Qualifiers
REGION                  1..6
                        note = source = /note="Description of Artificial Sequence:
```

-continued

```
                          Synthetic peptide"
source                    1..6
                          mol_type = protein
                          organism = synthetic construct
SEQUENCE: 172
RIGFPI                                                                6

SEQ ID NO: 173            moltype = AA  length = 113
FEATURE                   Location/Qualifiers
REGION                    1..113
                          note = source = /note="Description of Artificial Sequence:
                           Synthetic polypeptide"
source                    1..113
                          mol_type = protein
                          organism = synthetic construct
SEQUENCE: 173
DIVMTQTPLS LPVTPGEPAS ISCRSSQSLL DSDDGNTYLD WYLQKPGQSP QLLIYTLSFR  60
ASGVPDRFSG SGSGTDFTLK IRRVEAEDVG VYYCMQRIGF PITFGQGTRL EIK         113

SEQ ID NO: 174            moltype = DNA  length = 339
FEATURE                   Location/Qualifiers
misc_feature              1..339
                          note = source = /note="Description of Artificial Sequence:
                           Synthetic polynucleotide"
source                    1..339
                          mol_type = other DNA
                          organism = synthetic construct
SEQUENCE: 174
gatatcgtga tgacccagac tcccctgtcc ctgcctgtga ctcccggaga accagcctcc  60
atttcctgcc ggtcctccca gtccctgctg gacagcgacg acggcaacac ttacctggac  120
tggtacttgc agaagccggg ccaatcgcct cagctgctga tctataccct gtcattccgg  180
gcctcaggag tgcctgaccg cttctcggga tcagggagcg ggaccgattt caccctgaaa  240
attaggcgag tggaagccga ggacgtcgga gtgtactact gcatgcagcg catcggcttc  300
ccgattacgt ttggacaggg tacccggctt gagatcaag                         339

SEQ ID NO: 175            moltype = AA  length = 251
FEATURE                   Location/Qualifiers
REGION                    1..251
                          note = source = /note="Description of Artificial Sequence:
                           Synthetic polypeptide"
source                    1..251
                          mol_type = protein
                          organism = synthetic construct
SEQUENCE: 175
EVQLVESGGG LVKPGGSLRL SCAASGFTFS SFRMNWVRQA PGKGLEWVSS ISSSSSYIYY  60
ADSVKGRFTI SRDNAKNSLY LQMNSLRAED TAVYYCARWL SYYGMDVWGQ GTTVTVSSGG  120
GGSGGGGSGG GGSGGGGSDI VMTQTPLSLP VTPGEPASIS CRSSQSLLDS DDGNTYLDWY  180
LQKPGQSPQL LIYTLSFRAS GVPDRFSGSG SGTDFTLKIR RVEAEDVGVY YCMQRIGFPI  240
TFGQGTRLEI K                                                       251

SEQ ID NO: 176            moltype = DNA  length = 753
FEATURE                   Location/Qualifiers
misc_feature              1..753
                          note = source = /note="Description of Artificial Sequence:
                           Synthetic polynucleotide"
source                    1..753
                          mol_type = other DNA
                          organism = synthetic construct
SEQUENCE: 176
gaagtgcaac tggtggagag cggtggaggg cttgtcaagc ccggaggatc gctgcggctg  60
tcctgtgctg cgtccgggtt caccttctcc tcgttccgca tgaactgggt cagacaggca  120
ccgggaaagg gcctcgaatg ggtgtcctca atctcatcgt cctcgtccta catctactac  180
gccgactccg tgaaaggccg cttcaccatc tcccgggaca acgccaagaa ctcgctgtac  240
ctccaaatga atagcctcag ggcggaagat actgctgtgt attactgcgc acgctggctt  300
tcctactacg gcatggacgt ctggggccaa gggaccactg tgaccgtgtc tagcggaggc  360
ggaggttcag gggcggtgg atcaggcgga ggaggatcgg ggggtggtgg atcggatatc  420
gtgatgaccc agactcccct gtccctgcct gtgactcccg gagaaccagc ctccatttcc  480
tgccggtcct cccagtccct gctggacagc gacgacggca acacttacct ggactggtac  540
ttgcagaagc cgggccaatc gcctcagctg ctgatctata ccctgtcatt ccgggcctca  600
ggagtgcctg accgcttctc gggatcaggg agcgggaccg atttcaccct gaaaattagg  660
cgagtggaag ccgaggacgt cggagtgtac tactgcatgc agcgcatcgg cttcccgatt  720
acgtttggac agggtacccg gcttgagatc aag                               753

SEQ ID NO: 177            moltype = AA  length = 474
FEATURE                   Location/Qualifiers
REGION                    1..474
                          note = source = /note="Description of Artificial Sequence:
                           Synthetic polypeptide"
source                    1..474
```

```
                         mol_type = protein
                         organism = synthetic construct
SEQUENCE: 177
EVQLVESGGG LVKPGGSLRL SCAASGFTFS SFRMNWVRQA PGKGLEWVSS ISSSSSYIYY  60
ADSVKGRFTI SRDNAKNSLY LQMNSLRAED TAVYYCARWL SYYGMDVWGQ GTTVTVSSGG  120
GGSGGGGSGG GGSGGGGSDI VMTQTPLSLP VTPGEPASIS CRSSQSLLDS DDGNTYLDWY  180
LQKPGQSPQL LIYTLSFRAS GVPDRFSGSG SGTDFTLKIR RVEAEDVGVY YCMQRIGFPI  240
TFGQGTRLEI KTTTPAPRPP TPAPTIASQP LSLRPEACRP AAGGAVHTRG LDFACDIYIW  300
APLAGTCGVL LLSLVITLYC KRGRKKLLYI FKQPFMRPVQ TTQEEDGCSC RFPEEEEGGC  360
ELRVKFSRSA DAPAYQQGQN QLYNELNLGR REEYDVLDKR RGRDPEMGGK PRRKNPQEGL  420
YNELQKDKMA EAYSEIGMKG ERRRGKGHDG LYQGLSTATK DTYDALHMQA LPPR        474

SEQ ID NO: 178           moltype = DNA  length = 1422
FEATURE                  Location/Qualifiers
misc_feature             1..1422
                         note = source = /note="Description of Artificial Sequence:
                          Synthetic polynucleotide"
source                   1..1422
                         mol_type = other DNA
                         organism = synthetic construct
SEQUENCE: 178
gaagtgcaac tggtggagag cggtggaggg cttgtcaagc ccggaggatc gctgcggctg  60
tcctgtgctg cgtccgggtt caccttctcc tcgttccgca tgaactgggt cagacaggca  120
ccgggaaagg gcctcgaatg ggtgtcctca atctcatcgt cctcgtccta catctactac  180
gccgactccg tgaaaggccg cttcaccatc tcccgggaca acgccaagaa ctcgctgtac  240
ctccaaatga atagcctcag ggcggaagat actgctgtgt attactgcgc acgctggctt  300
tcctactacg gcatggacgt ctggggccaa gggaccactg tgaccgtgtc tagcggaggc  360
ggaggttcag gggcggtgg atcaggcgga ggaggatcgg ggggtggtgg atcggatatc  420
gtgatgaccc agactcccct gtccctgcct gtgactcccg gagaaccagc ctccatttcc  480
tgccggtcct cccagtccct gctggacagc gacgacggca acacttacct ggactggtac  540
ttgcagaagc cgggccaatc gcctcagctg ctgatctata ccctgtcatt ccgggcctca  600
ggagtgcctg accgcttctc gggatcaggg agcgggaccg atttcaccct gaaaattagg  660
cgagtggaag ccgaggacgt cggagtgtac tactgcatgc agcgcatcgg cttcccgatt  720
acgtttggac agggtacccg gcttgagatc aagaccacta ccccagcacc gaggccaccc  780
accccggctc ctaccatcgc ctcccagcct ctgtccctgc gtccggaggc atgtagaccc  840
gcagctggtg gggccgtgca tacccggggt cttgacttcg cctgcgatat ctacatttgg  900
gcccctctgg ctggtacttg cggggtcctg ctgctttcac tcgtgatcac tctttactgt  960
aagcgcggtc ggaagaagct gctgtacatc tttaagcaac ccttcatgag gcctgtgcag  1020
actactcaag aggaggacgg ctgttcatgc cggttcccag aggaggagga aggcggctgc  1080
gaactgcgcg tgaaattcag ccgcagcgca gatgctccag cctaccagca ggggcagaac  1140
cagctctaca acgaactcaa tcttggtcgg agagaggagt acgacgtgct ggacaagcgg  1200
agaggacggg acccagaaat gggcgggaag ccgcgcagaa agaatcccca agagggcctg  1260
tacaacgagc tccaaaagga taagatggca gaagcctata gcgagattgg tatgaaaggg  1320
gaacgcagaa gaggcaaagg ccacgacgga ctgtaccagg gactcagcac cgccaccaag  1380
gacacctatg acgctcttca catgcaggcc ctgccgcctc gg                    1422

SEQ ID NO: 179           moltype = AA  length = 5
FEATURE                  Location/Qualifiers
VARIANT                  1
                         note = /replace="Ser"
VARIANT                  3
                         note = /replace="Arg"
VARIANT                  5
                         note = /replace="Asn"
SITE                     1..5
                         note = /note="Variant residues given in the sequence have
                          no preference with respect to those in the annotations for
                          variant positions"
REGION                   1..5
                         note = source = /note="Description of Artificial Sequence:
                          Synthetic peptide"
source                   1..5
                         mol_type = protein
                         organism = synthetic construct
SEQUENCE: 179
GFWMS                                                             5

SEQ ID NO: 180           moltype = AA  length = 17
FEATURE                  Location/Qualifiers
VARIANT                  1
                         note = /replace="Ser"
VARIANT                  3
                         note = /replace="Ser"
VARIANT                  4
                         note = /replace="Ser"
VARIANT                  5
                         note = /replace="Ser"
VARIANT                  6
                         note = /replace="Ser"
```

```
VARIANT                 8
                        note = /replace="Tyr"
VARIANT                 9
                        note = /replace="Ile"
VARIANT                 12
                        note = /replace="Ala"
VARIANT                 16
                        note = /replace="Lys"
SITE                    1..17
                        note = /note="Variant residues given in the sequence have
                         no preference with respect to those in the annotations for
                         variant positions"
REGION                  1..17
                        note = source = /note="Description of Artificial Sequence:
                         Synthetic peptide"
source                  1..17
                        mol_type = protein
                        organism = synthetic construct
SEQUENCE: 180
NIKQDGSEKY YVDSVRG                                                   17

SEQ ID NO: 181          moltype = AA  length = 9
FEATURE                 Location/Qualifiers
VARIANT                 1
                        note = /replace="Trp"
VARIANT                 3
                        note = /replace="Ser"
SITE                    1..9
                        note = /note="Variant residues given in the sequence have
                         no preference with respect to those in the annotations for
                         variant positions"
REGION                  1..9
                        note = source = /note="Description of Artificial Sequence:
                         Synthetic peptide"
source                  1..9
                        mol_type = protein
                        organism = synthetic construct
SEQUENCE: 181
ALDYYGMDV                                                            9

SEQ ID NO: 182          moltype = AA  length = 7
FEATURE                 Location/Qualifiers
VARIANT                 4
                        note = /replace="Phe"
SITE                    1..7
                        note = /note="Variant residues given in the sequence have
                         no preference with respect to those in the annotations for
                         variant positions"
REGION                  1..7
                        note = source = /note="Description of Artificial Sequence:
                         Synthetic peptide"
source                  1..7
                        mol_type = protein
                        organism = synthetic construct
SEQUENCE: 182
TLSYRAS                                                              7

SEQ ID NO: 183          moltype = AA  length = 10
FEATURE                 Location/Qualifiers
VARIANT                 1
                        note = /replace="Met"
VARIANT                 4
                        note = /replace="Ile"
VARIANT                 5
                        note = /replace="Gly"
VARIANT                 8
                        note = /replace=" "
SITE                    1..10
                        note = /note="Variant residues given in the sequence have
                         no preference with respect to those in the annotations for
                         variant positions"
REGION                  1..10
                        note = source = /note="Description of Artificial Sequence:
                         Synthetic peptide"
source                  1..10
                        mol_type = protein
                        organism = synthetic construct
SEQUENCE: 183
TQRLEFPSIT                                                           10
```

```
SEQ ID NO: 184          moltype = AA  length = 7
FEATURE                 Location/Qualifiers
VARIANT                 6
                        note = /replace="Ser"
SITE                    1..7
                        note = /note="Variant residues given in the sequence have
                         no preference with respect to those in the annotations for
                         variant positions"
REGION                  1..7
                        note = source = /note="Description of Artificial Sequence:
                         Synthetic peptide"
source                  1..7
                        mol_type = protein
                        organism = synthetic construct
SEQUENCE: 184
GFTFSGF                                                                     7

SEQ ID NO: 185          moltype = AA  length = 6
FEATURE                 Location/Qualifiers
VARIANT                 1
                        note = /replace="Ser"
VARIANT                 2
                        note = /replace="Ser"
VARIANT                 3
                        note = /replace="Ser"
VARIANT                 4
                        note = /replace="Ser"
VARIANT                 6
                        note = /replace="Tyr"
SITE                    1..6
                        note = /note="Variant residues given in the sequence have
                         no preference with respect to those in the annotations for
                         variant positions"
REGION                  1..6
                        note = source = /note="Description of Artificial Sequence:
                         Synthetic peptide"
source                  1..6
                        mol_type = protein
                        organism = synthetic construct
SEQUENCE: 185
KQDGSE                                                                      6

SEQ ID NO: 186          moltype = AA  length = 7
FEATURE                 Location/Qualifiers
VARIANT                 2
                        note = /replace="Ile"
VARIANT                 3
                        note = /replace="Gly"
VARIANT                 6
                        note = /replace=" "
SITE                    1..7
                        note = /note="Variant residues given in the sequence have
                         no preference with respect to those in the annotations for
                         variant positions"
REGION                  1..7
                        note = source = /note="Description of Artificial Sequence:
                         Synthetic peptide"
source                  1..7
                        mol_type = protein
                        organism = synthetic construct
SEQUENCE: 186
RLEFPSI                                                                     7

SEQ ID NO: 187          moltype = AA  length = 8
FEATURE                 Location/Qualifiers
VARIANT                 6
                        note = /replace="Ser"
VARIANT                 8
                        note = /replace="Arg"
SITE                    1..8
                        note = /note="Variant residues given in the sequence have
                         no preference with respect to those in the annotations for
                         variant positions"
REGION                  1..8
                        note = source = /note="Description of Artificial Sequence:
                         Synthetic peptide"
source                  1..8
                        mol_type = protein
```

```
                        organism = synthetic construct
SEQUENCE: 187
GFTFSGFW                                                                        8

SEQ ID NO: 188          moltype = AA   length = 8
FEATURE                 Location/Qualifiers
VARIANT                 2
                        note = /replace="Ser"
VARIANT                 3
                        note = /replace="Ser"
VARIANT                 4
                        note = /replace="Ser"
VARIANT                 5
                        note = /replace="Ser"
VARIANT                 7
                        note = /replace="Tyr"
VARIANT                 8
                        note = /replace="Ile"
SITE                    1..8
                        note = /note="Variant residues given in the sequence have
                         no preference with respect to those in the annotations for
                         variant positions"
REGION                  1..8
                        note = source = /note="Description of Artificial Sequence:
                         Synthetic peptide"
source                  1..8
                        mol_type = protein
                        organism = synthetic construct
SEQUENCE: 188
IKQDGSEK                                                                        8

SEQ ID NO: 189          moltype = AA   length = 11
FEATURE                 Location/Qualifiers
VARIANT                 3
                        note = /replace="Trp"
VARIANT                 5
                        note = /replace="Ser"
SITE                    1..11
                        note = /note="Variant residues given in the sequence have
                         no preference with respect to those in the annotations for
                         variant positions"
REGION                  1..11
                        note = source = /note="Description of Artificial Sequence:
                         Synthetic peptide"
source                  1..11
                        mol_type = protein
                        organism = synthetic construct
SEQUENCE: 189
ARALDYYGMD V                                                                   11

SEQ ID NO: 190          moltype = DNA   length = 521
FEATURE                 Location/Qualifiers
misc_feature            1..521
                        note = source = /note="Description of Unknown: PGK Promoter
                         sequence"
source                  1..521
                        mol_type = unassigned DNA
                        organism = unidentified
SEQUENCE: 190
acccctctct ccagccacta agccagttgc tccctcggct gacggctgca cgcgaggcct      60
ccgaacgtct tacgccttgt ggcgcgcccg tccttgtccc gggtgtgatg gcggggtgtg     120
gggcggaggg cgtggcgggg aagggccggc gacgagagcc gcgcgggacg actcgtcggc    180
gataaccggt gtcgggtagc gccagccgcg cgacggtaac gagggaccgc gacaggcaga    240
cgctcccatg atcactctgc acgccgaagg caaatagtgc aggccgtgcg gcgcttggcg    300
ttccttggaa gggctgaatc cccgcctcgt ccttcgcagc ggccccccgg gtgttcccat    360
cgccgcttct aggcccactg cgacgcttgc ctgcacttct tacacgctct gggtcccagc    420
cgcggcgacg caaagggcct tggtgcgggt ctcgtcggcg cagggacgcg tttgggtccc    480
gacggaacct tttccgcgtt ggggttgggg caccataagc t                        521

SEQ ID NO: 191          moltype = DNA   length = 221
FEATURE                 Location/Qualifiers
misc_feature            1..221
                        note = source = /note="Description of Artificial Sequence:
                         Synthetic polynucleotide"
source                  1..221
                        mol_type = other DNA
                        organism = synthetic construct
SEQUENCE: 191
acccctctct ccagccacta agccagttgc tccctcggct gacggctgca cgcgaggcct      60
```

```
ccgaacgtct tacgccttgt ggcgcgcccg tccttgtccc gggtgtgatg gcggggtgtg  120
gggcggaggg cgtggcgggg aagggccggc gacgagagcc gcgcgggacg actcgtcggc  180
gataaccggt gtcgggtagc gccagccgcg cgacggtaac g                      221

SEQ ID NO: 192         moltype = DNA  length = 324
FEATURE                Location/Qualifiers
misc_feature           1..324
                       note = source = /note="Description of Artificial Sequence:
                        Synthetic polynucleotide"
source                 1..324
                       mol_type = other DNA
                       organism = synthetic construct
SEQUENCE: 192
acccctctct ccagccacta agccagttgc tccctcggct gacggctgca cgcgaggcct  60
ccgaacgtct tacgccttgt ggcgcgcccg tccttgtccc gggtgtgatg gcggggtgtg  120
gggcggaggg cgtggcgggg aagggccggc gacgagagcc gcgcgggacg actcgtcggc  180
gataaccggt gtcgggtagc gccagccgcg cgacggtaac gagggaccgc gacaggcaga  240
cgctcccatg atcactctgc acgccgaagg caaatagtgc aggccgtgcg gcgcttggcg  300
ttccttggaa gggctgaatc cccg                                         324

SEQ ID NO: 193         moltype = DNA  length = 422
FEATURE                Location/Qualifiers
misc_feature           1..422
                       note = source = /note="Description of Artificial Sequence:
                        Synthetic polynucleotide"
source                 1..422
                       mol_type = other DNA
                       organism = synthetic construct
SEQUENCE: 193
acccctctct ccagccacta agccagttgc tccctcggct gacggctgca cgcgaggcct  60
ccgaacgtct tacgccttgt ggcgcgcccg tccttgtccc gggtgtgatg gcggggtgtg  120
gggcggaggg cgtggcgggg aagggccggc gacgagagcc gcgcgggacg actcgtcggc  180
gataaccggt gtcgggtagc gccagccgcg cgacggtaac gagggaccgc gacaggcaga  240
cgctcccatg atcactctgc acgccgaagg caaatagtgc aggccgtgcg gcgcttggcg  300
ttccttggaa gggctgaatc cccgcctcgt ccttcgcagc ggccccccgg gtgttcccat  360
cgccgcttct aggcccactg cgacgcttgc ctgcacttct tacacgctct gggtcccagc  420
cg                                                                 422

SEQ ID NO: 194         moltype = AA  length = 21
FEATURE                Location/Qualifiers
SITE                   1..3
                       note = /note="This region may or may not be present"
REGION                 1..21
                       note = source = /note="Description of Artificial Sequence:
                        Synthetic peptide"
source                 1..21
                       mol_type = protein
                       organism = synthetic construct
SEQUENCE: 194
GSGEGRGSLL TCGDVEENPG P                                            21

SEQ ID NO: 195         moltype = AA  length = 22
FEATURE                Location/Qualifiers
SITE                   1..3
                       note = /note="This region may or may not be present"
REGION                 1..22
                       note = source = /note="Description of Artificial Sequence:
                        Synthetic peptide"
source                 1..22
                       mol_type = protein
                       organism = synthetic construct
SEQUENCE: 195
GSGATNFSLL KQAGDVEENP GP                                           22

SEQ ID NO: 196         moltype = AA  length = 23
FEATURE                Location/Qualifiers
SITE                   1..3
                       note = /note="This region may or may not be present"
REGION                 1..23
                       note = source = /note="Description of Artificial Sequence:
                        Synthetic peptide"
source                 1..23
                       mol_type = protein
                       organism = synthetic construct
SEQUENCE: 196
GSGQCTNYAL LKLAGDVESN PGP                                          23

SEQ ID NO: 197         moltype = AA  length = 25
FEATURE                Location/Qualifiers
```

```
SITE                    1..3
                        note = /note="This region may or may not be present"
REGION                  1..25
                        note = source = /note="Description of Artificial Sequence:
                         Synthetic peptide"
source                  1..25
                        mol_type = protein
                        organism = synthetic construct
SEQUENCE: 197
GSGVKQTLNF DLLKLAGDVE SNPGP                                        25

SEQ ID NO: 198          moltype = DNA  length = 118
FEATURE                 Location/Qualifiers
misc_feature            1..118
                        note = source = /note="Description of Artificial Sequence:
                         Synthetic polynucleotide"
source                  1..118
                        mol_type = other DNA
                        organism = synthetic construct
SEQUENCE: 198
acccctctct ccagccacta agccagttgc tccctcggct gacggctgca cgcgaggcct  60
ccgaacgtct tacgccttgt ggcgcgcccg tccttgtccc gggtgtgatg gcggggtg    118

SEQ ID NO: 199          moltype =   length =
SEQUENCE: 199
000

SEQ ID NO: 200          moltype =   length =
SEQUENCE: 200
000

SEQ ID NO: 201          moltype =   length =
SEQUENCE: 201
000

SEQ ID NO: 202          moltype = AA  length = 69
FEATURE                 Location/Qualifiers
REGION                  1..69
                        note = source = /note="Description of Artificial Sequence:
                         Synthetic polypeptide"
source                  1..69
                        mol_type = protein
                        organism = synthetic construct
SEQUENCE: 202
TTTPAPRPPT PAPTIASQPL SLRPEACRPA AGGAVHTRGL DFACDIYIWA PLAGTCGVLL  60
LSLVITLYC                                                          69

SEQ ID NO: 203          moltype =   length =
SEQUENCE: 203
000

SEQ ID NO: 204          moltype =   length =
SEQUENCE: 204
000

SEQ ID NO: 205          moltype =   length =
SEQUENCE: 205
000

SEQ ID NO: 206          moltype =   length =
SEQUENCE: 206
000

SEQ ID NO: 207          moltype =   length =
SEQUENCE: 207
000

SEQ ID NO: 208          moltype =   length =
SEQUENCE: 208
000

SEQ ID NO: 209          moltype =   length =
SEQUENCE: 209
000

SEQ ID NO: 210          moltype =   length =
SEQUENCE: 210
000
```

SEQ ID NO: 211 moltype = length =
SEQUENCE: 211
000

SEQ ID NO: 212 moltype = length =
SEQUENCE: 212
000

SEQ ID NO: 213 moltype = length =
SEQUENCE: 213
000

SEQ ID NO: 214 moltype = length =
SEQUENCE: 214
000

SEQ ID NO: 215 moltype = length =
SEQUENCE: 215
000

SEQ ID NO: 216 moltype = length =
SEQUENCE: 216
000

SEQ ID NO: 217 moltype = length =
SEQUENCE: 217
000

SEQ ID NO: 218 moltype = length =
SEQUENCE: 218
000

SEQ ID NO: 219 moltype = length =
SEQUENCE: 219
000

SEQ ID NO: 220 moltype = length =
SEQUENCE: 220
000

SEQ ID NO: 221 moltype = length =
SEQUENCE: 221
000

SEQ ID NO: 222 moltype = length =
SEQUENCE: 222
000

SEQ ID NO: 223 moltype = length =
SEQUENCE: 223
000

SEQ ID NO: 224 moltype = length =
SEQUENCE: 224
000

SEQ ID NO: 225 moltype = length =
SEQUENCE: 225
000

SEQ ID NO: 226 moltype = length =
SEQUENCE: 226
000

SEQ ID NO: 227 moltype = length =
SEQUENCE: 227
000

SEQ ID NO: 228 moltype = length =
SEQUENCE: 228
000

SEQ ID NO: 229 moltype = length =
SEQUENCE: 229
000

SEQ ID NO: 230 moltype = length =
SEQUENCE: 230
000

SEQ ID NO: 231 moltype = length =
SEQUENCE: 231
000

SEQ ID NO: 232 moltype = length =
SEQUENCE: 232
000

SEQ ID NO: 233 moltype = length =
SEQUENCE: 233
000

SEQ ID NO: 234 moltype = length =
SEQUENCE: 234
000

SEQ ID NO: 235 moltype = length =
SEQUENCE: 235
000

SEQ ID NO: 236 moltype = length =
SEQUENCE: 236
000

SEQ ID NO: 237 moltype = length =
SEQUENCE: 237
000

SEQ ID NO: 238 moltype = length =
SEQUENCE: 238
000

SEQ ID NO: 239 moltype = length =
SEQUENCE: 239
000

SEQ ID NO: 240 moltype = length =
SEQUENCE: 240
000

SEQ ID NO: 241 moltype = length =
SEQUENCE: 241
000

SEQ ID NO: 242 moltype = length =
SEQUENCE: 242
000

SEQ ID NO: 243 moltype = length =
SEQUENCE: 243
000

SEQ ID NO: 244 moltype = length =
SEQUENCE: 244
000

SEQ ID NO: 245 moltype = length =
SEQUENCE: 245
000

SEQ ID NO: 246 moltype = length =
SEQUENCE: 246
000

SEQ ID NO: 247 moltype = length =
SEQUENCE: 247
000

SEQ ID NO: 248 moltype = length =
SEQUENCE: 248
000

SEQ ID NO: 249 moltype = length =
SEQUENCE: 249
000

SEQ ID NO: 250 moltype = length =
SEQUENCE: 250

```
000

SEQ ID NO: 251          moltype =   length =
SEQUENCE: 251
000

SEQ ID NO: 252          moltype = DNA  length = 63
FEATURE                 Location/Qualifiers
misc_feature            1..63
                        note = source = /note="Description of Artificial Sequence:
                         Synthetic oligonucleotide"
source                  1..63
                        mol_type = other DNA
                        organism = synthetic construct
SEQUENCE: 252
atggccctcc ctgtcaccgc tctgttgctg ccgcttgctc tgctgctcca cgcagcgcga  60
ccg                                                                63

SEQ ID NO: 253          moltype = DNA  length = 747
FEATURE                 Location/Qualifiers
misc_feature            1..747
                        note = source = /note="Description of Artificial Sequence:
                         Synthetic polynucleotide"
source                  1..747
                        mol_type = other DNA
                        organism = synthetic construct
SEQUENCE: 253
caggtacaat tgcaggagtc tggaggcggt gtggtgcaac ccggtcgcag cttgcgcctg  60
agttgtgctg cgtctggatt tacattttca tcttacggaa tgcattgggt acgccaggca  120
ccggggaaag gccttgaatg ggtggctgta atttcatacg atggttccaa caaatactat  180
gctgactcag tcaagggtcg atttacaatt agtcgggaca actccaagaa caccctttat  240
cttcaaatga attcccttag agcagaggat acggcggtct attactgtgg tggcagtggt  300
tatgcacttc atgatgatta ctatggcttg gatgtctggg ggcaagggac gcttgtaact  360
gtatcctctg gtggtggtgg tagtggtggg ggaggctccg gcggtggcgg ctctcaatct  420
gctctgactc aaccagcaag cgtatcaggg tcaccgggac agagtattac cataagttgc  480
acggggacct ctagcgatgt aggggggtat aattatgtat cttggtatca acaacacccc  540
gggaaagccc ctaaattgat gatctacgac gtgagcaatc gacctagtgg cgtatcaaat  600
cgcttctctg gtagcaagag tgggaatacg gcgtccctta ctattagcgg attgcaagca  660
gaagatgagg ccgattacta ctgcagctcc tatactagct cttctacatt gtacgtcttt  720
gggagcggaa caaaagtaac agtactc                                      747

SEQ ID NO: 254          moltype = DNA  length = 207
FEATURE                 Location/Qualifiers
misc_feature            1..207
                        note = source = /note="Description of Artificial Sequence:
                         Synthetic polynucleotide"
source                  1..207
                        mol_type = other DNA
                        organism = synthetic construct
SEQUENCE: 254
acaacaacac ctgccccgag accgcctaca ccagccccga ctattgccag ccagcctctg  60
agcctcaggc ctgaggcctg taggcccgca gcgggcggcg cagttcatac acggggcttg  120
gatttcgctt gtgatattta tatttgggct cctttggcgg ggacatgtgg cgtgctgctt  180
ctgtcacttg ttattacact gtactgt                                      207

SEQ ID NO: 255          moltype = DNA  length = 126
FEATURE                 Location/Qualifiers
misc_feature            1..126
                        note = source = /note="Description of Artificial Sequence:
                         Synthetic polynucleotide"
source                  1..126
                        mol_type = other DNA
                        organism = synthetic construct
SEQUENCE: 255
aaacgcgggc gaaaaaaatt gctgtatatt tttaagcagc catttatgag gcccgttcag  60
acgacgcagg aggaggacgg ttgctcttgc aggttcccag aagaggaaga agggggctgt  120
gaattg                                                             126

SEQ ID NO: 256          moltype = DNA  length = 336
FEATURE                 Location/Qualifiers
misc_feature            1..336
                        note = source = /note="Description of Artificial Sequence:
                         Synthetic polynucleotide"
source                  1..336
                        mol_type = other DNA
                        organism = synthetic construct
SEQUENCE: 256
cgggttaaat tttcaagatc cgcagacgct ccagcatacc aacagggaca aaaccaactc  60
tataacgagc tgaatcttgg aagaagggag gaatatgatg tgctggataa acggcgcggt  120
```

```
agagatccgg agatgggcgg aaaaccaagg cgaaaaaacc ctcaggaggg actctacaac  180
gaactgcaga aagacaaaat ggcggaggct tattccgaaa taggcatgaa gggcgagcgg  240
aggcgagggga aagggcacga cggactgtat caaggcctct caaccgcgac taaggatacg  300
tacgacgccc tgcacatgca ggccctgcct ccgaga                              336

SEQ ID NO: 257          moltype = AA  length = 493
FEATURE                 Location/Qualifiers
REGION                  1..493
                        note = source = /note="Description of Artificial Sequence:
                         Synthetic polypeptide"
source                  1..493
                        mol_type = protein
                        organism = synthetic construct
SEQUENCE: 257
MALPVTALLL PLALLLHAAR PQVQLQESGG GVVQPGRSLR LSCAASGFTF SSYGMHWVRQ  60
APGKGLEWVA VISYDGSNKY YADSVKGRFT ISRDNSKNTL YLQMNSLRAE DTAVYYCGGS  120
GYALHDDYYG LDVWGQGTLV TVSSGGGGSG GGGSGGGGSQ SALTQPASVS GSPGQSITIS  180
CTGTSSDVGG YNYVSWYQQH PGKAPKLMIY DVSNRPSGVS NRFSGSKSGN TASLTISGLQ  240
AEDEADYYCS SYTSSSTLYV FGSGTKVTVL TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                       493

SEQ ID NO: 258          moltype = DNA  length = 1479
FEATURE                 Location/Qualifiers
misc_feature            1..1479
                        note = source = /note="Description of Artificial Sequence:
                         Synthetic polynucleotide"
source                  1..1479
                        mol_type = other DNA
                        organism = synthetic construct
SEQUENCE: 258
atggccctcc ctgtcaccgc tctgttgctg ccgcttgctc tgctgctcca cgcagcgcga  60
ccgcaggtac aattgcagga gtctggaggc ggtgtggtgc aacccggtcg cagcttgcgc  120
ctgagttgtg ctgcgtctgg atttacattt tcatcttacg gaatgcattg ggtacgccag  180
gcaccgggga aaggccttga atgggtggct gtaatttcat acgatggttc caacaaatac  240
tatgctgact cagtcaaggg tcgatttaca attagtcggg acaactccaa gaacaccctt  300
tatcttcaaa tgaattccct tagagcagag gatacggcgg tctattactg tggtggcagt  360
ggttatgcac ttcatgatga ttactatggc ttggatgtct gggggcaagg gacgcttgta  420
actgtatcct ctggtggtgg tggtagtggt gggggaggct ccggcggtgg cggctctcaa  480
tctgctctga ctcaaccagc aagcgtatca gggtcaccgg gacagagtat taccataagt  540
tgcacgggga cctctagcga tgtagggggg tataattatg tatcttggta tcaacaacac  600
cccgggaaag cccctaaatt gatgatctac gacgtgagca atcgacctag tggcgtatca  660
aatcgcttct ctggtagcaa gagtgggaat acggcgtccc ttactattag cggattgcaa  720
gcagaagatg aggccgatta ctactgcagc tcctatacta gctcttctac attgtacgtc  780
tttgggagcg gaacaaaagt aacagtactc acaacaacac ctgccccgag accgcctaca  840
ccagccccga ctattgccag ccagcctctg agcctcaggc ctgaggcctg taggcccgca  900
gcgggcggcg cagttcatac acggggcttg gatttcgctt gtgatattta tatttgggct  960
cctttggcgg ggacatgtgg cgtgctgctt ctgtcacttg ttattacact gtactgtaaa  1020
cgcgggcgaa aaaaattgct gtatattttt aagcagccat ttatgaggcc cgttcagacg  1080
acgcaggagg aggacggttg ctcttgcagg ttcccagaag aggaagaagg gggctgtgaa  1140
ttgcgggtta aattttcaag atccgcagac gctccagcat accaacaggg acaaaaccaa  1200
ctctataacg agctgaatct tggaagaagg gaggaatatg atgtgctgga taaacggcgc  1260
ggtagagatc cggagatggg cggaaaacca aggcgaaaaa accctcagga gggactctac  1320
aacgaactgc agaaagacaa aatggcggag gcttattccg aaataggcat gaagggcgag  1380
cggaggcgag ggaaagggca cgacggactg tatcaaggcc tctcaaccgc gactaaggat  1440
acgtacgacg ccctgcacat gcaggccctg cctccgaga                           1479

SEQ ID NO: 259          moltype = DNA  length = 1416
FEATURE                 Location/Qualifiers
misc_feature            1..1416
                        note = source = /note="Description of Artificial Sequence:
                         Synthetic polynucleotide"
source                  1..1416
                        mol_type = other DNA
                        organism = synthetic construct
SEQUENCE: 259
caggtacaat tgcaggagtc tggaggcggt gtggtgcaac ccggtcgcag cttgcgcctg  60
agttgtgctg cgtctggatt tacattttca tcttacggaa tgcattgggt acgccaggca  120
ccggggaaag gccttgaatg ggtggctgta atttcatacg atggttccaa caaatactat  180
gctgactcag tcaagggtcg atttacaatt agtcgggaca actccaagaa cacccttttat  240
cttcaaatga attcccttag agcagaggat acggcggtct attactgtgg tggcagtggt  300
tatgcacttc atgatgatta ctatggcttg gatgtctggg ggcaagggac gcttgtaact  360
gtatcctctg gtggtggtgg tagtggtggg ggaggctccg gcggtggcgg ctctcaatct  420
gctctgactc aaccagcaag cgtatcaggg tcaccgggac agagtattac cataagttgc  480
acggggacct ctagcgatgt aggggggtat aattatgtat cttggtatca acaacacccc  540
gggaaagccc ctaaattgat gatctacgac gtgagcaatc gacctagtgg cgtatcaaat  600
cgcttctctg gtagcaagag tgggaatacg gcgtccctta ctattagcgg attgcaagca  660
```

-continued

```
gaagatgagg ccgattacta ctgcagctcc tatactagct cttctacatt gtacgtcttt  720
gggagcggaa caaaagtaac agtactcaca acaacacctg ccccgagacc gcctacacca  780
gccccgacta ttgccagcca gcctctgagc ctcaggcctg aggcctgtag gcccgcagcg  840
ggcggcgcag ttcatacacg gggcttggat ttcgcttgtg atatttatat ttgggctcct  900
ttggcgggga catgtggcgt gctgcttctg tcacttgtta ttacactgta ctgtaaacgc  960
gggcgaaaaa aattgctgta tatttttaag cagccattta tgaggcccgt tcagacgacg  1020
caggaggagg acggttgctc ttgcaggttc ccagaagagg aagaaggggg ctgtgaattg  1080
cgggttaaat tttcaagatc cgcagacgct ccagcatacc aacagggaca aaaccaactc  1140
tataacgagc tgaatcttgg aagaagggag gaatatgatg tgctggataa acggcgcggt  1200
agagatccgg agatgggcgg aaaaccaagg cgaaaaaacc ctcaggaggg actctacaac  1260
gaactgcaga aagacaaaat ggcggaggct tattccgaaa taggcatgaa gggcgagcgg  1320
aggcgaggga aagggcacga cggactgtat caaggcctct caaccgcgac taaggatacg  1380
tacgacgccc tgcacatgca ggccctgcct ccgaga                          1416

SEQ ID NO: 260          moltype = DNA  length = 369
FEATURE                 Location/Qualifiers
misc_feature            1..369
                        note = source = /note="Description of Artificial Sequence:
                         Synthetic polynucleotide"
source                  1..369
                        mol_type = other DNA
                        organism = synthetic construct
SEQUENCE: 260
caggtacaat tgcaggagtc tggaggcggt gtggtgcaac ccggtcgcag cttgcgcctg  60
agttgtgctg cgtctggatt tacattttca tcttacggaa tgcattgggt acgccaggca  120
ccggggaaag gccttgaatg ggtggctgta atttcatacg atggttccaa caaatactat  180
gctgactcag tcaagggtcg atttacaatt agtcgggaca actccaagaa caccctttat  240
cttcaaatga attcccttag agcagaggat acggcggtct attactgtgg tggcagtggt  300
tatgcacttc atgatgatta ctatggcttg gatgtctggg ggcaagggac gcttgtaact  360
gtatcctct                                                        369

SEQ ID NO: 261          moltype = DNA  length = 333
FEATURE                 Location/Qualifiers
misc_feature            1..333
                        note = source = /note="Description of Artificial Sequence:
                         Synthetic polynucleotide"
source                  1..333
                        mol_type = other DNA
                        organism = synthetic construct
SEQUENCE: 261
caatctgctc tgactcaacc agcaagcgta tcagggtcac cgggacagag tattaccata  60
agttgcacgg ggacctctag cgatgtaggg gggtataatt atgtatcttg gtatcaacaa  120
caccccggga aagcccctaa attgatgatc tacgacgtga gcaatcgacc tagtggcgta  180
tcaaatcgct tctctggtag caagagtggg aatacggcgt cccttactat tagcggattg  240
caagcagaag atgaggccga ttactactgc agctcctata ctagctcttc tacattgtac  300
gtctttggga gcggaacaaa agtaacagta ctc                             333

SEQ ID NO: 262          moltype =   length =
SEQUENCE: 262
000

SEQ ID NO: 263          moltype =   length =
SEQUENCE: 263
000

SEQ ID NO: 264          moltype =   length =
SEQUENCE: 264
000

SEQ ID NO: 265          moltype =   length =
SEQUENCE: 265
000

SEQ ID NO: 266          moltype =   length =
SEQUENCE: 266
000

SEQ ID NO: 267          moltype =   length =
SEQUENCE: 267
000

SEQ ID NO: 268          moltype =   length =
SEQUENCE: 268
000

SEQ ID NO: 269          moltype =   length =
SEQUENCE: 269
000
```

```
SEQ ID NO: 270         moltype =   length =
SEQUENCE: 270
000

SEQ ID NO: 271         moltype =   length =
SEQUENCE: 271
000

SEQ ID NO: 272         moltype =   length =
SEQUENCE: 272
000

SEQ ID NO: 273         moltype =   length =
SEQUENCE: 273
000

SEQ ID NO: 274         moltype =   length =
SEQUENCE: 274
000

SEQ ID NO: 275         moltype = AA  length = 132
FEATURE                Location/Qualifiers
REGION                 1..132
                       note = source = /note="Description of Artificial Sequence:
                        Synthetic polypeptide"
source                 1..132
                       mol_type = protein
                       organism = synthetic construct
SEQUENCE: 275
DVPDYASLGG PSSPKKKRKV SRGVQVETIS PGDGRTFPKR GQTCVVHYTG MLEDGKKFDS  60
SRDRNKPFKF MLGKQEVIRG WEEGVAQMSV GQRAKLTISP DYAYGATGHP GIIPPHATLV  120
FDVELLKLET SY                                                     132

SEQ ID NO: 276         moltype = AA  length = 108
FEATURE                Location/Qualifiers
REGION                 1..108
                       note = source = /note="Description of Artificial Sequence:
                        Synthetic polypeptide"
source                 1..108
                       mol_type = protein
                       organism = synthetic construct
SEQUENCE: 276
VQVETISPGD GRTFPKRGQT CVVHYTGMLE DGKKFDSSRD RNKPFKFMLG KQEVIRGWEE  60
GVAQMSVGQR AKLTISPDYA YGATGHPGII PPHATLVFDV ELLKLETS               108

SEQ ID NO: 277         moltype = AA  length = 93
FEATURE                Location/Qualifiers
REGION                 1..93
                       note = source = /note="Description of Artificial Sequence:
                        Synthetic polypeptide"
source                 1..93
                       mol_type = protein
                       organism = synthetic construct
SEQUENCE: 277
ILWHEMWHEG LEEASRLYFG ERNVKGMFEV LEPLHAMMER GPQTLKETSF NQAYGRDLME  60
AQEWCRKYMK SGNVKDLTQA WDLYYHVFRR ISK                              93

SEQ ID NO: 278         moltype = AA  length = 95
FEATURE                Location/Qualifiers
REGION                 1..95
                       note = source = /note="Description of Artificial Sequence:
                        Synthetic polypeptide"
source                 1..95
                       mol_type = protein
                       organism = synthetic construct
SEQUENCE: 278
ILWHEMWHEG LIEASRLYFG ERNVKGMFEV LEPLHAMMER GPQTLKETSF NQAYGRDLME  60
AQEWCRKYMK SGNVKDLTQA WDLYYHVFRR ISKTS                            95

SEQ ID NO: 279         moltype = AA  length = 95
FEATURE                Location/Qualifiers
REGION                 1..95
                       note = source = /note="Description of Artificial Sequence:
                        Synthetic polypeptide"
source                 1..95
                       mol_type = protein
                       organism = synthetic construct
SEQUENCE: 279
ILWHEMWHEG LLEASRLYFG ERNVKGMFEV LEPLHAMMER GPQTLKETSF NQAYGRDLME  60
```

-continued

```
AQEWCRKYMK SGNVKDLTQA WDLYYHVFRR ISKTS                         95

SEQ ID NO: 280         moltype = AA  length = 95
FEATURE                Location/Qualifiers
REGION                 1..95
                       note = source = /note="Description of Artificial Sequence:
                        Synthetic polypeptide"
source                 1..95
                       mol_type = protein
                       organism = synthetic construct
SEQUENCE: 280
ILWHEMWHEG LEEASRLYFG ERNVKGMFEV LEPLHAMMER GPQTLKETSF NQAYGRDLME  60
AQEWCRKYMK SGNVKDLLQA WDLYYHVFRR ISKTS                         95

SEQ ID NO: 281         moltype = AA  length = 95
FEATURE                Location/Qualifiers
MOD_RES                12
                       note = Any amino acid
MOD_RES                78
                       note = Any amino acid
REGION                 1..95
                       note = source = /note="Description of Artificial Sequence:
                        Synthetic polypeptide"
source                 1..95
                       mol_type = protein
                       organism = synthetic construct
SEQUENCE: 281
ILWHEMWHEG LXEASRLYFG ERNVKGMFEV LEPLHAMMER GPQTLKETSF NQAYGRDLME  60
AQEWCRKYMK SGNVKDLXQA WDLYYHVFRR ISKTS                         95

SEQ ID NO: 282         moltype = AA  length = 95
FEATURE                Location/Qualifiers
REGION                 1..95
                       note = source = /note="Description of Artificial Sequence:
                        Synthetic polypeptide"
source                 1..95
                       mol_type = protein
                       organism = synthetic construct
SEQUENCE: 282
ILWHEMWHEG LIEASRLYFG ERNVKGMFEV LEPLHAMMER GPQTLKETSF NQAYGRDLME  60
AQEWCRKYMK SGNVKDLLQA WDLYYHVFRR ISKTS                         95

SEQ ID NO: 283         moltype = AA  length = 95
FEATURE                Location/Qualifiers
REGION                 1..95
                       note = source = /note="Description of Artificial Sequence:
                        Synthetic polypeptide"
source                 1..95
                       mol_type = protein
                       organism = synthetic construct
SEQUENCE: 283
ILWHEMWHEG LLEASRLYFG ERNVKGMFEV LEPLHAMMER GPQTLKETSF NQAYGRDLME  60
AQEWCRKYMK SGNVKDLLQA WDLYYHVFRR ISKTS                         95

SEQ ID NO: 284         moltype = AA  length = 1132
FEATURE                Location/Qualifiers
source                 1..1132
                       mol_type = protein
                       organism = Homo sapiens
SEQUENCE: 284
MPRAPRCRAV RSLLRSHYRE VLPLATFVRR LGPQGWRLVQ RGDPAAFRAL VAQCLVCVPW  60
DARPPPAAPS FRQVSCLKEL VARVLQRLCE RGAKNVLAFG FALLDGARGG PPEAFTTSVR  120
SYLPNTVTDA LRGSGAWGLL LRRVGDDVLV HLLARCALFV LVAPSCAYQV CGPPLYQLGA  180
ATQARPPPHA SGPRRRLGCE RAWNHSVREA GVPLGLPAPG ARRRGGSASR SLPLPKRPRR  240
GAAPEPERTP VGQGSWAHPG RTRGPSDRGF CVVSPARPAE EATSLEGALS GTRHSHPSVG  300
RQHHAGPPST SRPPRPWDTP CPPVYAETKH FLYSSGDKEQ LRPSFLLSSL RPSLTGARRL  360
VETIFLGSRP WMPGTPRRLP RLPQRYWQMR PLFLELLGNH AQCPYGVLLK THCPLRAAVT  420
PAAGVCAREK PQGSVAAPEE EDTDPRRLVQ LLRQHSSPWQ VYGFVRACLR RLVPPGLWGS  480
RHNERRFLRN TKKFISLGKH AKLSLQELTW KMSVRGCAWL RRSPGVGCVP AAEHRLREEI  540
LAKFLHWLMS VYVVELLRSF FYVTETTFQK NRLFFYRKSV WSKLQSIGIR QHLKRVQLRE  600
LSEAEVRQHR EARPALLTSR LRFIPKPDGL RPIVNMDYVV GARTFRREKR AERLTSRVKA  660
LFSVLNYERA RRPGLLGASV LGLDDIHRAW RTFVLRVRAQ DPPPELYFVK VDVTGAYDTI  720
PQDRLTEVIA SIIKPQNTYC VRRYAVVQKA AHGHVRKAFK SHVSTLTDLQ PYMRQFVAHL  780
QETSPLRDAV VIEQSSSLNE ASSGLFDVFL RFMCHHAVRI RGKSYVQCQG IPQGSILSTL  840
LCSLCYGDME NKLFAGIRRD GLLLRLVDDF LLVTPHLTHA KTFLRTLVRG VPEYGCVVNL  900
RKTVVNFPVE DEALGGTAFV QMPAHGLFPW CGLLLDTRTL EVQSDYSSYA RTSIRASLTF  960
NRGFKAGRNM RRKLFGVLRL KCHSLFLDLQ VNSLQTVCTN IYKILLLQAY RFHACVLQLP  1020
FHQQVWKNPT FFLRVISDTA SLCYSILKAK NAGMSLGAKG AAGPLPSEAV QWLCHQAFLL  1080
KLTRHRVTYV PLLGSLRTAQ TQLSRKLPGT TLTALEAAAN PALPSDFKTI LD          1132
```

-continued

```
SEQ ID NO: 285          moltype = AA  length = 4
FEATURE                 Location/Qualifiers
REGION                  1..4
                        note = source = /note="Description of Artificial Sequence:
                         Synthetic peptide"
source                  1..4
                        mol_type = protein
                        organism = synthetic construct
SEQUENCE: 285
RGDS                                                                        4
```

What is claimed is:

1. A method of providing an anti-tumor immunity in a subject having BCMA-expressing cancer cells, the method comprising administering to the subject an effective amount of cells comprising a chimeric antigen receptor (CAR), wherein the CAR comprises an anti-BCMA binding domain, a transmembrane domain, and an intracellular signaling domain comprising a primary signaling domain and a costimulatory signaling domain, wherein:

(a) the anti-BCMA binding domain comprises a heavy chain variable region (VH) comprising a heavy chain complementarity determining region 1 (HC CDR1) of SEQ ID NO: 86, a heavy chain complementarity determining region 2 (HC CDR2) of SEQ ID NO: 87, and a heavy chain complementarity determining region 3 (HC CDR3) of SEQ ID NO: 88, and a light chain variable region (VL) comprising a light chain complementarity determining region 1 (LC CDR1) of SEQ ID NO: 95, a light chain complementarity determining region 2 (LC CDR2) of SEQ ID NO: 96, and a light chain complementarity determining region 3 (LC CDR3) of SEQ ID NO: 97;

(b) the primary signaling domain comprises:

(i) a functional signaling domain of CD3 zeta or FcR gamma; or (ii) an amino acid sequence having at least 85% sequence identity to SEQ ID NO: 9 or 10; and (c) the costimulatory signaling domain comprises:

(i) a functional signaling domain of 4-1BB (CD137), OX40, CD2, CD27, CD28, ICAM-1, LFA-1, or ICOS (CD278); or (ii) an amino acid sequence having at least 85% sequence identity to SEQ ID NO: 7.

2. The method of claim 1, wherein the cells comprising the CAR are autologous T cells.

3. The method of claim 1, further comprising administering to the subject a second therapeutic agent.

4. The method of claim 3, wherein the second therapeutic agent is:

(a) a PD-1 inhibitor;

(b) a PD-L1 inhibitor;

(c) a LAG-3 inhibitor;

(d) a TIM-3 inhibitor;

(e) a CTLA-4 inhibitor;

(f) an interleukin-15 (IL-15) polypeptide, an interleukin-15 receptor alpha (IL-15Ra) polypeptide, or a combination of both an IL-15 polypeptide and an IL-15Ra polypeptide;

(g) an interleukin-12 (IL-12) polypeptide; or (h) an mTOR inhibitor.

5. The method of claim 4, wherein:

(a) the PD-1 inhibitor is selected from the group consisting of PDR001, nivolumab, pembrolizumab, MEDI0680, REGN2810, TSR-042, PF-06801591, and AMP-224;

(b) the PD-L1 inhibitor is selected from the group consisting of FAZ053, atezolizumab, avelumab, durvalumab, and BMS-936559;

(c) the LAG-3 inhibitor is selected from the group consisting of LAG525, BMS-986016, TSR-033, MK-4280 and REGN3767;

(d) the TIM-3 inhibitor is selected from the group consisting of MBG453, TSR-022, and LY3321367;

(e) the CTLA-4 inhibitor is ipilimumab or tremelimumab;

(f) the combination of both an IL-15 polypeptide and an IL-15Ra polypeptide is hetIL-15; or (g) the mTOR inhibitor is RAD001 or rapamycin.

6. A method of treating a subject having a cancer comprising BCMA-expressing cancer cells, the method comprising administering to the subject an effective amount of cells comprising a CAR, wherein the CAR comprises an anti-BCMA binding domain, a transmembrane domain, and an intracellular signaling domain comprising a primary signaling domain and a costimulatory signaling domain, wherein:

(a) the anti-BCMA binding domain comprises a VH comprising an HC CDR1 of SEQ ID NO: 86, an HC CDR2 of SEQ ID NO: 87, and an HC CDR3 of SEQ ID NO: 88, and a VL comprising an LC CDR1 of SEQ ID NO: 95, an LC CDR2 of SEQ ID NO: 96, and an LC CDR3 of SEQ ID NO: 97;

(b) the primary signaling domain comprises:

(i) a functional signaling domain of CD3 zeta or FcR gamma; or (ii) an amino acid sequence having at least 85% sequence identity to SEQ ID NO: 9 or 10; and (c) the costimulatory signaling domain comprises:

(i) a functional signaling domain of 4-1BB (CD137), OX40, CD2, CD27, CD28, ICAM-1, LFA-1, or ICOS (CD278); or (ii) an amino acid sequence having at least 85% sequence identity to SEQ ID NO: 7.

7. The method of claim 6, wherein the cells comprising the CAR are autologous T cells.

8. The method of claim 6, wherein the cancer is a hematologic cancer or a solid cancer.

9. The method of claim 6, wherein the cancer is multiple myeloma, acute leukemia, B-cell acute lymphoblastic leukemia (BALL), T-cell acute lymphoblastic leukemia (TALL), acute lymphoblastic leukemia (ALL), chronic myelogenous leukemia (CML), chronic lymphocytic leukemia (CLL), B cell prolymphocytic leukemia, blastic plasmacytoid dendritic cell neoplasm, Burkitt's lymphoma, diffuse large B cell lymphoma, follicular lymphoma, hairy cell leukemia, small cell- or large cell-follicular lymphoma, malignant lymphoproliferative conditions, MALT lymphoma, mantle cell lymphoma, marginal zone lymphoma, myelodysplasia and myelodysplastic syndrome, non-Hodgkin's lymphoma, plasmablastic lymphoma, plasmacytoid dendritic cell neoplasm, Waldenstrom macroglobulinemia, prostate cancer, pancreatic cancer, lung cancer, a plasma cell proliferative disorder, or a combination thereof.

10. The method of claim 9, wherein the cancer is multiple myeloma.

11. The method of claim 6, further comprising administering to the subject a second therapeutic agent.

12. The method of claim 11, wherein the second therapeutic agent is:

(a) a PD-1 inhibitor;
(b) a PD-L1 inhibitor;
(c) a LAG-3 inhibitor;
(d) a TIM-3 inhibitor;
(e) a CTLA-4 inhibitor;
(f) an IL-15 polypeptide, an IL-15Ra polypeptide, or a combination of both an IL-15 polypeptide and an IL-15Ra polypeptide;
(g) an IL-12 polypeptide; or
(h) an mTOR inhibitor.

13. The method of claim 12, wherein:

(a) the PD-1 inhibitor is selected from the group consisting of PDR001, nivolumab, pembrolizumab, MEDI0680, REGN2810, TSR-042, PF-06801591, and AMP-224;
(b) the PD-L1 inhibitor is selected from the group consisting of FAZ053, atezolizumab, avelumab, durvalumab, and BMS-936559;
(c) the LAG-3 inhibitor is selected from the group consisting of LAG525, BMS-986016, TSR-033, MK-4280 and REGN3767;
(d) the TIM-3 inhibitor is selected from the group consisting of MBG453, TSR-022, and LY3321367;
(e) the CTLA-4 inhibitor is ipilimumab or tremelimumab;
(f) the combination of both an IL-15 polypeptide and an IL-15Ra polypeptide is hetIL-15; or
(g) the mTOR inhibitor is RAD001 or rapamycin.

14. A method of treating a subject having a cancer comprising BCMA-expressing cancer cells, the method comprising administering to the subject an effective amount of cells comprising a CAR that binds to BCMA, wherein the CAR comprises, from N-terminus to C-terminus:

(a) an HC CDR1 of SEQ ID NO: 86;
(b) an HC CDR2 of SEQ ID NO: 87;
(c) an HC CDR3 of SEQ ID NO: 88;
(d) an LC CDR1 of SEQ ID NO: 95;
(e) an LC CDR2 of SEQ ID NO: 96;
(f) an LC CDR3 of SEQ ID NO: 97;
(g) a CD8 transmembrane domain and hinge of SEQ ID NO: 202;
(h) a functional signaling domain of 4-1BB of SEQ ID NO: 7; and
(i) a functional signaling domain of CD3 zeta of SEQ ID NO: 10.

15. The method of claim 14, wherein the CAR comprises:

(a) a VH comprising the amino acid sequence of SEQ ID NO: 93 and a VL comprising the amino acid sequence of SEQ ID NO: 1-102; and/or
(b) an scFv comprising the amino acid sequence of SEQ ID NO: 105.

16. The method of claim 15, wherein the CAR comprises the amino acid sequence of SEQ ID NO: 257 or SEQ ID NO: 107.

17. The method of claim 14, wherein the cells comprising the CAR are autologous T cells.

18. The method of claim 1, wherein:

(a) the VH comprises an amino acid sequence having at least 85% sequence identity to SEQ ID NO: 93; and/or
(b) the VL comprises an amino acid sequence having at least 85% sequence identity to SEQ ID NO: 102.

19. The method of claim 18, wherein:

(a) the VH comprises the amino acid sequence of SEQ ID NO: 93; and/or
(b) the VL comprises the amino acid sequence of SEQ ID NO: 102.

20. The method of claim 1, wherein the anti-BCMA binding domain is an scFv.

21. The method of claim 20, wherein the scFv is a fully human scFv.

22. The method of claim 20, wherein the scFv comprises an amino acid sequence having at least 85% sequence identity to SEQ ID NO: 105.

23. The method of claim 22, wherein the scFv comprises the amino acid sequence of SEQ ID NO: 105.

24. The method of claim 1, wherein the transmembrane domain comprises:

(a) a transmembrane domain of a protein selected from the group consisting of a T cell receptor alpha chain, a T cell receptor beta chain, a T cell receptor zeta chain, CD28, CD3 epsilon, CD45, CD4, CD5, CD8, CD9, CD16, CD22, CD33, CD37, CD64, CD80, CD86, CD134, CD137, and CD154; or
(b) an amino acid sequence having at least 85% identity to SEQ ID NO: 6.

25. The method of claim 24, wherein the transmembrane domain comprises the amino acid sequence of SEQ ID NO: 6.

26. The method of claim 1, wherein the anti-BCMA binding domain is connected to the transmembrane domain by a hinge region comprising the amino acid sequence of SEQ ID NO: 2, 3, or 4.

27. The method of claim 1, wherein:

(a) the primary signaling domain comprises the amino acid sequence of SEQ ID NO: 9 or 10; and/or
(b) the costimulatory signaling domain comprises the amino acid sequence of SEQ ID NO: 7.

28. The method of claim 1, wherein the CAR comprises an amino acid sequence having at least 85% sequence identity to SEQ ID NO: 107 or at least 85% sequence identity to SEQ ID NO: 257.

29. The method of claim 28, wherein the CAR comprises the amino acid sequence of SEQ ID NO: 107 or SEQ ID NO: 257.

30. The method of claim 1, wherein the effective amount of the cells is $10^4$ to $10^9$ cells per kg body weight.

31. The method of claim 30, wherein the effective amount of the cells is $10^5$ to $10^6$ cells per kg body weight.

32. The method of claim 1, wherein the cells comprising the CAR are allogeneic T cells.

33. The method of claim 1, wherein the cells comprising the CAR, or progeny of the cells comprising the CAR, persist in the subject for at least six months after administration.

34. The method of claim 1, wherein the subject has multiple myeloma.

35. The method of claim 1, wherein the subject is a human.

36. The method of claim 6, wherein:

(a) the VH comprises an amino acid sequence having at least 85% sequence identity to SEQ ID NO: 93; and/or
(b) the VL comprises an amino acid sequence having at least 85% sequence identity to SEQ ID NO: 102.

37. The method of claim 36, wherein:

(a) the VH comprises the amino acid sequence of SEQ ID NO: 93; and/or (b) the VL comprises the amino acid sequence of SEQ ID NO: 102.

38. The method of claim 1, wherein the anti-BCMA binding domain is an scFv.

39. The method of claim 38, wherein the scFv is a fully human scFv.

40. The method of claim 38, wherein the scFv comprises an amino acid sequence having at least 85% sequence identity to SEQ ID NO: 105.

41. The method of claim 40, wherein the scFv comprises the amino acid sequence of SEQ ID NO: 105.

42. The method of claim 6, wherein the transmembrane domain comprises:

(a) a transmembrane domain of a protein selected from the group consisting of a T cell receptor alpha chain, a T cell receptor beta chain, a T cell receptor zeta chain, CD28, CD3 epsilon, CD45, CD4, CD5, CD8, CD9, CD16, CD22, CD33, CD37, CD64, CD80, CD86, CD134, CD137, and CD154; or (b) an amino acid sequence having at least 85% identity to SEQ ID NO: 6.

43. The method of claim 42, wherein the transmembrane domain comprises the amino acid sequence of SEQ ID NO: 6.

44. The method of claim 6, wherein the anti-BCMA binding domain is connected to the transmembrane domain by a hinge region comprising the amino acid sequence of SEQ ID NO: 2, 3, or 4.

45. The method of claim 6, wherein:

(a) the primary signaling domain comprises the amino acid sequence of SEQ ID NO: 9 or 10; and/or (b) the costimulatory signaling domain comprises the amino acid sequence of SEQ ID NO: 7.

46. The method of claim 6, wherein the CAR comprises an amino acid sequence having at least 85% sequence identity to SEQ ID NO: 107 or at least 85% sequence identity to SEQ ID NO: 257.

47. The method of claim 46, wherein the CAR comprises the amino acid sequence of SEQ ID NO: 107 or SEQ ID NO: 257.

48. The method of claim 6, wherein the effective amount of the cells is $10^4$ to $10^9$ cells per kg body weight.

49. The method of claim 48, wherein the effective amount of the cells is $10^5$ to $10^6$ cells per kg body weight.

50. The method of claim 6, wherein the cells comprising the CAR are allogeneic T cells.

51. The method of claim 6, wherein the cells comprising the CAR, or progeny of the cells comprising the CAR, persist in the subject for at least six months after administration.

52. The method of claim 6, wherein the subject is a human.

53. The method of claim 6, further comprising administering to the subject a soluble factor-neutralizing agent.

54. The method of claim 53, wherein the soluble factor-neutralizing agent is a corticosteroid, an inhibitor of IL-6, or a combination thereof.

55. The method of claim 54, wherein the inhibitor of IL-6 is tocilizumab.

56. The method of claim 14, wherein the CAR comprises an N-terminal leader sequence of SEQ ID NO: 1.

57. The method of claim 14, wherein the cancer is multiple myeloma, acute leukemia, B-cell acute lymphoblastic leukemia (BALL), T-cell acute lymphoblastic leukemia (TALL), acute lymphoblastic leukemia (ALL), chronic myelogenous leukemia (CML), chronic lymphocytic leukemia (CLL), B cell prolymphocytic leukemia, blastic plasmacytoid dendritic cell neoplasm, Burkitt's lymphoma, diffuse large B cell lymphoma, follicular lymphoma, hairy cell leukemia, small cell- or large cell-follicular lymphoma, malignant lymphoproliferative conditions, MALT lymphoma, mantle cell lymphoma, marginal zone lymphoma, myelodysplasia and myelodysplastic syndrome, non-Hodgkin's lymphoma, plasmablastic lymphoma, plasmacytoid dendritic cell neoplasm, Waldenstrom macroglobulinemia, prostate cancer, pancreatic cancer, lung cancer, a plasma cell proliferative disorder, or a combination thereof.

58. The method of claim 14, wherein the effective amount of the cells is $10^4$ to $10^9$ cells per kg body weight.

59. The method of claim 58, wherein the effective amount of the cells is $10^5$ to $10^6$ cells per kg body weight.

60. The method of claim 14, wherein the cells comprising the CAR are allogeneic T cells.

61. The method of claim 14, wherein the cells comprising the CAR, or progeny of the cells comprising the CAR, persist in the subject for at least six months after administration.

62. The method of claim 14, wherein the subject is a human.

63. A method of treating a subject having a multiple myeloma, the method comprising administering to the subject an effective amount of autologous T cells comprising a CAR, wherein the CAR comprises an anti-BCMA binding domain, a transmembrane domain, and an intracellular signaling domain comprising a primary signaling domain and a costimulatory signaling domain, wherein:

(a) the anti-BCMA binding domain comprises a VH comprising an HC CDR1 of SEQ ID NO: 86, a HC CDR2 of SEQ ID NO: 87, and a HC CDR3 of SEQ ID NO: 88, and a VL comprising an LC CDR1 of SEQ ID NO: 95, a LC CDR2 of SEQ ID NO: 96, and an LC CDR3 of SEQ ID NO: 97;

(b) the primary signaling domain comprises a functional signaling domain of CD3 zeta; and (c) the costimulatory signaling domain comprises a functional signaling domain of 4-1BB (CD137).

64. The method of claim 63, wherein:

(a) the VH comprises an amino acid sequence having at least 85% sequence identity to SEQ ID NO: 93; and/or (b) the VL comprises an amino acid sequence having at least 85% sequence identity to SEQ ID NO: 102.

65. The method of claim 64, wherein:

(a) the VH comprises the amino acid sequence of SEQ ID NO: 93; and/or (b) the VL comprises the amino acid sequence of SEQ ID NO: 102.

66. The method of claim 63, wherein the anti-BCMA binding domain is an scFv.

67. The method of claim 66, wherein the scFv is a fully human scFv.

68. The method of claim 67, wherein the scFv comprises an amino acid sequence having at least 85% sequence identity to SEQ ID NO: 105.

69. The method of claim 68, wherein the scFv comprises the amino acid sequence of SEQ ID NO: 105.

70. The method of claim 63, wherein the transmembrane domain comprises:

(a) a transmembrane domain of a protein selected from the group consisting of a T cell receptor alpha chain, a T cell receptor beta chain, a T cell receptor zeta chain, CD28, CD3 epsilon, CD45, CD4, CD5, CD8, CD9, CD16, CD22, CD33, CD37, CD64, CD80, CD86, CD134, CD137, and CD154; or (b) an amino acid sequence having at least 85% identity to SEQ ID NO: 6.

71. The method of claim 70, wherein the transmembrane domain comprises the amino acid sequence of SEQ ID NO: 6.

72. The method of claim 63, wherein the anti-BCMA binding domain is connected to the transmembrane domain by a hinge region comprising the amino acid sequence of SEQ ID NO: 2, 3, or 4.

73. The method of claim 63, wherein:

(a) the primary signaling domain comprises the amino acid sequence of SEQ ID NO: 9 or 10; and/or (b) the costimulatory signaling domain comprises the amino acid sequence of SEQ ID NO: 7.

74. The method of claim 63, wherein the CAR comprises an amino acid sequence having at least 85% sequence identity to SEQ ID NO: 107 or at least 85% sequence identity to SEQ ID NO: 257.

75. The method of claim 74, wherein the CAR comprises the amino acid sequence of SEQ ID NO: 107 or SEQ ID NO: 257.

76. The method of claim 63, wherein the effective amount of the autologous T cells is $10^4$ to $10^9$ cells per kg body weight.

77. The method of claim 76, wherein the effective amount of the autologous T cells is $10^5$ to $10^6$ cells per kg body weight.

78. The method of claim 63, wherein the autologous T cells comprising the CAR, or progeny of the autologous T cells comprising the CAR, persist in the subject for at least six months after administration.

79. The method of claim 63, wherein the subject is a human.

80. The method of claim 63, further comprising administering to the subject a soluble factor-neutralizing agent.

81. The method of claim 80, wherein the soluble factor-neutralizing agent is a corticosteroid, an inhibitor of IL-6, or a combination thereof.

82. The method of claim 81, wherein the inhibitor of IL-6 is tocilizumab.

83. A method of treating a subject having a multiple myeloma, the method comprising administering to the subject an effective amount of autologous T cells comprising a CAR that binds to BCMA, wherein the CAR comprises, from N-terminus to C-terminus:

(a) an HC CDR1 of SEQ ID NO: 86;

(b) an HC CDR2 of SEQ ID NO: 87;

(c) an HC CDR3 of SEQ ID NO: 88;

(d) an LC CDR1 of SEQ ID NO: 95;

(e) an LC CDR2 of SEQ ID NO: 96;

(f) an LC CDR3 of SEQ ID NO: 97;

(g) a CD8 transmembrane domain and hinge of SEQ ID NO: 202;

(h) a functional signaling domain of 4-1BB of SEQ ID NO: 7; and (i) a functional signaling domain of CD3 zeta of SEQ ID NO: 10.

84. The method of claim 83, wherein the CAR comprises:

(a) a VH comprising the amino acid sequence of SEQ ID NO: 93 and a VL comprising the amino acid sequence of SEQ ID NO: 102; and/or (b) an scFv comprising the amino acid sequence of SEQ ID NO: 105.

85. The method of claim 84, wherein the CAR comprises the amino acid sequence of SEQ ID NO: 257 or SEQ ID NO: 107.

86. The method of claim 83, wherein the effective amount of the autologous T cells is $10^4$ to $10^9$ cells per kg body weight.

87. The method of claim 86, wherein the effective amount of the autologous T cells is $10^5$ to $10^6$ cells per kg body weight.

88. The method of claim 83, wherein the autologous T cells comprising the CAR, or progeny of the autologous T cells comprising the CAR, persist in the subject for at least six months after administration.

89. The method of claim 83, wherein the subject is a human.

90. The method of claim 57, wherein the cancer is a multiple myeloma.

* * * * *

UNITED STATES PATENT AND TRADEMARK OFFICE

CERTIFICATE OF CORRECTION

PATENT NO. : 11,939,389 B2
APPLICATION NO. : 18/170969
DATED : March 26, 2024
INVENTOR(S) : Aida Abujoub et al.

It is certified that error appears in the above-identified patent and that said Letters Patent is hereby corrected as shown below:

In the Claims

At Column 313, Claim number 15, Line number 60, delete "of SEQ ID NO:1-102; and/or" and insert --of SEQ ID NO:102; and/or--

Signed and Sealed this
Third Day of September, 2024

Katherine Kelly Vidal
*Director of the United States Patent and Trademark Office*